US008119130B2

(12) United States Patent
Barry et al.

(10) Patent No.: US 8,119,130 B2
(45) Date of Patent: Feb. 21, 2012

(54) TARGETED BINDING AGENTS DIRECTED TO KDR AND USES THEREOF—035

(75) Inventors: Simon Thomas Barry, Macclesfield (GB); Vahe Bedian, Framingham, MA (US); Bradley Hedberg, Vancouver (CA); Jaspal Singh Kang, Surrey (CA); Qing Zhou, Fremont, CA (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 12/669,724

(22) PCT Filed: Jul. 23, 2008

(86) PCT No.: PCT/GB2008/050615

§ 371 (c)(1), (2), (4) Date: Jun. 22, 2010

(87) PCT Pub. No.: WO2009/013543

PCT Pub. Date: Jan. 29, 2009

(65) Prior Publication Data

US 2010/0260765 A1 Oct. 14, 2010

Related U.S. Application Data

(60) Provisional application No. 60/951,805, filed on Jul. 25, 2007.

(51) Int. Cl.

*A61K 39/395* (2006.01)
*A61K 39/00* (2006.01)
*C12P 21/08* (2006.01)
*C07K 16/00* (2006.01)
*C07K 16/28* (2006.01)

(52) U.S. Cl. ............... 424/130.1; 424/141.1; 424/142.1; 424/143.1; 530/387.1; 530/388.1; 530/388.15; 530/388.22

(58) Field of Classification Search ........................ None
See application file for complete search history.

(56) References Cited

U.S. PATENT DOCUMENTS

| | | | | |
|---|---|---|---|---|
| 7,498,414 | B2 * | 3/2009 | Zhu | 530/387.1 |
| 2004/0242851 | A1 * | 12/2004 | Zhu | 530/388.22 |
| 2005/0234225 | A1 * | 10/2005 | Zhu | 530/388.22 |

FOREIGN PATENT DOCUMENTS

| | | | |
|---|---|---|---|
| WO | WO/02/102973 | A2 | 12/2002 |
| WO | WO/2009/013543 | A2 | 1/2009 |

OTHER PUBLICATIONS

Stancovski et al, Proceedings of the National Academy of Science USA 88: 8691-8695, 1991.*
Cochran et al, J. Immunol. Meth. 287: 147-158, 2004.*
Riemer et al, Mol. lmmunol. 42: 1121-1124, 2005.*
Alam, Antoine et al., 2004, "Heterodimerization with vascular endothelial growth factor receptor-2 (VEGFR-2) is necessary for VEGFR-3 activity", Biochemical and Biophysical Research Communication, 324:909-915.
Autiero, Monica et al., 2003, "Role of PIGF in the intra- and intermolecular cross talk between the VEGF receptors Flt1 and Flk1", Nature Medicine, 9(7):936-943.
Baka, Sofia et al., 2006, "A review of the lastest clinical compounds to inhibit VEGF in pathological angiogenesis", Expert Opinion Therapeutic Targets, 10(6):867-876.
Carmeliet, Peter et al., 2001, "Synergism between vascular endothelial growth factor and placental growth factor contributes to angiogenesis and plasma extravasation in pathological conditions", Nature Medicine, vol. 7., No. 5, 575-583.
Castellone, Maria Domenica, et al., 2008, "Receptor tyrosine kinase inhibitors in thyroid cancer", Best Practice & Research Clinical Endocrinology & Metabolism, 22(6):1023-1038.
Christinger, Hans W. et al., 2004, "The Crystal Structure of Placental Growth Factor in Complex with Domain 2 of Vascular Endothelial Growth Factor Receptor-1", The Journal of Biological Chemistry, 279(11):10382-10388.
Eskens, Ferry A.L.M., et al., 2006, "The clinical toxicity profile of vascular endothelial growth factor (VEGF) and vascular endothelial growth factor receptor (VEGFR) targeting angiogenesis inhibitors; A review", European Journal of Cancer, 42:3127-3139.
Fuh, Germaine, et al., 1998, "Requirements for Binding and Signaling of the Kinase Domain Receptor for Vascular Endothelial Growth Factor", The Journal of Biological Chemistry, 273(18):11197-11204.
Heldin, Carl-Henrik, 1995, "Dimerization of Cell Surface Receptors in Signal Transduction", Cell, 80:213-223.
Huang, Tiffany T., et al., 2009, "Targeted Therapy for Malignant Glioma Patients: Lessons Learned and the Road Ahead", Neurotherapeutics: The Journal of the American Society for Experimental NeuroTherapeutics, 6:500-512.
Imclone Systems Incorporated: "Phase II Study of IMC-1121B fro Advanced Renal Cell Cancer Opens for Patient Enrollment", Internet Citation (Press Release) [Online] Aug. 24, 2007.
Lu, Dan et al., 2003, "Tailoring in Vitro Selection for a Picomolar Affinity Human Antibody Directed against Vascular Endothelial Growth Factor Receptor 2 for Enhanced Neutralizing Activity", The Journal of Biological Chemistry, 278(44):43496-43507.
Notification of Transmittal of the International Search Report and the Written Opinon of the International Searching Authority, or the Declaration for PCT/GB2008/050615 mailed Oct. 3, 2010.
Notification Concerning Transmittal of International Preliminary Report on Patentability for PCT/GB2008/050615 mailed Apr. 1, 2010.
Olsson, Anna-Karin et al., 2006, "VEGF receptor signalling—in control of vascular function", Nature Reviews/Molecular Cell Biology, 7:359-371.
Prewett, Marie, et al., 1999, "Antivascular Endothelial Growth Factor Receptor (Fetal Liver Kinase 1) Monoclonal Antibody Inhibits Tumor Angiogenesis and Growth of Several Mouse and Human Tumors", Cancer Research, 59:5209-5218.
Roskoski, Robert Jr., 2007, "Vascular endothelial growth factor (VEGF) signaling in tumor progression", Critical Reviews in Oncology/Hematology, 62:179-213.
Waltenberger, Johannes et al., 1994, "Different Signal Transduction Properties of KDR and Flt1, Two Receptors for Vascular Endothelial Growth Factor", The Journal of Biological Chemistry, 269(43):26988-26995.

* cited by examiner

*Primary Examiner* — Phuong Huynh

(57) ABSTRACT

The invention relates to targeted binding agents against KDR and uses of such agents. More specifically, the invention relates to fully human monoclonal antibodies directed to KDR. The described targeted binding agents are useful in the treatment of diseases associated with the activity and/or overproduction of KDR and as diagnostics.

4 Claims, 2 Drawing Sheets

TARGETED BINDING AGENTS DIRECTED TO KDR AND USES THEREOF—035

CROSS REFERENCE TO RELATED APPLICATIONS

This application is a National Stage Application of International Application No. PCT/GB08/50615, filed Jul. 23, 2008, said International Application No. PCT/GB08/50615 claims the benefit of U.S. Appl. Ser. No. 60/951,805 filed Jul. 25, 2007, all of which are hereby incorporated by reference in their entirety for all purposes.

BACKGROUND OF THE INVENTION

1. Field of the Invention

The invention relates to targeted binding agents against KDR and uses of such agents. More specifically, the invention relates to fully human monoclonal antibodies directed to KDR. The described targeted binding agents are useful in the treatment of diseases associated with the activity and/or overproduction of KDR and as diagnostics.

2. Description of the Related Art

The vascular endothelial growth factor-A (VEGF-A) plays a critical role in inducing vascular growth and remodeling during development, and in a number of pathological conditions including the angiogenesis required to support solid tumour growth. VEGF-A signaling is predominantly mediated through activation of VEGF receptor 2 (VEGFR2; KDR/flk-1), which can stimulate endothelial cell proliferation, migration, vascular permeability, and neovascular survival (reviewed in Olsson et al., Nat. Rev. Mol. Cell. Biol. 2006; 7:359-71.). The broader VEGFR family of tyrosine kinase receptors consists of three members: VEGFR1, VEGFR2 and VEGFR3, also known as Flt-1, KDR/Flk-1 and Flt4, respectively. Known VEGFR ligands exhibit differential, well-defined selectivity for each VEGFR. For example, VEGF-A binds both VEGFR1 and VEGFR2, VEGF-B and P1GF primarily bind VEGFR1, and VEGF-C and D are specific activators of VEGFR3. There are also a number of non-physiological VEGFs that also activate the VEGFR, for example VEGF-E specifically activates VEGFR2 while VEGF-F will activate VEGFR1 and VEGFR2.

Dimerization of VEGFR drives a complex series of signaling events leading to activation of many common growth factor signaling pathways (Olsson et al Nat. Rev. Mol. Cell Biol. 2006; 7:359-71). At the molecular level, there is a complex relationship between ligand expression, receptor dimerization and activation, and the downstream consequences in different cell types. VEGFR signaling is of primary importance to endothelial cells, although the receptors have been implicated in regulating the function of other cells. For example Flt-1 plays a role in mediating monocyte transmigration and, when expressed, can promote tumour cell migration.

All three receptors form both homo- and heterodimers (with the exception of VEGFR1/3 heterodimers), allowing signals from the various VEGF ligands to be integrated. KDR appears to be the receptor that is central to many of these signaling events, as it is the common VEGFR expressed on blood and lymphatic vessels. KDR can also offset low VEGFR-1 signaling activity. VEGFR1 itself has low intrinsic kinase activity, and deletion of the VEGFR1 kinase domain does not affect normal development. Experiments have shown that VEGFR1 can synergize with KDR and facilitate full activation of KDR signaling (Carmeliet et al, Nat Med 2001, 7, 575; Auterio et al, 2003 Nat Med, 9, 936). It is possible that this is achieved through heterodimerisation, which is prevented by an inhibitor of KDR dimerization. VEGFR3 has also been shown to form a heterodimer with KDR (Alam et al, BBRC, 2004, 324, 909). However, the mechanisms by which the various homo- and heterodimers of VEGFR1, KDR and VEGFR3 interact to drive physiological effects is unclear. Inhibition of VEGFR/VEGF signaling may effect different disease states (reviewed in Baka et al Expert Opin Ther Targets 2006, 10, 867).

VEGFRs consist of seven immunoglobin-like extracellular domains. Ligands, (e.g. VEGFA and P1GF) that specifically bind VEGFRs have immunoglobin-like domains 2 and 3, with domain 2 making the primary contact and domain 3 determining the specificity of binding (Christinger et al JBC, 2004, 279, 10382; Fuh et al JBC 1998, 273, 11197). In contrast, domains 4-6 are involved in dimerization of the receptor complexes. Ligand binding that stabilizes the receptor complexes can prolong dimerization, allowing productive signaling to proceed. As receptor activation is a function of both binding and dimerization, receptor activation can be inhibited by inhibiting ligand-receptor binding or by blocking dimerization. Antibodies that block binding of ligand to the receptors have been described previously, for example, IMC1121b and its murine equivalent, DC101, both of which block binding of VEGF-A to KDR, and thereby block VEGF-A signaling through KDR, and are known to deliver an anti-tumour effect (Prewett et al Cancer Res 1999, 59, 5209; Lu et al, JBC 2003, 278, 43496). It has been reported both pre-clinically and clinically that as a direct consequence of inhibiting KDR signaling, there is a rebound increase in circulating VEGF-A levels. Antibodies such as IMC1121b which block VEGF-A binding to KDR are expected to be less efficacious under conditions of increasing VEGF-A concentrations, where competition for binding to KDR may be won over by VEGF-A rather than the antibody.

Thus there is a need to identify new means of inhibiting KDR signaling.

SUMMARY OF THE INVENTION

The present invention relates to targeted binding agents that specifically bind to KDR and inhibit the biological activity of KDR. Embodiments of the invention relate to targeted binding agents that specifically bind to KDR and inhibit receptor dimerisation. Embodiments of the invention also relate to targeted binding agents that specifically bind to KDR and inhibit binding of VEGF to KDR. Embodiments of the invention relate to fully human isolated targeted binding agents that specifically bind to KDR and inhibit binding of VEGF to KDR Inhibition of KDR signaling by inhibition of receptor dimerisation is expected to have advantages over inhibition of VEGF-A binding to KDR. Targeted binding agents which inhibit receptor dimerisation, such as those described here, are anticipated to be able to maximally inhibit the KDR signaling axis by blocking KDR:KDR homodimer and KDR:Flt-1 heterodimer formation and hence block VEGF-A, VEGF-B and P1GF signaling through both KDR and Flt-1. In addition, increasing VEGF-A levels should have no direct impact on the efficacy of agents that inhibit receptor dimerization.

Embodiments of the invention relate to targeted binding agents that specifically bind to KDR and inhibit receptor dimerisation. In one embodiment the targeted binding agent that inhibits receptor dimerisation and binding of VEGF to KDR. In one embodiment of the invention the targeted binding agent specifically binds to KDR and inhibits KDR homodimer formation. In one embodiment of the invention the targeted binding agent specifically binds to KDR and inhibits KDR heterodimer formation. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of KDR receptor dimerisation that would occur in the absence of the targeted binding agent.

In one embodiment of the invention the targeted binding agent specifically binds to KDR and inhibits binding of VEGF. In one embodiment of the invention the targeted binding agent specifically binds to KDR and inhibits binding of VEGF-A. In one embodiment of the invention the targeted binding agent specifically binds to KDR and inhibits binding of PLGF. In one embodiment of the invention the targeted binding agent specifically binds to KDR and inhibits binding of VEGF-C, VEGF-D and/or VEGF-E.

In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of VEGF or VEGF-C binding to KDR that would occur in the absence of the targeted binding agent.

In one embodiment of the invention the targeted binding agent specifically binds to KDR and inhibits VEGF-mediated prostaglandin release. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of VEGF-mediated prostaglandin release that would occur in the absence of the targeted binding agent.

In some embodiments of the invention, the targeted binding agent at 133 nM inhibits greater than 50% of VEGF-165-mediated tyrosine phosphorylation induced by 2 nM VEGF-165 in human umbilical vein endothelial cells (HUVECs). In some embodiments of the invention, the targeted binding agent at 133 nM inhibits greater than 50% of VEGF-165-mediated tyrosine phosphorylation induced by 2 nM VEGF-165 in human umbilical vein endothelial cells (HUVECs) as measured in an assay wherein the HUVECs are firstly incubated in FCS supplemented media, which is then replaced with supplement-free media overnight, the targeted binding agent is then added and after a pre-incubation period with the targeted binding agent, the cells are stimulated by addition of the VEGF-165. In some embodiments of the invention, the targeted binding agent inhibits greater than 50% of VEGF-165-mediated tyrosine phosphorylation in human umbilical vein endothelial cells (HUVECs) as measured in an assay as described in Example 11 herein.

In some embodiments of the invention, the targeted binding agent at a 1/20 dilution of hybridoma supernatant inhibits greater than 40% of VEGF-E mediated tyrosine phosphorylation induced by 2 nM VEGF-E in HUVECs. In some embodiments of the invention, the targeted binding agent at a 1/20 dilution of hybridoma supernatant inhibits greater than 40% of VEGF-E mediated tyrosine phosphorylation induced by 2 nM VEGF-E in HUVECs as measured in an assay wherein the HUVECs are firstly incubated in FCS plus growth supplements media, which is then replaced by supplement-free media overnight, followed by addition of the targeted binding agent and finally by replacement with the VEGF-E. In some embodiments of the invention, the targeted binding agent inhibits greater than 40% of VEGF-E mediated tyrosine phosphorylation in HUVECs as measured in an assay as described in Example 8 herein.

In some embodiments, the targeted binding agent at a 1/20 dilution of hybridoma supernatant inhibits greater than 55% of VEGF-E mediated cell survival as induced by 1 nM VEGF-E in HUVECs. In some embodiments, the targeted binding agent at a 1/20 dilution of hybridoma supernatant inhibits greater than 55% of VEGF-E mediated cell survival as induced by 1 nM VEGF-E in HUVECs as measured in an assay wherein the HUVECs are firstly incubated in FCS plus growth supplements media, followed by addition of the targeted binding agent and after a pre-incubation period, addition of VEGF-E. In some embodiments, the targeted binding agent inhibits greater than 55% of VEGF-E mediated cell survival in HUVECs as measured in an assay as described in Example 8 herein.

In some embodiments of the invention, the targeted binding agent at 20 μg/mL, 5 μg/mL, 1.25 μg/mL or 0.3125 μg/mL inhibits greater than 50% of endothelial cell tube formation in comparison with a control antibody. In some embodiments of the invention, the targeted binding agent at 20 μg/mL, 5 μg/mL, 1.25 μg/mL or 0.3125 μg/mL inhibits greater than 50% of endothelial cell tube formation as measured in an assay wherein the targeted binding agent is introduced to co-cultures of HUVECs and human diploid fibroblasts maintained in either TCS Optimised Medium or MCDB131 medium supplemented with 2% foetal calf serum, 1% glutamine and 1% penicillin/streptomycin. In some embodiments of the invention, the targeted binding agent at 20 μg/mL, 5 μg/mL, 1.25 μg/mL or 0.3125 μg/mL inhibits greater than 50% of endothelial cell tube formation as measured in an assay as described in Example 23. In some embodiments of the invention, the targeted binding agent at 20 μg/mL, 5 μg/mL, 1.25 μg/mL or 0.3125 μg/mL inhibits greater than 60%, 70%, 80% or 90% of endothelial cell tube formation.

In some embodiments of the invention, the targeted binding agent dosed at 10 mg/kg or 1 mg/kg twice weekly inhibits greater than 50% of angiogenesis in vivo. In some embodiments of the invention, the targeted binding agent dosed at 10 mg/kg or 1 mg/kg twice weekly inhibits greater than 50% of angiogenesis in vivo in a spheroid-based in vivo angiogenesis assay. In some embodiments of the invention, the targeted binding agent inhibits greater than 50% of angiogenesis in vivo as measured in an assay wherein HUVEC spheroids are mixed in a Matrigel/fibrin solution with single HUVECs to reach a final number of 100,000 ECs as spheroids and 200,000 single ECs per injected plug; VEGF-A and FGF added at a final concentration of 1000 ng/ml and the 500 μl of cell/matrix suspension injected into the study animal, with treatment with the targeted binding agent commenced the following day and ceased at day 21. In some embodiments of the invention, the targeted binding agent inhibits greater than 50% of angiogenesis in vivo as measured in an assay as described in Example 24. In some embodiments of the invention, the targeted binding agent inhibits greater than 60%, 70%, 80% or 90% of angiogenesis in vivo.

In some embodiments of the invention, the targeted binding agent binds KDR with a binding affinity (Kd) of less than 5 nanomolar (nM). In other embodiments, the targeted binding agent binds with a Kd of less than 4 nM, 3 nM, 2 nM or 1 nM. In some embodiments of the invention, the targeted binding agent binds KDR with a Kd of less than 950 picomolar (pM). In some embodiments of the invention, the targeted binding agent binds KDR with a Kd of less than 900 pM. In other embodiments, the targeted binding agent binds with a Kd of less than 800 pM, 700 pM or 600 pM. In some embodiments of the invention, the targeted binding agent binds KDR with a Kd of less than 500 pM. In other embodiments, the targeted binding agent binds with a Kd of less than 400 pM. In still other embodiments, the targeted binding agent binds with a Kd of less than 300 pM. In some other embodiments, the targeted binding agent binds with a Kd of less than 200 pM. The Kd may be assessed using a method described herein or known to one of skill in the art (e.g., a BIAcore assay, ELISA) (Biacore International AB, Uppsala, Sweden).

The binding properties of the targeted binding agent or antibody of the invention may also be measured by reference to the dissociation or association rates ($k_{off}$ and $k_{on}$ respectively).

In one embodiment of the invention, a targeted binding agent or an antibody may have an $k_{on}$ rate (antibody (Ab)+antigen $(Ag)^{k_{on}}\rightarrow$Ab–Ag) of at least $10^4M^{-1}s^{-1}$, at least $5\times10^4M^{-1}s^{-1}$, at least $10^5M^{-1}s^{-1}$, at least $2\times10^5M^{-1}s^{-1}$, at least $5\times10^5M^{-1}s^{-1}$, at least $10^6M^{-1}s^{-1}$, at least $5\times10^6M^{-1}s^{-1}$, at least $10^7M^{-1}s^{-1}$, at least $5\times10^7M^{-1}s^{-1}$, or at least $10^8M^{-1}s^{-1}$.

In another embodiment of the invention, targeted binding agent or an antibody may have a $k_{off}$ rate ($(Ab-Ag)^{k_{off}}\rightarrow$antibody (Ab)+antigen (Ag)) of less than $5\times10^{-1}s^{-1}$, less than $10^{-1}s^{-1}$, less than $5\times10^{-2}s^{-1}$, less than $10^{-2}s^{-1}$, less than $5\times10^{-3}s^{-1}$, less than $10^{-3}s^{-1}$, less than $5\times10^{-4}s^{-1}$, less than $10^{-4}s^{-1}$, less than $5\times10^{-5}s^{-1}$, less than $10^{-5}s^{-1}$, less than $5\times10^{-6}s^{-1}$, less than $10^{-6}s^{-1}$, less than $5\times10^{-7}s^{-1}$, less than $10^{-7}s^{-1}$, less than $5\times10^{-8}s^{-1}$, less than $10^{-8}s^{-1}$, less than $5\times10^{-9}s^{-1}$, less than $10^{-9}s^{-1}$, or less than $10^{-10}s^{-1}$.

In some embodiments of the invention, the targeted binding agent inhibits tumour growth and/or metastasis in a mammal. In other embodiments, the targeted binding agent ameliorates symptoms associated with inflammatory disorders in a mammal In one embodiment, the targeted binding agent ameliorates symptoms associated with inflammatory disorders selected from rheumatoid arthritis or psoriasis in a mammal. Symptoms that may be ameliorated include, but are not limited to, angiogenesis and synovitis. In still other embodiments, the targeted binding agent ameliorates symptoms associated with cardiovascular disease in a mammal In still other embodiments, the targeted binding agent ameliorates symptoms associated with a cardiovascular disease such as atherosclerosis in a mammal. Symptoms that may be ameliorated include, but are not limited to, inflammation and angiogenesis. In some other embodiments, the targeted binding agent ameliorates symptoms associated with sepsis in a mammal. Symptoms that may be ameliorated include, but are not limited to, uncontrolled vascular permeability, vascular leakage and angiogenesis. In some other embodiments, the targeted binding agent ameliorates symptoms associated with ocular disease. In some other embodiments, the targeted binding agent ameliorates symptoms associated with an ocular disease, such as ischaemic retinopathy or age-related macular degeneration. Symptoms that may be ameliorated include, but are not limited to, uncontrolled vascular permeability and vascular leakage.

In some embodiments of the invention, the targeted binding agent is an antibody. In some embodiments of the invention, the targeted binding agent is a monoclonal antibody. In one embodiment of the invention, the targeted binding agent is a fully human monoclonal antibody. In another embodiment of the invention, the targeted binding agent is a fully human monoclonal antibody of the IgG1, IgG2, IgG3 or IgG4 isotype. In another embodiment of the invention, the targeted binding agent is a fully human monoclonal antibody of the IgG2 isotype. This isotype has reduced potential to elicit effector function in comparison with other isotypes, which may lead to reduced toxicity. In another embodiment of the invention, the targeted binding agent is a fully human monoclonal antibody of the IgG1 isotype. The IgG1 isotype has increased potential to elicit ADCC in comparison with other isotypes, which may lead to improved efficacy. The IgG1 isotype has improved stability in comparison with other isotypes, e.g. IgG4, which may lead to improved bioavailability, or improved ease of manufacture or a longer half-life. In one embodiment, the fully human monoclonal antibody of the IgG1 isotype is of the z, za or f allotype.

A further embodiment is a targeted binding agent or an antibody that specifically binds to KDR and comprises a sequence comprising one of the complementarity determining regions (CDR) sequences shown in Table 20. Embodiments of the invention include a targeted binding agent or antibody comprising a sequence comprising: any one of a CDR1, a CDR2 or a CDR3 sequence as shown in Table 20. A further embodiment is a targeted binding agent or an antibody that specifically binds to KDR and comprises a sequence comprising two of the CDR sequences shown in Table 20. In another embodiment the targeted binding agent or antibody comprises a sequence comprising a CDR1, a CDR2 and a CDR3 sequence as shown in Table 20. In another embodiment the targeted binding agent or antibody comprises a sequence comprising one of the CDR sequences shown in Table 21. Embodiments of the invention include a targeted binding agent or antibody comprising a sequence comprising: any one of a CDR1, a CDR2 or a CDR3 sequence as shown in Table 21. In another embodiment the targeted binding agent or antibody comprises a sequence comprising two of the CDR sequences shown in Table 21. In another embodiment the targeted binding agent or antibody comprises a sequence comprising a CDR1, a CDR2 and a CDR3 sequence as shown in Table 21. In another embodiment the targeted binding agent or antibody may comprise a sequence comprising a CDR1, a CDR2 and a CDR3 sequence as shown in Table 20 and a CDR1, a CDR2 and a CDR3 sequence as shown in Table 21. In some embodiments, the targeted binding agent is an antibody. In certain embodiments, the targeted binding agent is a fully human monoclonal antibody. In certain other embodiments, the targeted binding agent is a binding fragment of a fully human monoclonal antibody.

For the avoidance of doubt, the term "Table 20" as used herein includes Table 20a and Table 20b.

For the avoidance of doubt, the term "Table 21" as used herein includes Table 21a and Table 21b.

It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3. Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains.

In one embodiment, the targeted binding agent or antibody comprises a sequence comprising any one of the heavy chain sequences shown in Table 20. In another embodiment, the targeted binding agent or antibody comprises a sequence comprising any one of the heavy chain sequences of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4. Light-chain promiscuity is well established in the art, thus, a targeted binding agent or antibody comprising a sequence comprising any one of the heavy chain sequences of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4 or another antibody as disclosed herein, may further comprise any one of the light chain sequences shown in Table 21 or of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4, or another antibody as disclosed herein. In some embodiments, the antibody is a fully human monoclonal antibody.

In one embodiment, the targeted binding agent or antibody comprises a sequence comprising any one of the light chain sequences shown in Table 21. In another embodiment, the targeted binding agent or antibody comprises a sequence comprising any one of the light chain sequences of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4. In some embodiments, the antibody is a fully human monoclonal antibody.

In some embodiments, the targeting binding agent is a monoclonal antibody selected from the group consisting of: 24B3, 27D10 and 33C3. In one embodiment, the targeted binding agent comprises one or more of fully human monoclonal antibodies 24B3, 27D10 or 33C3. In certain embodiments, the targeting binding agent is monoclonal antibody 24B3. In certain other embodiments, the targeting binding agent is monoclonal antibody 27D10. In still other embodiments, the targeting binding agent is monoclonal antibody 33C3. In additional embodiments, the targeted binding agent is derivable from any of the foregoing monoclonal antibodies.

In one embodiment a targeted binding agent or an antibody may comprise a sequence comprising a heavy chain CDR1, CDR2 and CDR3 selected from any one of the sequences shown in Table 20. In one embodiment a targeted binding agent or an antibody may comprise a sequence comprising a light chain CDR1, CDR2 and CDR3 selected from any one of the sequences shown in Table 21. In one embodiment a targeted binding agent or an antibody may comprise a sequence comprising a heavy chain CDR1, CDR2 and CDR3 selected from any one of the CDRs of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4. In one embodiment a targeted binding agent or an antibody may comprise a sequence comprising a light chain CDR1, CDR2 and CDR3 selected from any one of the CDRs of antibodies 33D5, 29H3, 29F7, 33C3, 31E11, 21A1, 21H6, 24C9, 32G7, 24B3, 33B1, 29A11, 30H10, 32B2, 32C11, 30E3, 1G6, 30F6, 30D7, 21H9, 29A3, 33E1, 22B8, 27A3, 27D10, 30A1, 32F4 or 29D4.

In another embodiment the targeted binding agent or antibody may comprise a sequence comprising any one of a CDR1, a CDR2 or a CDR3 of any one of the fully human monoclonal antibodies 24B3, 27D10 or 33C3, as shown in Table 20. In another embodiment the targeted binding agent or antibody may comprise a sequence comprising any one of a CDR1, a CDR2 or a CDR3 of any one of the fully human monoclonal antibodies 24B3, 27D10 or 33C3, as shown in Table 21. In one embodiment the targeted binding agent or antibody may comprise a sequence comprising a CDR1, a CDR2 and a CDR3 of fully human monoclonal antibody 24B3, 27D10 or 33C3, as shown in Table 20. In another embodiment the targeted binding agent or antibody may comprise a sequence comprising a CDR1, a CDR2 and a CDR3 of fully human monoclonal antibody 24B3, 27D10 or 33C3, as shown in Table 21. In another embodiment the targeted binding agent or antibody may comprise a sequence comprising a CDR1, a CDR2 and a CDR3 of fully human monoclonal antibody 24B3, 27D10 or 33C3, as shown in Table 20, and a CDR1, a CDR2 and a CDR3 sequence of fully human monoclonal antibody 24B3, 27D10 or 33C3, as shown in Table 21. In some embodiments, the antibody is a fully human monoclonal antibody.

In another embodiment the targeted binding agent or antibody comprises a sequence comprising the CDR1, CDR2 and CDR3 sequence of fully human monoclonal antibody 24B3 as shown in Table 20 and the CDR1, CDR2 and CDR3 sequence of fully human monoclonal antibody 24B3 as shown in Table 21. In another embodiment the targeted binding agent or antibody comprises a sequence comprising the CDR1, CDR2 and CDR3 sequence of fully human monoclonal antibody 27D10 as shown in Table 20 and the CDR1, CDR2 and CDR3 sequence of fully human monoclonal antibody 27D10 as shown in Table 21. In another embodiment the targeted binding agent or antibody comprises a sequence comprising the CDR1, CDR2 and CDR3 sequence of fully human monoclonal antibody 33C3 as shown in Table 20 and the CDR1, CDR2 and CDR3 sequence of fully human monoclonal antibody 33C3 as shown in Table 21. In some embodiments, the antibody is a fully human monoclonal antibody.

A further embodiment of the invention is a targeted binding agent or antibody comprising a sequence comprising the contiguous sequence spanning the framework regions and CDRs, specifically from FR1 through FR4 or CDR1 through CDR3, of any one of the sequences as shown in Table 20 or Table 21. In one embodiment the targeted binding agent or antibody comprises a sequence comprising the contiguous sequences spanning the framework regions and CDRs, specifically from FR1 through FR4 or CDR1 through CDR3, of any one of the sequences of monoclonal antibodies 24B3, 27D10 or 33C3, as shown in Table 20 or Table 21. In some embodiments, the antibody is a fully human monoclonal antibody.

One embodiment provides a targeted binding agent or antibody, or antigen-binding portion thereof, wherein the agent or antibody, or antigen-binding portion thereof, comprises a heavy chain polypeptide comprising the sequence of SEQ ID NO.:42. In one embodiment, the agent or antibody, or antigen-binding portion thereof, further comprises a light chain polypeptide comprising the sequence of SEQ ID NO.:44. In some embodiments, the antibody is a fully human monoclonal antibody.

In another embodiment the agent or antibody, or antigen-binding portion thereof, comprises a heavy chain polypeptide comprising the sequence of SEQ ID NO.:14. In one embodiment, the agent or antibody, or antigen-binding portion thereof, further comprises a light chain polypeptide comprising the sequence of SEQ ID NO.:16. In some embodiments, the antibody is a fully human monoclonal antibody.

In another embodiment the agent or antibody, or antigen-binding portion thereof, comprises a heavy chain polypeptide comprising the sequence of SEQ ID NO.:74. In another embodiment, the agent or antibody, or antigen-binding portion thereof, further comprises a light chain polypeptide comprising the sequence of SEQ ID NO.:76. In some embodiments, the antibody is a fully human monoclonal antibody.

In one embodiment the targeted binding agent or antibody comprises as many as twenty, sixteen, ten, nine or fewer, e.g. one, two, three, four or five, amino acid additions, substitutions, deletions, and/or insertions within the disclosed CDRs or heavy or light chain sequences. Such modifications may potentially be made at any residue within the CDRs. In some embodiments, the antibody is a fully human monoclonal antibody.

In one embodiment, the targeted binding agent or antibody comprises variants or derivatives of the CDRs disclosed herein, the contiguous sequences spanning the framework regions and CDRs (specifically from FR1 through FR4 or CDR1 through CDR3), the light or heavy chain sequences disclosed herein, or the antibodies disclosed herein. Variants include targeted binding agents or antibodies comprising sequences which have as many as twenty, sixteen, ten, nine or fewer, e.g. one, two, three, four, five or six amino acid additions, substitutions, deletions, and/or insertions in any of the CDR1, CDR2 or CDR3s as shown in Table 20 or Table 21, the contiguous sequences spanning the framework regions and CDRs (specifically from FR1 through FR4 or CDR1 through CDR3) as shown in Table 20 or Table 21, the light or heavy chain sequences disclosed herein, or with the monoclonal antibodies disclosed herein. Variants include targeted binding agents or antibodies comprising sequences which have at least about 60, 70, 80, 85, 90, 95, 98 or about 99% amino acid sequence identity with any of the CDR1, CDR2 or CDR3s as shown in Table 20 or Table 21, the contiguous sequences spanning the framework regions and CDRs (specifically from FR1 through FR4 or CDR1 through CDR3) as shown in Table 20 or Table 21, the light or heavy chain sequences disclosed herein, or with the monoclonal antibodies disclosed herein. The percent identity of two amino acid sequences can be determined by any method known to one skilled in the art, including, but not limited to, pairwise protein alignment. In one embodiment variants comprise changes in the CDR sequences or light or heavy chain polypeptides disclosed herein that are naturally occurring or are introduced by in vitro engineering of native sequences using recombinant DNA techniques or mutagenesis techniques. Naturally occurring variants include those which are generated in vivo in the corresponding germline nucleotide sequences during the generation of an antibody to a foreign antigen. In one embodiment the derivative may be a heteroantibody, that is an antibody in which two or more antibodies are linked together. Derivatives include antibodies which have been chemically modified. Examples include covalent attachment of one or more polymers, such as water-soluble polymers, N-linked, or O-linked carbohydrates, sugars, phosphates, and/or other such molecules. The derivatives are modified in a manner that is different from the naturally occurring or starting antibody, either in the type or location of the molecules attached. Derivatives further include deletion of one or more chemical groups which are naturally present on the antibody.

In one embodiment, the targeted binding agent is a bispecific antibody. A bispecific antibody is an antibody that has binding specificity for at least two different epitopes. Methods for making bispecific antibodies are known in the art. (See, for example, Millstein et al., *Nature,* 305:537-539 (1983); Traunecker et al., *EMBO J.,* 10:3655-3659 (1991); Suresh et al., *Methods in Enzymology,* 121:210 (1986); Kostelny et al., *J. Immunol.,* 148(5):1547-1553 (1992); Hollinger et al., *Proc. Natl. Acad. Sci. USA,* 90:6444-6448 (1993); Gruber et al., *J. Immunol.,* 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In some embodiments of the invention, the targeted binding agent or antibody comprises a sequence comprising SEQ ID NO.: 42. In certain embodiments, SEQ ID NO.:42 comprises any one of the combinations of germline and non-germline residues indicated by each row of Table 17. In some embodiments, SEQ ID NO:42 comprises any one, any two, any three, any four, any five, any six, any seven, any eight or all nine of the germline residues as indicated in Table 17. In certain embodiments, SEQ ID NO.:42 comprises any one of the unique combinations of germline and non-germline residues indicated by each row of Table 17a. In other embodiments, the targeted binding agent or antibody is derived from a germline sequence with VH3-21, D3-10 and JH4B domains, wherein one or more residues has been mutated to yield the corresponding germline residue at that position.

In some embodiments of the invention, the targeted binding agent or antibody comprises a sequence comprising SEQ ID NO.:44. In certain embodiments, SEQ ID NO.:44 comprises any one of the unique combinations of germline and non-germline residues indicated by each row of Table 16. In some embodiments, SEQ ID NO:44 comprises any one, any two or all three of the germline residues as indicated in Table 16. In certain embodiments, SEQ ID NO.:44 comprises any one of the unique combinations of germline and non-germline residues indicated by each row of Table 16a. In other embodiments, the targeted binding agent or antibody is derived from a germline sequence with A30 and JK1 domains, wherein one or more residues has been mutated to yield the corresponding germline residue at that position.

In some embodiments of the invention, in the targeted binding agent or antibody comprises a sequence comprising SEQ ID NO.:14. In certain embodiments, SEQ ID NO.:14 comprises any one of the unique combinations of germline and non-germline residues indicated by each row of Table 15. In some embodiments, SEQ ID NO:14 comprises any one, any two, any three, any four, any five or all six of the germline residues as indicated in Table 15. In certain embodiments, SEQ ID NO.:14 comprises any one of the unique combinations of germline and non-germline residues indicated by each row of Table 15a. In other embodiments, the targeted binding agent or antibody is derived from a germline sequence with VH4-39, D6-6 and JH4B domains, wherein one or more residues has been mutated to yield the corresponding germline residue at that position.

In some embodiments of the invention, the targeted binding agent or antibody comprises a sequence comprising SEQ ID NO.:16. In certain embodiments, the targeted binding agent or antibody is derived from a germline sequence with A27 and JK4 domains, wherein one or more residues has been mutated to yield the corresponding germline residue at that position.

In some embodiments of the invention, the targeted binding agent or antibody comprises a sequence comprising SEQ ID NO.:74. In certain embodiments, SEQ ID NO.:74 comprises any one of the unique combinations of germline and non-germline residues indicated by each row of Table 19. In some embodiments, SEQ ID NO:74 comprises any one, any two, any three, any four, any five, any six, any seven or all eight of the germline residues as indicated in Table 19. In certain embodiments, SEQ ID NO.:74 comprises any one of the unique combinations of germline and non-germline residues indicated by each row of Table 19a. In other embodiments, the targeted binding agent or antibody is derived from a germline sequence with VH3-11, D3-3 and JH5B domains, wherein one or more residues has been mutated to yield the corresponding germline residue at that position.

In some embodiments of the invention, the targeted binding agent or antibody comprises a sequence comprising SEQ ID NO.:76. In certain embodiments, SEQ ID NO.:76 comprises any one of the unique combinations of germline and non-germline residues indicated by each row of Table 18. In some embodiments, SEQ ID NO:76 comprises any one, any two, any three, any four, any five, any six, any seven, any eight or all nine of the germline residues as indicated in Table 18. In certain embodiments, SEQ ID NO.:76 comprises any one of the unique combinations of germline and non-germline residues indicated by each row of Table 18a. In other embodiments, the targeted binding agent or antibody is derived from a germline sequence with O2 and JK4 domains, wherein one or more residues has been mutated to yield the corresponding germline residue at that position.

A further embodiment of the invention is a targeted binding agent or antibody which competes for binding to KDR with the targeted binding agent or antibodies of the invention. In another embodiment of the invention there is an antibody which competes for binding to KDR with the targeted binding agent or antibodies of the invention. In another embodiment the targeted binding agent or antibody competes for binding to KDR with any one of fully human monoclonal antibodies 24B3, 27D10 or 33C3. "Competes" indicates that the targeted binding agent or antibody competes for binding to KDR with any one of fully human monoclonal antibodies 24B3, 27D10 and 33C3, i.e. competition is unidirectional.

Embodiments of the invention include a targeted binding agent or antibody which cross competes with any one of fully human monoclonal antibodies 24B3, 27D10 and 33C3 for binding to KDR. "Cross competes" indicates that the targeted binding agent or antibody competes for binding to KDR with any one of fully human monoclonal antibodies 24B3, 27D10 and 33C3, and vice versa, i.e. competition is bidirectional.

A further embodiment of the invention is a targeted binding agent or antibody which competes for binding to the dimerisation domain of KDR. In another embodiment of the invention there is a targeted binding agent or antibody which cross-competes with the targeted binding agent or antibodies of the invention for binding to the dimerisation domain of KDR.

A further embodiment of the invention is a targeted binding agent or antibody that binds to the same epitope on KDR as the targeted binding agent or antibodies of the invention. Embodiments of the invention also include a targeted binding agent or antibody that binds to the same epitope on KDR as any one of fully human monoclonal antibodies 24B3, 27D10 and 33C3.

Other embodiments of the invention include isolated nucleic acid molecules encoding any of the targeted binding agents or antibodies described herein, vectors having isolated nucleic acid molecules encoding the targeted binding agents or antibodies described herein or a host cell transformed with any of such nucleic acid molecules. Embodiments of the invention include a nucleic acid molecule encoding a fully human isolated targeted binding agent that specifically bind to KDR and inhibit binding of VEGF to KDR. The invention also encompasses polynucleotides that hybridize under stringent or lower stringency hybridization conditions, as defined herein, to polynucleotides that encode any of the targeted binding agents or antibodies described herein. Embodiments of the invention also include a vector comprising the nucleic acid molecule encoding the binding agent. Additional embodiments include a host cell comprising the vector of comprising the nucleic acid molecule.

As known in the art, antibodies can advantageously be, for example, polyclonal, oligoclonal, monoclonal, chimeric, humanised, and/or fully human antibodies.

It will be appreciated that embodiments of the invention are not limited to any particular form of an antibody or method of generation or production. In some embodiments of the invention, the targeted binding agent is a binding fragment of a fully human monoclonal antibody. For example, the targeted binding agent can be a full-length antibody (e.g., having an intact human Fc region) or an antibody binding fragment (e.g., a Fab, Fab' or $F(ab')_2$, FV or dAb). In addition, the antibodies can be single-domain antibodies such as camelid or human single VH or VL domains that bind to KDR, such as a dAb fragment.

Embodiments of the invention described herein also provide cells for producing these antibodies. Examples of cells include hybridomas, or recombinantly created cells, such as Chinese hamster ovary (CHO) cells, variants of CHO cells (for example DG44) and NS0 cells that produce antibodies against KDR. Additional information about variants of CHO cells can be found in Andersen and Reilly (2004) *Current Opinion in Biotechnology* 15, 456-462 which is incorporated herein in its entirety by reference. The antibody can be manufactured from a hybridoma that secretes the antibody, or from a recombinantly engineered cell that has been transformed or transfected with a gene or genes encoding the antibody.

In addition, one embodiment of the invention is a method of producing an antibody of the invention by culturing host cells under conditions wherein a nucleic acid molecule is expressed to produce the antibody followed by recovering the antibody. It should be realised that embodiments of the invention also include any nucleic acid molecule which encodes an antibody or fragment of an antibody of the invention including nucleic acid sequences optimised for increasing yields of antibodies or fragments thereof when transfected into host cells for antibody production.

A further embodiment herein includes a method of producing antibodies that specifically bind to KDR and inhibit the biological activity of KDR, by immunising a mammal with cells expressing human KDR, isolated cell membranes containing human KDR, purified human KDR, or a fragment thereof, and/or one or more orthologous sequences or fragments thereof.

In other embodiments the invention provides compositions, including a targeted binding agent or antibody of the invention or binding fragment thereof, and a pharmaceutically acceptable carrier or diluent.

Still further embodiments of the invention include methods of effectively treating an animal suffering from a proliferative, angiogenic, cell adhesion or invasion-related disease by administering to the animal a therapeutically effective dose of a targeted binding agent that specifically binds to KDR. In certain embodiments the method further comprises selecting an animal in need of treatment for a proliferative, angiogenic, cell adhesion or invasion-related disease, and administering to the animal a therapeutically effective dose of a targeted binding agent that specifically binds to KDR.

Still further embodiments of the invention include methods of effectively treating an animal suffering from a neoplastic disease by administering to the animal a therapeutically effective dose of a targeted binding agent that specifically binds to KDR. In certain embodiments the method further comprises selecting an animal in need of treatment for a neoplastic disease, and administering to the animal a therapeutically effective dose of a targeted binding agent that specifically binds to KDR.

Still further embodiments of the invention include methods of effectively treating an animal suffering from a non-neoplastic disease by administering to the animal a therapeutically effective dose of a targeted binding agent that specifically binds to KDR. In certain embodiments the method further comprises selecting an animal in need of treatment for a non-neoplastic disease, and administering to the animal a therapeutically effective dose of a targeted binding agent that specifically binds to KDR.

Still further embodiments of the invention include methods of effectively treating an animal suffering from a malignant tumour by administering to the animal a therapeutically effective dose of a targeted binding agent that specifically binds to KDR. In certain embodiments the method further comprises selecting an animal in need of treatment for a malignant tumour, and administering to the animal a therapeutically effective dose of a targeted binding agent that specifically binds to KDR.

Still further embodiments of the invention include methods of effectively treating an animal suffering from a disease or condition associated with KDR expression by administering to the animal a therapeutically effective dose of a targeted binding agent that specifically binds to KDR. In certain embodiments the method further comprises selecting an animal in need of treatment for a disease or condition associated with KDR expression, and administering to the animal a therapeutically effective dose of a targeted binding agent that specifically binds to KDR.

Still further embodiments of the invention include methods of effectively treating an animal suffering from KDR induced disease-related VEGF activation by administering to the animal a therapeutically effective dose of a targeted binding agent that specifically binds to KDR. In certain embodiments the method further comprises selecting an animal in need of treatment for KDR induced disease-related VEGF activation, and administering to the animal a therapeutically effective dose of a targeted binding agent that specifically binds to KDR.

A malignant tumour may be selected from the group consisting of: melanoma, small cell lung cancer, non-small cell lung cancer, glioma, hepatocellular (liver) carcinoma, thyroid tumour, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Treatable proliferative, angiogenic, cell adhesion or invasion-related diseases include neoplastic diseases, such as, melanoma, small cell lung cancer, non-small cell lung cancer, glioma, hepatocellular (liver) carcinoma, thyroid tumour, gastric (stomach) cancer, gallbladder cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies, epidermoid carcinoma and leukaemia, including chronic myelogenous leukaemia.

In one embodiment, the neoplastic disease is melanoma, colon cancer or chronic myelogenous leukaemia.

Non-neoplastic diseases include inflammatory disorders such as rheumatoid arthritis or psoriasis, cardiovascular disease such as atherosclerosis, sepsis, ocular disease such as ischaemic retinopathy or age-related macular degeneration.

In one embodiment the present invention is suitable for use in inhibiting KDR, in patients with a tumour which is dependent alone, or in part, on KDR.

Still further embodiments of the invention include use of a targeted binding agent or antibody of the invention in the preparation of a medicament for the treatment of an animal suffering from a proliferative, angiogenic, cell adhesion or invasion-related disease. In certain embodiments the use further comprises selecting an animal in need of treatment for a proliferative, angiogenic, cell adhesion or invasion-related disease.

Still further embodiments of the invention include use of a targeted binding agent or antibody of the invention in the preparation of a medicament for the treatment of an animal suffering from a neoplastic disease. In certain embodiments the use further comprises selecting an animal in need of treatment for a neoplastic disease.

Still further embodiments of the invention include use of a targeted binding agent or antibody of the invention in the preparation of a medicament for the treatment of an animal suffering from a non-neoplastic disease. In certain embodiments the use further comprises selecting an animal in need of treatment for a non-neoplastic disease.

Still further embodiments of the invention include use of a targeted binding agent or antibody of the invention in the preparation of a medicament for the treatment of an animal suffering from a malignant tumour. In certain embodiments the use further comprises selecting an animal in need of treatment for a malignant tumour.

Still further embodiments of the invention include use of a targeted binding agent or antibody of the invention in the preparation of a medicament for the treatment of an animal suffering from a disease or condition associated with KDR expression. In certain embodiments the use further comprises selecting an animal in need of treatment for a disease or condition associated with KDR expression.

Still further embodiments of the invention include use of a targeted binding agent or antibody of the invention in the preparation of a medicament for the treatment of an animal suffering from KDR induced disease-related VEGF activation. In certain embodiments the use further comprises selecting an animal in need of treatment for KDR induced disease-related VEGF activation.

Still further embodiments of the invention include a targeted binding agent or antibody of the invention for use as a medicament for the treatment of an animal suffering from a proliferative, angiogenic, cell adhesion or invasion-related disease.

Still further embodiments of the invention include a targeted binding agent or antibody of the invention for use as a medicament for the treatment of an animal suffering from a neoplastic disease.

Still further embodiments of the invention include a targeted binding agent or antibody of the invention for use as a medicament for the treatment of an animal suffering from a non-neoplastic disease.

Still further embodiments of the invention include a targeted binding agent or antibody of the invention for use as a medicament for the treatment of an animal suffering from a malignant tumour.

Still further embodiments of the invention include a targeted binding agent or antibody of the invention for use as a medicament for the treatment of an animal suffering from a disease or condition associated with KDR expression.

Still further embodiments of the invention include a targeted binding agent or antibody of the invention for use as a medicament for the treatment of an animal suffering from KDR induced disease-related VEGF activation.

In one embodiment treatment of a a proliferative, angiogenic, cell adhesion or invasion-related disease;

a neoplastic disease;

a non-neoplastic disease;

a malignant tumour;

a disease or condition associated with KDR expression; or

KDR induced disease-related VEGF activation, comprises managing, ameliorating, preventing, any of the aforementioned diseases or conditions.

In one embodiment treatment of a neoplastic disease comprises inhibition of tumour growth, tumour growth delay, regression of tumour, shrinkage of tumour, increased time to regrowth of tumour on cessation of treatment, increased time to tumour recurrence, slowing of disease progression.

In some embodiments of the invention, the animal to be treated is a human.

In some embodiments of the invention, the targeted binding agent is a fully human monoclonal antibody.

In some embodiments of the invention, the targeted binding agent is selected from the group consisting of fully human monoclonal antibodies 24B3, 27D10 and 33C3.

Embodiments of the invention include a conjugate comprising the targeted binding agent as described herein, and a therapeutic agent. In some embodiments of the invention, the therapeutic agent is a toxin. In other embodiments, the therapeutic agent is a radioisotope. In still other embodiments, the therapeutic agent is a pharmaceutical composition.

In another aspect, a method of selectively killing a cancerous cell in a patient is provided. The method comprises administering a fully human antibody conjugate to a patient. The fully human antibody conjugate comprises an antibody that can bind to KDR and an agent. The agent is either a toxin, a radioisotope, or another substance that will kill a cancer cell. The antibody conjugate thereby selectively kills the cancer cell.

In one aspect, a conjugated fully human antibody that specifically binds to KDR is provided. Attached to the antibody is an agent, and the binding of the antibody to a cell results in the delivery of the agent to the cell. In one embodiment, the above conjugated fully human antibody binds to an extracellular domain of KDR. In another embodiment, the antibody and conjugated toxin are internalised by a cell that expresses KDR. In another embodiment, the agent is a cytotoxic agent. In another embodiment, the agent is, for example saporin, or auristatin, pseudomonas exotoxin, gelonin, ricin, calicheamicin or maytansine-based immunoconjugates, and the like. In still another embodiment, the agent is a radioisotope.

The targeted binding agent or antibody of the invention can be administered alone, or can be administered in combination with additional antibodies or chemotherapeutic drugs or radiation therapy. For example, a monoclonal, oligoclonal or polyclonal mixture of KDR antibodies that block cell adhesion, invasion, angiogenesis or proliferation can be administered in combination with a drug shown to inhibit tumour cell proliferation.

Another embodiment of the invention includes a method of diagnosing diseases or conditions in which an antibody as disclosed herein is utilised to detect the level of KDR in a patient or patient sample. In one embodiment, the patient sample is blood or blood serum or urine. In further embodiments, methods for the identification of risk factors, diagnosis of disease, and staging of disease is presented which involves the identification of the expression and/or overexpression of KDR using anti-KDR antibodies. In some embodiments, the methods comprise administering to a patient a fully human antibody conjugate that selectively binds to KDR on a cell. The antibody conjugate comprises an antibody that specifically binds to KDR and a label. The methods further comprise observing the presence of the label in the patient. A relatively high amount of the label will indicate a relatively high risk of the disease and a relatively low amount of the label will indicate a relatively low risk of the disease. In one embodiment, the label is a green fluorescent protein.

The invention further provides methods for assaying the level of KDR in a patient sample, comprising contacting an antibody as disclosed herein with a biological sample from a patient, and detecting the level of binding between said antibody and KDR in said sample. In more specific embodiments, the biological sample is blood, plasma or serum.

Another embodiment of the invention includes a method for diagnosing a condition associated with the expression of KDR in a cell by contacting the serum or a cell with an antibody as disclosed herein, and thereafter detecting the presence of KDR. In one embodiment the condition can be a proliferative, angiogenic, cell adhesion or invasion-related disease including, but not limited to, a neoplastic disease.

In another embodiment, the invention includes an assay kit for detecting KDR in mammalian tissues, cells, or body fluids to screen for KDR-related diseases. The kit includes an antibody as disclosed herein and a means for indicating the reaction of the antibody with KDR, if present. In one embodiment the antibody is a monoclonal antibody. In one embodiment, the antibody that binds KDR is labelled. In another embodiment the antibody is an unlabelled primary antibody and the kit further includes a means for detecting the primary antibody. In one embodiment, the means for detecting includes a labelled second antibody that is an anti-immunoglobulin. The antibody may be labelled with a marker selected from the group consisting of a fluorochrome, an enzyme, a radionuclide and a radiopaque material.

In some embodiments, the targeted binding agents or antibodies as disclosed herein can be modified to enhance their capability of fixing complement and participating in complement-dependent cytotoxicity (CDC). In other embodiments, the targeted binding agents or antibodies can be modified to enhance their capability of activating effector cells and participating in antibody-dependent cytotoxicity (ADCC). In yet other embodiments, the targeted binding agents or antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the targeted binding agents or antibodies as disclosed herein can be modified to reduce their capability of fixing complement and participating in complement-dependent cytotoxicity (CDC). In other embodiments, the targeted binding agents or antibodies can be modified to reduce their capability of activating effector cells and participating in antibody-dependent cytotoxicity (ADCC). In yet other embodiments, the targeted binding agents or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In certain embodiments, the half-life of a targeted binding agent or antibody as disclosed herein and of compositions of the invention is at least about 4 to 7 days. In certain embodiments, the mean half-life of a targeted binding agent or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a targeted binding agent or antibody as disclosed herein and of compositions of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of a targeted binding agent or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/3461.

In another embodiment, the invention provides an article of manufacture including a container. The container includes a composition containing a targeted binding agent or antibody as disclosed herein, and a package insert or label indicating that the composition can be used to treat cell adhesion, invasion, angiogenesis, and/or proliferation-related diseases, including, but not limited to, diseases characterised by the expression or overexpression of KDR.

In other embodiments, the invention provides a kit comprising a composition containing a targeted binding agent or antibody as disclosed herein, and instructions to administer the composition to a subject in need of treatment.

The present invention provides formulation of proteins comprising a variant Fc region. That is, a non-naturally occurring Fc region, for example an Fc region comprising one or more non naturally occurring amino acid residues. Also encompassed by the variant Fc regions of present invention are Fc regions which comprise amino acid deletions, additions and/or modifications.

The serum half-life of proteins comprising Fc regions may be increased by increasing the binding affinity of the Fc region for FcRn. In one embodiment, the Fc variant protein has enhanced serum half life relative to comparable molecule.

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat. In a further specific embodiment, an Fc variant of the invention comprises the 234F, 235F, and 331S non naturally occurring amino acid residues, as numbered by the EU index as set forth in Kabat. In another specific embodiment, an Fc variant of the invention comprises the 234F, 235Y, and 331S non naturally occurring amino acid residues, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci. USA* 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments of the invention, the glycosylation patterns of the antibodies provided herein are modified to enhance ADCC and CDC effector function. See Shields R L et al., (2002) JBC. 277:26733; Shinkawa T et al., (2003) JBC. 278:3466 and Okazaki A et al., (2004) J. Mol. Biol., 336: 1239. In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It is also known in the art that the glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). Accordingly, in one embodiment the Fc regions of the antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867).

DETAILED DESCRIPTION OF THE PREFERRED EMBODIMENT

Figure 1:
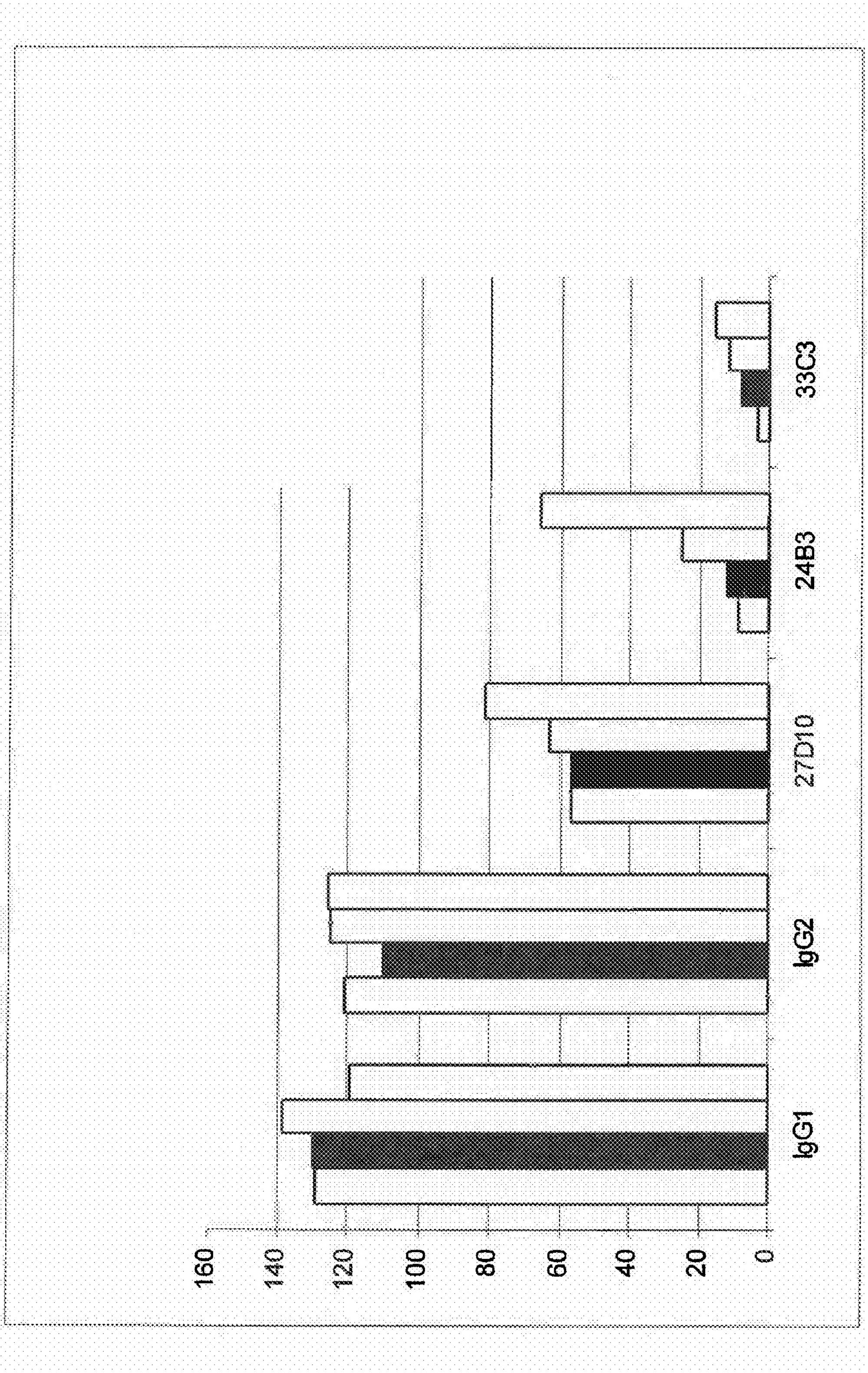
FIG. 1 is a bar chart showing the effect of inhibitory KDR antibodies on endothelial cell tube formation in a vessel length endothelial tube formation assay. Antibodies are indicated on the X axis and concentrations from left to right in each group of bars are 20 μg/mL, 5 μg/mL, 1.25 μg/mL and 0.3125 μg/mL.

Embodiments of the invention relate to a novel set of VEGFR blocking molecules, such as, for example, antibodies, that inhibit VEGFR signaling without blocking binding of ligand to its receptor. Such molecules can be used as single agents, or alternatively, in combination with VEGF-A binding antibodies/agents, antibodies that inhibit receptor-ligand binding and small molecule inhibitors of VEGFRs. They can also be used in combination with any standard or novel anticancer agents.

Embodiments of the invention relate to targeted binding agents that bind to KDR. In some embodiments, the targeted binding agents bind to KDR and inhibit the binding of the protein product of vascular endothelial growth factor (VEGF) to KDR. In some embodiments, the targeted binding agents bind to KDR and inhibit receptor dimerisation. In some embodiments, the targeted binding agents bind to KDR and inhibit receptor dimerisation and binding of VEGF to KDR. In one embodiment, the targeted binding agents are monoclonal antibodies, or binding fragments thereof. Such monoclonal antibodies may be referred to as anti-KDR antibodies herein.

Other embodiments of the invention include fully human anti-KDR antibodies, and antibody preparations that are therapeutically useful. In one embodiment, preparations of the anti-KDR antibody of the invention have desirable therapeutic properties, including strong binding affinity for KDR, the ability to inhibit KDR tyrosine phosphorylation in vitro, and the ability to inhibit KDR-induced cell activity in vitro and in vivo.

In addition, embodiments of the invention include methods of using these antibodies for treating diseases. Anti-KDR antibodies of the invention are useful for preventing KDR-mediated tumourigenesis and tumour invasion of healthy tissue. In addition KDR antibodies can be useful for treating diseases associated with angiogenesis such as ocular disease such as AMD, inflammatory disorders such as rheumatoid arthritis, and cardiovascular disease and sepsis as well as neoplastic diseases. While not being limited to any particular theory, the mechanism of action of this inhibition can include inhibition of VEGF from binding to KDR and/or by inhibiting dimerisation of the receptor, thereby preventing productive signaling and activation of proliferative signals. Diseases that are treatable through this inhibition mechanism include, but are not limited to a neoplastic disease. Any disease that is characterized by any type of malignant tumour, including metastatic cancers, lymphatic tumours, and blood cancers, can also be treated by this inhibition mechanism. Exemplary cancers in humans include a bladder tumour, breast tumour, prostate tumour, basal cell carcinoma, biliary tract cancer, bladder cancer, bone cancer, brain and CNS cancer (e.g., glioma tumour), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Malignant disorders commonly diagnosed in dogs, cats, and other pets include, but are not limited to, lymphosarcoma, osteosarcoma, mammary tumours, mastocytoma, brain tumour, melanoma, adenosquamous carcinoma, carcinoid lung tumour, bronchial gland tumour, bronchiolar adenocarcinoma, fibroma, myxochondroma, pulmonary sarcoma, neurosarcoma, osteoma, papilloma, retinoblastoma, Ewing's sarcoma, Wilm's tumour, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumour, testicular tumour, seminoma, Sertoli cell tumour, hemangiopericytoma, histiocytoma, chloroma (e.g., granulocytic sarcoma), corneal papilloma, corneal squamous cell carcinoma, hemangiosarcoma, pleural mesothelioma, basal cell tumour, thymoma, stomach tumour, adrenal gland carcinoma, oral papillomatosis, hemangioendothelioma and cystadenoma, follicular lymphoma, intestinal lymphosarcoma, fibrosarcoma and pulmonary squamous cell carcinoma. In rodents, such as a ferret, exemplary cancers include insulinoma, lymphoma, sarcoma, neuroma, pancreatic islet cell tumour, gastric MALT lymphoma and gastric adenocarcinoma. Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulo-endotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium *Corynebacterium pseudotuberculosis*, and contagious lung tumour of sheep caused by jaagsiekte.

Other embodiments of the invention include diagnostic assays for specifically determining the quantity of KDR in a biological sample. The assay kit can include a targeted binding agent or antibody as disclosed herein along with the necessary labels for detecting such antibodies. These diagnostic assays are useful to screen for cell adhesion, invasion, angiogenesis or proliferation-related diseases including, but not limited to, neoplastic diseases.

Another aspect of the invention is an antagonist of the biological activity of KDR wherein the antagonist binds to KDR. In one embodiment, the antagonist is a targeted binding agent, such as an antibody. The antagonist may bind to:

i) KDR; or ii) the KDR/VEGF complex, or a combination of these. In one embodiment the antagonist is able to antagonize the biological activity of KDR in vitro and in vivo. The antagonist may be selected from an antibody described herein, for example, antibody 27D10, 24B3 or 33C3.

In one embodiment the antagonist of the biological activity of KDR may bind to KDR and thereby inhibit or suppress KDR receptor tyrosine kinase activity, thereby inhibiting cell adhesion and/or invasion and/or angiogenesis and/or proliferation. The mechanism of action of this inhibition may include binding of the antagonist to KDR and inhibiting the binding of a native KDR-specific ligand, such as, for example VEGF, to KDR. The mechanism of action of this inhibition may include binding of the antagonist to KDR and inhibiting dimerisation of KDR. Without wishing to be bound by any particular theoretical considerations, mechanisms by which antagonism of the biological activity of KDR can be achieved include, but are not limited to, inhibition of binding of VEGF to KDR, and/or inhibition of receptor dimerisation or inhibition of KDR-VEGF mediated signaling activity.

One embodiment is a targeted binding agent which binds to the same epitope or epitopes as fully human monoclonal antibody 27D10, 24B3 or 33C3.

One embodiment is an antibody which binds to the same epitope or epitopes as fully human monoclonal antibody 27D10, 24B3 or 33C3.

One embodiment is a hybridoma that produces the targeted binding agent as described hereinabove. In one embodiment is a hybridoma that produces the light chain and/or the heavy chain of the antibodies as described hereinabove. In one embodiment the hybridoma produces the light chain and/or the heavy chain of a fully human monoclonal antibody. In another embodiment the hybridoma produces the light chain and/or the heavy chain of fully human monoclonal antibody 27D10, 24B3 or 33C3. Alternatively the hybridoma may produce an antibody which binds to the same epitope or epitopes as fully human monoclonal antibody 27D10, 24B3 or 33C3.

Another embodiment is a nucleic acid molecule encoding the targeted binding agent as described hereinabove. In one embodiment is a nucleic acid molecule encoding the light chain or the heavy chain of an antibody as described hereinabove. In one embodiment the nucleic acid molecule encodes the light chain or the heavy chain of a fully human monoclonal antibody. Still another embodiment is a nucleic acid molecule encoding the light chain or the heavy chain of a fully human monoclonal antibody selected from antibodies 27D10, 24B3 or 33C3.

Another embodiment of the invention is a vector comprising a nucleic acid molecule or molecules as described hereinabove, wherein the vector encodes a targeted binding agent as defined hereinabove. In one embodiment of the invention is a vector comprising a nucleic acid molecule or molecules as described hereinabove, wherein the vector encodes a light chain and/or a heavy chain of an antibody as defined hereinabove.

Yet another embodiment of the invention is a host cell comprising a vector as described hereinabove. Alternatively the host cell may comprise more than one vector.

In addition, one embodiment of the invention is a method of producing a targeted binding agent of the invention by culturing host cells under conditions wherein a nucleic acid molecule is expressed to produce the targeted binding agent, followed by recovery of the targeted binding agent. In one embodiment of the invention is a method of producing an antibody of the invention by culturing host cells under conditions wherein a nucleic acid molecule is expressed to produce the antibody, followed by recovery of the antibody.

In one embodiment the invention includes a method of making an targeted binding agent by transfecting at least one host cell with at least one nucleic acid molecule encoding the targeted binding agent as described hereinabove, expressing the nucleic acid molecule in the host cell and isolating the targeted binding agent. In one embodiment the invention includes a method of making an antibody by transfecting at least one host cell with at least one nucleic acid molecule encoding the antibody as described hereinabove, expressing the nucleic acid molecule in the host cell and isolating the antibody.

According to another aspect, the invention includes a method of antagonising the biological activity of KDR by administering an antagonist as described herein. The method may include selecting an animal in need of treatment for disease-related cell adhesion and/or invasion and/or angiogenesis and/or proliferation, and administering to the animal a therapeutically effective dose of an antagonist of the biological activity of KDR.

Another aspect of the invention includes a method of antagonising the biological activity of KDR by administering a targeted binding agent as described hereinabove. The method may include selecting an animal in need of treatment for disease-related cell adhesion and/or invasion and/or angiogenesis and/or proliferation, and administering to the animal a therapeutically effective dose of a targeted binding agent which antagonises the biological activity of KDR.

Another aspect of the invention includes a method of antagonising the biological activity of KDR by administering an antibody as described hereinabove. The method may include selecting an animal in need of treatment for disease-related cell adhesion and/or invasion and/or angiogenesis and/or proliferation, and administering to the animal a therapeutically effective dose of an antibody which antagonises the biological activity of KDR.

According to another aspect there is provided a method of treating disease-related cell adhesion and/or invasion and/or angiogenesis and/or proliferation in an animal by administering a therapeutically effective amount of an antagonist of the biological activity of KDR. The method may include selecting an animal in need of treatment for disease-related cell adhesion and/or invasion and/or angiogenesis and/or proliferation, and administering to the animal a therapeutically effective dose of an antagonist of the biological activity of KDR.

According to another aspect there is provided a method of treating disease-related cell adhesion and/or invasion and/or angiogenesis and/or proliferation in an animal by administering a therapeutically effective amount of a targeted binding agent which antagonizes the biological activity of KDR. The method may include selecting an animal in need of treatment for disease-related cell adhesion and/or invasion and/or angiogenesis and/or proliferation, and administering to the animal a therapeutically effective dose of a targeted binding agent which antagonises the biological activity of KDR. The targeted binding agent can be administered alone, or can be administered in combination with additional antibodies or chemotherapeutic drugs or radiation therapy.

According to another aspect there is provided a method of treating disease-related cell adhesion and/or invasion and/or angiogenesis and/or proliferation in an animal by administering a therapeutically effective amount of an antibody which antagonizes the biological activity of KDR. The method may include selecting an animal in need of treatment for disease-related cell adhesion and/or invasion and/or angiogenesis and/or proliferation, and administering to the animal a therapeutically effective dose of an antibody which antagonises the biological activity of KDR. The antibody can be administered alone, or can be administered in combination with additional antibodies or chemotherapeutic drugs or radiation therapy.

According to another aspect there is provided a method of treating cancer in an animal by administering a therapeutically effective amount of an antagonist of the biological activity of KDR. The method may include selecting an animal in need of treatment for cancer, and administering to the animal a therapeutically effective dose of an antagonist which antagonises the biological activity of KDR. The antagonist can be administered alone, or can be administered in combination with additional antibodies or chemotherapeutic drugs or radiation therapy.

According to another aspect there is provided a method of treating cancer in an animal by administering a therapeutically effective amount of a targeted binding agent which antagonizes the biological activity of KDR. The method may include selecting an animal in need of treatment for cancer, and administering to the animal a therapeutically effective dose of a targeted binding agent which antagonises the biological activity of KDR. The targeted binding agent can be administered alone, or can be administered in combination with additional antibodies or chemotherapeutic drugs or radiation therapy.

According to another aspect there is provided a method of treating cancer in an animal by administering a therapeutically effective amount of an antibody which antagonizes the biological activity of KDR. The method may include selecting an animal in need of treatment for cancer, and administering to the animal a therapeutically effective dose of an antibody which antagonises the biological activity of KDR. The antibody can be administered alone, or can be administered in combination with additional antibodies or chemotherapeutic drugs or radiation therapy.

According to another aspect there is provided a method of reducing or inhibiting tumour cell proliferation, adhesion, invasion and/or angiogenesis, in an animal by administering a therapeutically effective amount of an antibody which antagonizes the biological activity of KDR. The method may include selecting an animal in need of a reduction or inhibition of proliferation, cell adhesion, invasion and/or angiogenesis, and administering to the animal a therapeutically effective dose of an antibody which antagonises the biological activity of KDR. The antibody can be administered alone, or can be administered in combination with additional antibodies or chemotherapeutic drugs or radiation therapy.

According to another aspect there is provided a method of reducing tumour growth and/or metastasis, in an animal by administering a therapeutically effective amount of an antibody which antagonizes the biological activity of KDR. The method may include selecting an animal in need of a reduction of tumour growth and/or metastasis, and administering to the animal a therapeutically effective dose of an antibody which antagonises the biological activity of KDR. The antibody can be administered alone, or can be administered in combination with additional antibodies or chemotherapeutic drugs or radiation therapy.

According to another aspect of the invention there is provided the use of an antagonist of the biological activity of KDR for the manufacture of a medicament for the treatment of disease-related cell adhesion and/or invasion and/or angiogenesis and/or proliferation. In one embodiment the antagonist of the biological activity of KDR is a targeted binding agent of the invention. In one embodiment the antagonist of the biological activity of KDR is an antibody of the invention.

According to another aspect of the invention there is provided an antagonist of the biological activity of KDR for use as a medicament for the treatment of disease-related cell adhesion and/or invasion and/or angiogenesis and/or proliferation. In one embodiment the antagonist of the biological activity of KDR is a targeted binding agent of the invention. In one embodiment the antagonist of the biological activity of KDR is an antibody of the invention.

According to another aspect of the invention there is provided the use of a targeted binding agent or an antibody which antagonizes the biological activity of KDR for the manufacture of a medicament for the treatment of disease-related cell adhesion and/or invasion and/or angiogenesis and/or proliferation.

According to another aspect of the invention there is provided a targeted binding agent or an antibody which antagonizes the biological activity of KDR for use as a medicament for the treatment of disease-related cell adhesion and/or invasion and/or angiogenesis and/or proliferation.

According to another aspect of the invention there is provided the use of a targeted binding agent or an antibody which antagonizes the biological activity of KDR for the manufacture of a medicament for the treatment of disease-related cell adhesion and/or invasion and/or angiogenesis and/or proliferation.

According to another aspect of the invention there is provided an antibody which antagonizes the biological activity of KDR for use as a medicament for the treatment of disease-related cell adhesion and/or invasion and/or angiogenesis and/or proliferation.

According to another aspect of the invention there is provided the use of an antagonist of the biological activity of KDR for the manufacture of a medicament for the treatment of cancer in a mammal In one embodiment the antagonist of the biological activity of KDR is a targeted binding agent of the invention. In one embodiment the antagonist of the biological activity of KDR is an antibody of the invention.

According to another aspect of the invention there is provided an antagonist of the biological activity of KDR for use as a medicament for the treatment of cancer in a mammal. In one embodiment the antagonist of the biological activity of KDR is a targeted binding agent of the invention. In one embodiment the antagonist of the biological activity of KDR is an antibody of the invention.

According to another aspect of the invention there is provided the use of a targeted binding agent which antagonizes the biological activity of KDR for the manufacture of a medicament for the treatment of cancer in a mammal.

According to another aspect of the invention there is provided a targeted binding agent which antagonizes the biological activity of KDR for use as a medicament for the treatment of cancer in a mammal.

According to another aspect of the invention there is provided the use of an antibody which antagonizes the biological activity of KDR for the manufacture of a medicament for the treatment of cancer in a mammal.

According to another aspect of the invention there is provided an antibody which antagonizes the biological activity of KDR for use as a medicament for the treatment of cancer in a mammal.

According to another aspect there is provided the use of a targeted binding agent or an antibody which antagonizes the biological activity of KDR for the manufacture of a medicament for the reduction or inhibition proliferation, cell adhesion, invasion and/or angiogenesis in an animal.

According to another aspect there is provided a targeted binding agent or an antibody which antagonizes the biological activity of KDR for use as a medicament for the reduction or inhibition proliferation, cell adhesion, invasion and/or angiogenesis in an animal.

According to another aspect there is provided the use of a targeted binding agent or an antibody which antagonizes the biological activity of KDR for the manufacture of a medicament for reducing tumour growth and/or metastasis, in an animal.

According to another aspect there is provided a targeted binding agent or an antibody which antagonizes the biological activity of KDR for use as a medicament for reducing tumour growth and/or metastasis, in an animal.

In one embodiment the present invention is particularly suitable for use in antagonizing KDR, in patients with a tumour which is dependent alone, or in part, on KDR receptor tyrosine kinase.

According to another aspect of the invention there is provided a pharmaceutical composition comprising an antagonist of the biological activity of KDR, and a pharmaceutically acceptable carrier. In one embodiment the antagonist comprises an antibody. According to another aspect of the invention there is provided a pharmaceutical composition comprising an antagonist of the biological activity of KDR, and a pharmaceutically acceptable carrier. In one embodiment the antagonist comprises an antibody.

In some embodiments, following administration of the antibody that specifically binds to KDR, a clearing agent is administered, to remove excess circulating antibody from the blood.

Anti-KDR antibodies are useful in the detection of KDR in patient samples and accordingly are useful as diagnostics for disease states as described herein. In addition, based on their ability to significantly inhibit KDR-mediated signaling activity (as demonstrated in the Examples below), anti-KDR antibodies have therapeutic effects in treating symptoms and conditions resulting from KDR expression. In specific embodiments, the antibodies and methods herein relate to the treatment of symptoms resulting from KDR induced cell adhesion, invasion, angiogenesis, proliferation and/or intracellular signaling. Further embodiments involve using the antibodies and methods described herein to treat cell adhesion, invasion, angiogenesis and/or proliferation-related diseases including neoplastic diseases, such as, melanoma, small cell lung cancer, non-small cell lung cancer, glioma, hepatocellular (liver) carcinoma, thyroid tumour, gastric (stomach) cancer, prostate cancer, breast cancer, ovarian cancer, bladder cancer, lung cancer, glioblastoma, endometrial cancer, kidney cancer, colon cancer, and pancreatic cancer. The antibodies may also be useful in treating cell adhesion and/or invasion in arthritis, atherosclerosis and diseases involving angiogenesis.

Another embodiment of the invention includes an assay kit for detecting KDR in mammalian tissues, cells, or body fluids to screen for cell adhesion-, invasion-, angiogenesis- or proliferation related diseases. The kit includes a targeted binding agent that binds to KDR and a means for indicating the reaction of the targeted binding agent with KDR, if present. In one embodiment, the targeted binding agent that binds KDR is labeled. In another embodiment the targeted binding agent is an unlabeled and the kit further includes a means for detecting the targeted binding agent. Preferably the targeted binding agent is labeled with a marker selected from the group consisting of a fluorochrome, an enzyme, a radionuclide and a radio-opaque material.

Another embodiment of the invention includes an assay kit for detecting KDR in mammalian tissues, cells, or body fluids to screen for cell adhesion-, invasion-, angiogenesis or proliferation-related diseases. The kit includes an antibody that binds to KDR and a means for indicating the reaction of the antibody with KDR, if present. The antibody may be a monoclonal antibody. In one embodiment, the antibody that binds KDR is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding the antibodies as disclosed herein are provided in additional detail below.

Sequence Listing

Embodiments of the invention include the specific antibodies listed below in Table 1. This table reports the identification number of each anti-KDR antibody, along with the SEQ ID number of the variable domain of the corresponding heavy chain and light chain genes and polypeptides, respectively. Each antibody has been given an identification number.

TABLE 1

| MAb ID No.: | Sequence | SEQ ID NO: |
|---|---|---|
| 30D7 | Nucleotide sequence encoding the variable region of the heavy chain | 1 |
| | Amino acid sequence of the variable region of the heavy chain | 2 |
| | Nucleotide sequence encoding the variable region of the light chain | 3 |
| | Amino acid sequence of the variable region of the light chain | 4 |
| 21H9 | Nucleotide sequence encoding the variable region of the heavy chain | 5 |
| | Amino acid sequence of the variable region of the heavy chain | 6 |
| | Nucleotide sequence encoding the variable region of the light chain | 7 |
| | Amino acid sequence of the variable region of the light chain | 8 |
| 27A3 | Nucleotide sequence encoding the variable region of the heavy chain | 9 |
| | Amino acid sequence of the variable region of the heavy chain | 10 |
| | Nucleotide sequence encoding the variable region of the light chain | 11 |
| | Amino acid sequence of the variable region of the light chain | 12 |
| 27D10 | Nucleotide sequence encoding the variable region of the heavy chain | 13 |
| | Amino acid sequence of the variable region of the heavy chain | 14 |
| | Nucleotide sequence encoding the variable region of the light chain | 15 |
| | Amino acid sequence of the variable region of the light chain | 16 |
| 32F4 | Nucleotide sequence encoding the variable region of the heavy chain | 17 |
| | Amino acid sequence of the variable region of the heavy chain | 18 |
| | Nucleotide sequence encoding the variable region of the light chain | 19 |
| | Amino acid sequence of the variable region of the light chain | 20 |
| 29D4 | Nucleotide sequence encoding the variable region of the heavy chain | 21 |
| | Amino acid sequence of the variable region of the heavy chain | 22 |
| | Nucleotide sequence encoding the variable region of the light chain | 23 |
| | Amino acid sequence of the variable region of the light chain | 24 |
| 30A1 | Nucleotide sequence encoding the variable region of the heavy chain | 25 |
| | Amino acid sequence of the variable region of the heavy chain | 26 |
| | Nucleotide sequence encoding the variable region of the light chain | 27 |
| | Amino acid sequence of the variable region of the light chain | 28 |
| 22B8 | Nucleotide sequence encoding the variable region of the heavy chain | 29 |
| | Amino acid sequence of the variable region of the heavy chain | 30 |
| | Nucleotide sequence encoding the variable region of the light chain | 31 |
| | Amino acid sequence of the variable region of the light chain | 32 |
| 24C9 | Nucleotide sequence encoding the variable region of the heavy chain | 33 |
| | Amino acid sequence of the variable region of the heavy chain | 34 |
| | Nucleotide sequence encoding the variable region of the light chain | 35 |
| | Amino acid sequence of the variable region of the light chain | 36 |
| 32G7 | Nucleotide sequence encoding the variable region of the heavy chain | 37 |
| | Amino acid sequence of the variable region of the heavy chain | 38 |
| | Nucleotide sequence encoding the variable region of the light chain | 39 |
| | Amino acid sequence of the variable region of the light chain | 40 |

TABLE 1-continued

| MAb ID No.: | Sequence | SEQ ID NO: |
|---|---|---|
| 24B3 | Nucleotide sequence encoding the variable region of the heavy chain | 41 |
| | Amino acid sequence of the variable region of the heavy chain | 42 |
| | Nucleotide sequence encoding the variable region of the light chain | 43 |
| | Amino acid sequence of the variable region of the light chain | 44 |
| 33B1 | Nucleotide sequence encoding the variable region of the heavy chain | 45 |
| | Amino acid sequence of the variable region of the heavy chain | 46 |
| | Nucleotide sequence encoding the variable region of the light chain | 47 |
| | Amino acid sequence of the variable region of the light chain | 48 |
| 33E1 | Nucleotide sequence encoding the variable region of the heavy chain | 49 |
| | Amino acid sequence of the variable region of the heavy chain | 50 |
| | Nucleotide sequence encoding the variable region of the light chain | 51 |
| | Amino acid sequence of the variable region of the light chain | 52 |
| 29H3 | Nucleotide sequence encoding the variable region of the heavy chain | 53 |
| | Amino acid sequence of the variable region of the heavy chain | 54 |
| | Nucleotide sequence encoding the variable region of the light chain | 55 |
| | Amino acid sequence of the variable region of the light chain | 56 |
| 33D5 | Nucleotide sequence encoding the variable region of the heavy chain | 57 |
| | Amino acid sequence of the variable region of the heavy chain | 58 |
| | Nucleotide sequence encoding the variable region of the light chain | 59 |
| | Amino acid sequence of the variable region of the light chain | 60 |
| 29F7 | Nucleotide sequence encoding the variable region of the heavy chain | 61 |
| | Amino acid sequence of the variable region of the heavy chain | 62 |
| | Nucleotide sequence encoding the variable region of the light chain | 63 |
| | Amino acid sequence of the variable region of the light chain | 64 |
| 21A1 | Nucleotide sequence encoding the variable region of the heavy chain | 65 |
| | Amino acid sequence of the variable region of the heavy chain | 66 |
| | Nucleotide sequence encoding the variable region of the light chain | 67 |
| | Amino acid sequence of the variable region of the light chain | 68 |
| 31E11 | Nucleotide sequence encoding the variable region of the heavy chain | 69 |
| | Amino acid sequence of the variable region of the heavy chain | 70 |
| | Nucleotide sequence encoding the variable region of the light chain | 71 |
| | Amino acid sequence of the variable region of the light chain | 72 |
| 33C3 | Nucleotide sequence encoding the variable region of the heavy chain | 73 |
| | Amino acid sequence of the variable region of the heavy chain | 74 |
| | Nucleotide sequence encoding the variable region of the light chain | 75 |
| | Amino acid sequence of the variable region of the light chain | 76 |
| 30F6 | Nucleotide sequence encoding the variable region of the heavy chain | 77 |
| | Amino acid sequence of the variable region of the heavy chain | 78 |
| | Nucleotide sequence encoding the variable region of the light chain | 79 |
| | Amino acid sequence of the variable region of the light chain | 80 |
| 32B2 | Nucleotide sequence encoding the variable region of the heavy chain | 81 |
| | Amino acid sequence of the variable region of the heavy chain | 82 |
| | Nucleotide sequence encoding the variable region of the light chain | 83 |
| | Amino acid sequence of the variable region of the light chain | 84 |
| 30E3 | Nucleotide sequence encoding the variable region of the heavy chain | 85 |
| | Amino acid sequence of the variable region of the heavy chain | 86 |
| | Nucleotide sequence encoding the variable region of the light chain | 87 |
| | Amino acid sequence of the variable region of the light chain | 88 |
| 29A11 | Nucleotide sequence encoding the variable region of the heavy chain | 89 |
| | Amino acid sequence of the variable region of the heavy chain | 90 |
| | Nucleotide sequence encoding the variable region of the light chain | 91 |
| | Amino acid sequence of the variable region of the light chain | 92 |
| 30H10 | Nucleotide sequence encoding the variable region of the heavy chain | 93 |
| | Amino acid sequence of the variable region of the heavy chain | 94 |
| | Nucleotide sequence encoding the variable region of the light chain | 95 |
| | Amino acid sequence of the variable region of the light chain | 96 |
| 32C11 | Nucleotide sequence encoding the variable region of the heavy chain | 97 |
| | Amino acid sequence of the variable region of the heavy chain | 98 |
| | Nucleotide sequence encoding the variable region of the light chain | 99 |
| | Amino acid sequence of the variable region of the light chain | 100 |
| 29A3 | Nucleotide sequence encoding the variable region of the heavy chain | 101 |
| | Amino acid sequence of the variable region of the heavy chain | 102 |
| | Nucleotide sequence encoding the variable region of the light chain | 103 |
| | Amino acid sequence of the variable region of the light chain | 104 |
| 1G6 | Nucleotide sequence encoding the variable region of the heavy chain | 105 |
| | Amino acid sequence of the variable region of the heavy chain | 131 |
| | Nucleotide sequence encoding the variable region of the light chain | 107 |
| | Amino acid sequence of the variable region of the light chain | 108 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

An antagonist or inhibitor may be a polypeptide, nucleic acid, carbohydrate, lipid, small molecular weight compound, an oligonucleotide, an oligopeptide, RNA interference (RNAi), antisense, a recombinant protein, an antibody, or fragments thereof or conjugates or fusion proteins thereof. For a review of RNAi see Milhavet O, Gary D S, Mattson M P. (Pharmacol Rev. 2003 December; 55(4):629-48. Review) and antisense (see Opalinska J B, Gewirtz A M. (Sci STKE. 2003 Oct. 28; 2003 (206):pe47.)

Disease-related cell adhesion and/or invasion and/or angiogenesis and/or proliferation may be any abnormal, undesirable or pathological cell adhesion and/or invasion and/or angiogenesis and/or proliferation, for example tumour-related cell adhesion and/or invasion and/or angiogenesis and/or proliferation. Cell adhesion- and/or invasion and/or angiogenesis- and/or proliferation-related diseases include, but are not limited to, non-solid tumours such as leukemia, multiple myeloma or lymphoma, and also solid tumours such as melanoma, small cell lung cancer, non-small cell lung cancer, glioma, hepatocellular (liver) carcinoma, glioblastoma, carcinoma of the thyroid, bile duct, bone, gastric, brain/CNS, head and neck, hepatic system, stomach, prostate, breast, renal, testicle, ovary, skin, cervix, lung, muscle, neuron, esophageal, bladder, lung, uterus, vulva, endometrium, kidney, colorectum, pancreas, pleural/peritoneal membranes, salivary gland, and epidermous.

A compound refers to any small molecular weight compound with a molecular weight of less than about 2000 Daltons.

The term "KDR" refers to the molecule that is KDR protein, also known as VEGFR2 and KDR receptor-like tyrosine kinase.

The terms "neutralizing" or "inhibits" when referring to a targeted binding agent, such as an antibody, relates to the ability of an antibody to eliminate, reduce, or significantly reduce, the activity of a target antigen. Accordingly, a "neutralizing" anti-KDR antibody of the invention is capable of eliminating or significantly reducing the activity of KDR. A neutralizing KDR antibody may, for example, act by blocking the binding of a native KDR-specific ligand, such as, for example, VEGF, to KDR. By blocking this binding, KDR signal-mediated activity is significantly, or completely, eliminated. Ideally, a neutralizing antibody against KDR inhibits cell adhesion and/or invasion and/or angiogenesis and/or proliferation.

An "antagonist of the biological activity of KDR" is capable of eliminating, reducing or significantly reducing the activity of KDR. An "antagonist of the biological activity of KDR" is capable of eliminating, reducing or significantly reducing KDR signaling. An "antagonist of the biological activity of KDR" may eliminate or significantly reduce cell adhesion and/or invasion and/or angiogenesis and/or proliferation.

"Reducing KDR signaling" encompasses a reduction of KDR signaling by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% in comparison with the level of signaling in the absence of a targeted binding agent, antibody or antagonist of the invention.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The terms "native" or "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridise" referred to herein means to detectably and specifically bind. Polynucleotides, oligonucleotides and fragments thereof selectively hybridise to nucleic acid strands under hybridisation and wash conditions that minimise appreciable amounts of detectable binding to nonspecific nucleic acids. High stringency conditions can be used to achieve selective hybridisation conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Stringent hybridization conditions include, but are not limited to, hybridization to filter-bound DNA in 6× sodium chloride/sodium citrate (SSC) (0.9 M NaCl/90 mM NaCitrate, pH 7.0) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3). Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-,$\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

In general, cysteine residues in proteins are either engaged in cysteine-cysteine disulfide bonds or sterically protected from the disulfide bond formation when they are a part of folded protein region. Disulfide bond formation in proteins is a complex process, which is determined by the redox potential of the environment and specialized thiol-disulfide exchanging enzymes (Creighton, Methods Enzymol. 107, 305-329, 1984; Houee-Levin, Methods Enzymol. 353, 35-44, 2002). When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

Additionally, such methods may be used to make amino acid substitutions or deletions of one or more variable region cysteine residues participating in an intrachain disulfide bond to generate antibody molecules lacking one or more intrachain disulfide bonds.

The term "CDR region" or "CDR" is intended to indicate the hypervariable regions of the heavy and light chains of an antibody which confer antigen-binding specificity to the antibody. CDRs may be defined according to the Kabat system (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognises.

The third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Kabat et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3.

Variants of the VH and VL domains and CDRs of the present invention, including those for which amino acid sequences are set out herein, and which can be employed in targeting agents and antibodies for KDR can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralisation of an antigen activity relative to known antibodies which are specific for the antigen if the activity is known; specified competitive ability with a known antibody or ligand to the antigen at a specific molar ratio; ability to immunoprecipitate ligand-receptor complex; ability to bind to a specified epitope; linear epitope, e.g. peptide sequence identified using peptide-binding scan, e.g. using peptides screened in linear and/or constrained conformation; conformational epitope, formed by non-continuous residues; ability to modulate a new biological activity of KDR, or downstream molecule; ability to bind and/or neutralise KDR and/or for any other desired property.

The techniques required to make substitutions within amino acid sequences of CDRs, antibody VH or VL domains and antigen binding sites are available in the art. Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Arup K. & Viswanadhan, Vellarkad N. Combinatorial Library Design and Evaluation Principles, Software, Tools, and Applications in Drug Discovery). In some cases the properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimisation experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity or confer other desirable properties.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to KDR, under suitable binding conditions, (2) ability to block appropriate VEGF/KDR binding, or (3) ability to inhibit KDR receptor tyrosine kinase activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species.

As used herein, the terms "antibody" and "antibodies" (immunoglobulins) encompass monoclonal antibodies (including full-length monoclonal antibodies), polyclonal antibodies, camelised antibodies and chimeric antibodies. As used herein, the term "antibody" or "antibodies" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. chain. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. The variable regions of each light/heavy chain pair form an antibody binding site. Such antibodies may be derived from any mammal, including, but not limited to, humans, monkeys, pigs, horses, rabbits, dogs, cats, mice, etc.

The term "antibody" or "antibodies" includes binding fragments of the antibodies of the invention, exemplary fragments include single-chain Fvs (scFv), single-chain antibodies, single domain antibodies, domain antibodies, Fv fragments, Fab fragments, F(ab') fragments, F(ab')2 fragments, antibody fragments that exhibit the desired biological activity, disulfide-stabilised variable region (dsFv), dimeric variable region (Diabody), anti-idiotypic (anti-Id) antibodies (including, e.g., anti-Id antibodies to antibodies of the invention), intrabodies, linear antibodies, single-chain antibody molecules and multispecific antibodies formed from antibody fragments and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a $F(ab')_2$ fragment in which the two arms of the antibody molecule remain linked and comprise two-antigen binding sites. The $F(ab')_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" when used herein refers to a fragment of an antibody that comprises the constant domain of the light chain and the CH1 domain of the heavy chain.

"dAb" when used herein refers to a fragment of an antibody that is the smallest functional binding unit of a human antibodies. A "dAb" is a single domain antibody and comprises either the variable domain of an antibody heavy chain (VH domain) or the variable domain of an antibody light chain (VL domain). Each dAb contains three of the six naturally occurring CDRs (Ward et al., Binding activities of a repertoire of single immunoglobulin variable domains secreted from *Escherichia coli. Nature* 341, 544-546 (1989); Holt, et al., Domain antibodies: protein for therapy, *Trends Biotechnol.* 21, 484-49 (2003)). With molecular weights ranging from 11 to 15 kDa, they are four times smaller than a fragment antigen binding (Fab)2 and half the size of a single chain Fv (scFv) molecule.

"Camelid" when used herein refers to antibody molecules are composed of heavy-chain dimers which are devoid of light chains, but nevertheless have an extensive antigen-binding repertoire (Hamers-Casterman C, Atarhouch T, Muyldermans S, Robinson G, Hamers C, Songa E B, Bendahman N, Hamers R (1993) Naturally occurring antibodies devoid of light chains. Nature 363:446-448).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al (1990) Nature, 348, 552-554, Holt et al (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426, Huston et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448,). Fv, scFv or diabody molecules may be stabilised by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see, Kabat et al., Sequences of Proteins of Immunological Interest, 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework" or "FR" residues are those variable domain residues flanking the CDRs. FR residues are present in chimeric, humanized, human, domain antibodies, diabodies, vaccibodies, linear antibodies, and bispecific antibodies.

As used herein, targeted binding agent, targeted binding protein, specific binding protein and like terms refer to an antibody, or binding fragment thereof that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', $F(ab')_2$, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leqq 1$ μM, preferably $\leqq 100$ nM and most preferably $\leqq 10$ nM.

The term "agent" is used herein to denote a chemical compound, a mixture of chemical compounds, a biological macromolecule, or an extract made from biological materials.

"Active" or "activity" in regard to an KDR polypeptide refers to a portion of an KDR polypeptide that has a biological or an immunological activity of a native KDR polypeptide. "Biological" when used herein refers to a biological function that results from the activity of the native KDR polypeptide. A preferred KDR biological activity includes, for example, KDR induced cell adhesion and invasion and/or angiogenesis and/or proliferation.

"Mammal" when used herein refers to any animal that is considered a mammal Preferably, the mammal is human.

"Animal" when used herein encompasses animals considered a mammal Preferably the is animal is human.

The term "mAb" refers to monoclonal antibody.

"Liposome" when used herein refers to a small vesicle that may be useful for delivery of drugs that may include the KDR polypeptide of the invention or antibodies to such an KDR polypeptide to a mammal "Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^{3}H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, monocytes, neutrophils, and macrophages) recognise bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarised in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *PNAS* (*USA*) 95:652-656 (1988). "Complement dependent cytotoxicity" and "CDC" refer to the mechanism by which antibodies carry out their cell-killing function. It is initiated by the binding of C1q, a constituent of the first component of complement, to the Fc domain of Igs, IgG or IgM, which are in complex with antigen (Hughs-Jones, N.C., and B. Gardner. 1979. Mol. Immunol. 16:697). C1q is a large, structurally complex glycoprotein of ~410 kDa present in human serum at a concentration of 70 μg/ml (Cooper, N. R. 1985. Adv. Immunol. 37:151). Together with two serine proteases, C1r and C1s, C1q forms the complex C1, the first component of complement. At least two of the N-terminal globular heads of C1q must be bound to the Fc of Igs for C1 activation, hence for initiation of the complement cascade (Cooper, N. R. 1985. Adv. Immunol. 37:151).

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and μ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate in humans. Human light chain constant regions may be classified into two major classes, kappa and lambda.

If desired, the isotype of an antibody that specifically binds KDR can be switched, for example to take advantage of a biological property of a different isotype. For example, in some circumstances it can be desirable in connection with the generation of antibodies as therapeutic antibodies against KDR that the antibodies be capable of fixing complement and participating in complement-dependent cytotoxicity (CDC).

There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable in connection with the generation of antibodies as therapeutic antibodies against KDR that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-KDR antibodies discussed herein are fully human antibodies. If an antibody possessed desired binding to KDR, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

"Whole blood assays" use unfractionated blood as a source of natural effectors. Blood contains complement in the plasma, together with FcR-expressing cellular effectors, such as polymorphonuclear cells (PMNs) and mononuclear cells (MNCs). Thus, whole blood assays allow simultaneous evaluation of the synergy of both ADCC and CDC effector mechanisms in vitro.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Bispecific antibodies do not exist in the form of fragments having a single binding site (e.g., Fab, Fab', and Fv).

Typically, a VH domain is paired with a VL domain to provide an antibody antigen-binding site, although a VH or VL domain alone may be used to bind antigen. The VH domain (see Table 12) may be paired with the VL domain (see Table 13), so that an antibody antigen-binding site is formed comprising both the VH and VL domains.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Amgen, Inc. (Fremont, Calif., U.S.A).

Such mice, then, are capable of producing human immunoglobulin molecules and antibodies and are deficient in the production of murine immunoglobulin molecules and antibodies. Technologies utilised for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

The production of the XenoMouse® strains of mice is further discussed and delineated in U.S. patent application Ser. No. 07/466,008, filed Jan. 12, 1990, U.S. patent application Ser. No. 07/610,515, filed Nov. 8, 1990, U.S. patent application Ser. No. 07/919,297, filed Jul. 24, 1992, U.S. patent application Ser. No. 07/922,649, filed Jul. 30, 1992, U.S. patent application Ser. No. 08/031,801, filed Mar. 15, 1993, U.S. patent application Ser. No. 08/112,848, filed Aug. 27, 1993, U.S. patent application Ser. No. 08/234,145, filed Apr. 28, 1994, U.S. patent application Ser. No. 08/376,279, filed Jan. 20, 1995, U.S. patent application Ser. No. 08/430, 938, filed Apr. 27, 1995, U.S. patent application Ser. No. 08/464,584, filed Jun. 5, 1995, U.S. patent application Ser. No. 08/464,582, filed Jun. 5, 1995, U.S. patent application Ser. No. 08/463,191, filed Jun. 5, 1995, U.S. patent application Ser. No. 08/462,837, filed Jun. 5, 1995, U.S. patent application Ser. No. 08/486,853, filed Jun. 5, 1995, U.S. patent application Ser. No. 08/486,857, filed Jun. 5, 1995, U.S. patent application Ser. No. 08/486,859, filed Jun. 5, 1995, U.S. patent application Ser. No. 08/462,513, filed Jun. 5, 1995, U.S. patent application Ser. No. 08/724,752, filed Oct. 2, 1996, U.S. patent application Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilised a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, U.S. patent application Ser. No. 07/575,962, filed Aug. 31, 1990, U.S. patent application Ser. No. 07/810,279, filed Dec. 17, 1991, U.S. patent application Ser. No. 07/853,408, filed Mar. 18, 1992, U.S. patent application Ser. No. 07/904,068, filed Jun. 23, 1992, U.S. patent application Ser. No. 07/990,860, filed Dec. 16, 1992, U.S. patent application Ser. No. 08/053,131, filed Apr. 26, 1993, U.S. patent application Ser. No. 08/096,762, filed Jul. 22, 1993, U.S. patent application Ser. No. 08/155, 301, filed Nov. 18, 1993, U.S. patent application Ser. No. 08/161,739, filed Dec. 3, 1993, U.S. patent application Ser. No. 08/165,699, filed Dec. 10, 1993, U.S. patent application Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™-mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (Medimmune, Morphosys, Dyax, Biosite/Medarex, Xoma, Symphogen, Alexion (formerly Proliferon), Affimed) ribosome display (Medimmune), yeast display, and the like.

Preparation of Antibodies

Antibodies, as described herein, were prepared through the utilization of the XenoMouse® technology, as described below. Such mice are capable of producing human immunoglobulin molecules and antibodies and are deficient in the production of murine immunoglobulin molecules and antibodies. Technologies utilised for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunised with an antigen of interest (e.g. KDR), lymphatic cells (such as B-cells) are recovered from the hyperimmunised mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to KDR. Further, provided herein are characterisation of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the KDR immunogen. The supernatants might also be screened for immunoreactivity against fragments of KDR to further map the different antibodies for binding to domains of functional interest on KDR. The antibodies may also be screened other related human endoglycosidases and against the rat, the mouse, and non-human primate, such as Cynomolgus monkey, orthologues of KDR, the last to determine species cross-reactivity. B cells from wells containing antibodies of interest may be immortalised by various methods including fusion to make hybridomas either from individual or from pooled wells, or by infection with EBV or transfection by known immortalising genes and then plating in suitable medium. Alternatively, single plasma cells secreting antibodies with the desired specificities are then isolated using an KDR-specific hemolytic plaque assay (see for example Babcook et al., *Proc. Natl. Acad. Sci. USA* 93:7843-48 (1996)). Cells targeted for lysis are preferably sheep red blood cells (SRBCs) coated with the KDR antigen.

In the presence of a B-cell culture containing plasma cells secreting the immunoglobulin of interest and complement, the formation of a plaque indicates specific KDR-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

As will be appreciated, antibodies that specifically bind KDR can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive KDR binding properties.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Therapeutic Administration and Formulations

Embodiments of the invention include sterile pharmaceutical formulations of anti-KDR antibodies that are useful as treatments for diseases. Such formulations would inhibit the binding of a native KDR-specific ligand such as, for example, VEGF, to KDR, thereby effectively treating pathological conditions where, for example, serum or tissue KDR expression is abnormally elevated. Anti-KDR antibodies preferably possess adequate affinity to potently inhibit native KDR-specific ligands such as, for example, VEGF, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumour site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine;

monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* ($20^{th}$ ed, Lippincott Williams & Wilkens Publishers (2003)). For example, dissolution or suspension of the active compound in a pharmaceutically acceptable carrier such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res*., (1981) 15:167-277 and Langer, *Chem. Tech*., (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.0001 mg/kg, 0.001 mg/kg, 0.01 mg/kg, 0.1 mg/kg, 1 mg/kg, 10 mg/kg to up to 100 mg/kg, 1000 mg/kg, 10000 mg/kg or more, of the patient's body weight depending on the factors mentioned above. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight depending on the factors mentioned above. Typically, the clinician will administer the therapeutic antibody until a dosage is reached that achieves the desired effect. The progress of this therapy is easily monitored by conventional assays or as described herein.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™) DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to KDR, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, antibody fragments, such as a Fab, Fab', $F(ab')_2$, Fv or dAb, generation of peptide therapeutics, KDR binding domains in novel scaffolds, gene therapies, particularly intrabodies, antisense therapeutics, and small molecules.

An antigen binding site may be provided by means of arrangement of CDRs on non-antibody protein scaffolds, such as fibronectin or cytochrome B etc. (Haan & Maggos (2004) BioCentury, 12(5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12(42), A1-A7, 2004). Typical are proteins having a stable backbone and one or more variable loops, in which the amino acid sequence of the loop or loops specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

For example, bispecific antibodies can be generated that comprise (i) two antibodies one with a specificity to KDR and another to a second molecule that are conjugated together, (ii) a single antibody that has one chain specific to KDR and a second chain specific to a second molecule, or (iii) a single chain antibody that has specificity to KDR and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer* (*Suppl.*) 7:51-52 (1992). In each case, the second specificity can be made to the heavy chain activation receptors, including, without limitation, CD16 or CD64 (see e.g., Deo et al. *Immunol. Today* 18:127 (1997)) or CD89 (see e.g., Valerius et al. *Blood* 90:4485-4492 (1997)).

Antibodies can also be modified to act as immunotoxins, utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each immunotoxin or radiolabeled molecule would be likely to kill cells expressing the desired multimeric enzyme subunit oligomerisation domain.

When an antibody is linked to an agent (e.g., radioisotope, pharmaceutical composition, or a toxin), it is contemplated that the agent possess a pharmaceutical property selected from the group of antimitotic, alkylating, antimetabolite, antiangiogenic, apoptotic, alkaloid, COX-2, and antibiotic agents and combinations thereof. The drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

Examples of toxins further include gelonin, *Pseudomonas* exotoxin (PE), PE40, PE38, diphtheria toxin, ricin, abrin, alpha toxin, saporin, ribonuclease (RNase), DNase I, Staphylococcal enterotoxin-A, pokeweed antiviral protein, gelonin, *Pseudomonas* endotoxin, members of the enediyne family of molecules, such as calicheamicin and esperamicin, as well as derivatives, combinations and modifications thereof. Chemical toxins can also be taken from the group consisting of duocarmycin (see, e.g., U.S. Pat. Nos. 5,703,080 and 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

Examples of radioisotopes include gamma-emitters, positron-emitters, and x-ray emitters that can be used for localisation and/or therapy, and beta-emitters and alpha-emitters that can be used for therapy. The radioisotopes described previously as useful for diagnostics, prognostics and staging are also useful for therapeutics.

Non-limiting examples of anti-cancer or anti-leukemia agents include anthracyclines such as doxorubicin (adriamycin), daunorubicin (daunomycin), idarubicin, detorubicin, caminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. Preferably, the anti-cancer or anti-leukemia is doxorubicin, morpholinodoxorubicin, or morpholinodaunorubicin.

The antibodies of the invention also encompass antibodies that have half-lives (e.g., serum half-lives) in a mammal, preferably a human, of greater than that of an unmodified antibody. Said antibody half life may be greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatisation that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

As will be appreciated by one of skill in the art, in the above embodiments, while affinity values can be important, other factors can be as important or more so, depending upon the particular function of the antibody. For example, for an immunotoxin (toxin associated with an antibody), the act of binding of the antibody to the target can be useful; however, in some embodiments, it is the internalisation of the toxin into the cell that is the desired end result. As such, antibodies with a high percent internalisation can be desirable in these situations. Thus, in one embodiment, antibodies with a high efficiency in internalisation are contemplated. A high efficiency of internalisation can be measured as a percent internalised antibody, and can be from a low value to 100%. For example, in varying embodiments, 0.1-5, 5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of KDR expression in mammalian tissues or cells in order to screen for a disease or disorder associated with changes in expression of KDR. The kit comprises an antibody that binds KDR and means for indicating the reaction of the antibody with the antigen, if present.

Combinations

The targeted binding agent or antibody defined herein may be applied as a sole therapy or may involve, in addition to the compounds of the invention, conventional surgery or radiotherapy or chemotherapy. Such chemotherapy may include one or more of the following categories of anti tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or, inhibitors of cathepsins, inhibitors of serine proteases for example matriptase, hepsin, urokinase, inhibitors of heparanase);

(iv) cytotoxic agents such as fludarabine, 2-chlorodeoxyadenosine, chlorambucil or doxorubicin and combination thereof such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CNOP: cyclophosphamide+mitoxantrone+vincristine+prednisone, m-BACOD: methotrexate+bleomycin+doxorubicin+cyclophosphamide+vincristine+dexamethasone+leucovorin., MACOP-B: methotrexate+doxorubicin+cyclophosphamide+vincristine+prednisone fixed dose+bleomycin+leucovorin, or ProMACE CytaBOM: prednisone+doxorubicin+cyclophosphamide+etoposide+cytarabine+bleomycin+vincristine+methotrexate+leucovorin.

(v) inhibitors of growth factor function, for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) -quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors, aurora kinase inhibitors (for example AZD1152, PH739358, VX-680, MLN8054, R763, MP235, MP529, VX-528 and AX39459), cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin αvβ3 function and angiostatin)] or colony stimulating factor 1 (CSF1) or CSF1 receptor.;

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as G-3139 (Genasense), an anti bcl2 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including for example treatment with Alemtuzumab (campath-1H™), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumour cell lines and approaches using anti idiotypic antibodies.

(xi) inhibitors of protein degradation such as proteasome inhibitor such as Velcade (bortezomid).

(xii) biotherapeutic therapeutic approaches for example those which use peptides or proteins (such as antibodies or soluble external receptor domain constructions) which either sequester receptor ligands, block ligand binding to receptor or decrease receptor signalling (e.g. to due to enhanced receptor degradation or lowered expression levels).

In one embodiment the anti-tumour treatment defined herein may involve, in addition to the compounds of the invention, treatment with other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin).

In one embodiment the anti-tumour treatment defined herein may involve, in addition to the compounds of the invention, treatment with gemcitabine.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunization

Immunizations were conducted using soluble KDR (VEGF Receptor $2_{D1-7}$, Cat. #676490, Calbiochem). For the campaign, 10 μg/mouse of soluble protein was provided in the initial boost, followed by 5 μg/mouse in subsequent boosts, for immunization in XenoMouse™. The immunization was carried out according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. The immunization programs are summarized in Table 2.

Selection of Animals for Harvest by Titer

Titers of the antibody against human KDR were tested by FACS staining for native antigen binding using Human Umbilical Vein Endothelial Cells (HUVEC) or by ELISA assay for binding to immobilized soluble KDR. At the end of the immunization program, fusions were performed using mouse myeloma cells and lymphocytes isolated from the spleens and lymph nodes of the immunized mice by means of electroporation, as described in Example 2.

TABLE 2

Summary of Immunization Programs

| Campaign | Group | Immunogen | Strain | No of mice | Immunization routes |
|---|---|---|---|---|---|
| 1 | 1 | Soluble KDR (Calbiochem #676490) | IgG2 | 10 | IP/Tail/BIP, twice/wk, ×8 wks, followed by IP/Tail/BIP, once/every 2 weeks, × 6 wks |
| 1 | 2 | Soluble KDR (Calbiochem #676490) | IgG4 | 10 | IP/Tail/BIP, twice/wk, ×8 wks, followed by IP/Tail/BIP, once/every 2 weeks, ×6 wks |

"IP" refers to "intraperitoneal"
"BIP" refers to "Base of Tail/Intraperitoneal"

Example 2

Recovery of Lymphocytes, B-Cell Isolations, Fusions and Generation of Hybridomas Immunized mice were sacrificed by cervical dislocation, and the draining lymph nodes harvested and pooled from each cohort. There were two harvests performed for this program. Harvest 1 used six mice with ID numbers 157166, 157168, 157597, 157599, 157600, 157602. Harvest 2 used five mice with ID numbers 157662, 157663, 157665, 157672, 157694.

The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 μl of CD90+magnetic beads per 100 million cells, the cells were labeled by incubating the cells with the magnetic beads at 4° C. for 15 minutes. The magnetically labeled cell suspension containing up to $10^8$ positive cells (or up to $2\times10^9$ total cells) was loaded onto a LS+column and the column washed with DMEM. The total effluent was collected as the CD90-negative fraction (most of these cells were expected to be B cells).

The fusion was performed by mixing washed enriched Day 6 B cells with nonsecretory myeloma P3X63Ag8.653 cells purchased from ATCC, cat. # CRL 1580 (Kearney et al, J. Immunol. 123, 1979, 1548-1550) at a ratio of 1:4. The cell mixture was gently pelleted by centrifugation at 400×g for 4 minutes. After decanting of the supernatant, the cells were gently mixed using a 1 ml pipette. Preheated PEG (1 ml per $10^6$ B-cells) was slowly added with gentle agitation over 1 minute followed by 1 minute of mixing. Preheated IDMEM (2 ml per $10^6$ B-cells) was then added over 2 minutes with gentle agitation. Finally preheated IDMEM (8 ml per $10^6$ B-cells) was added over 3 minutes.

The fused cells were spun down at 400×g for 6 minutes and resuspended in 20 ml of Selection media (DMEM (Invitrogen), 15% FBS (Hyclone), supplemented with L-glutamine, pen/strep, MEM Non-essential amino acids, Sodium Pyruvate, 2-Mercaptoethanol (all from Invitrogen), HA-Azaserine Hypoxanthine and OPI (oxaloacetate, pyruvate, bovine insulin) (both from Sigma) and IL-6 (Boehringer Mannheim)) per $10^6$ B-cells. Cells were incubated for 20-30 minutes at 37° C. and then resuspended in 200 ml Selection media and cultured for 3-4 days in a T175 flask.

Day 3 post fusion the cells were collected, spun for 8 minutes at 400×g and resuspended in 10 ml Selection media per $10^6$ fused B-cells. FACS analysis of hybridoma population was performed, and cells were subsequently frozen down.

Hybridomas were grown as routine in the selective medium. Exhaustive supernatants collected from the hybridomas that potentially produce anti-human KDR antibodies were subjected to subsequent screening assays.

Example 3

Antibody Titer Measurement

Native Antigen Binding of Human Umbilical Vein Endothelial Cells (HUVEC)

FACS analysis was performed on human umbilical vein endothelial cells (HUVECs) to measure the titers of antibody against human KDR produced as described in Examples 1 and 2. HUVECs were seeded at 60,000 cells/well and incubated with 2 μL of sample (at 1:50 dilution) for one hour at 4° C. The wells were then washed and incubated with Cy5-conjugated goat anti-human antibody at 5 μg/mL and 7-Amino-Actinomycin (7AAD) at 5 μg/mL for 15 minutes at 4° C. Bound KDR was detected using FACS analysis. The positive control was goat anti-KDR antibody (R&D Systems, Inc.), and negative controls included negative controls included naïve XMG2 sera and naïve XMG4 (XM3C-1) sera. Animals with the greatest FACS Geometric Mean Fluorescence were selected for subsequent hybridoma generation. Table 3 lists the FACS data obtained from analysis of the HUVECs.

TABLE 3

Titers of antibody against human KDR as measured by FACS analysis of HUVECs

| Mouse | FACS Geometric Mean |
|---|---|
| P157166 | 18.97 |
| P157168 | 15.82 |
| P157169 | 10.43 |
| P157597 | 24.34 |
| P157598 | 11.29 |

TABLE 3-continued

| Titers of antibody against human KDR as measured by FACS analysis of HUVECs | |
|---|---|
| Mouse | FACS Geometric Mean |
| P157599 | 19.66 |
| P157600 | 42.11 |
| P157602 | 33.2 |
| P157661 | 10.64 |
| P157662 | 20.18 |
| P157663 | 24.63 |
| P157664 | 7.59 |
| P157665 | 17.25 |
| P157672 | 28.64 |
| P157692 | 12.94 |
| P157693 | 11.1 |
| P157694 | 31.69 |
| P157695 | 7.71 |
| Naïve G2 | 3.73 |
| Naïve G4 | 3.06 |
| Control: Goat anti-KDR (2 μg/mL) | 21.68 |
| Control: Goat anti-KDR (0.2 μg/mL) | 8.23 |
| Control: Goat anti-KDR (0.02 μg/mL) | 4.25 |
| Control: Goat isotype (2 μg/mL) | 3.28 |

Example 4

Antibody Titer Measurement

Binding to Immobilized Soluble KDR

ELISA assay of binding to immobilized soluble KDR was used to measure titers of antibody produced as described in Examples 1 and 2.

To measure the titers of antibody, plates were coated with KDR (Calbiochem) at 1 μg/mL overnight at 4° C. Serum containing antibodies were then titrated 1:3 in duplicate starting at 1:100 dilution in blocking buffer (1×PBS/1% milk). The plates containing sera were incubated for one hour at room temperature, washed, and subsequently incubated with secondary antibody (goat anti-human IgG Fc POD—Jackson Laboratories) for one hour at room temperature. The positive control was goat anti-KDR (Catalog #AF357, R&D Systems, Inc.), and negative controls included naïve XMG2 sera and naïve XMG4 (XM3C-1) sera. Table 4 provides a summary of the ELISA readings obtained from analysis of the bound antibodies.

TABLE 4

| Titers of antibody against immobilized soluble KDR as measured by ELISA assay | |
|---|---|
| Mouse | Coating: KDR @ 1 μg/mL |
| P157166 | 13400 |
| P157168 | 14144 |
| P157169 | 2309 |
| P157597 | 11027 |
| P157598 | 2080 |
| P157599 | 21053 |
| P157600 | 11507 |
| P157602 | 67697 |
| P157661 | 2393 |
| P157662 | 3207 |
| P157663 | 6816 |
| P157664 | 2171 |
| P157665 | 2488 |
| P157672 | 7197 |
| P157692 | 7060 |
| P157693 | 2340 |
| P157694 | 6568 |

TABLE 4-continued

| Titers of antibody against immobilized soluble KDR as measured by ELISA assay | |
|---|---|
| Mouse | Coating: KDR @ 1 μg/mL |
| P157695 | 2051 |
| Naïve G2 | <100 @ OD 0.217 |
| Naïve G4 | <100 @ OD 0.244 |

Example 5

Hybridoma Supernatant Screening by Binding Assay

Hybridoma supernatants containing antibody, produced as described in Examples 1 and 2, were screened by assays that measure binding to both immobilized soluble human KDR and to the Ig4-7 domain of KDR.

To screen by binding to immobilized soluble KDR, plates were coated with KDR (Calbiochem) at 250 ng/mL overnight at 4° C. After blocking and washing the coated plates, the candidate hybridoma supernatants (at 1:5 dilution) were transferred to the plates and incubated for one hour at room temperature. The plates were then washed and incubated with secondary antibody (at 1:4000 dilution) for one hour at room temperature. Table 5 provides a summary of the ELISA readings obtained from analysis of the bound antibodies for the screening.

TABLE 5

| ELISA results (substrate: immobilized soluble human KDR) | |
|---|---|
| MAb ID | KDR OD(450 nm) |
| 1G6 | 6.000 |
| 21A1 | 0.967 |
| 21H6 | 0.620 |
| 21H9 | 1.647 |
| 22B8 | 1.183 |
| 24B3 | 6.000 |
| 24C9 | 0.550 |
| 27A3 | 3.749 |
| 27D10 | 3.238 |
| 29A3 | 0.814 |
| 29H3 | 0.830 |
| 29D4 | 1.001 |
| 29F7 | 1.222 |
| 29A11 | 3.527 |
| 30A1 | 0.786 |
| 30E3 | 4.178 |
| 30F6 | 0.454 |
| 30D7 | 3.448 |
| 30H10 | 0.943 |
| 31E11 | 1.137 |
| 32B2 | 1.111 |
| 32F4 | 0.907 |
| 32G7 | 1.066 |
| 32C11 | 0.924 |
| 33B1 | 1.111 |
| 33E1 | 4.555 |
| 33C3 | 1.154 |
| 33D5 | 3.587 |

For this experiment, a KDR antibody containing the Ig4-7 domain (b-KDRIg4-7-myc-his) was obtained by cloning the extracellular domains 4-7 of the KDR antibody into pSecTag DNA expression constructs. The constructs were transiently transfected and expressed in 293T cells, and the expressed his-tagged protein was purified by nickel (Ni) column chromatography.

To screen by binding to the Ig4-7 domain of KDR, plates were first coated with neutravadin (Pierce) at 4 μg/mL and incubated overnight at 4° C. The plates were then blocked and subsequently incubated with b-KDRIg4-7-myc-his at 1 μg/mL for one hour at room temperature. Candidate hybridoma supernatants (at 1:5 dilution) were transferred to the plates and incubated for one hour at room temperature. The plates were then washed and incubated with goat anti-human IgG Fc POD (at 1:4000 dilution) for one hour at room temperature. Table 6 provides a summary of the ELISA readings obtained from analysis of the bound antibodies for the screening.

TABLE 6

ELISA results (substrate: Ig4-7 domain of KDR)

| MAb ID | b-KDRIg4-7 OD(450 nm) |
|---|---|
| 1G6 | 0.056 |
| 21A1 | 1.274 |
| 21H6 | 0.935 |
| 21H9 | 0.052 |
| 22B8 | 2.815 |
| 24B3 | 0.065 |
| 24C9 | 0.066 |
| 27A3 | 1.820 |
| 27D10 | 2.031 |
| 29A3 | 0.201 |
| 29H3 | 0.071 |
| 29D4 | 2.608 |
| 29F7 | 0.082 |
| 29A11 | 0.062 |
| 30A1 | 1.209 |
| 30E3 | 0.049 |
| 30F6 | 0.093 |
| 30D7 | 0.056 |
| 30H10 | 0.047 |
| 31E11 | 1.279 |
| 32B2 | 0.061 |
| 32F4 | 2.291 |
| 32G7 | 0.068 |
| 32C11 | 0.050 |
| 33B1 | 0.058 |
| 33E1 | 0.620 |
| 33C3 | 3.659 |
| 33D5 | 0.107 |

Example 6

Cross-Reactivity to Human VEGF-Receptor-1 (Flt-1) and Mouse KDR (Flk-1)

The cross-reactivity of antibodies in the hybridoma supernatant was tested against KDR mouse ortholog (mouse VEGFR2, or Flk-1) and human VEGFR1 (Flt-1). Cross-reactivity was measured using an ELISA based assay. Cross-reactivity to KDR mouse ortholog (Flk-1) was desired. However, antibodies that selected over Flt-1 were chosen for further analysis.

Plates were coated with human VEGFR1 (Flt-1)/Fc (Flt-1, Cat. #321-FL/CF, R&D Systems, Inc.) or mouse KDR (Flk-1)/Fc (Flk-1, Cat. #443-KD/CF, R&D Systems, Inc.) at 500 ng/mL and incubated overnight at 4° C. After washing and blocking the plates, the antibody-containing supernatants were added (at 1:5 dilution) into the coated wells and incubated for one hour at room temperature. The plates were then incubated with mouse anti-human IgG 2, 3 and 4 and subsequently with goat anti-mouse IgG Fc POD, to detect and measure bound antibodies. Table 7 provides the results of the ELISA cross-reactivity assay for each substrate.

TABLE 7

ELISA Cross-Reactivity Assay Results Against Mouse KDR (Flk-1) and Human VEGFR1 (Flt-1)

| MAb ID | Flk-1 (mouse KDR), OD (450 nm) | Flt-1 (human VEGFR1), OD (450 nm) |
|---|---|---|
| 1G6 | 0.055 | 0.054 |
| 21A1 | 0.270 | 0.180 |
| 21H6 | 0.193 | 0.086 |
| 21H9 | 0.139 | 0.134 |
| 22B8 | 0.074 | 0.078 |
| 24B3 | 0.094 | 0.068 |
| 24C9 | 0.098 | 0.080 |
| 27A3 | 0.156 | 0.068 |
| 27D10 | 0.166 | 0.140 |
| 29A3 | 0.416 | 0.069 |
| 29H3 | 0.096 | 0.071 |
| 29D4 | 0.100 | 0.079 |
| 29F7 | 0.093 | 0.061 |
| 29A11 | 0.261 | 0.080 |
| 30A1 | 0.107 | 0.067 |
| 30E3 | 0.112 | 0.058 |
| 30F6 | 0.067 | 0.075 |
| 30D7 | 0.135 | 0.062 |
| 30H10 | 0.338 | 0.097 |
| 31E11 | 0.162 | 0.134 |
| 32B2 | 0.274 | 0.114 |
| 32F4 | 0.094 | 0.090 |
| 32G7 | 0.092 | 0.085 |
| 32C11 | 0.083 | 0.063 |
| 33B1 | 0.108 | 0.085 |
| 33E1 | 0.097 | 0.075 |
| 33C3 | 0.076 | 0.067 |
| 33D5 | 0.201 | 0.093 |

Example 7

Native Binding to Human Umbilical Vein Endothelial Cells (HUVECs)

FACS analysis was performed on human umbilical vein endothelial cells (HUVECs) to confirm native binding of antibody in the hybrodima supernatant produced as described in Examples 1 and 2. HUVECs were seeded at 15,000 cells/well and incubated with 100 μL of sample supernatant (at 1:50 dilution) for one hour at 4° C. The positive control was goat anti-KDR antibody (R&D Systems, Inc.), and negative controls included irrelevant hybridoma supernatants at the same dilution. The cells were then washed and incubated with Cy5-conjugated goat anti-human antibody at 5 μg/mL and 7-Amino-Actinomycin D (7AAD) at 5 μg/mL for 15 minutes at 4° C. Bound KDR was detected using FACS analysis. Table 8 lists the FACS data obtained from analysis of the HUVECs. Antibodies with strong binding to HUVEC cells were considered as having higher relative avidity.

TABLE 8

Native binding to HUVECs as measured by FACS

| MAb ID | FACS Geometric Mean (1:50 dilution of hybridoma supernatant) |
|---|---|
| 1G6 | 32 |
| 21A1 | 14 |
| 21H6 | 18 |
| 21H9 | 29 |
| 22B8 | 24 |
| 24B3 | 26 |
| 24C9 | 33 |
| 27A3 | 25 |

TABLE 8-continued

Native binding to HUVECs as measured by FACS

| MAb ID | FACS Geometric Mean (1:50 dilution of hybridoma supernatant) |
|---|---|
| 27D10 | 24 |
| 29A3 | 30 |
| 29H3 | 27 |
| 29D4 | 26 |
| 29F7 | 32 |
| 29A11 | 31 |
| 30A1 | 25 |
| 30E3 | 36 |
| 30F6 | 21 |
| 30D7 | 31 |
| 30H10 | 31 |
| 31E11 | 18 |
| 32B2 | 26 |
| 32F4 | 27 |
| 32G7 | 28 |
| 32C11 | 26 |
| 33B1 | 25 |
| 33E1 | 14 |
| 33C3 | 20 |
| 33D5 | 24 |

Example 8

Determination of Relative Potency of Antibody-Containing Supernatants

The relative potency of the various antibody-containing supernatants was compared by measuring how well the antibodies blocked KDR phosphorylation in an endogenously KDR-expressing normal cell line (HUVEC). The assays were conducted using a supernatant dilution of 1:20 and included examination of the blockade of both VEGF165-mediated and VEGF-E mediated KDR tyrosine phosphorylation. VEGF165 binds to both KDR:KDR homodimers and to KDR:VEGF-Receptor-1 hetrodimers. VEGF-E is an Orf virus homologue of VEGF165; however, unlike VEGF165, VEGF-E is specifically binds to KDR, therefore providing selective analysis of KDR dimerization (*Endocrine Reviews*, August 2004, 25(4): 581-611).

The relative potencies of the different antibody containing supernatants were also examined for their ability to block survival of serum-deprived HUVEC cells as mediated by both VEGF165 and VEGF-E. These assays were also performed at a supernatant dilution of 1:20. All incubations with HUVEC cells took place at 37° C. and 5% $CO_2$.

Assay to Measure Inhibition of VEGF165-Mediated KDR Activity

HUVEC cells were seeded at 25,000 cells/well and incubated overnight in Endothelial Cell Basal Medium-2 (EBM-2, Clonetics EGM-2 BulletKit, catalog #CC-3162)+2% FCS+the following growth supplements: hydrocortisone, hFGF-B, R3-IGF-1, ascorbic acid, heparin, FBS, hEGF, and GA-1000. The cells were then washed and incubated in supplement-free media overnight. On the third day, the various antibody-containing supernatants were added to the HUVEC cells and incubated for 2 hours. The supernatant volumes were then removed and replaced by 50 μL of VEGF165 at 2 nM final concentration. After incubation with VEGF165 for 7 minutes, the cells were lysed, and the cell lysates were measured for inhibition of VEGF165-mediated KDR activity. Table 9 provides a listing of average (n=3) ELISA readings indicating the level of inhibition of VEGF165-mediated KDR tyrosine phosphorylation.

TABLE 9

Inhibition of VEGF165-mediated KDR tyrosine phosphorylation in HUVEC cells

| MAb ID | % Inhibition of VEGF165-mediated pTyr Activity n = 1 | n = 2 | n = 3 | Average | St. Dev. | % CV |
|---|---|---|---|---|---|---|
| 1G6 | 89 | 67 | 58 | 71 | 16 | 23 |
| 21A1 | 71 | 77 | 68 | 72 | 5 | 7 |
| 21H6 | 85 | 65 | 68 | 72 | 11 | 15 |
| 21H9 | 80 | 70 | 61 | 70 | 9 | 13 |
| 22B8 | 82 | 65 | 53 | 67 | 15 | 22 |
| 24B3 | 69 | 51 | 33 | 51 | 18 | 35 |
| 24C9 | 55 | 45 | 38 | 46 | 8 | 18 |
| 27A3 | 60 | 68 | 59 | 62 | 5 | 8 |
| 27D10 | 62 | 48 | 63 | 58 | 8 | 15 |
| 29A3 | 92 | 66 | 72 | 77 | 14 | 18 |
| 29H3 | 89 | 72 | 66 | 76 | 12 | 16 |
| 29D4 | 85 | 67 | 63 | 72 | 12 | 16 |
| 29F7 | 90 | 67 | 77 | 78 | 12 | 15 |
| 29A11 | 96 | 72 | 66 | 78 | 16 | 20 |
| 30A1 | 86 | 59 | 52 | 65 | 18 | 27 |
| 30E3 | 89 | 67 | 58 | 71 | 16 | 23 |
| 30F6 | 98 | 60 | 52 | 70 | 24 | 35 |
| 30D7 | 99 | 71 | 59 | 76 | 21 | 27 |
| 30H10 | 92 | 77 | 59 | 76 | 17 | 22 |
| 31E11 | 81 | 80 | 59 | 74 | 12 | 17 |
| 32B2 | 91 | 75 | 66 | 77 | 13 | 17 |
| 32F4 | 88 | 76 | 56 | 73 | 16 | 22 |
| 32G7 | 73 | 47 | 11 | 44 | 31 | 71 |
| 32C11 | 84 | 75 | 57 | 72 | 14 | 19 |
| 33B1 | 76 | 56 | 31 | 54 | 23 | 42 |
| 33E1 | 88 | 78 | 52 | 73 | 19 | 26 |
| 33C3 | 87 | 75 | 50 | 71 | 19 | 27 |
| 33D5 | 95 | 72 | 63 | 77 | 16 | 21 |

Assay to Measure Inhibition of VEGF-E-Mediated KDR Activity

HUVEC cells were seeded and incubated with antibody-containing supernatants as described above. The supernatant volumes were then removed and replaced by 50 μL of VEGF-E at 2 nM final concentration. After incubation with VEGF-E for 7 minutes, the cells were lysed, and the cell lysates were measured for inhibition of VEGF-E-mediated KDR activity. Table 10 provides a listing of ELISA readings indicating the level of inhibition of VEGF-E-mediated KDR tyrosine phosphorylation.

TABLE 10

Inhibition of VEGF-E-mediated KDR tyrosine phosphorylation in HUVEC cells

| MAb ID | % Inhibition of VEGF-E-mediated pTyr Activity |
|---|---|
| 1G6 | 24 |
| 21A1 | 67 |
| 21H6 | 70 |
| 21H9 | 6 |
| 22B8 | 61 |
| 24B3 | 40 |
| 24C9 | 51 |
| 27A3 | 60 |
| 27D10 | 63 |
| 29A3 | 22 |
| 29H3 | 18 |
| 29D4 | 67 |
| 29F7 | 45 |
| 29A11 | 15 |
| 30A1 | 50 |
| 30E3 | 19 |
| 30F6 | 56 |
| 30D7 | 24 |
| 30H10 | 20 |

TABLE 10-continued

| Inhibition of VEGF-E-mediated KDR tyrosine phosphorylation in HUVEC cells | |
|---|---|
| MAb ID | % Inhibition of VEGF-E-mediated pTyr Activity |
| 31E11 | 67 |
| 32B2 | 15 |
| 32F4 | 62 |
| 32G7 | 57 |
| 32C11 | 17 |
| 33B1 | 54 |
| 33E1 | 46 |
| 33C3 | 66 |
| 33D5 | 30 |

Assay to Measure Ability of Antibody to Block Survival of Serum-Deprived HUVEC Cells as Mediated by VEGF165

HUVEC cells were seeded at 10,000 cells/well and incubated overnight in EBM-2+2% FCS+all supplements except VEGF (see above). The cells were then washed and the various antibody-containing supernatants (at either 1:10 or 1:20 dilution in 50 μL of basal EBM-2 media) were added to the HUVEC cells and incubated for 2 hours. Fifty (50) μL of VEGF165 (1 nM final concentration) with chloroquine (25 nM final concentration, Sigma-Aldrich) and 0.01% FCS (final concentration) was added to the cells, and the cells were incubated for 4 days at 37° C. and 5% $CO_2$. Cell survival was then measured by addition of luminescent substrate (Cell Titer Glo, Promega) per manufacturer's protocol and detected using a luminometer. Antibody inhibition of HUVEC survival is indicated by lower Relative Luminscence Unit (RLU) values. Table 11 provides a listing of (n=2) luminometer readings indicating HUVEC survival by VEGF165-mediated KDR activity.

TABLE 11

| Survival of HUVEC Cells by VEGF165-mediated KDR Activity | | |
|---|---|---|
| MAb ID | HUVEC survival (n = 1) 1:10 dilution of supernatant (RLU) | HUVEC survival (n = 2) 1:20 dilution of supernatant (RLU) |
| 1G6 | 47799 | 10197 |
| 21A1 | 8871 | 2673 |
| 21H6 | 10200 | 247 |
| 21H9 | 43793 | 10269 |
| 22B8 | 12860 | 3260 |
| 24B3 | 14148 | 2459 |
| 24C9 | 14615 | 9180 |
| 27A3 | 17291 | 4563 |
| 27D10 | 20114 | 9713 |
| 29A3 | 36363 | 2450 |
| 29H3 | 32652 | 544 |
| 29D4 | 12886 | 5384 |
| 29F7 | 44127 | 23984 |
| 29A11 | 34648 | 27654 |
| 30A1 | 14389 | 9728 |
| 30E3 | 37528 | 30447 |
| 30F6 | 14832 | 1348 |
| 30D7 | 28288 | 2524 |
| 30H10 | 39549 | 21110 |
| 31E11 | 9135 | 6979 |
| 32B2 | 19290 | 400 |
| 32F4 | 20111 | 5026 |
| 32G7 | 24875 | 11898 |
| 32C11 | 44831 | 8574 |
| 33B1 | 19422 | 12454 |
| 33E1 | 25742 | 2308 |
| 33C3 | 6539 | 4708 |
| 33D5 | 43395 | 706 |

Assay to Measure Ability of Antibody to Block Survival of Serum-Deprived HUVEC Cells as Mediated by VEGF-E HUVEC cells were seeded and incubated with antibody-containing supernatants as described above. The cells were then washed and the various antibody-containing supernatants (at 1:10 dilution in basal EBM-2 media) were added to the HUVEC cells and incubated for 2 hours. VEGF-E (Cederlane) was added to the cells to a final concentration of 1 nM, and the cells were incubated for 4 days. Cell survival was then measured as above by addition of luminescent substrate and luminometer assay. Table 12 provides a listing of the degree of inhibition observed as a percentage of VEGF-E maximal activity. Values approaching 100% are equivalent to complete inhibition of VEGF-E activity.

TABLE 12

| Survival of HUVEC Cells by VEGF-E-mediated KDR Activity | | | | | |
|---|---|---|---|---|---|
| | VEGF-E-mediated Survival % Inhibition | | | | |
| MAb ID | n = 1 | n = 2 | Average | St. Dev. | % CV |
| 1G6 | −2 | 6 | 2 | 6 | 324 |
| 21A1 | 45 | 40 | 42 | 4 | 8 |
| 21H6 | 56 | 53 | 55 | 2 | 4 |
| 21H9 | −3 | 1 | −1 | 3 | −506 |
| 22B8 | 57 | 53 | 55 | 3 | 5 |
| 24B3 | 65 | 66 | 66 | 1 | 1 |
| 24C9 | 72 | 72 | 72 | 1 | 1 |
| 27A3 | 63 | 52 | 58 | 8 | 13 |
| 27D10 | 50 | 64 | 57 | 10 | 18 |
| 29A3 | −1 | −20 | −10 | 13 | −129 |
| 29H3 | −19 | −11 | −15 | 6 | −42 |
| 29D4 | 64 | 67 | 66 | 2 | 3 |
| 29F7 | 15 | 6 | 11 | 6 | 60 |
| 29A11 | 8 | 1 | 5 | 5 | 112 |
| 30A1 | 58 | 59 | 58 | 1 | 2 |
| 30E3 | −21 | −7 | −14 | 10 | −68 |
| 30F6 | 31 | 43 | 37 | 8 | 23 |
| 30D7 | −27 | −22 | −24 | 4 | −14 |
| 30H10 | −21 | 2 | −10 | 17 | −175 |
| 31E11 | 56 | 54 | 55 | 1 | 3 |
| 32B2 | −2 | −9 | −6 | 5 | −83 |
| 32F4 | 64 | 64 | 64 | 0 | 0 |
| 32G7 | 69 | 54 | 62 | 11 | 18 |
| 32C11 | 5 | 7 | 6 | 2 | 27 |
| 33B1 | 66 | 68 | 67 | 2 | 2 |
| 33E1 | 66 | 54 | 60 | 9 | 14 |
| 33C3 | 78 | 69 | 74 | 7 | 9 |
| 33D5 | −2 | 2 | 0 | 3 | −678 |

Example 9

Kinetic Assays

These experiments were conducted to identify high affinity/high potency antibodies in the hybridoma supernatants obtained as described in Example 2. The experiments were performed using soluble KDR extracellular domain (ECD) (Calbiochem).

High Antigen (HA) Quantitation (ELISA)

ELISA plates were coated with a greater amount of KDR (at 500 ng/mL) in comparison with the Limited Antigen Quantitation assay described below. Sample containing antibody (Ab) was titrated on the KDR-coated ELISA plates and was incubated overnight at 4° C. to allow Ab binding to approach equilibrium. Titration of Ab in sample covered a dilution range of 1:25 to 1:18,225. A standard curve of KDR-specific antibody of known concentration was used to define the linear range of the assay. Data within the linear range were used to derive the relative concentration of KDR-specific Ab in each titrated sample. The high KDR concentration and the overnight incubation limited the effect of Ab affinity, allowing quantitation of the relative amount of KDR-specific Ab present in each sample.

Limited Antigen (LA) Quantitation (ELISA)

ELISA plates were coated with a lower amount of KDR (3.125, 6.25, 12.5, 25 and 50 ng/mL) in comparison with the High Antigen Quantitation assay described above. Samples containing one concentration of antibody (Ab) (1:25 dilution) were incubated overnight to allow Ab binding to approach equilibrium. The low antigen concentration limited the effect of antibody concentration, allowing ranking of the antibodies based on their relative affinity.

Tables 13 and 14 summarize the results for the hybridoma lines that had the desired neutralizing activity and preferred binding kinetics.

TABLE 13

High Antigen Supernatant Dilution ELISA Assay Results

| MAb ID | High Antigen Hybridoma Supernatant Dilution 1:25 | 1:75 | 1:225 | 1:675 | 1:2025 | 1:6075 | 1:18,225 | HA Derived Conc. (μg/mL) | Std. Dev. | % CV |
|---|---|---|---|---|---|---|---|---|---|---|
| 1G6 | 6.000 | 6.000 | 4.490 | 2.240 | 0.690 | 0.340 | 0.260 | 5.1 | 1.5 | 28.6 |
| 21A1 | 4.450 | 4.430 | 4.140 | 3.360 | 1.660 | 0.560 | 0.250 | 13.0 | 1.1 | 8.6 |
| 21H6 | 6.000 | 4.190 | 5.570 | 4.020 | 2.910 | 1.170 | 0.540 | 30.7 | 3.9 | 12.6 |
| 21H9 | 6.000 | 4.340 | 3.410 | 1.560 | 0.700 | 0.260 | 0.120 | 3.7 | 2.0 | 55.3 |
| 22B8 | 6.000 | 6.000 | 6.000 | 3.490 | 1.270 | 0.310 | 0.200 | 7.0 | 4.5 | 64.4 |
| 24B3 | 2.330 | 1.580 | 1.160 | 0.790 | 0.310 | 0.130 | 0.080 | 1.0 | 0.7 | 68.6 |
| 24C9 | 3.670 | 2.480 | 2.140 | 1.450 | 0.540 | 0.200 | 0.110 | 2.7 | 1.5 | 56.3 |
| 27A3 | 4.790 | 4.720 | 5.260 | 3.930 | 2.050 | 0.960 | 0.400 | 20.5 | 2.7 | 13.0 |
| 27D10 | 4.090 | 4.020 | 3.950 | 3.790 | 1.870 | 0.890 | 0.410 | 19.9 | 3.7 | 18.6 |
| 29A3 | 3.890 | 4.060 | 3.850 | 3.320 | 1.910 | 0.570 | 0.240 | 13.6 | 2.3 | 17.1 |
| 29H3 | 4.520 | 4.960 | 4.290 | 2.830 | 1.420 | 0.470 | 0.210 | 10.1 | 1.3 | 12.9 |
| 29D4 | 4.240 | 5.570 | 6.000 | 4.090 | 2.060 | 0.660 | 0.250 | 16.3 | 2.0 | 12.5 |
| 29F7 | 4.420 | 4.490 | 4.260 | 3.760 | 1.680 | 0.570 | 0.220 | 13.2 | 1.1 | 8.2 |
| 29A11 | 4.660 | 6.000 | 6.000 | 5.090 | 4.330 | 2.160 | 0.990 | 63.5 | 10.0 | 15.7 |
| 30A1 | 4.520 | 4.780 | 6.000 | 4.280 | 3.370 | 1.580 | 1.110 | 59.7 | 29.4 | 49.2 |
| 30E3 | 6.000 | 4.780 | 4.450 | 2.120 | 0.860 | 0.320 | 0.180 | 5.7 | 1.4 | 23.9 |
| 30F6 | 3.040 | 3.120 | 2.420 | 0.930 | 0.350 | 0.160 | 0.090 | 1.7 | 0.9 | 53.2 |
| 30D7 | 4.660 | 5.090 | 6.000 | 4.240 | 2.790 | 1.020 | 0.820 | 36.2 | 18.6 | 51.3 |
| 30H10 | 4.420 | 6.000 | 6.000 | 4.610 | 2.520 | 1.180 | 0.640 | 31.6 | 10.6 | 33.3 |
| 31E11 | 4.480 | 6.000 | 4.610 | 3.600 | 1.810 | 0.620 | 0.310 | 13.8 | 1.5 | 10.6 |
| 32B2 | 6.000 | 6.000 | 6.000 | 6.000 | 3.330 | 1.540 | 0.800 | 43.3 | 10.9 | 25.3 |
| 32F4 | 4.790 | 5.560 | 6.000 | 4.610 | 2.710 | 0.970 | 0.500 | 26.5 | 4.1 | 15.4 |
| 32G7 | 2.030 | 1.270 | 0.960 | 0.550 | 0.380 | 0.240 | 0.110 | 1.0 | 0.8 | 80.7 |
| 32C11 | 4.360 | 6.000 | 4.280 | 2.020 | 0.820 | 0.270 | 0.140 | 4.6 | 2.6 | 55.4 |
| 33B1 | 2.710 | 2.320 | 1.620 | 1.100 | 0.550 | 0.250 | 0.200 | 1.9 | 1.5 | 80.8 |
| 33E1 | 4.060 | 4.240 | 4.070 | 3.510 | 2.090 | 0.980 | 0.490 | 23.8 | 6.0 | 25.2 |
| 33C3 | 4.960 | 4.960 | 4.310 | 2.550 | 0.840 | 0.310 | 0.180 | 6.1 | 2.0 | 31.8 |
| 33D5 | 4.610 | 4.560 | 4.780 | 6.000 | 3.650 | 1.700 | 0.870 | 52.1 | 13.9 | 26.6 |

TABLE 14

Limited Antigen Coating Concentration ELISA Assay Results

| MAb ID | Limited Antigen Coating Concentration (ng/mL) 50 | 25 | 12.5 | 6.25 | 3.125 |
|---|---|---|---|---|---|
| 1G6 | 1.380 | 0.650 | 0.320 | 0.200 | 0.120 |
| 21A1 | 2.650 | 1.470 | 0.810 | 0.380 | 0.230 |
| 21H6 | 1.830 | 0.970 | 0.520 | 0.230 | 0.150 |
| 21H9 | 2.280 | 1.460 | 0.820 | 0.390 | 0.220 |
| 22B8 | 3.360 | 1.840 | 0.910 | 0.420 | 0.210 |
| 24B3 | 0.380 | 0.210 | 0.120 | 0.080 | 0.070 |
| 24C9 | 0.500 | 0.230 | 0.130 | 0.090 | 0.070 |
| 27A3 | 2.300 | 1.260 | 0.540 | 0.260 | 0.150 |
| 27D10 | 1.360 | 0.540 | 0.250 | 0.140 | 0.120 |
| 29A3 | 2.270 | 1.130 | 0.490 | 0.270 | 0.160 |
| 29H3 | 2.130 | 1.030 | 0.400 | 0.240 | 0.160 |
| 29D4 | 3.310 | 1.870 | 0.800 | 0.410 | 0.230 |
| 29F7 | 3.540 | 2.190 | 1.000 | 0.510 | 0.250 |
| 29A11 | 3.430 | 1.900 | 1.050 | 0.590 | 0.300 |
| 30A1 | 1.770 | 0.870 | 0.500 | 0.270 | 0.150 |
| 30E3 | 2.710 | 1.370 | 0.730 | 0.430 | 0.240 |
| 30F6 | 0.520 | 0.310 | 0.250 | 0.130 | 0.100 |
| 30D7 | 2.930 | 1.510 | 0.790 | 0.480 | 0.270 |
| 30H10 | 2.210 | 1.180 | 0.520 | 0.310 | 0.170 |
| 31E11 | 2.370 | 1.240 | 0.680 | 0.390 | 0.200 |
| 32B2 | 2.900 | 1.690 | 0.860 | 0.420 | 0.250 |
| 32F4 | 2.220 | 1.090 | 0.740 | 0.360 | 0.230 |
| 32G7 | 0.190 | 0.150 | 0.110 | 0.080 | 0.070 |
| 32C11 | 2.480 | 1.120 | 0.690 | 0.350 | 0.200 |
| 33B1 | 0.230 | 0.200 | 0.120 | 0.080 | 0.080 |
| 33E1 | 0.850 | 0.360 | 0.150 | 0.110 | 0.070 |
| 33C3 | 3.000 | 1.320 | 0.720 | 0.370 | 0.200 |
| 33D5 | 3.810 | 2.200 | 1.320 | 0.610 | 0.330 |

Example 10

Structural Analysis of KDR Antibodies

The variable heavy chains and the variable light chains of the antibodies were sequenced to determine their DNA sequences. The complete sequence information for the anti-KDR antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 20 is a table comparing the antibody heavy chain regions to their cognate germ line heavy chain region. Table 21 is a table comparing the antibody kappa light chain regions to their cognate germ line light chain region. It should be appreciated that amino acid sequences among the sister clones collected from each hybridoma are identical. As an example, the heavy chain and light chain sequences for 30E3.3 would be identical to the sequences for 30E3.1 and 30E3.2. For ease of viewing Tables 20 and 21, sister clones are grouped together and identified by their common chain name. For example, the sequences for 30E3.1, 30E3.2 and 30E3.3 are listed as a common sequence under the chain name "30E3".

The variable (V) regions of immunoglobulin chains are encoded by multiple germ line DNA segments, which are joined into functional variable regions ($V_HDJ_H$ or $V_KJ_K$) during B-cell ontogeny. The molecular and genetic diversity of the antibody response to KDR was studied in detail. These assays revealed several points specific to anti-KDR antibodies. It is of note that monoclonal antibodies 29A11, 32B2, 30E3, 30H10 and 32C11 appear to use D1-14 in the reverse complement orientation.

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 16 shows that the light chain sequence of mAb 24B3 (SEQ ID NO.: 44) differs from the corresponding germline sequence (SEQ ID NO.:124) through a Ser to Asn mutation (mutation 1) in the CDR1 region, a Thr to Ala mutation (mutation 2) in the CDR2 region and an Arg to Ser mutation (mutation 3) in the CDR3 region. Thus, the amino acid or nucleotide sequence encoding the light chain of mAb 24B3 can be modified to change mutation 1 to yield the germline sequence at the site of mutation 1. Further, the amino acid or nucleotide sequence encoding the light chain of mAb 24B3 can be modified to change mutation 2 or mutation 3 to yield the germline sequence at the site of mutation 2 or mutation 3. Still further, the amino acid or nucleotide sequence encoding the light chain of mAb 24B3 can be modified to change both mutation 1 and mutation 2, or any other combination of two or more mutations to yield the germline sequence at those particular sites. Tables 15-19 below illustrate the positions of such variations from the germline for mAb 27D10, 24B3 and 33C3. Tables 15a-19a illustrate the positions of such variations from the germline for mAb 27D10, 24B3 and 33C3. Each row represents a unique combination of germline and non-germline residues at the position indicated by bold type.

TABLE 15

Exemplary Mutations of mAB 27D10 Heavy Chain (SEQ ID NO: 14) to Germline at the Indicated Residue Number

| 34 | 39 | 57 | 69 | 113 | 114 |
|---|---|---|---|---|---|
| R | Y | T | Y | L | # |
| S | D | S | F | # | Y |

TABLE 15a

Exemplary Mutations of mAB 27D10 Heavy Chain (SEQ ID NO: 14) to Germline at the Indicated Residue Number

| 32 | 34 | 52 | 60 | 104 | 105 |
|---|---|---|---|---|---|
| R | D | T | F | L | Y |
| S | D | T | F | L | Y |
| R | Y | T | F | L | Y |
| S | Y | T | F | L | Y |
| R | D | S | F | L | Y |
| S | D | S | F | L | Y |
| R | Y | S | F | L | Y |
| S | Y | S | F | L | Y |
| R | D | T | Y | L | Y |
| S | D | T | Y | L | Y |
| R | Y | T | Y | L | Y |
| S | Y | T | Y | L | Y |
| R | D | S | Y | L | Y |
| S | D | S | Y | L | Y |
| R | Y | S | Y | L | Y |
| S | Y | S | Y | L | Y |
| R | D | T | F | — | Y |
| S | D | T | F | — | Y |
| R | Y | T | F | — | Y |
| S | Y | T | F | — | Y |
| R | D | S | F | — | Y |
| S | D | S | F | — | Y |
| R | Y | S | F | — | Y |
| S | Y | S | F | — | Y |
| R | D | T | Y | — | Y |
| S | D | T | Y | — | Y |
| R | Y | T | Y | — | Y |
| S | Y | T | Y | — | Y |
| R | D | S | Y | — | Y |
| S | D | S | Y | — | Y |
| R | Y | S | Y | — | Y |
| S | Y | S | Y | — | Y |
| R | D | T | F | L | — |
| S | D | T | F | L | — |
| R | Y | T | F | L | — |
| S | Y | T | F | L | — |
| R | D | S | F | L | — |
| S | D | S | F | L | — |
| R | Y | S | F | L | — |
| S | Y | S | F | L | — |
| R | D | T | Y | L | — |
| S | D | T | Y | L | — |
| R | Y | T | Y | L | — |
| S | Y | T | Y | L | — |
| R | D | S | Y | L | — |
| S | D | S | Y | L | — |
| R | Y | S | Y | L | — |
| S | Y | S | Y | L | — |
| R | D | T | F | — | — |
| S | D | T | F | — | — |
| R | Y | T | F | — | — |
| S | Y | T | F | — | — |
| R | D | S | F | — | — |
| S | D | S | F | — | — |
| R | Y | S | F | — | — |
| S | Y | S | F | — | — |
| R | D | T | Y | — | — |
| S | D | T | Y | — | — |
| R | Y | T | Y | — | — |
| S | Y | T | Y | — | — |
| R | D | S | Y | — | — |
| S | D | S | Y | — | — |

TABLE 15a-continued

| Exemplary Mutations of mAB 27D10 Heavy Chain (SEQ ID NO: 14) to Germline at the Indicated Residue Number | | | | | |
|---|---|---|---|---|---|
| 32 | 34 | 52 | 60 | 104 | 105 |
| R | Y | S | Y | — | — |
| S | Y | S | Y | — | — |

"—" indicates the absence of a residue at that position with reference to SEQ ID NO: 14

TABLE 16

| Exemplary Mutations of mAB 24B3 Light Chain (SEQ ID NO: 44) to Germline at the Indicated Residue Number | | |
|---|---|---|
| 33 | 67 | 111 |
| S | T | R |

TABLE 16a

| Exemplary Mutations of mAB 24B3 Light Chain (SEQ ID NO: 44) to Germline at the Indicated Residue Number | | |
|---|---|---|
| 31 | 51 | 93 |
| S | T | R |
| N | T | R |
| S | A | R |
| N | A | R |
| S | T | S |
| N | T | S |
| S | A | S |
| N | A | S |

TABLE 17

| Exemplary Mutations of mAB 24B3 Heavy Chain (SEQ ID NO: 42) to Germline at the Indicated Residue Number | | | | | | | | |
|---|---|---|---|---|---|---|---|---|
| 33 | 57 | 60 | 61 | 107 | 108 | 109 | 110 | 113 |
| S | F | S | S | A | R | D | # | G |
| S | S | G | S | A | R | # | D | G |
| T | S | S | R | A | R | # | # | E |

TABLE 17a

| Exemplary Mutations of mAB 24B3 Heavy Chain (SEQ ID NO: 42) to Germline at the Indicated Residue Number | | | | | | | | |
|---|---|---|---|---|---|---|---|---|
| 31 | 50 | 53 | 54 | 97 | 98 | 99 | 100 | 103 |
| T | F | G | R | S | K | D | D | E |
| S | F | G | R | S | K | D | D | E |
| T | S | G | R | S | K | D | D | E |
| S | S | G | R | S | K | D | D | E |
| T | F | S | R | S | K | D | D | E |
| S | F | S | R | S | K | D | D | E |
| T | S | S | R | S | K | D | D | E |
| S | S | S | R | S | K | D | D | E |
| T | F | G | S | S | K | D | D | E |
| S | F | G | S | S | K | D | D | E |
| T | S | G | S | S | K | D | D | E |
| S | S | G | S | S | K | D | D | E |
| T | F | S | S | S | K | D | D | E |
| S | F | S | S | S | K | D | D | E |
| T | S | S | S | S | K | D | D | E |
| S | S | S | S | S | K | D | D | E |
| T | F | G | R | A | K | D | D | E |

TABLE 17a-continued

| Exemplary Mutations of mAB 24B3 Heavy Chain (SEQ ID NO: 42) to Germline at the Indicated Residue Number | | | | | | | | |
|---|---|---|---|---|---|---|---|---|
| 31 | 50 | 53 | 54 | 97 | 98 | 99 | 100 | 103 |
| S | F | G | R | A | K | D | D | E |
| T | S | G | R | A | K | D | D | E |
| S | S | G | R | A | K | D | D | E |
| T | F | S | R | A | K | D | D | E |
| S | F | S | R | A | K | D | D | E |
| T | S | S | R | A | K | D | D | E |
| S | S | S | R | A | K | D | D | E |
| T | F | G | S | A | K | D | D | E |
| S | F | G | S | A | K | D | D | E |
| T | S | G | S | A | K | D | D | E |
| S | S | G | S | A | K | D | D | E |
| T | F | S | S | A | K | D | D | E |
| S | F | S | S | A | K | D | D | E |
| T | S | S | S | A | K | D | D | E |
| S | S | S | S | A | K | D | D | E |
| T | F | G | R | S | R | D | D | E |
| S | F | G | R | S | R | D | D | E |
| T | S | G | R | S | R | D | D | E |
| S | S | G | R | S | R | D | D | E |
| T | F | S | R | S | R | D | D | E |
| S | F | S | R | S | R | D | D | E |
| T | S | S | R | S | R | D | D | E |
| S | S | S | R | S | R | D | D | E |
| T | F | G | S | S | R | D | D | E |
| S | F | G | S | S | R | D | D | E |
| T | S | G | S | S | R | D | D | E |
| S | S | G | S | S | R | D | D | E |
| T | F | S | S | S | R | D | D | E |
| S | F | S | S | S | R | D | D | E |
| T | S | S | S | S | R | D | D | E |
| S | S | S | S | S | R | D | D | E |
| T | F | G | R | A | R | D | D | E |
| S | F | G | R | A | R | D | D | E |
| T | S | G | R | A | R | D | D | E |
| S | S | G | R | A | R | D | D | E |
| T | F | S | R | A | R | D | D | E |
| S | F | S | R | A | R | D | D | E |
| T | S | S | R | A | R | D | D | E |
| S | S | S | R | A | R | D | D | E |
| T | F | G | S | A | R | D | D | E |
| S | F | G | S | A | R | D | D | E |
| T | S | G | S | A | R | D | D | E |
| S | S | G | S | A | R | D | D | E |
| T | F | S | S | A | R | D | D | E |
| S | F | S | S | A | R | D | D | E |
| T | S | S | S | A | R | D | D | E |
| S | S | S | S | A | R | D | D | E |
| T | F | G | R | S | K | — | D | E |
| S | F | G | R | S | K | — | D | E |
| T | S | G | R | S | K | — | D | E |
| S | S | G | R | S | K | — | D | E |
| T | F | S | R | S | K | — | D | E |
| S | F | S | R | S | K | — | D | E |
| T | S | S | R | S | K | — | D | E |
| S | S | S | R | S | K | — | D | E |
| T | F | G | S | S | K | — | D | E |
| S | F | G | S | S | K | — | D | E |
| T | S | G | S | S | K | — | D | E |
| S | S | G | S | S | K | — | D | E |
| T | F | S | S | S | K | — | D | E |
| S | F | S | S | S | K | — | D | E |
| T | S | S | S | S | K | — | D | E |
| S | S | S | S | S | K | — | D | E |
| T | F | G | R | A | K | — | D | E |
| S | F | G | R | A | K | — | D | E |
| T | S | G | R | A | K | — | D | E |
| S | S | G | R | A | K | — | D | E |
| T | F | S | R | A | K | — | D | E |
| S | F | S | R | A | K | — | D | E |
| T | S | S | R | A | K | — | D | E |
| S | S | S | R | A | K | — | D | E |
| T | F | G | S | A | K | — | D | E |
| S | F | G | S | A | K | — | D | E |
| T | S | G | S | A | K | — | D | E |
| S | S | G | S | A | K | — | D | E |

TABLE 17a-continued

| Exemplary Mutations of mAB 24B3 Heavy Chain (SEQ ID NO: 42) to Germline at the Indicated Residue Number | | | | | | | | |
|---|---|---|---|---|---|---|---|---|
| 31 | 50 | 53 | 54 | 97 | 98 | 99 | 100 | 103 |
| T | F | S | S | A | K | — | D | E |
| S | F | S | S | A | K | — | D | E |
| T | S | S | S | A | K | — | D | E |
| S | S | S | S | A | K | — | D | E |
| T | F | G | R | S | R | — | D | E |
| S | F | G | R | S | R | — | D | E |
| T | S | G | R | S | R | — | D | E |
| S | S | G | R | S | R | — | D | E |
| T | F | S | R | S | R | — | D | E |
| S | F | S | R | S | R | — | D | E |
| T | S | S | R | S | R | — | D | E |
| S | S | S | R | S | R | — | D | E |
| T | F | G | S | S | R | — | D | E |
| S | F | G | S | S | R | — | D | E |
| T | S | G | S | S | R | — | D | E |
| S | S | G | S | S | R | — | D | E |
| T | F | S | S | S | R | — | D | E |
| S | F | S | S | S | R | — | D | E |
| T | S | S | S | S | R | — | D | E |
| S | S | S | S | S | R | — | D | E |
| T | F | G | R | A | R | — | D | E |
| S | F | G | R | A | R | — | D | E |
| T | S | G | R | A | R | — | D | E |
| S | S | G | R | A | R | — | D | E |
| T | F | S | R | A | R | — | D | E |
| S | F | S | R | A | R | — | D | E |
| T | S | S | R | A | R | — | D | E |
| S | S | S | R | A | R | — | D | E |
| T | F | G | S | A | R | — | D | E |
| S | F | G | S | A | R | — | D | E |
| T | S | G | S | A | R | — | D | E |
| S | S | G | S | A | R | — | D | E |
| T | F | S | S | A | R | — | D | E |
| S | F | S | S | A | R | — | D | E |
| T | S | S | S | A | R | — | D | E |
| S | S | S | S | A | R | — | D | E |
| T | F | G | R | S | K | D | — | E |
| S | F | G | R | S | K | D | — | E |
| T | S | G | R | S | K | D | — | E |
| S | S | G | R | S | K | D | — | E |
| T | F | S | R | S | K | D | — | E |
| S | F | S | R | S | K | D | — | E |
| T | S | S | R | S | K | D | — | E |
| S | S | S | R | S | K | D | — | E |
| T | F | G | S | S | K | D | — | E |
| S | F | G | S | S | K | D | — | E |
| T | S | G | S | S | K | D | — | E |
| S | S | G | S | S | K | D | — | E |
| T | F | S | S | S | K | D | — | E |
| S | F | S | S | S | K | D | — | E |
| T | S | S | S | S | K | D | — | E |
| S | S | S | S | S | K | D | — | E |
| T | F | G | R | A | K | D | — | E |
| S | F | G | R | A | K | D | — | E |
| T | S | G | R | A | K | D | — | E |
| S | S | G | R | A | K | D | — | E |
| T | F | S | R | A | K | D | — | E |
| S | F | S | R | A | K | D | — | E |
| T | S | S | R | A | K | D | — | E |
| S | S | S | R | A | K | D | — | E |
| T | F | G | S | A | K | D | — | E |
| S | F | G | S | A | K | D | — | E |
| T | S | G | S | A | K | D | — | E |
| S | S | G | S | A | K | D | — | E |
| T | F | S | S | A | K | D | — | E |
| S | F | S | S | A | K | D | — | E |
| T | S | S | S | A | K | D | — | E |
| S | S | S | S | A | K | D | — | E |
| T | F | G | R | S | R | D | — | E |
| S | F | G | R | S | R | D | — | E |
| T | S | G | R | S | R | D | — | E |
| S | S | G | R | S | R | D | — | E |
| T | F | S | R | S | R | D | — | E |
| S | F | S | R | S | R | D | — | E |
| T | S | S | R | S | R | D | — | E |

TABLE 17a-continued

| Exemplary Mutations of mAB 24B3 Heavy Chain (SEQ ID NO: 42) to Germline at the Indicated Residue Number | | | | | | | | |
|---|---|---|---|---|---|---|---|---|
| 31 | 50 | 53 | 54 | 97 | 98 | 99 | 100 | 103 |
| S | S | S | R | S | R | D | — | E |
| T | F | G | S | S | R | D | — | E |
| S | F | G | S | S | R | D | — | E |
| T | S | G | S | S | R | D | — | E |
| S | S | G | S | S | R | D | — | E |
| T | F | S | S | S | R | D | — | E |
| S | F | S | S | S | R | D | — | E |
| T | S | S | S | S | R | D | — | E |
| S | S | S | S | S | R | D | — | E |
| T | F | G | R | A | R | D | — | E |
| S | F | G | R | A | R | D | — | E |
| T | S | G | R | A | R | D | — | E |
| S | S | G | R | A | R | D | — | E |
| T | F | S | R | A | R | D | — | E |
| S | F | S | R | A | R | D | — | E |
| T | S | S | R | A | R | D | — | E |
| S | S | S | R | A | R | D | — | E |
| T | F | G | S | A | R | D | — | E |
| S | F | G | S | A | R | D | — | E |
| T | S | G | S | A | R | D | — | E |
| S | S | G | S | A | R | D | — | E |
| T | F | S | S | A | R | D | — | E |
| S | F | S | S | A | R | D | — | E |
| T | S | S | S | A | R | D | — | E |
| S | S | S | S | A | R | D | — | E |
| T | F | G | R | S | K | — | — | E |
| S | F | G | R | S | K | — | — | E |
| T | S | G | R | S | K | — | — | E |
| S | S | G | R | S | K | — | — | E |
| T | F | S | R | S | K | — | — | E |
| S | F | S | R | S | K | — | — | E |
| T | S | S | R | S | K | — | — | E |
| S | S | S | R | S | K | — | — | E |
| T | F | G | S | S | K | — | — | E |
| S | F | G | S | S | K | — | — | E |
| T | S | G | S | S | K | — | — | E |
| S | S | G | S | S | K | — | — | E |
| T | F | S | S | S | K | — | — | E |
| S | F | S | S | S | K | — | — | E |
| T | S | S | S | S | K | — | — | E |
| S | S | S | S | S | K | — | — | E |
| T | F | G | R | A | K | — | — | E |
| S | F | G | R | A | K | — | — | E |
| T | S | G | R | A | K | — | — | E |
| S | S | G | R | A | K | — | — | E |
| T | F | S | R | A | K | — | — | E |
| S | F | S | R | A | K | — | — | E |
| T | S | S | R | A | K | — | — | E |
| S | S | S | R | A | K | — | — | E |
| T | F | G | S | A | K | — | — | E |
| S | F | G | S | A | K | — | — | E |
| T | S | G | S | A | K | — | — | E |
| S | S | G | S | A | K | — | — | E |
| T | F | S | S | A | K | — | — | E |
| S | F | S | S | A | K | — | — | E |
| T | S | S | S | A | K | — | — | E |
| S | S | S | S | A | K | — | — | E |
| T | F | G | R | S | R | — | — | E |
| S | F | G | R | S | R | — | — | E |
| T | S | G | R | S | R | — | — | E |
| S | S | G | R | S | R | — | — | E |
| T | F | S | R | S | R | — | — | E |
| S | F | S | R | S | R | — | — | E |
| T | S | S | R | S | R | — | — | E |
| S | S | S | R | S | R | — | — | E |
| T | F | G | S | S | R | — | — | E |
| S | F | G | S | S | R | — | — | E |
| T | S | G | S | S | R | — | — | E |
| S | S | G | S | S | R | — | — | E |
| T | F | S | S | S | R | — | — | E |
| S | F | S | S | S | R | — | — | E |
| T | S | S | S | S | R | — | — | E |
| S | S | S | S | S | R | — | — | E |
| T | F | G | R | A | R | — | — | E |
| S | F | G | R | A | R | — | — | E |

TABLE 17a-continued

Exemplary Mutations of mAB 24B3 Heavy Chain (SEQ ID NO: 42) to Germline at the Indicated Residue Number

| 31 | 50 | 53 | 54 | 97 | 98 | 99 | 100 | 103 |
|---|---|---|---|---|---|---|---|---|
| T | S | G | R | A | R | — | — | E |
| S | S | G | R | A | R | — | — | E |
| T | F | S | R | A | R | — | — | E |
| S | F | S | R | A | R | — | — | E |
| T | S | S | R | A | R | — | — | E |
| S | S | S | R | A | R | — | — | E |
| T | F | G | S | A | R | — | — | E |
| S | F | G | S | A | R | — | — | E |
| T | S | G | S | A | R | — | — | E |
| S | S | G | S | A | R | — | — | E |
| T | F | S | S | A | R | — | — | E |
| S | F | S | S | A | R | — | — | E |
| T | S | S | S | A | R | — | — | E |
| S | S | S | S | A | R | — | — | E |
| T | F | G | R | S | K | D | D | G |
| S | F | G | R | S | K | D | D | G |
| T | S | G | R | S | K | D | D | G |
| S | S | G | R | S | K | D | D | G |
| T | F | S | R | S | K | D | D | G |
| S | F | S | R | S | K | D | D | G |
| T | S | S | R | S | K | D | D | G |
| S | S | S | R | S | K | D | D | G |
| T | F | G | S | S | K | D | D | G |
| S | F | G | S | S | K | D | D | G |
| T | S | G | S | S | K | D | D | G |
| S | S | G | S | S | K | D | D | G |
| T | F | S | S | S | K | D | D | G |
| S | F | S | S | S | K | D | D | G |
| T | S | S | S | S | K | D | D | G |
| S | S | S | S | S | K | D | D | G |
| T | F | G | R | A | K | D | D | G |
| S | F | G | R | A | K | D | D | G |
| T | S | G | R | A | K | D | D | G |
| S | S | G | R | A | K | D | D | G |
| T | F | S | R | A | K | D | D | G |
| S | F | S | R | A | K | D | D | G |
| T | S | S | R | A | K | D | D | G |
| S | S | S | R | A | K | D | D | G |
| T | F | G | S | A | K | D | D | G |
| S | F | G | S | A | K | D | D | G |
| T | S | G | S | A | K | D | D | G |
| S | S | G | S | A | K | D | D | G |
| T | F | S | S | A | K | D | D | G |
| S | F | S | S | A | K | D | D | G |
| T | S | S | S | A | K | D | D | G |
| S | S | S | S | A | K | D | D | G |
| T | F | G | R | S | R | D | D | G |
| S | F | G | R | S | R | D | D | G |
| T | S | G | R | S | R | D | D | G |
| S | S | G | R | S | R | D | D | G |
| T | F | S | R | S | R | D | D | G |
| S | F | S | R | S | R | D | D | G |
| T | S | S | R | S | R | D | D | G |
| S | S | S | R | S | R | D | D | G |
| T | F | G | S | S | R | D | D | G |
| S | F | G | S | S | R | D | D | G |
| T | S | G | S | S | R | D | D | G |
| S | S | G | S | S | R | D | D | G |
| T | F | S | S | S | R | D | D | G |
| S | F | S | S | S | R | D | D | G |
| T | S | S | S | S | R | D | D | G |
| S | S | S | S | S | R | D | D | G |
| T | F | G | R | A | R | D | D | G |
| S | F | G | R | A | R | D | D | G |
| T | S | G | R | A | R | D | D | G |
| S | S | G | R | A | R | D | D | G |
| T | F | S | R | A | R | D | D | G |
| S | F | S | R | A | R | D | D | G |
| T | S | S | R | A | R | D | D | G |
| S | S | S | R | A | R | D | D | G |
| T | F | G | S | A | R | D | D | G |
| S | F | G | S | A | R | D | D | G |
| T | S | G | S | A | R | D | D | G |
| S | S | G | S | A | R | D | D | G |
| T | F | S | S | A | R | D | D | G |

TABLE 17a-continued

Exemplary Mutations of mAB 24B3 Heavy Chain (SEQ ID NO: 42) to Germline at the Indicated Residue Number

| 31 | 50 | 53 | 54 | 97 | 98 | 99 | 100 | 103 |
|---|---|---|---|---|---|---|---|---|
| S | F | S | S | A | R | D | D | G |
| T | S | S | S | A | R | D | D | G |
| S | S | S | S | A | R | D | D | G |
| T | F | G | R | S | K | — | D | G |
| S | F | G | R | S | K | — | D | G |
| T | S | G | R | S | K | — | D | G |
| S | S | G | R | S | K | — | D | G |
| T | F | S | R | S | K | — | D | G |
| S | F | S | R | S | K | — | D | G |
| T | S | S | R | S | K | — | D | G |
| S | S | S | R | S | K | — | D | G |
| T | F | G | S | S | K | — | D | G |
| S | F | G | S | S | K | — | D | G |
| T | S | G | S | S | K | — | D | G |
| S | S | G | S | S | K | — | D | G |
| T | F | S | S | S | K | — | D | G |
| S | F | S | S | S | K | — | D | G |
| T | S | S | S | S | K | — | D | G |
| S | S | S | S | S | K | — | D | G |
| T | F | G | R | A | K | — | D | G |
| S | F | G | R | A | K | — | D | G |
| T | S | G | R | A | K | — | D | G |
| S | S | G | R | A | K | — | D | G |
| T | F | S | R | A | K | — | D | G |
| S | F | S | R | A | K | — | D | G |
| T | S | S | R | A | K | — | D | G |
| S | S | S | R | A | K | — | D | G |
| T | F | G | S | A | K | — | D | G |
| S | F | G | S | A | K | — | D | G |
| T | S | G | S | A | K | — | D | G |
| S | S | G | S | A | K | — | D | G |
| T | F | S | S | A | K | — | D | G |
| S | F | S | S | A | K | — | D | G |
| T | S | S | S | A | K | — | D | G |
| S | S | S | S | A | K | — | D | G |
| T | F | G | R | S | R | — | D | G |
| S | F | G | R | S | R | — | D | G |
| T | S | G | R | S | R | — | D | G |
| S | S | G | R | S | R | — | D | G |
| T | F | S | R | S | R | — | D | G |
| S | F | S | R | S | R | — | D | G |
| T | S | S | R | S | R | — | D | G |
| S | S | S | R | S | R | — | D | G |
| T | F | G | S | S | R | — | D | G |
| S | F | G | S | S | R | — | D | G |
| T | S | G | S | S | R | — | D | G |
| S | S | G | S | S | R | — | D | G |
| T | F | S | S | S | R | — | D | G |
| S | F | S | S | S | R | — | D | G |
| T | S | S | S | S | R | — | D | G |
| S | S | S | S | S | R | — | D | G |
| T | F | G | R | A | R | — | D | G |
| S | F | G | R | A | R | — | D | G |
| T | S | G | R | A | R | — | D | G |
| S | S | G | R | A | R | — | D | G |
| T | F | S | R | A | R | — | D | G |
| S | F | S | R | A | R | — | D | G |
| T | S | S | R | A | R | — | D | G |
| S | S | S | R | A | R | — | D | G |
| T | F | G | S | A | R | — | D | G |
| S | F | G | S | A | R | — | D | G |
| T | S | G | S | A | R | — | D | G |
| S | S | G | S | A | R | — | D | G |
| T | F | S | S | A | R | — | D | G |
| S | F | S | S | A | R | — | D | G |
| T | S | S | S | A | R | — | D | G |
| S | S | S | S | A | R | — | D | G |
| T | F | G | R | S | K | D | — | G |
| S | F | G | R | S | K | D | — | G |
| T | S | G | R | S | K | D | — | G |
| S | S | G | R | S | K | D | — | G |
| T | F | S | R | S | K | D | — | G |
| S | F | S | R | S | K | D | — | G |
| T | S | S | R | S | K | D | — | G |
| S | S | S | R | S | K | D | — | G |

TABLE 17a-continued

Exemplary Mutations of mAB 24B3 Heavy Chain (SEQ ID NO: 42) to Germline at the Indicated Residue Number

| 31 | 50 | 53 | 54 | 97 | 98 | 99 | 100 | 103 |
|---|---|---|---|---|---|---|---|---|
| T | F | G | S | S | K | D | — | G |
| S | F | G | S | S | K | D | — | G |
| T | S | G | S | S | K | D | — | G |
| S | S | G | S | S | K | D | — | G |
| T | F | S | S | S | K | D | — | G |
| S | F | S | S | S | K | D | — | G |
| T | S | S | S | S | K | D | — | G |
| S | S | S | S | S | K | D | — | G |
| T | F | G | R | A | K | D | — | G |
| S | F | G | R | A | K | D | — | G |
| T | S | G | R | A | K | D | — | G |
| S | S | G | R | A | K | D | — | G |
| T | F | S | R | A | K | D | — | G |
| S | F | S | R | A | K | D | — | G |
| T | S | S | R | A | K | D | — | G |
| S | S | S | R | A | K | D | — | G |
| T | F | G | S | A | K | D | — | G |
| S | F | G | S | A | K | D | — | G |
| T | S | G | S | A | K | D | — | G |
| S | S | G | S | A | K | D | — | G |
| T | F | S | S | A | K | D | — | G |
| S | F | S | S | A | K | D | — | G |
| T | S | S | S | A | K | D | — | G |
| S | S | S | S | A | K | D | — | G |
| T | F | G | R | S | R | D | — | G |
| S | F | G | R | S | R | D | — | G |
| T | S | G | R | S | R | D | — | G |
| S | S | G | R | S | R | D | — | G |
| T | F | S | R | S | R | D | — | G |
| S | F | S | R | S | R | D | — | G |
| T | S | S | R | S | R | D | — | G |
| S | S | S | R | S | R | D | — | G |
| T | F | G | S | S | R | D | — | G |
| S | F | G | S | S | R | D | — | G |
| T | S | G | S | S | R | D | — | G |
| S | S | G | S | S | R | D | — | G |
| T | F | S | S | S | R | D | — | G |
| S | F | S | S | S | R | D | — | G |
| T | S | S | S | S | R | D | — | G |
| S | S | S | S | S | R | D | — | G |
| T | F | G | R | A | R | D | — | G |
| S | F | G | R | A | R | D | — | G |
| T | S | G | R | A | R | D | — | G |
| S | S | G | R | A | R | D | — | G |
| T | F | S | R | A | R | D | — | G |
| S | F | S | R | A | R | D | — | G |
| T | S | S | R | A | R | D | — | G |
| S | S | S | R | A | R | D | — | G |
| T | F | G | S | A | R | D | — | G |
| S | F | G | S | A | R | D | — | G |
| T | S | G | S | A | R | D | — | G |
| S | S | G | S | A | R | D | — | G |
| T | F | S | S | A | R | D | — | G |
| S | F | S | S | A | R | D | — | G |
| T | S | S | S | A | R | D | — | G |
| S | S | S | S | A | R | D | — | G |
| T | F | G | R | S | K | — | — | G |
| S | F | G | R | S | K | — | — | G |
| T | S | G | R | S | K | — | — | G |
| S | S | G | R | S | K | — | — | G |
| T | F | S | R | S | K | — | — | G |
| S | F | S | R | S | K | — | — | G |
| T | S | S | R | S | K | — | — | G |
| S | S | S | R | S | K | — | — | G |
| T | F | G | S | S | K | — | — | G |
| S | F | G | S | S | K | — | — | G |
| T | S | G | S | S | K | — | — | G |
| S | S | G | S | S | K | — | — | G |
| T | F | S | S | S | K | — | — | G |
| S | F | S | S | S | K | — | — | G |
| T | S | S | S | S | K | — | — | G |
| S | S | S | S | S | K | — | — | G |
| T | F | G | R | A | K | — | — | G |
| S | F | G | R | A | K | — | — | G |
| T | S | G | R | A | K | — | — | G |
| S | S | G | R | A | K | — | — | G |
| T | F | S | R | A | K | — | — | G |
| S | F | S | R | A | K | — | — | G |
| T | S | S | R | A | K | — | — | G |
| S | S | S | R | A | K | — | — | G |
| T | F | G | S | A | K | — | — | G |
| S | F | G | S | A | K | — | — | G |
| T | S | G | S | A | K | — | — | G |
| S | S | G | S | A | K | — | — | G |
| T | F | S | S | A | K | — | — | G |
| S | F | S | S | A | K | — | — | G |
| T | S | S | S | A | K | — | — | G |
| S | S | S | S | A | K | — | — | G |
| T | F | G | R | S | R | — | — | G |
| S | F | G | R | S | R | — | — | G |
| T | S | G | R | S | R | — | — | G |
| S | S | G | R | S | R | — | — | G |
| T | F | S | R | S | R | — | — | G |
| S | F | S | R | S | R | — | — | G |
| T | S | S | R | S | R | — | — | G |
| S | S | S | R | S | R | — | — | G |
| T | F | G | S | S | R | — | — | G |
| S | F | G | S | S | R | — | — | G |
| T | S | G | S | S | R | — | — | G |
| S | S | G | S | S | R | — | — | G |
| T | F | S | S | S | R | — | — | G |
| S | F | S | S | S | R | — | — | G |
| T | S | S | S | S | R | — | — | G |
| S | S | S | S | S | R | — | — | G |
| T | F | G | R | A | R | — | — | G |
| S | F | G | R | A | R | — | — | G |
| T | S | G | R | A | R | — | — | G |
| S | S | G | R | A | R | — | — | G |
| T | F | S | R | A | R | — | — | G |
| S | F | S | R | A | R | — | — | G |
| T | S | S | R | A | R | — | — | G |
| S | S | S | R | A | R | — | — | G |
| T | F | G | S | A | R | — | — | G |
| S | F | G | S | A | R | — | — | G |
| T | S | G | S | A | R | — | — | G |
| S | S | G | S | A | R | — | — | G |
| T | F | S | S | A | R | — | — | G |
| S | F | S | S | A | R | — | — | G |
| T | S | S | S | A | R | — | — | G |
| S | S | S | S | A | R | — | — | G |

"—" indicates the absence of a residue at that position with reference to SEQ ID NO: 42

TABLE 18

Exemplary Mutations of mAB 33C3 Light Chain (SEQ ID NO: 76) to Germline at the Indicated Residue Number

| 7 | 9 | 40 | 45 | 58 | 67 | 109 | 112 | 144 |
|---|---|---|---|---|---|---|---|---|
| S | S | Y | Q | G | A | T | T | K |
| S | S | Y | Q | A | T | S | I | K |
| S | S | F | Q | A | A | S | T | K |

TABLE 18a

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| Y | L | F | H | G | T | T | I | N |
| S | L | F | H | G | T | T | I | N |
| Y | S | F | H | G | T | T | I | N |
| S | S | F | H | G | T | T | I | N |
| Y | L | Y | H | G | T | T | I | N |

TABLE 18a-continued

| Exemplary Mutations of mAB 33C3 Light Chain (SEQ ID NO: 76) to Germline at the Indicated Residue Number | | | | | | | | |
|---|---|---|---|---|---|---|---|---|
| 7 | 9 | 32 | 37 | 50 | 51 | 91 | 94 | 103 |
| S | L | Y | H | G | T | T | I | N |
| Y | S | Y | H | G | T | T | I | N |
| S | S | Y | H | G | T | T | I | N |
| Y | L | F | Q | G | T | T | I | N |
| S | L | F | Q | G | T | T | I | N |
| Y | S | F | Q | G | T | T | I | N |
| S | S | F | Q | G | T | T | I | N |
| Y | L | Y | Q | G | T | T | I | N |
| S | L | Y | Q | G | T | T | I | N |
| Y | S | Y | Q | G | T | T | I | N |
| S | S | Y | Q | G | T | T | I | N |
| Y | L | F | H | A | T | T | I | N |
| S | L | F | H | A | T | T | I | N |
| Y | S | F | H | A | T | T | I | N |
| S | S | F | H | A | T | T | I | N |
| Y | L | Y | H | A | T | T | I | N |
| S | L | Y | H | A | T | T | I | N |
| Y | S | Y | H | A | T | T | I | N |
| S | S | Y | H | A | T | T | I | N |
| Y | L | F | Q | A | T | T | I | N |
| S | L | F | Q | A | T | T | I | N |
| Y | S | F | Q | A | T | T | I | N |
| S | S | F | Q | A | T | T | I | N |
| Y | L | Y | Q | A | T | T | I | N |
| S | L | Y | Q | A | T | T | I | N |
| Y | S | Y | Q | A | T | T | I | N |
| S | S | Y | Q | A | T | T | I | N |
| Y | L | F | H | G | A | T | I | N |
| S | L | F | H | G | A | T | I | N |
| Y | S | F | H | G | A | T | I | N |
| S | S | F | H | G | A | T | I | N |
| Y | L | Y | H | G | A | T | I | N |
| S | L | Y | H | G | A | T | I | N |
| Y | S | Y | H | G | A | T | I | N |
| S | S | Y | H | G | A | T | I | N |
| Y | L | F | Q | G | A | T | I | N |
| S | L | F | Q | G | A | T | I | N |
| Y | S | F | Q | G | A | T | I | N |
| S | S | F | Q | G | A | T | I | N |
| Y | L | Y | Q | G | A | T | I | N |
| S | L | Y | Q | G | A | T | I | N |
| Y | S | Y | Q | G | A | T | I | N |
| S | S | Y | Q | G | A | T | I | N |
| Y | L | F | H | A | A | T | I | N |
| S | L | F | H | A | A | T | I | N |
| Y | S | F | H | A | A | T | I | N |
| S | S | F | H | A | A | T | I | N |
| Y | L | Y | H | A | A | T | I | N |
| S | L | Y | H | A | A | T | I | N |
| Y | S | Y | H | A | A | T | I | N |
| S | S | Y | H | A | A | T | I | N |
| Y | L | F | Q | A | A | T | I | N |
| S | L | F | Q | A | A | T | I | N |
| Y | S | F | Q | A | A | T | I | N |
| S | S | F | Q | A | A | T | I | N |
| Y | L | Y | Q | A | A | T | I | N |
| S | L | Y | Q | A | A | T | I | N |
| Y | S | Y | Q | A | A | T | I | N |
| S | S | Y | Q | A | A | T | I | N |
| Y | L | F | H | G | T | S | I | N |
| S | L | F | H | G | T | S | I | N |
| Y | S | F | H | G | T | S | I | N |
| S | S | F | H | G | T | S | I | N |
| Y | L | Y | H | G | T | S | I | N |
| S | L | Y | H | G | T | S | I | N |
| Y | S | Y | H | G | T | S | I | N |
| S | S | Y | H | G | T | S | I | N |
| Y | L | F | Q | G | T | S | I | N |
| S | L | F | Q | G | T | S | I | N |
| Y | S | F | Q | G | T | S | I | N |
| S | S | F | Q | G | T | S | I | N |
| Y | L | Y | Q | G | T | S | I | N |
| S | L | Y | Q | G | T | S | I | N |
| Y | S | Y | Q | G | T | S | I | N |
| S | S | Y | Q | G | T | S | I | N |

TABLE 18a-continued

| Exemplary Mutations of mAB 33C3 Light Chain (SEQ ID NO: 76) to Germline at the Indicated Residue Number | | | | | | | | |
|---|---|---|---|---|---|---|---|---|
| 7 | 9 | 32 | 37 | 50 | 51 | 91 | 94 | 103 |
| Y | L | F | H | A | T | S | I | N |
| S | L | F | H | A | T | S | I | N |
| Y | S | F | H | A | T | S | I | N |
| S | S | F | H | A | T | S | I | N |
| Y | L | Y | H | A | T | S | I | N |
| S | L | Y | H | A | T | S | I | N |
| Y | S | Y | H | A | T | S | I | N |
| S | S | Y | H | A | T | S | I | N |
| Y | L | F | Q | A | T | S | I | N |
| S | L | F | Q | A | T | S | I | N |
| Y | S | F | Q | A | T | S | I | N |
| S | S | F | Q | A | T | S | I | N |
| Y | L | Y | Q | A | T | S | I | N |
| S | L | Y | Q | A | T | S | I | N |
| Y | S | Y | Q | A | T | S | I | N |
| S | S | Y | Q | A | T | S | I | N |
| Y | L | F | H | G | A | S | I | N |
| S | L | F | H | G | A | S | I | N |
| Y | S | F | H | G | A | S | I | N |
| S | S | F | H | G | A | S | I | N |
| Y | L | Y | H | G | A | S | I | N |
| S | L | Y | H | G | A | S | I | N |
| Y | S | Y | H | G | A | S | I | N |
| S | S | Y | H | G | A | S | I | N |
| Y | L | F | Q | G | A | S | I | N |
| S | L | F | Q | G | A | S | I | N |
| Y | S | F | Q | G | A | S | I | N |
| S | S | F | Q | G | A | S | I | N |
| Y | L | Y | Q | G | A | S | I | N |
| S | L | Y | Q | G | A | S | I | N |
| Y | S | Y | Q | G | A | S | I | N |
| S | S | Y | Q | G | A | S | I | N |
| Y | L | F | H | A | A | S | I | N |
| S | L | F | H | A | A | S | I | N |
| Y | S | F | H | A | A | S | I | N |
| S | S | F | H | A | A | S | I | N |
| Y | L | Y | H | A | A | S | I | N |
| S | L | Y | H | A | A | S | I | N |
| Y | S | Y | H | A | A | S | I | N |
| S | S | Y | H | A | A | S | I | N |
| Y | L | F | Q | A | A | S | I | N |
| S | L | F | Q | A | A | S | I | N |
| Y | S | F | Q | A | A | S | I | N |
| S | S | F | Q | A | A | S | I | N |
| Y | L | Y | Q | A | A | S | I | N |
| S | L | Y | Q | A | A | S | I | N |
| Y | S | Y | Q | A | A | S | I | N |
| S | S | Y | Q | A | A | S | I | N |
| Y | L | F | H | G | T | T | T | N |
| S | L | F | H | G | T | T | T | N |
| Y | S | F | H | G | T | T | T | N |
| S | S | F | H | G | T | T | T | N |
| Y | L | Y | H | G | T | T | T | N |
| S | L | Y | H | G | T | T | T | N |
| Y | S | Y | H | G | T | T | T | N |
| S | S | Y | H | G | T | T | T | N |
| Y | L | F | Q | G | T | T | T | N |
| S | L | F | Q | G | T | T | T | N |
| Y | S | F | Q | G | T | T | T | N |
| S | S | F | Q | G | T | T | T | N |
| Y | L | Y | Q | G | T | T | T | N |
| S | L | Y | Q | G | T | T | T | N |
| Y | S | Y | Q | G | T | T | T | N |
| S | S | Y | Q | G | T | T | T | N |
| Y | L | F | H | A | T | T | T | N |
| S | L | F | H | A | T | T | T | N |
| Y | S | F | H | A | T | T | T | N |
| S | S | F | H | A | T | T | T | N |
| Y | L | Y | H | A | T | T | T | N |
| S | L | Y | H | A | T | T | T | N |
| Y | S | Y | H | A | T | T | T | N |
| S | S | Y | H | A | T | T | T | N |
| Y | L | F | Q | A | T | T | T | N |
| S | L | F | Q | A | T | T | T | N |
| Y | S | F | Q | A | T | T | T | N |

TABLE 18a-continued

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| S | S | F | Q | A | T | T | T | N |
| Y | L | Y | Q | A | T | T | T | N |
| S | L | Y | Q | A | T | T | T | N |
| Y | S | Y | Q | A | T | T | T | N |
| S | S | Y | Q | A | T | T | T | N |
| Y | L | F | H | G | A | T | T | N |
| S | L | F | H | G | A | T | T | N |
| Y | S | F | H | G | A | T | T | N |
| S | S | F | H | G | A | T | T | N |
| Y | L | Y | H | G | A | T | T | N |
| S | L | Y | H | G | A | T | T | N |
| Y | S | Y | H | G | A | T | T | N |
| S | S | Y | H | G | A | T | T | N |
| Y | L | F | Q | G | A | T | T | N |
| S | L | F | Q | G | A | T | T | N |
| Y | S | F | Q | G | A | T | T | N |
| S | S | F | Q | G | A | T | T | N |
| Y | L | Y | Q | G | A | T | T | N |
| S | L | Y | Q | G | A | T | T | N |
| Y | S | Y | Q | G | A | T | T | N |
| S | S | Y | Q | G | A | T | T | N |
| Y | L | F | H | A | A | T | T | N |
| S | L | F | H | A | A | T | T | N |
| Y | S | F | H | A | A | T | T | N |
| S | S | F | H | A | A | T | T | N |
| Y | L | Y | H | A | A | T | T | N |
| S | L | Y | H | A | A | T | T | N |
| Y | S | Y | H | A | A | T | T | N |
| S | S | Y | H | A | A | T | T | N |
| Y | L | F | Q | A | A | T | T | N |
| S | L | F | Q | A | A | T | T | N |
| Y | S | F | Q | A | A | T | T | N |
| S | S | F | Q | A | A | T | T | N |
| Y | L | Y | Q | A | A | T | T | N |
| S | L | Y | Q | A | A | T | T | N |
| Y | S | Y | Q | A | A | T | T | N |
| S | S | Y | Q | A | A | T | T | N |
| Y | L | F | H | G | T | S | T | N |
| S | L | F | H | G | T | S | T | N |
| Y | S | F | H | G | T | S | T | N |
| S | S | F | H | G | T | S | T | N |
| Y | L | Y | H | G | T | S | T | N |
| S | L | Y | H | G | T | S | T | N |
| Y | S | Y | H | G | T | S | T | N |
| S | S | Y | H | G | T | S | T | N |
| Y | L | F | Q | G | T | S | T | N |
| S | L | F | Q | G | T | S | T | N |
| Y | S | F | Q | G | T | S | T | N |
| S | S | F | Q | G | T | S | T | N |
| Y | L | Y | Q | G | T | S | T | N |
| S | L | Y | Q | G | T | S | T | N |
| Y | S | Y | Q | G | T | S | T | N |
| S | S | Y | Q | G | T | S | T | N |
| Y | L | F | H | A | T | S | T | N |
| S | L | F | H | A | T | S | T | N |
| Y | S | F | H | A | T | S | T | N |
| S | S | F | H | A | T | S | T | N |
| Y | L | Y | H | A | T | S | T | N |
| S | L | Y | H | A | T | S | T | N |
| Y | S | Y | H | A | T | S | T | N |
| S | S | Y | H | A | T | S | T | N |
| Y | L | F | Q | A | T | S | T | N |
| S | L | F | Q | A | T | S | T | N |
| Y | S | F | Q | A | T | S | T | N |
| S | S | F | Q | A | T | S | T | N |
| Y | L | Y | Q | A | T | S | T | N |
| S | L | Y | Q | A | T | S | T | N |
| Y | S | Y | Q | A | T | S | T | N |
| S | S | Y | Q | A | T | S | T | N |
| Y | L | F | H | G | A | S | T | N |
| S | L | F | H | G | A | S | T | N |
| Y | S | F | H | G | A | S | T | N |
| S | S | F | H | G | A | S | T | N |
| Y | L | Y | H | G | A | S | T | N |
| S | L | Y | H | G | A | S | T | N |

TABLE 18a-continued

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| Y | S | Y | H | G | A | S | T | N |
| S | S | Y | H | G | A | S | T | N |
| Y | L | F | Q | G | A | S | T | N |
| S | L | F | Q | G | A | S | T | N |
| Y | S | F | Q | G | A | S | T | N |
| S | S | F | Q | G | A | S | T | N |
| Y | L | Y | Q | G | A | S | T | N |
| S | L | Y | Q | G | A | S | T | N |
| Y | S | Y | Q | G | A | S | T | N |
| S | S | Y | Q | G | A | S | T | N |
| Y | L | F | H | A | A | S | T | N |
| S | L | F | H | A | A | S | T | N |
| Y | S | F | H | A | A | S | T | N |
| S | S | F | H | A | A | S | T | N |
| Y | L | Y | H | A | A | S | T | N |
| S | L | Y | H | A | A | S | T | N |
| Y | S | Y | H | A | A | S | T | N |
| S | S | Y | H | A | A | S | T | N |
| Y | L | F | Q | A | A | S | T | N |
| S | L | F | Q | A | A | S | T | N |
| Y | S | F | Q | A | A | S | T | N |
| S | S | F | Q | A | A | S | T | N |
| Y | L | Y | Q | A | A | S | T | N |
| S | L | Y | Q | A | A | S | T | N |
| Y | S | Y | Q | A | A | S | T | N |
| S | S | Y | Q | A | A | S | T | N |
| Y | L | F | H | G | T | T | I | K |
| S | L | F | H | G | T | T | I | K |
| Y | S | F | H | G | T | T | I | K |
| S | S | F | H | G | T | T | I | K |
| Y | L | Y | H | G | T | T | I | K |
| S | L | Y | H | G | T | T | I | K |
| Y | S | Y | H | G | T | T | I | K |
| S | S | Y | H | G | T | T | I | K |
| Y | L | F | Q | G | T | T | I | K |
| S | L | F | Q | G | T | T | I | K |
| Y | S | F | Q | G | T | T | I | K |
| S | S | F | Q | G | T | T | I | K |
| Y | L | Y | Q | G | T | T | I | K |
| S | L | Y | Q | G | T | T | I | K |
| Y | S | Y | Q | G | T | T | I | K |
| S | S | Y | Q | G | T | T | I | K |
| Y | L | F | H | A | T | T | I | K |
| S | L | F | H | A | T | T | I | K |
| Y | S | F | H | A | T | T | I | K |
| S | S | F | H | A | T | T | I | K |
| Y | L | Y | H | A | T | T | I | K |
| S | L | Y | H | A | T | T | I | K |
| Y | S | Y | H | A | T | T | I | K |
| S | S | Y | H | A | T | T | I | K |
| Y | L | F | Q | A | T | T | I | K |
| S | L | F | Q | A | T | T | I | K |
| Y | S | F | Q | A | T | T | I | K |
| S | S | F | Q | A | T | T | I | K |
| Y | L | Y | Q | A | T | T | I | K |
| S | L | Y | Q | A | T | T | I | K |
| Y | S | Y | Q | A | T | T | I | K |
| S | S | Y | Q | A | T | T | I | K |
| Y | L | F | H | G | A | T | I | K |
| S | L | F | H | G | A | T | I | K |
| Y | S | F | H | G | A | T | I | K |
| S | S | F | H | G | A | T | I | K |
| Y | L | Y | H | G | A | T | I | K |
| S | L | Y | H | G | A | T | I | K |
| Y | S | Y | H | G | A | T | I | K |
| S | S | Y | H | G | A | T | I | K |
| Y | L | F | Q | G | A | T | I | K |
| S | L | F | Q | G | A | T | I | K |
| Y | S | F | Q | G | A | T | I | K |
| S | S | F | Q | G | A | T | I | K |
| Y | L | Y | Q | G | A | T | I | K |
| S | L | Y | Q | G | A | T | I | K |
| Y | S | Y | Q | G | A | T | I | K |
| S | S | Y | Q | G | A | T | I | K |
| Y | L | F | H | A | A | T | I | K |

TABLE 18a-continued

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| S | L | F | H | A | A | T | I | K |
| Y | S | F | H | A | A | T | I | K |
| S | S | F | H | A | A | T | I | K |
| Y | L | Y | H | A | A | T | I | K |
| S | L | Y | H | A | A | T | I | K |
| Y | S | Y | H | A | A | T | I | K |
| S | S | Y | H | A | A | T | I | K |
| Y | L | F | Q | A | A | T | I | K |
| S | L | F | Q | A | A | T | I | K |
| Y | S | F | Q | A | A | T | I | K |
| S | S | F | Q | A | A | T | I | K |
| Y | L | Y | Q | A | A | T | I | K |
| S | L | Y | Q | A | A | T | I | K |
| Y | S | Y | Q | A | A | T | I | K |
| S | S | Y | Q | A | A | T | I | K |
| Y | L | F | H | G | T | S | I | K |
| S | L | F | H | G | T | S | I | K |
| Y | S | F | H | G | T | S | I | K |
| S | S | F | H | G | T | S | I | K |
| Y | L | Y | H | G | T | S | I | K |
| S | L | Y | H | G | T | S | I | K |
| Y | S | Y | H | G | T | S | I | K |
| S | S | Y | H | G | T | S | I | K |
| Y | L | F | Q | G | T | S | I | K |
| S | L | F | Q | G | T | S | I | K |
| Y | S | F | Q | G | T | S | I | K |
| S | S | F | Q | G | T | S | I | K |
| Y | L | Y | Q | G | T | S | I | K |
| S | L | Y | Q | G | T | S | I | K |
| Y | S | Y | Q | G | T | S | I | K |
| S | S | Y | Q | G | T | S | I | K |
| Y | L | F | H | A | T | S | I | K |
| S | L | F | H | A | T | S | I | K |
| Y | S | F | H | A | T | S | I | K |
| S | S | F | H | A | T | S | I | K |
| Y | L | Y | H | A | T | S | I | K |
| S | L | Y | H | A | T | S | I | K |
| Y | S | Y | H | A | T | S | I | K |
| S | S | Y | H | A | T | S | I | K |
| Y | L | F | Q | A | T | S | I | K |
| S | L | F | Q | A | T | S | I | K |
| Y | S | F | Q | A | T | S | I | K |
| S | S | F | Q | A | T | S | I | K |
| Y | L | Y | Q | A | T | S | I | K |
| S | L | Y | Q | A | T | S | I | K |
| Y | S | Y | Q | A | T | S | I | K |
| S | S | Y | Q | A | T | S | I | K |
| Y | L | F | H | G | A | S | I | K |
| S | L | F | H | G | A | S | I | K |
| Y | S | F | H | G | A | S | I | K |
| S | S | F | H | G | A | S | I | K |
| Y | L | Y | H | G | A | S | I | K |
| S | L | Y | H | G | A | S | I | K |
| Y | S | Y | H | G | A | S | I | K |
| S | S | Y | H | G | A | S | I | K |
| Y | L | F | Q | G | A | S | I | K |
| S | L | F | Q | G | A | S | I | K |
| Y | S | F | Q | G | A | S | I | K |
| S | S | F | Q | G | A | S | I | K |
| Y | L | Y | Q | G | A | S | I | K |
| S | L | Y | Q | G | A | S | I | K |
| Y | S | Y | Q | G | A | S | I | K |
| S | S | Y | Q | G | A | S | I | K |
| Y | L | F | H | A | A | S | I | K |
| S | L | F | H | A | A | S | I | K |
| Y | S | F | H | A | A | S | I | K |
| S | S | F | H | A | A | S | I | K |
| Y | L | Y | H | A | A | S | I | K |
| S | L | Y | H | A | A | S | I | K |
| Y | S | Y | H | A | A | S | I | K |
| S | S | Y | H | A | A | S | I | K |
| Y | L | F | Q | A | A | S | I | K |
| S | L | F | Q | A | A | S | I | K |
| Y | S | F | Q | A | A | S | I | K |
| S | S | F | Q | A | A | S | I | K |

TABLE 18a-continued

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| Y | L | Y | Q | A | A | S | I | K |
| S | L | Y | Q | A | A | S | I | K |
| Y | S | Y | Q | A | A | S | I | K |
| S | S | Y | Q | A | A | S | I | K |
| Y | L | F | H | G | T | T | T | K |
| S | L | F | H | G | T | T | T | K |
| Y | S | F | H | G | T | T | T | K |
| S | S | F | H | G | T | T | T | K |
| Y | L | Y | H | G | T | T | T | K |
| S | L | Y | H | G | T | T | T | K |
| Y | S | Y | H | G | T | T | T | K |
| S | S | Y | H | G | T | T | T | K |
| Y | L | F | Q | G | T | T | T | K |
| S | L | F | Q | G | T | T | T | K |
| Y | S | F | Q | G | T | T | T | K |
| S | S | F | Q | G | T | T | T | K |
| Y | L | Y | Q | G | T | T | T | K |
| S | L | Y | Q | G | T | T | T | K |
| Y | S | Y | Q | G | T | T | T | K |
| S | S | Y | Q | G | T | T | T | K |
| Y | L | F | H | A | T | T | T | K |
| S | L | F | H | A | T | T | T | K |
| Y | S | F | H | A | T | T | T | K |
| S | S | F | H | A | T | T | T | K |
| Y | L | Y | H | A | T | T | T | K |
| S | L | Y | H | A | T | T | T | K |
| Y | S | Y | H | A | T | T | T | K |
| S | S | Y | H | A | T | T | T | K |
| Y | L | F | Q | A | T | T | T | K |
| S | L | F | Q | A | T | T | T | K |
| Y | S | F | Q | A | T | T | T | K |
| S | S | F | Q | A | T | T | T | K |
| Y | L | Y | Q | A | T | T | T | K |
| S | L | Y | Q | A | T | T | T | K |
| Y | S | Y | Q | A | T | T | T | K |
| S | S | Y | Q | A | T | T | T | K |
| Y | L | F | H | G | A | T | T | K |
| S | L | F | H | G | A | T | T | K |
| Y | S | F | H | G | A | T | T | K |
| S | S | F | H | G | A | T | T | K |
| Y | L | Y | H | G | A | T | T | K |
| S | L | Y | H | G | A | T | T | K |
| Y | S | Y | H | G | A | T | T | K |
| S | S | Y | H | G | A | T | T | K |
| Y | L | F | Q | G | A | T | T | K |
| S | L | F | Q | G | A | T | T | K |
| Y | S | F | Q | G | A | T | T | K |
| S | S | F | Q | G | A | T | T | K |
| Y | L | Y | Q | G | A | T | T | K |
| S | L | Y | Q | G | A | T | T | K |
| Y | S | Y | Q | G | A | T | T | K |
| S | S | Y | Q | G | A | T | T | K |
| Y | L | F | H | A | A | T | T | K |
| S | L | F | H | A | A | T | T | K |
| Y | S | F | H | A | A | T | T | K |
| S | S | F | H | A | A | T | T | K |
| Y | L | Y | H | A | A | T | T | K |
| S | L | Y | H | A | A | T | T | K |
| Y | S | Y | H | A | A | T | T | K |
| S | S | Y | H | A | A | T | T | K |
| Y | L | F | Q | A | A | T | T | K |
| S | L | F | Q | A | A | T | T | K |
| Y | S | F | Q | A | A | T | T | K |
| S | S | F | Q | A | A | T | T | K |
| Y | L | Y | Q | A | A | T | T | K |
| S | L | Y | Q | A | A | T | T | K |
| Y | S | Y | Q | A | A | T | T | K |
| S | S | Y | Q | A | A | T | T | K |
| Y | L | F | H | G | T | S | T | K |
| S | L | F | H | G | T | S | T | K |
| Y | S | F | H | G | T | S | T | K |
| S | S | F | H | G | T | S | T | K |
| Y | L | Y | H | G | T | S | T | K |
| S | L | Y | H | G | T | S | T | K |
| Y | S | Y | H | G | T | S | T | K |

TABLE 18a-continued

Exemplary Mutations of mAB 33C3 Light Chain (SEQ ID NO: 76) to Germline at the Indicated Residue Number

| 7 | 9 | 32 | 37 | 50 | 51 | 91 | 94 | 103 |
|---|---|---|---|---|---|---|---|---|
| S | S | Y | H | G | T | S | T | K |
| Y | L | F | Q | G | T | S | T | K |
| S | L | F | Q | G | T | S | T | K |
| Y | S | F | Q | G | T | S | T | K |
| S | S | F | Q | G | T | S | T | K |
| Y | L | Y | Q | G | T | S | T | K |
| S | L | Y | Q | G | T | S | T | K |
| Y | S | Y | Q | G | T | S | T | K |
| S | S | Y | Q | G | T | S | T | K |
| Y | L | F | H | A | T | S | T | K |
| S | L | F | H | A | T | S | T | K |
| Y | S | F | H | A | T | S | T | K |
| S | S | F | H | A | T | S | T | K |
| Y | L | Y | H | A | T | S | T | K |
| S | L | Y | H | A | T | S | T | K |
| Y | S | Y | H | A | T | S | T | K |
| S | S | Y | H | A | T | S | T | K |
| Y | L | F | Q | A | T | S | T | K |
| S | L | F | Q | A | T | S | T | K |
| Y | S | F | Q | A | T | S | T | K |
| S | S | F | Q | A | T | S | T | K |
| Y | L | Y | Q | A | T | S | T | K |
| S | L | Y | Q | A | T | S | T | K |
| Y | S | Y | Q | A | T | S | T | K |
| S | S | Y | Q | A | T | S | T | K |
| Y | L | F | H | G | A | S | T | K |
| S | L | F | H | G | A | S | T | K |
| Y | S | F | H | G | A | S | T | K |
| S | S | F | H | G | A | S | T | K |
| Y | L | Y | H | G | A | S | T | K |
| S | L | Y | H | G | A | S | T | K |
| Y | S | Y | H | G | A | S | T | K |
| S | S | Y | H | G | A | S | T | K |
| Y | L | F | Q | G | A | S | T | K |
| S | L | F | Q | G | A | S | T | K |
| Y | S | F | Q | G | A | S | T | K |
| S | S | F | Q | G | A | S | T | K |
| Y | L | Y | Q | G | A | S | T | K |
| S | L | Y | Q | G | A | S | T | K |
| Y | S | Y | Q | G | A | S | T | K |
| S | S | Y | Q | G | A | S | T | K |
| Y | L | F | H | A | A | S | T | K |
| S | L | F | H | A | A | S | T | K |
| Y | S | F | H | A | A | S | T | K |
| S | S | F | H | A | A | S | T | K |
| Y | L | Y | H | A | A | S | T | K |
| S | L | Y | H | A | A | S | T | K |
| Y | S | Y | H | A | A | S | T | K |
| S | S | Y | H | A | A | S | T | K |
| Y | L | F | Q | A | A | S | T | K |
| S | L | F | Q | A | A | S | T | K |
| Y | S | F | Q | A | A | S | T | K |
| S | S | F | Q | A | A | S | T | K |
| Y | L | Y | Q | A | A | S | T | K |
| S | L | Y | Q | A | A | S | T | K |
| Y | S | Y | Q | A | A | S | T | K |
| S | S | Y | Q | A | A | S | T | K |

TABLE 19

Exemplary Mutations of mAB 33C3 Heavy Chain (SEQ ID NO: 74) to Germline at the Indicated Residue Number

| 17 | 60 | 61 | 98 | 105 | 109 | 117 | 143 |
|---|---|---|---|---|---|---|---|
| G | H | S | A | Y | D | # | T |
| G | S | G | A | Y | # | F | T |
| E | S | S | A | Y | # | # | T |

TABLE 19a

Exemplary Mutations of mAB 33C3 Heavy Chain (SEQ ID NO: 74) to Germline at the Indicated Residue Number

| 16 | 53 | 54 | 88 | 95 | 99 | 107 | 117 |
|---|---|---|---|---|---|---|---|
| E | H | G | V | F | D | F | A |
| G | H | G | V | F | D | F | A |
| E | S | G | V | F | D | F | A |
| G | S | G | V | F | D | F | A |
| E | H | S | V | F | D | F | A |
| G | H | S | V | F | D | F | A |
| E | S | S | V | F | D | F | A |
| G | S | S | V | F | D | F | A |
| E | H | G | A | F | D | F | A |
| G | H | G | A | F | D | F | A |
| E | S | G | A | F | D | F | A |
| G | S | G | A | F | D | F | A |
| E | H | S | A | F | D | F | A |
| G | H | S | A | F | D | F | A |
| E | S | S | A | F | D | F | A |
| G | S | S | A | F | D | F | A |
| E | H | G | V | Y | D | F | A |
| G | H | G | V | Y | D | F | A |
| E | S | G | V | Y | D | F | A |
| G | S | G | V | Y | D | F | A |
| E | H | S | V | Y | D | F | A |
| G | H | S | V | Y | D | F | A |
| E | S | S | V | Y | D | F | A |
| G | S | S | V | Y | D | F | A |
| E | H | G | A | Y | D | F | A |
| G | H | G | A | Y | D | F | A |
| E | S | G | A | Y | D | F | A |
| G | S | G | A | Y | D | F | A |
| E | H | S | A | Y | D | F | A |
| G | H | S | A | Y | D | F | A |
| E | S | S | A | Y | D | F | A |
| G | S | S | A | Y | D | F | A |
| E | H | G | V | F | — | F | A |
| G | H | G | V | F | — | F | A |
| E | S | G | V | F | — | F | A |
| G | S | G | V | F | — | F | A |
| E | H | S | V | F | — | F | A |
| G | H | S | V | F | — | F | A |
| E | S | S | V | F | — | F | A |
| G | S | S | V | F | — | F | A |
| E | H | G | A | F | — | F | A |
| G | H | G | A | F | — | F | A |
| E | S | G | A | F | — | F | A |
| G | S | G | A | F | — | F | A |
| E | H | S | A | F | — | F | A |
| G | H | S | A | F | — | F | A |
| E | S | S | A | F | — | F | A |
| G | S | S | A | F | — | F | A |
| E | H | G | V | Y | — | F | A |
| G | H | G | V | Y | — | F | A |
| E | S | G | V | Y | — | F | A |
| G | S | G | V | Y | — | F | A |
| E | H | S | V | Y | — | F | A |
| G | H | S | V | Y | — | F | A |
| E | S | S | V | Y | — | F | A |
| G | S | S | V | Y | — | F | A |
| E | H | G | A | Y | — | F | A |
| G | H | G | A | Y | — | F | A |
| E | S | G | A | Y | — | F | A |
| G | S | G | A | Y | — | F | A |
| E | H | S | A | Y | — | F | A |
| G | H | S | A | Y | — | F | A |
| E | S | S | A | Y | — | F | A |
| G | S | S | A | Y | — | F | A |
| E | H | G | V | F | D | — | A |
| G | H | G | V | F | D | — | A |
| E | S | G | V | F | D | — | A |
| G | S | G | V | F | D | — | A |
| E | H | S | V | F | D | — | A |
| G | H | S | V | F | D | — | A |
| E | S | S | V | F | D | — | A |
| G | S | S | V | F | D | — | A |
| E | H | G | A | F | D | — | A |
| G | H | G | A | F | D | — | A |

TABLE 19a-continued

| Exemplary Mutations of mAB 33C3 Heavy Chain (SEQ ID NO: 74) to Germline at the Indicated Residue Number | | | | | | | |
|---|---|---|---|---|---|---|---|
| 16 | 53 | 54 | 88 | 95 | 99 | 107 | 117 |
| E | S | G | A | F | D | — | A |
| G | S | G | A | F | D | — | A |
| E | H | S | A | F | D | — | A |
| G | H | S | A | F | D | — | A |
| E | S | S | A | F | D | — | A |
| G | S | S | A | F | D | — | A |
| E | H | G | V | Y | D | — | A |
| G | H | G | V | Y | D | — | A |
| E | S | G | V | Y | D | — | A |
| G | S | G | V | Y | D | — | A |
| E | H | S | V | Y | D | — | A |
| G | H | S | V | Y | D | — | A |
| E | S | S | V | Y | D | — | A |
| G | S | S | V | Y | D | — | A |
| E | H | G | A | Y | D | — | A |
| G | H | G | A | Y | D | — | A |
| E | S | G | A | Y | D | — | A |
| G | S | G | A | Y | D | — | A |
| E | H | S | A | Y | D | — | A |
| G | H | S | A | Y | D | — | A |
| E | S | S | A | Y | D | — | A |
| G | S | S | A | Y | D | — | A |
| E | H | G | V | F | — | — | A |
| G | H | G | V | F | — | — | A |
| E | S | G | V | F | — | — | A |
| G | S | G | V | F | — | — | A |
| E | H | S | V | F | — | — | A |
| G | H | S | V | F | — | — | A |
| E | S | S | V | F | — | — | A |
| G | S | S | V | F | — | — | A |
| E | H | G | A | F | — | — | A |
| G | H | G | A | F | — | — | A |
| E | S | G | A | F | — | — | A |
| G | S | G | A | F | — | — | A |
| E | H | S | A | F | — | — | A |
| G | H | S | A | F | — | — | A |
| E | S | S | A | F | — | — | A |
| G | S | S | A | F | — | — | A |
| E | H | G | V | Y | — | — | A |
| G | H | G | V | Y | — | — | A |
| E | S | G | V | Y | — | — | A |
| G | S | G | V | Y | — | — | A |
| E | H | S | V | Y | — | — | A |
| G | H | S | V | Y | — | — | A |
| E | S | S | V | Y | — | — | A |
| G | S | S | V | Y | — | — | A |
| E | H | G | A | Y | — | — | A |
| G | H | G | A | Y | — | — | A |
| E | S | G | A | Y | — | — | A |
| G | S | G | A | Y | — | — | A |
| E | H | S | A | Y | — | — | A |
| G | H | S | A | Y | — | — | A |
| E | S | S | A | Y | — | — | A |
| G | S | S | A | Y | — | — | A |
| E | H | G | V | F | D | F | A |
| G | H | G | V | F | D | F | A |
| E | S | G | V | F | D | F | A |
| G | S | G | V | F | D | F | A |
| E | H | S | V | F | D | F | A |
| G | H | S | V | F | D | F | A |
| E | S | S | V | F | D | F | A |
| G | S | S | V | F | D | F | A |
| E | H | G | A | F | D | F | A |
| G | H | G | A | F | D | F | A |
| E | S | G | A | F | D | F | A |
| G | S | G | A | F | D | F | A |
| E | H | S | A | F | D | F | A |
| G | H | S | A | F | D | F | A |
| E | S | S | A | F | D | F | A |
| G | S | S | A | F | D | F | A |
| E | H | G | V | Y | D | F | A |
| G | H | G | V | Y | D | F | A |
| E | S | G | V | Y | D | F | A |
| G | S | G | V | Y | D | F | A |

TABLE 19a-continued

| Exemplary Mutations of mAB 33C3 Heavy Chain (SEQ ID NO: 74) to Germline at the Indicated Residue Number | | | | | | | |
|---|---|---|---|---|---|---|---|
| 16 | 53 | 54 | 88 | 95 | 99 | 107 | 117 |
| E | H | S | V | Y | D | F | A |
| G | H | S | V | Y | D | F | A |
| E | S | S | V | Y | D | F | A |
| G | S | S | V | Y | D | F | A |
| E | H | G | A | Y | D | F | A |
| G | H | G | A | Y | D | F | A |
| E | S | G | A | Y | D | F | A |
| G | S | G | A | Y | D | F | A |
| E | H | S | A | Y | D | F | A |
| G | H | S | A | Y | D | F | A |
| E | S | S | A | Y | D | F | A |
| G | S | S | A | Y | D | F | A |
| E | H | G | V | F | — | F | A |
| G | H | G | V | F | — | F | A |
| E | S | G | V | F | — | F | A |
| G | S | G | V | F | — | F | A |
| E | H | S | V | F | — | F | A |
| G | H | S | V | F | — | F | A |
| E | S | S | V | F | — | F | A |
| G | S | S | V | F | — | F | A |
| E | H | G | A | F | — | F | A |
| G | H | G | A | F | — | F | A |
| E | S | G | A | F | — | F | A |
| G | S | G | A | F | — | F | A |
| E | H | S | A | F | — | F | A |
| G | H | S | A | F | — | F | A |
| E | S | S | A | F | — | F | A |
| G | S | S | A | F | — | F | A |
| E | H | G | V | Y | — | F | A |
| G | H | G | V | Y | — | F | A |
| E | S | G | V | Y | — | F | A |
| G | S | G | V | Y | — | F | A |
| E | H | S | V | Y | — | F | A |
| G | H | S | V | Y | — | F | A |
| E | S | S | V | Y | — | F | A |
| G | S | S | V | Y | — | F | A |
| E | H | G | A | Y | — | F | A |
| G | H | G | A | Y | — | F | A |
| E | S | G | A | Y | — | F | A |
| G | S | G | A | Y | — | F | A |
| E | H | S | A | Y | — | F | A |
| G | H | S | A | Y | — | F | A |
| E | S | S | A | Y | — | F | A |
| G | S | S | A | Y | — | F | A |
| E | H | G | V | F | D | — | A |
| G | H | G | V | F | D | — | A |
| E | S | G | V | F | D | — | A |
| G | S | G | V | F | D | — | A |
| E | H | S | V | F | D | — | A |
| G | H | S | V | F | D | — | A |
| E | S | S | V | F | D | — | A |
| G | S | S | V | F | D | — | A |
| E | H | G | A | F | D | — | A |
| G | H | G | A | F | D | — | A |
| E | S | G | A | F | D | — | A |
| G | S | G | A | F | D | — | A |
| E | H | S | A | F | D | — | A |
| G | H | S | A | F | D | — | A |
| E | S | S | A | F | D | — | A |
| G | S | S | A | F | D | — | A |
| E | H | G | V | Y | D | — | A |
| G | H | G | V | Y | D | — | A |
| E | S | G | V | Y | D | — | A |
| G | S | G | V | Y | D | — | A |
| E | H | S | V | Y | D | — | A |
| G | H | S | V | Y | D | — | A |
| E | S | S | V | Y | D | — | A |
| G | S | S | V | Y | D | — | A |
| E | H | G | A | Y | D | — | A |
| G | H | G | A | Y | D | — | A |
| E | S | G | A | Y | D | — | A |
| G | S | G | A | Y | D | — | A |
| E | H | S | A | Y | D | — | A |
| G | H | S | A | Y | D | — | A |

TABLE 19a-continued

| Exemplary Mutations of mAB 33C3 Heavy Chain (SEQ ID NO: 74) to Germline at the Indicated Residue Number | | | | | | | |
|---|---|---|---|---|---|---|---|
| 16 | 53 | 54 | 88 | 95 | 99 | 107 | 117 |
| E | S | S | A | Y | D | — | A |
| G | S | S | A | Y | D | — | A |
| E | H | G | V | F | — | — | A |
| G | H | G | V | F | — | — | A |
| E | S | G | V | F | — | — | A |
| G | S | G | V | F | — | — | A |
| E | H | S | V | F | — | — | A |
| G | H | S | V | F | — | — | A |
| E | S | S | V | F | — | — | A |
| G | S | S | V | F | — | — | A |
| E | H | G | A | F | — | — | A |
| G | H | G | A | F | — | — | A |
| E | S | G | A | F | — | — | A |
| G | S | G | A | F | — | — | A |
| E | H | S | A | F | — | — | A |
| G | H | S | A | F | — | — | A |
| E | S | S | A | F | — | — | A |
| G | S | S | A | F | — | — | A |
| E | H | G | V | Y | — | — | A |
| G | H | G | V | Y | — | — | A |
| E | S | G | V | Y | — | — | A |
| G | S | G | V | Y | — | — | A |
| E | H | S | V | Y | — | — | A |
| G | H | S | V | Y | — | — | A |
| E | S | S | V | Y | — | — | A |
| G | S | S | V | Y | — | — | A |
| E | H | G | A | Y | — | — | A |
| G | H | G | A | Y | — | — | A |
| E | S | G | A | Y | — | — | A |
| G | S | G | A | Y | — | — | A |
| E | H | S | A | Y | — | — | A |
| G | H | S | A | Y | — | — | A |
| E | S | S | A | Y | — | — | A |
| G | S | S | A | Y | — | — | A |
| E | H | G | V | F | D | F | T |
| G | H | G | V | F | D | F | T |
| E | S | G | V | F | D | F | T |
| G | S | G | V | F | D | F | T |
| E | H | S | V | F | D | F | T |
| G | H | S | V | F | D | F | T |
| E | S | S | V | F | D | F | T |
| G | S | S | V | F | D | F | T |
| E | H | G | A | F | D | F | T |
| G | H | G | A | F | D | F | T |
| E | S | G | A | F | D | F | T |
| G | S | G | A | F | D | F | T |
| E | H | S | A | F | D | F | T |
| G | H | S | A | F | D | F | T |
| E | S | S | A | F | D | F | T |
| G | S | S | A | F | D | F | T |
| E | H | G | V | Y | D | F | T |
| G | H | G | V | Y | D | F | T |
| E | S | G | V | Y | D | F | T |
| G | S | G | V | Y | D | F | T |
| E | H | S | V | Y | D | F | T |
| G | H | S | V | Y | D | F | T |
| E | S | S | V | Y | D | F | T |
| G | S | S | V | Y | D | F | T |
| E | H | G | A | Y | D | F | T |
| G | H | G | A | Y | D | F | T |
| E | S | G | A | Y | D | F | T |
| G | S | G | A | Y | D | F | T |
| E | H | S | A | Y | D | F | T |
| G | H | S | A | Y | D | F | T |
| E | S | S | A | Y | D | F | T |
| G | S | S | A | Y | D | F | T |
| E | H | G | V | F | — | F | T |
| G | H | G | V | F | — | F | T |
| E | S | G | V | F | — | F | T |
| G | S | G | V | F | — | F | T |
| E | H | S | V | F | — | F | T |
| G | H | S | V | F | — | F | T |
| E | S | S | V | F | — | F | T |
| G | S | S | V | F | — | F | T |

TABLE 19a-continued

| Exemplary Mutations of mAB 33C3 Heavy Chain (SEQ ID NO: 74) to Germline at the Indicated Residue Number | | | | | | | |
|---|---|---|---|---|---|---|---|
| 16 | 53 | 54 | 88 | 95 | 99 | 107 | 117 |
| E | H | G | A | F | — | F | T |
| G | H | G | A | F | — | F | T |
| E | S | G | A | F | — | F | T |
| G | S | G | A | F | — | F | T |
| E | H | S | A | F | — | F | T |
| G | H | S | A | F | — | F | T |
| E | S | S | A | F | — | F | T |
| G | S | S | A | F | — | F | T |
| E | H | G | V | Y | — | F | T |
| G | H | G | V | Y | — | F | T |
| E | S | G | V | Y | — | F | T |
| G | S | G | V | Y | — | F | T |
| E | H | S | V | Y | — | F | T |
| G | H | S | V | Y | — | F | T |
| E | S | S | V | Y | — | F | T |
| G | S | S | V | Y | — | F | T |
| E | H | G | A | Y | — | F | T |
| G | H | G | A | Y | — | F | T |
| E | S | G | A | Y | — | F | T |
| G | S | G | A | Y | — | F | T |
| E | H | S | A | Y | — | F | T |
| G | H | S | A | Y | — | F | T |
| E | S | S | A | Y | — | F | T |
| G | S | S | A | Y | — | F | T |
| E | H | G | V | F | D | — | T |
| G | H | G | V | F | D | — | T |
| E | S | G | V | F | D | — | T |
| G | S | G | V | F | D | — | T |
| E | H | S | V | F | D | — | T |
| G | H | S | V | F | D | — | T |
| E | S | S | V | F | D | — | T |
| G | S | S | V | F | D | — | T |
| E | H | G | A | F | D | — | T |
| G | H | G | A | F | D | — | T |
| E | S | G | A | F | D | — | T |
| G | S | G | A | F | D | — | T |
| E | H | S | A | F | D | — | T |
| G | H | S | A | F | D | — | T |
| E | S | S | A | F | D | — | T |
| G | S | S | A | F | D | — | T |
| E | H | G | V | Y | D | — | T |
| G | H | G | V | Y | D | — | T |
| E | S | G | V | Y | D | — | T |
| G | S | G | V | Y | D | — | T |
| E | H | S | V | Y | D | — | T |
| G | H | S | V | Y | D | — | T |
| E | S | S | V | Y | D | — | T |
| G | S | S | V | Y | D | — | T |
| E | H | G | A | Y | D | — | T |
| G | H | G | A | Y | D | — | T |
| E | S | G | A | Y | D | — | T |
| G | S | G | A | Y | D | — | T |
| E | H | S | A | Y | D | — | T |
| G | H | S | A | Y | D | — | T |
| E | S | S | A | Y | D | — | T |
| G | S | S | A | Y | D | — | T |
| E | H | G | V | F | — | — | T |
| G | H | G | V | F | — | — | T |
| E | S | G | V | F | — | — | T |
| G | S | G | V | F | — | — | T |
| E | H | S | V | F | — | — | T |
| G | H | S | V | F | — | — | T |
| E | S | S | V | F | — | — | T |
| G | S | S | V | F | — | — | T |
| E | H | G | A | F | — | — | T |
| G | H | G | A | F | — | — | T |
| E | S | G | A | F | — | — | T |
| G | S | G | A | F | — | — | T |
| E | H | S | A | F | — | — | T |
| G | H | S | A | F | — | — | T |
| E | S | S | A | F | — | — | T |
| G | S | S | A | F | — | — | T |
| E | H | G | V | Y | — | — | T |
| G | H | G | V | Y | — | — | T |

TABLE 19a-continued

Exemplary Mutations of mAB 33C3 Heavy Chain (SEQ ID NO: 74) to Germline at the Indicated Residue Number

| 16 | 53 | 54 | 88 | 95 | 99 | 107 | 117 |
|---|---|---|---|---|---|---|---|
| E | S | G | V | Y | — | — | T |
| G | S | G | V | Y | — | — | T |
| E | H | S | V | Y | — | — | T |
| G | H | S | V | Y | — | — | T |
| E | S | S | V | Y | — | — | T |
| G | S | S | V | Y | — | — | T |
| E | H | G | A | Y | — | — | T |
| G | H | G | A | Y | — | — | T |
| E | S | G | A | Y | — | — | T |
| G | S | G | A | Y | — | — | T |
| E | H | S | A | Y | — | — | T |
| G | H | S | A | Y | — | — | T |
| E | S | S | A | Y | — | — | T |
| G | S | S | A | Y | — | — | T |
| E | H | G | V | F | D | F | T |
| G | H | G | V | F | D | F | T |
| E | S | G | V | F | D | F | T |
| G | S | G | V | F | D | F | T |
| E | H | S | V | F | D | F | T |
| G | H | S | V | F | D | F | T |
| E | S | S | V | F | D | F | T |
| G | S | S | V | F | D | F | T |
| E | H | G | A | F | D | F | T |
| G | H | G | A | F | D | F | T |
| E | S | G | A | F | D | F | T |
| G | S | G | A | F | D | F | T |
| E | H | S | A | F | D | F | T |
| G | H | S | A | F | D | F | T |
| E | S | S | A | F | D | F | T |
| G | S | S | A | F | D | F | T |
| E | H | G | V | Y | D | F | T |
| G | H | G | V | Y | D | F | T |
| E | S | G | V | Y | D | F | T |
| G | S | G | V | Y | D | F | T |
| E | H | S | V | Y | D | F | T |
| G | H | S | V | Y | D | F | T |
| E | S | S | V | Y | D | F | T |
| G | S | S | V | Y | D | F | T |
| E | H | G | A | Y | D | F | T |
| G | H | G | A | Y | D | F | T |
| E | S | G | A | Y | D | F | T |
| G | S | G | A | Y | D | F | T |
| E | H | S | A | Y | D | F | T |
| G | H | S | A | Y | D | F | T |
| E | S | S | A | Y | D | F | T |
| G | S | S | A | Y | D | F | T |
| E | H | G | V | F | — | F | T |
| G | H | G | V | F | — | F | T |
| E | S | G | V | F | — | F | T |
| G | S | G | V | F | — | F | T |
| E | H | S | V | F | — | F | T |
| G | H | S | V | F | — | F | T |
| E | S | S | V | F | — | F | T |
| G | S | S | V | F | — | F | T |
| E | H | G | A | F | — | F | T |
| G | H | G | A | F | — | F | T |
| E | S | G | A | F | — | F | T |
| G | S | G | A | F | — | F | T |
| E | H | S | A | F | — | F | T |
| G | H | S | A | F | — | F | T |
| E | S | S | A | F | — | F | T |
| G | S | S | A | F | — | F | T |
| E | H | G | V | Y | — | F | T |
| G | H | G | V | Y | — | F | T |
| E | S | G | V | Y | — | F | T |
| G | S | G | V | Y | — | F | T |
| E | H | S | V | Y | — | F | T |
| G | H | S | V | Y | — | F | T |
| E | S | S | V | Y | — | F | T |
| G | S | S | V | Y | — | F | T |
| E | H | G | A | Y | — | F | T |
| G | H | G | A | Y | — | F | T |
| E | S | G | A | Y | — | F | T |
| G | S | G | A | Y | — | F | T |
| E | H | S | A | Y | — | F | T |
| G | H | S | A | Y | — | F | T |
| E | S | S | A | Y | — | F | T |
| G | S | S | A | Y | — | F | T |
| E | H | G | V | F | D | — | T |
| G | H | G | V | F | D | — | T |
| E | S | G | V | F | D | — | T |
| G | S | G | V | F | D | — | T |
| E | H | S | V | F | D | — | T |
| G | H | S | V | F | D | — | T |
| E | S | S | V | F | D | — | T |
| G | S | S | V | F | D | — | T |
| E | H | G | A | F | D | — | T |
| G | H | G | A | F | D | — | T |
| E | S | G | A | F | D | — | T |
| G | S | G | A | F | D | — | T |
| E | H | S | A | F | D | — | T |
| G | H | S | A | F | D | — | T |
| E | S | S | A | F | D | — | T |
| G | S | S | A | F | D | — | T |
| E | H | G | V | Y | D | — | T |
| G | H | G | V | Y | D | — | T |
| E | S | G | V | Y | D | — | T |
| G | S | G | V | Y | D | — | T |
| E | H | S | V | Y | D | — | T |
| G | H | S | V | Y | D | — | T |
| E | S | S | V | Y | D | — | T |
| G | S | S | V | Y | D | — | T |
| E | H | G | A | Y | D | — | T |
| G | H | G | A | Y | D | — | T |
| E | S | G | A | Y | D | — | T |
| G | S | G | A | Y | D | — | T |
| E | H | S | A | Y | D | — | T |
| G | H | S | A | Y | D | — | T |
| E | S | S | A | Y | D | — | T |
| G | S | S | A | Y | D | — | T |
| E | H | G | V | F | — | — | T |
| G | H | G | V | F | — | — | T |
| E | S | G | V | F | — | — | T |
| G | S | G | V | F | — | — | T |
| E | H | S | V | F | — | — | T |
| G | H | S | V | F | — | — | T |
| E | S | S | V | F | — | — | T |
| G | S | S | V | F | — | — | T |
| E | H | G | A | F | — | — | T |
| G | H | G | A | F | — | — | T |
| E | S | G | A | F | — | — | T |
| G | S | G | A | F | — | — | T |
| E | H | S | A | F | — | — | T |
| G | H | S | A | F | — | — | T |
| E | S | S | A | F | — | — | T |
| G | S | S | A | F | — | — | T |
| E | H | G | V | Y | — | — | T |
| G | H | G | V | Y | — | — | T |
| E | S | G | V | Y | — | — | T |
| G | S | G | V | Y | — | — | T |
| E | H | S | V | Y | — | — | T |
| G | H | S | V | Y | — | — | T |
| E | S | S | V | Y | — | — | T |
| G | S | S | V | Y | — | — | T |
| E | H | G | A | Y | — | — | T |
| G | H | G | A | Y | — | — | T |
| E | S | G | A | Y | — | — | T |
| G | S | G | A | Y | — | — | T |
| E | H | S | A | Y | — | — | T |
| G | H | S | A | Y | — | — | T |
| E | S | S | A | Y | — | — | T |
| G | S | S | A | Y | — | — | T |

"—" indicates the absence of a residue at that position with reference to SEQ ID NO: 74

The skilled person will be aware that there are alternative methods of defining CDR boundaries. The starting residue of VH CDR1 in the Table 20a has been defined according to the method as described in Scaviner D, Barbie V, Ruiz M, Lefranc M-P. Protein Displays of the Human Immunoglobulin Heavy, Kappa and Lambda Variable and Joining Regions. Exp Clin Immunogenet 1999, 16:234-240. The remaining CDR boundaries in Table 20a and Table 21a are defined according to the Kabat definition.

All CDR boundaries in Table 20b and Table 21b are defined according to the Kabat definition.

TABLE 20a

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| | 109 | Germline | | | QVQLVQSGAEVKK PGASVKVSCKAS | GYTFTSY DIN | WVRQATG QGLEWMG | WMNPNSG NTGYAQK PCG | RVTMTRNTSIST AYMELSSLRSED TAVYYCAR | ##YS# ##WFD P | WGQGT LVTVS S |
| 33D5 | 58 | VH1-8 | D5-12 | JH5B | QVQLVQSGAEVKK PGASVKVSCKAS | GYTFGSY DIN | WVRQATG QGLEWMG | WMNPNSG NTGYAQK FCG | RVTLTRNTSIRT VYMELSSLRSED TAVYYCAR | GGYSN LGWFD P | WGQGS LVTVS S |
| 29H3 | 54 | VH1-8 | D6-13 | JH5B | QVQLVQSGAEVKK PGASVKVSCKAS | GYTFTSY DIN | WVRQATG QGLEWMG | WMNPNSG KTGYAQK FCG | RVTMTRNTSINT AYMELSSLRSED TAVYYCAR | GGYSN LGWFD P | WGQGT LVTVS S |
| 29F7 | 62 | VH1-8 | D6-13 | JH5B | QVQLVQSGAEVKK PGASVKVSCKAS | GYTFTSY DIN | WVRQATG QGLEWMG | WMNPNSG KTGYAQK FCG | RVTMTRSTSIST AYMELSSLRSED TAVYYCAR | GGYSN LGWFD P | WGQGT LVTVS S |
| | 110 | Germline | | | QVQLVESGGGLVK PGGSLRLSCAAS | GFTFSDY YMS | WIRQAPG KGLEWVS | YISSSGS TIYYADS VKG | RFTISRDNAKNS LYLQMNSLRAED TAVYYCAR | DDFWS GY##N WFDP | WGQGT LVTVS S |
| 33C3 | 74 | VH3-11 | D3-3 | JH5B | QVQKVESGGGKVK PGESLRLSCAAS | GFTFSDY YMS | WIRQAPG KGLEWVS | YISHGGS TIYYADS VKG | RFTISRDNAKNS LYLQMNSLRVED TAVYFCAR | DDFWS GYYFN WFDP | WGQGWA LVTVS S |
| 31E11 | 70 | VH3-11 | D3-3 | JH5B | QVQLVESGGGLVK PGGSLRLSCAAS | GFTFSDY YMS | WIRQAPG KGLEWVS | YISISGS TIYYADS VKG | RFTISRDNAKNS LYLQMNSLRAED TAVYYCAR | DDFWS GYYFN WFDP | WGQGT LVTVS S |
| | 111 | Germline | | | QVQLVESGGGLVK PGGSLRLSCAAS | GFTFSDY YMS | WIRQAPG KGLEWVS | YISSSGS TIYYADS VKG | RFTISRDNAKNS LYLQMSLRAED TAVYYCAR | ##YS# SGWY# #FDY | WGQGT LVTVS S |
| 21A1 | 66 | VH3-11 | D6-19 | JH4B | QVQLVESGGGLVK PGGSLRLSCAAS | GFTFSDY YMS | WIRQAPG KGLEWVS | YISNSGI TIYYADS VKG | RFTISRDNAKNS LYLQMNSLRAGD TAVYYCAR | EEWYS SSWYR NFDY | WGQGT LVTVS S |
| 21H6 | 66 | VH3-11 | D6-19 | JH4B | QVQLVESGGGLVK PGGSLRLSCAAS | GFTFSDY YMS | WIRAQPG KGLEWVS | YISNSGI TIYYADS VKG | RFTISRDNAKNS LYLQMNSLRAGD TAVYYCAR | EEWYS SSWYR NFDY | WGQGT LVTVS S |
| | 112 | Germline | | | EVQLVESGGGL VKPGGSLRLSC AAS | GFTFSSY SMN | WVRQAPG KGLEWVS | SISSSSS YIYYADS VKG | RFTISRDNAKNSL YLQMNSLRAEDTA VYYC## | ##WF### | WGQGTLV TVSS |
| 24C9 | 34 | VH3-21 | D3-10 | JH4B | EVQLVESGGGL VKPGGSLRLSC AAS | GFTFSTY SMN | WVRQAPG KGLEWVS | FISGRSS YIYYADS VKG | RFTISRDNAKNSL YLQMNSLRAEDTA VYYCSK | DDWFEEL | WGQGTLV TVSS |
| 32G7 | 38 | VH3-21 | D3-10 | JH4B | EVQLVESGGGL VKPGGSLRLSC AAS | GFTISSY SMN | WVRQAPG KGLEWVS | FISSRSN YIYYADS VKG | RFTISRDNAKNSL YLQMNSLRAEDTA VYYCSK | DDWFEEL | WGQGTLV TVSS |
| 24B3 | 42 | VH3-21 | D3-10 | JH4B | EVQLVESGGGL VKPGGSLRLSC AAS | GFTFSTY SMN | WVRQAPG KGLEWVS | FISGRSS YIYYADS VKG | RFTISRDNAKNSL YLQMNSLRAEDTA VYYCSK | DDWFEEL | WGQGTLV TVSS |
| 33B1 | 46 | VH3-21 | D3-10 | JH4B | EVQLVESGGGL VKPGGSLRLSC AAS | GFTFSSY TMN | WVRQAPG KGLEWVS | FIDSRSS YIYYADS VKG | RFTISRDNAKNSL YLQMNSLRAEDTA VYYCSK | DDWFEEL | WGQGTLV TVSS |
| | 113 | Germline | | | EVQLLESGGGL VQPGGSLRLSC AAS | GFTFSSY AMS | WVRQAPG KGLEWVS | AISGSGG STYYADS VKG | RFTISRDNSKNTL YLQMNSLRAEDTA VYYCAK | ##### | WGQGTLV TVSS |

TABLE 20a-continued

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| 29A11 | 90 | VH3-23 | | JH4B | EVQLLESGGGLVQPGGSLRLSCAAS | GFTFSNYAMN | WVRQAPGKGLEWVS | AISGGGSNTYYADSVKG | RFTISRDNSKNTLYLQMNRLRAEDTAVYYCAK | ASGDD | WGQGTLVTVSS |
| 30H10 | 94 | VH3-23 | | JH4B | EVQLLESGGGLVQPGGSLRLSCAAS | GFTFSNYAMS | WVRQAPGKGLEWVS | AISGSGGITYYADSVKG | RFTISRDNSKNTLFLQMNSLRAEDTAVYYCAK | ASGDD | WGQGTLVSVSS |
| 32B2 | 82 | VH3-23 | | JH4B | EVQLLESGGGLVQPGGSLRLSCAAS | GFTFSNYAMS | WVRQAPGKGLDWVS | AISGRGGSTYYADSVKG | RFTISRDNSKNTLFLLMNSLRAEDTAVYYCAK | ASGDD | WGQGTLVTVSS |
| 32C11 | 98 | VH3-23 | | JH4B | EVQLLESGGTLVQPGGSLRLSCAAS | GFTFSNYAMS | WVRQAPGKGLEWVS | AISGRAGSTYYADSVKG | RFTISRDNSKNTLFLQMNSLRAEDTAVYYCAK | ASGDD | WGQGTLVTVSS |
| 30E3 | 86 | VH3-23 | | JH4B | EVQLLESGGGLVQPGGSLRLSCAAS | GFTFSNYALS | WVRQAPGKGLEWVS | AISGSGRNTYYADSVKG | RFTLSRDNSKNTLFLQMNSLRAEDTAVYYCAK | ASGDD | WGWGTLVTVSS |
| | 114 | Germline | | | EVQLLESGGGLVQPGGSLRLSCAAS | GFTFSSYAMS | WVRQAPGKGLEWVS | AISGSGGSTYYADSVKG | RFTISRDNSKNTLYLQMNSLRAEDTAVYYCAK | VATDY | WGQGTLVTVSS |
| 1G6 | 106 | VH3-23 | D5-12 | JH4B | EVQLLESGGGLVQPGGSLRLSCAAS | GFTFSSYAMS | WVRQAPGKGLEWVS | AISGGGGNTYYADSVKG | RFTISRDNSKNTLYLQMNSLRAEDTAVYYCSK | VATDY | WGQGTLVTVSS |
| | 115 | Germline | | | QVQLVESGGGVVQPGRSLRLSCAAS | GFTFSSYGMH | WVRQAPGKGLEWVA | VIWYGDSNKYYADSVKG | RFTISRDNSKNTLTLQMNSLRAEDTAVYYCA# | ##WN##YYYGMDV | WGQGTTVTVSS |
| 30F6 | 78 | VH3-33 | D1-20 | JHB6 | QVQLVESGGGVVQPGRSLRLSCAAS | GFTFSTYGMH | WVRQAPGKGLEWVA | VIWYDGSNKYYADSVKG | RFTISRDNSKNTLYLQMNSLRAEDTAVYYCAC | SYWNDDYYYGMDV | WGQGTTVTVSS |
| | 116 | Germline | | | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | ##TMVRGVII##YYYGMDV | WGQGTTVTVSS |
| 30D7 | 2 | VH3-33 | D3-10 | JHB6 | QVPLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | GVTMVRGVIIARYYYGLDV | WGQGTTVTVSS |
| 21H9 | 6 | VH3-33 | D3-10 | JHB6 | QVPLVESGGGVVQPGRSLRLSCAAS | GFTFSSYGMH | WVRQAPGKGLEWVA | VIWYDGSNKYYADSVQG | RFTISRDNSKNTLYLQMNSLRAEDTAVYYCAR | GVTMVRGLIIARYYYGLDV | GWQGTTVTVSS |
| | 117 | Germline | | | QVQLQESGPGLVKPSETLSLTCTVS | GGSISSYYWS | WIRQPAGKGLEWIG | RIYTSGSTNYNPSLKS | RVTMSVDTSKNQFSLKLSSVTAADTAVYYCAR | ###WNY###FDY | WGQGTLVTVSS |
| 29A3 | 102 | VH4-4 | D1-7 | JH4B | QVQLQESGPGLVKPSETLSLTCTVS | GGSISSYFWS | WIRQPAGKGLEWIG | RIYFSGRTNYNPSLKS | RVTMSVETSKNQFSLKLNSVTAADTAVYYCAR | DGGWNYDVAFDY | WGQGTLVTVSS |
| | 118 | Germline | | | QVQLQESGPGLVKPSQTLSLTCTVS | GGSISSGGYYWS | WIRQHPGKLEWIG | YIYYSGSTYYNPSLKS | RVTISVDTSKNQFSLKLSSVTAADTAVYYCA# | ##SSSW##WYFDL | WGRGTLVTVSS |
| 33E1 | 50 | VH4-31 | D6-13 | JH2 | QVQLQESGPGLVKPSQTLSLTCTVS | GGSISSGDHYWS | WIRQHPGKLEWIG | HIYYSGSTDYNPSLKS | RVTISVDTSKNHFSLKLNSVTAADTAVYYCAR | TNSSSWSDWYFDL | WGRGTLVTVSS |
| | 119 | Germline | | | QLQLQESGPGLVKPSETLSLTCTVS | GGSISSSSYYWG | WIRQPPGKLEWIG | SIYYSGSTYYNPSLKS | RVTISVDTSKNQFSLKLSSVTAADTAVYYCA# | ##WLV##YFDY | WGQGTLVTVSS |
| 22B8 | 30 | VH4-39 | D6-13 | JH4B | QLQLQESGPGLVKPSETLSLTCTVS | GGSISSRYYYWG | WVRQPPGKGLEWIG | TIYYSGHTYYNPSLKT | RVTISVDTSKNQFSLKLISVTAADTAVYYCAT | QQLVLYYFDF | WGQGTLVTVSS |
| | 120 | Germline | | | QLQLQESGPGLVKPSETLSLTCTVS | GGSISSSSYYWG | WIRQPPGKGLEWIG | SIYYSGSTYYNPSLKS | RVTISVDTSKNQFSLKLSSVTAADTAVYYCAR | #QLV##YFDY | WGQGTLVTVSS |

TABLE 20a-continued

| Heavy chain analysis | | | | | | | | | | | |
|---|---|---|---|---|---|---|---|---|---|---|---|
| Chain Name | SEQ ID NO: | V | D | J | FR1 | CDR1 | FR2 | CDR2 | FR3 | CDR3 | FR4 |
| 27A3 | 10 | VH4-39 | D6-6 | JH4B | QLQLQESGPGLVKPSETLSLTCTVS | GGSISSRSDYWG | WIRQPPGKGLEWIG | TIYYSGDTYYNPSLKS | RVTISVDTSKNQFSLKLSSVTAADTAVYYCAR | QQLVLYYFDY | WGQGTLVTVSS |
| 27D10 | 14 | VH4-39 | D6-6 | JH4B | QLQLQESGPGLVKPSETLSLTCTVS | GGSISSRSDYWG | WIRQPPGKGLEWIG | TYYSGSTFYNPSLKS | RVTISVDTSKNQFSLKLSSVTAADTAVYYCAR | QQLVLYYFDY | WGQGTLVTVSS |
| 30A1 | 26 | VH4-39 | D6-6 | JH4B | QLQLQESGPGLVKPSETLSLTCTVS | GGSISSPNYYWG | WIRQPPGKGLEWIG | TIYYSGNTFYNPSLKS | RVTISVDTSKNQFSLKLSSVTAADTAVYYCAT | QQLVLYYFDF | WGQGTLVTVSS |
| 32F4 | 18 | VH4-39 | D6-6 | JH4B | QLQLQESGPGLVKPSGTLSLSCTVS | GGSISSRSDYWG | WIRQPPGKGLEWIG | TIYYSGNTFYNPSLKS | RVTISVDTSKKQFSLKLSSVTAADTAVYYCAR | QQLVLYYFDY | WGQGTLVTVSS |
| 29D4 | 22 | VH4-39 | D6-6 | JH4B | QLQLQESGPGLVKPSETLSLTCTVS | GGSISSRSNYWG | WIRQPPGKGLEWIG | TIYYSGHTYYNPSLKS | RVSISVDTSKNQFSLKLSSVTATDTALYYCAR | QQLVLYYFEY | QGQGTLVTVSS |

TABLE 20b

| Heavy chain analysis | | | | | | | | | | | |
|---|---|---|---|---|---|---|---|---|---|---|---|
| Chain Name | SEQ ID NO: | V | D | J | FR1 | CDR1 | FR2 | CDR2 | FR3 | CDR3 | FR4 |
| | 132 | | Germline | | QVQLQESGPGLVKPSSGGYYQTLSLTCTVSGGSIS | | WSWIRQHPGKGLEWIG | YIYYSGSTYYNPSLKS | RVTISVDTSKNQFSLKLSSVTAADTAVYYCAR | --SSSW--WYFDL | WGRGTLVTVSS |
| 33E1 | 50 | VH4-31 | D6-13 | JH2 | QVQLQESGPGLVKPSSGDHYQTLSLTCTVSGGSIS | | WSWIRQHPGKGLEWIG | HIYYSGSTDYNPSLKS | RVTSIDVTSKNHFSLKLNSVTAADTAVYYCAR | TNSSSWSDWYFDL | WGRGTLVTVSS |
| | 133 | | Germline | | EVQLLESGGGLVQPGSYAMS | | WVRQAPGKGLEWVS | AISGSGGSTYYADSVKG | RFTISRDNSKNTLYLQMNSLRAEDTAVYYCAK | GSGDY | WGQGTLVTVSS |
| 29A11 | 90 | VH3-23 | D1-14RC | JH4 | EVQLLESGGGLVQPGNYAMNGSLRLSCAASGFTFS | | WVRQAPGKGLEWVS | AISGGGGNTYYADSVKG | RFTISRDNSKNTLYLQMNRLRAEDTAVYYCAK | ASGDY | WGQGTLVTVSS |
| 32B2 | 82 | VH3-23 | D1-14RC | JH4 | EVQLLESGGGLVQPGNYAMSGSLRLSCAASGFTFS | | WVRQAPGKGLDWVS | AISGRGGSTYYADSVKG | RFTISRDNSKNTLFLLMNSLRAEDTAVYYCAK | ASGDD | WGQGTLVTVSS |
| 30E3 | 86 | VH3-23 | D1-14RC | JH4 | EVQLLESGGGLVQPGNYALSGSLRLSCAASGFTFS | | WVRQAPGKGLEWVS | AISGSGRNTYYADSVKG | RFTLSRDNSKNTLFLQMNSLRAEDTAVYYCAK | ASGDN | WGQGTLVTVSS |
| 30H10 | 94 | VH3-23 | D1-14RC | JH4 | EVQLLESGGGLVQPGNYAMSGSLRLSCAASGFTFS | | WVRQAPGKGLEWVS | AISGSGGITYYADSVKG | RFTISRDNSKNTLFLQMNSLRAEDTAVYYCAK | ASGDN | WGQGTLVSVSS |
| 32C11 | 98 | VH3-23 | D1-14RC | JH4 | EVQLLESGGTLVQPGNYAMSGSLRLSCAASGFTFS | | WVRQAPGKGLEWVS | AISGRAGSTYYADSVKG | RFTISRDNSKNTLFLQMNSLRAEDTAVYYCAK | ASGDD | WGQGTLVTVSS |
| | 134 | | Germline | | QLQLQESGPGLVKPSSSSYYWGETLSLTCTVSGGSIS | | WIRQPPGKGLEWIG | SIYYSGSTYYNPSLKS | RVTISVDTSKNQFSLKLSSVTAADTAVYYCAR | QQLV--YFDY | WGQGTLVTVSS |
| 22B8 | 30 | VH4-39 | D6-13 | JH4 | QLQLQESGPGLVKPSSRYYYWGETLSLTCTVSGGSIS | | WVRQPPGKGLEWIG | TIYYSGHTYYNPSLKT | RVTISVDTSKNQFSLKLISVTAADTAVYYCAT | QQLVLYYFDF | WGQGTLVTVSS |
| | 135 | | Germline | | QLQLQESGPGLVKPSSSSYYWGETLSLTCTVSGGSIS | | WIRQPPGKGLEWIG | SIYYSGSTYYNPSLKS | RVTISVDTSKNQFSLKLSSVTAADTAVYYCAR | QQLV--YFDY | WGQGTLVTVSS |

TABLE 20b-continued

| Heavy chain analysis | | | | | | | | | | | | |
|---|---|---|---|---|---|---|---|---|---|---|---|---|
| Chain Name | SEQ ID NO: | V | D | J | FR1 | CDR1 | FR2 | CDR2 | FR3 | CDR3 | FR4 |
| 30A1 | 26 | VH4-39 | D6-13 | JH4 | QLQLQESGPGLVKPSETLSLTCTVSGGSIS | SPNYYWG | WIRQPPGKGLEWIG | TIYYSGNTFYNPSLKS | RVTISVDTSKNQFSLKLSSVTAADTAVYYCAT | QQLVLYYFDF | WGQGTLVTVSS |
| 27A3 | 10 | VH4-39 | D6-13 | JH4 | QLQLQESGPGLVKPSETLSLTCTVSGGSIS | SRSDYWG | WIRQPPGKGLEWIG | TIYYSGDTYYNPSLKS | RVTISVDTSKNQFSLKLSSVTAADTAVYYCAR | QQLVLYYFDY | WGQGTLVTVSS |
| 27D10 | 14 | VH4-39 | D6-13 | JH4 | QLQLQESGPGLVKPSETLSLTCTVSGGSIS | SRSDYWG | WIRQPPGKGLEWIG | TIYYSGSTRYNPSLKS | RVTISVDTSKNQFSLKLSSVTAADTAVYYCAR | QQLVLYYFDY | QGQGTLVTVSS |
| 32F4 | 18 | VH4-39 | D6-13 | JH4 | QLQLQESGPGLVKPSGTLSLSCTVSGGSIS | SRSDYWG | WIRQPPGKGLEWIG | TIYYSGNTFYNPSLKS | RVTISVDTSKKQFSLKLSSVTAADTAVYYCAR | QQLVLYYFDY | QGQGTLVTVSS |
| 29D4 | 22 | VH4-39 | D6-13 | JH4 | QLQLQESGPGLVKPSETLSLTCTVSGGSIS | SRSNYWG | WIRQPPGKGLEWIG | TIYYSGHTYYNPSLKS | RVSISVDTSKNQFSLKLSSVTATDTALYYCAR | QQLVLYYFEY | WGQGTLVTVSS |
| | 136 | | Germline | | EVQLVESGGGLVKPGGSLRLSCAASGFTFS | SYSMN | WVRQAPGKGLEWVS | SISSSSSYIYYADSVKG | RFTISRDNAKNRLYLQMNSLRAEDTAVYYCAR | --WFGEL | WGQGTLVTVSS |
| 24B3 | 42 | VH3-21 | D3-10 | JH4 | EVQLVESGGGLVKPGGSLRLSCAASGFTFS | TYSMN | WVRQAPGKGLEWVS | FISGRSSYIYYADSVKG | RFTISRDNAKNSLYLQMNSLRAEDTAVYYCSK | DDWFEEL | WGQGTLVTVSS |
| 24C9 | 34 | VH3-21 | D3-10 | JH4 | EVQLVESGGGLVKPGGSLRLSCAASGFTFS | TYSMN | WVRQAPGKGLEWVS | FISGRSSYIYYADSVKG | RFTISRDNAKNSLYLQMNSLRAEDTAVYYCSK | DDWFEEL | WGQGTLVTVSS |
| 32G7 | 38 | VH3-21 | D3-10 | JH4 | EVQLVESGGGLVKPGGSLRLSCAASGFTIS | SYSMN | WVRQAPGKGLEWVS | FISSRSNYIYYADSVKG | RFTISRDNAKNSLYLQMNSLRAEDTAVYYCSK | DDFEEL | WGQGTLVTVSS |
| 33B1 | 46 | VH3-21 | D3-10 | JH4 | EVQLVESGGGLVKPGGSLRLSCAASGFTFS | SYTMN | WVRQAPGKGLEWVS | FIDSRSSYIYYADSVKG | RFTISRDNAKNSLYLQMNSLRAEDTAVYYCSK | DDWFEEL | WGQGTLVTVSS |
| | 137 | | Germline | | QVQLQESGPGLVKPSETLSLTCTVSGGSIS | SYYWS | WIRQPAGKGLEWIG | RIYTSGSTNYNPSLKS | RVTMSVDTSKNQFSLKLSSVTAADTAVYYCAR | ---WNY---FDY | WGQGTLVTVSS |
| 29A3 | 102 | VH4-4 | D1-7 | JH4 | QVQLQESGPGLVKPSETLSLTCTVSGGSIS | SYFWS | WIRQPAGKGLEWIG | RIYFSGRTNYNPSLKS | RVTMSVETSKNQFSLKLNSVTAADTAVYYCAR | DGGWNYDVAFDY | WGQGTLVTVSS |
| | 138 | | Germline | | QVQLVQSGAEVKKPGASVKVSCKASGYTFT | SYDIN | WVRQATGQGLEWMG | WMNPNSGNTGYAQKFQG | RVTMTRNTSISTAYMELSSLRSEDTAVYYCAR | -GYS---WFDP | WGQGTLVTVSS |
| 29F7 | 62 | VH1-08 | D6-13 | JH5 | QVQLVQSGAEVKKPGQSVKVSCKASGYTFT | SYDIN | WVRQATGQGLEWMG | WMNPNSGKTGYAQKFQG | RVTMTRSTSISTAYMELSSLRSEDTAVYYCAR | GGYSNLGWFDP | WGQGTLVTVSS |
| 33D5 | 58 | VH1-08 | D6-13 | JH5 | QVQLVQSGAEVKKPGASVKVSCKASGYTFG | SYDIN | WVRQATGQGLEWMG | WMNPNSGNTGYAQKFQG | RVTLTRNTSIRTVYMELSSLRSEDTAVYYCAR | GGYSNLGWFDP | WGQGSLVTVSS |
| 29H3 | 54 | VH1-08 | D6-13 | JH5 | QVQLVQSGAEVKKPGASVKVSCKASGYTFT | SYDIN | VWRQATGQGLEWMG | WMNPNSGKTGYAQKFQG | RVTMTRNTSINTAYMELSSLRSEDTAVYYCAR | GGYSNLGWFDP | WGQGTLVTVSS |
| | 139 | | Germline | | QVQLVESGGGLVKPGGSLRLSCAASGFTFS | DYYMS | WIRQAPGKGLEWVS | YISSSGSTIYYADSVKG | RFTISRDNAKNSLYLQMNSLRAEDTAVYYCAR | ---YSSGWY-YFDY | WGQGTLVTVSS |
| 21A1 = 21H6 | 66 | VH3-11 | D6-19 | JH4 | QVQLVESGGGLVKPGGSLRLSCAASGFTFS | DYYMS | WIRQAPGKGLEWVS | YISNSGITIYYADSVKG | RFTISRDNAKNSLYLQMNSLRAGDTAVYYCAR | EEWYSSSWYRNFDY | WGQGTLVTVSS |
| | 140 | | Germline | | QVQLVESGGGLVKPGGSLRLSCAASGFTFS | DYYMS | WIRQAPGKGLEWVS | YISSSGSTIYYADSVKG | RFTISRDNAKNSLYLQMNSLRAEDTAVYYCAR | -DFWSGYY-NWFDP | WGQGTLVTVSS |

TABLE 20b-continued

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| 31E11 | 70 | VH3-11 | D3-3 | JH5 | QVQLVESGGGLVKPGDYYMS GSLRLSCAASGFTFS | | WIRQAPGK GLEWVS | YISISGST IYYADSVK G | RFTISRDNAKN SLYLQMNSLRA EDTAVYYCAR | DDFWSGYYFN WFDP | WGQGTLVT VSS |
| 33C3 | 74 | VH3-11 | D3-3 | JH5 | QVQLVESGGGLVKPGDYYMS ESLRLSCAASGFTFS | | WIRQPAGK GLEWVS | YISHGGST IYYADSVK G | RFTISRDNAKN SLYLQMNSLRV EDTAVYFCAR | DDFWSGYYFN WFDP | WGQGALVT VSS |
| | 141 | | Germline | | QVQLVESGGGVVQPGSYGMH RSLRLSCAASGFTFS | | WVRQAPGK GLEWVA | VIWYDGSN KYYADSVK G | RFTISRDNSKN TLYLQMNSLRA EDTAVYYCAR | --TMVRGVII- -YYYGMDV | WGQGTTVT VSS |
| 21H9 | 6 | VH3-33 | D3-10 | JH6 | QVPLVESGGGVVQPGSYGMH RSLRLSCAASGFTFS | | WVRQAPGK GLEWVA | VIWYDGSN KYYADSVQ G | RFTISRDNSKN TLYLQMNSLRA EDTAVYYCAR | GVTMVRGLII ARYYYGLDV | WGQGTTVT VSS |
| 30D7 | 2 | VH3-33 | D3-10 | JH6 | QVPLVESGGGVVQPGSYGMH RSLRLSCAASGFTFS | | WVRQAPGK GLEWVA | VIWYDGSN KYYADSVK G | RFTISRDNSKN TLYLQMNSLRA EDTAVYYCAR | GVTMVRGVII ARYYYGLDV | WGQGTTVT VSS |
| | 142 | | Germline | | QVQLVESGGGVVQPGSYGMH RSLRLSCAASGFTFS | | WVRQAPGK GLEWVA | VIWYDGSN KYYADSVK G | RFTISRDNSKN TLYLQMNSLRA EDTAVYYCAR | --WND- YYYGMDV | WGQGTTVT VSS |
| 30F6 | 78 | VH3-33 | D1-20 | JH6 | QVQLVESGGGVVQPGTYGMH RSLRLSCAASGFTFS | | WVRQAPGK GLEWVA | VIWYDGSN KYYADSVK G | RFTISRDNSKN TLYLQMNSLRA EDTAVYYCAC | SYWNDDYYYG MDV | WGQGTTVT VSS |
| | 143 | | Germline | | EVQLLESGGGLVQPGSYAMS GSLRLSCAASGFTFS | | WVRQAPGK GLEWVS | AISGSGGS TYYADSVK G | RFTISRDNSKN TLYLQMNSLRA EDTAVYYCAK | VATDY | WGQGTLVT VSS |
| 1G6 | 131 | VH3-23 | D5-12 | JH4 | WVQLLESGGGLVQPGSYAMS GSLRLSCAASGFTFS | | WVRQAPGK GLEWVS | AISGGGGN TYYADSVK G | RFTISRDNSKN TLYLQMNSLRA EDTAVYYCSK | VATDY | WGQGTLVT VSS |

TABLE 21a

Light chain analysis

| Chain Name | SEQ ID NO: | V | J | FR1 | CDR1 | FR2 | CDR2 | FR3 | CDR3 | FR4 |
|---|---|---|---|---|---|---|---|---|---|---|
| | 121 | Germline | | DIVMTQTPLSSPV TLGQPASISC | RSSQSLVHS- DGN TYLS | WLQQRPGQPPR LLIY | KISNRFS | GVPDRFSGSGAGTDFT LKISRVEAEDVGVYYC | GQATQ FPLT | FGGGT KVEIK |
| 30D7 | 4 | A23 | JK4 | DIVMTQTPLSSPV TLGQPASISC | RSSQSLVHS- DGN TYLS | WLQQRPGQPPR LLIY | KISNRFF | GVPDRFSGSGAGTDFT LKIGRVEAEDVGLYYC | MQSTQ FPLT | FGGGT KVEIK |
| 21H9 | 8 | A23 | JK4 | DIVMTQTPLSSPV TFGQPASISC | RSSQLSVHS- DGN TYLS | WLQQRPGQPPR LLIY | KISNRFF | GVPDRFSGSGAGTDFT LKISRVEAEDVGLYYC | MQSTQ FPLT | FGGGT KVEIK |
| | 122 | Germline | | EIVLTQSPGTLSL SPGERATLSC | RASQSVSS- SYLA | WYQQKPGQAPR LLIY | GASSRAT | GIPDRFSGSGSGTDFT LTISRLEPEDFAVYYC | QQYGS SPPLT | FGGGT KVEIK |
| 27A3 | 12 | A27 | JK4 | EIVLTQSPGLTLSL SPGERATLSC | RASWSVSS- SYLA | WYQQKPGQAPR LLIY | ATSNRAT | GIPDRFSGSGSGTDFT LTISRLEPEDFAVYYC | QQHGS SPPLT | FGGGT KVEIK |
| 27D10 | 16 | A27 | JK4 | EIVLTQSPGTLSL SPGERATLSC | RASQSVSS- SYLA | WYQQKPGQAPR LLIY | GASSRAT | GIPDRFSGSGSGTDFT LTISRLEPEDFAVYYC | QQYGS SPPLT | FGGGT KVEIK |
| 32F4 | 20 | A27 | JK4 | EIVLTQSPGTLSL SPGERATLSC | RTSQSVSS- SYLA | WYQQKPGQAPR LLIY | GASSRAT | GVPDRFSGSGSGTDFS LTISRLEPEDFAVYYC | QQYGS SPPLT | FGGGT KVEIK |

TABLE 21a-continued

| Light chain analysis | | | | | | | | | | |
|---|---|---|---|---|---|---|---|---|---|---|
| Chain Name | SEQ ID NO: | V | J | FR1 | CDR1 | FR2 | CDR2 | FR3 | CDR3 | FR4 |
| 29D4 | 24 | A27 | JK4 | EIVLTQSPGTLSL SPGERATLSC | RASQSISR- SYLA | WYQQKPGQAPR LLIY | GASSRAT | GIPDRFSGSGSGTDFT LTISRLEPEDFAVYYC | QQYGS SPPLT | FGGGT KVEIK |
| | 123 | Germline | | EIVLTQSPGTLSL SPGERATLSC | RASQSVSS- SYLA | WYQQKPGQAPR LLIY | GASSRAT | GIPDRFSGSGSGTDFT LTISRLEPEDFAVYYC | QQYG# #IT | FGQGT RLEIK |
| 30A1 | 28 | A27 | JK5 | EIVLTQSPGTLSL SPGKRAALSC | RASQSISS- SYLA | WYQQKPGQAPR LLIY | GASSRAT | GIPDRFNGSGSGTDFT LTISRLEPEDFAVYYC | QQLGS SIT | FGQGT RLEIK |
| 22B8 | 32 | A27 | JK5 | EIVLTQSPGTLSL SPGERAALSC | RASQSISS- SYLA | WYQQRPGQAPR LLIY | GASSRAT | GIPDRFNGSGSGTDFT LTISRLEPEDFAVYYC | QQFGS SIT | FGQGT RLEIK |
| | 124 | Germline | | DIQMTQSPSSLSA SVGDRVTITC | RASQGRINDLG | WYQQKPGKAPK RLILY | AASSLQS | GVPSRFSGSGSGTEFT LTISSLQPEDFATYYC | LQHNS YPWT | FGQGT KVEIK |
| 24C9 | 36 | A30 | JK1 | DIQMTQSPSSLSA SVGDRVTITC | RASQGIRNDLG | WYQQKPGKAPK RLIY | ATFSLQS | GVPSRFSGSGSGTEFT LTISSLQPEDFATYYC | LQHNR YPWT | FGQGT KVEIK |
| 32G7 | 40 | A30 | JK1 | DIQMTQSPSSLSA SVGDRVTITC | RASQDIRNDLG | WYQQKPGKAPK RLIY | AASSLQS | GVPSRFSGSGSGTEFT LTISSLQPEDFATYYC | LQHNS FPWT | FGQGT KVEIK |
| 24B3 | 44 | A30 | JK1 | DIQMTQSPSSLSA SVGDRVTITC | RASQGIRSDLG | WYQQKPGKAPK RLIY | ATSSLQS | GVPSRFSGSGSGTEFT LTISSLQPEDFATYYC | LQHNR YPWT | FGQGT KVEIK |
| 33B1 | 48 | A30 | JK1 | DIQMTQSPSSLSA SVGDRVTITC | RASQGIRNDLG | WYQQKPGKAPK RLIY | ATSSLQS | GVPSRFSGSGSGTEFT LTISSLQPEDFATYYC | LHHNS FPWT | DGQGT KVEIK |
| | 125 | Germline | | DIVMTQSPDSLAV SLGERATINC | KSSQSV- LYSSNN KNYLA | WYQQKPGQPPK LLIY | WASTRES | GVPDRFSGSGSGTDFT LTISSLQAEDVAVYYC | QQYYS TPWT | FGQGT KVEIK |
| 33E1 | 52 | B3 | JK1 | DIVMTQSPDSLAV SLGERATINC | KSSQS- ILYSSNN KNYLA | WYQRKPGQPPI LLIH | WASTRES | GVPDRFSGSGSRTDFT LTISSLQAEDVAVYYC | QQYFI TPWT | FGQGT KVEIK |
| | 126 | Germline | | DIQMTQSPSSVSA SVGDRVTITC | RASQGISSWLA | WYQQKPGKAPK LLIY | AASSLQS | GVPSRFSGSGSGTDFT LTISSLQPEDFATYYC | QQANS FPFT | FGPGT KVDIK |
| 29H3 | 56 | L5 | JK3 | DIQMTQSPSSVSA SVGDRVTITC | RASQGISSWLV | WYHQKPGKAPK LLIY | GASSLQS | GVPSRFSGSGSGTDFT LTISSLQPEDFATYYC | QQANN FPFT | FGPGT KVDIK |
| 33D5 | 60 | L5 | JK3 | DIQMTQSPSSVSV SVGDRVTITC | RASQGISSWLA | WYQQKPGKAPK LLIY | AASSLQS | GVPSRFSGSGSGTDFT LTISSLQPEDFATYYC | QQANS FPFT | FGPGT KVDIK |
| 29F7 | 64 | L5 | JK3 | DIQMTQSPSSVFA SVGDRVTITC | RASQGISTWLA | WYQQKPGKAPK FLIY | AASSLQS | GVPSRFSGSGSGTDFT LTISSLQPDDFATYYC | QQANN FPFT | FGPGT KVDIK |
| | 127 | Germline | | DIQMTQSPSSLSA SVGDRVTITC | RASQSISSYLN | WYQQKPGKAPK LLIY | AASSLQS | GVPSRFSGSGSGTDFT LTISSLQPEDFATYYC | QQSYS T##T | FGGGT KVEIK |
| 21A1 | 68 | O2 | JK4 | DIQMTQFSSSLSA SVGDRVTITC | RASQSISRYLN | WYQQKPGKAPK LLIY | AASSLQS | GVPSRFNSGSGSGT- DFT LTISSLQPEDFATYYC | QQSYS APLT | FGGGT KVEIK |
| 21H6 | 68 | O2 | JK4 | DIQMTQFSSSLSA SVGDRVTITC | RASQSISRYLN | WYQQKPGKAPK LLIY | AASSLQS | GVPSRFNGSGSGTDFT LTISSLQPEDFATYYC | QQSYS APLT | FGGGT KVEIK |
| 31E11 | 72 | O2 | JK4 | DIQMTQFSSSLSA SVGDRVTITC | RANQTISTFLN | WYQQNPGKAPK LLIY | AASSLQS | GFPSRFSGSGSTDFT LTISSLQPEDFATYYC | QQTYI IPLT | FGGGT KVEIK |
| 33C3 | 76 | O2 | JK4 | DIQMTQYPLSLSA SVGDRVTITC | RASQSISSFLN | WYHQKPGKAPK LLIY | GTSSLQS | GVPSRFSGSGSGTDFT LTISSLQPEDFATYYC | QQTYS IPLT | FGGGT NVEIK |
| 30F6 | 80 | O2 | JK4 | DIQMTQSPSSLSA SVGDRVIITC | RASQNISSYLI | WYQQKPGKAPN LLIH | TTSSLQR | GVPSRFSGSGSGTDFT LTISSLQPEDFATYYC | QQSYS APLT | FGGGT KVEIK |
| | 128 | Germline | | QSVLTQPPSASGT PGQRVTISC | SGSSSNIG- SNTV N | WYQQLPGTAPK LLIY | SNNQRPS | GVPDRFSGSKSGTSAS LAISGLQSEDEADYYC | AAWDDS LNGYV | FGTGT KVTVL |

TABLE 21a-continued

Light chain analysis

| Chain Name | SEQ ID NO: | V | J | FR1 | CDR1 | FR2 | CDR2 | FR3 | CDR3 | FR4 |
|---|---|---|---|---|---|---|---|---|---|---|
| 32B2 | 84 | V1-16 | JL1 | QSVLTQPPSASGT PGQRVTISC | SGSSSNIG- SNTV N | WYQQLPGTAPK LLIY | LNNQRPS | GVPDRFSGSKSGTSAS LAISGLQSEDEADYYC | SAWDDS LNGYV | FGTGT KVTVL |
| 30E3 | 88 | V1-16 | JL1 | QSVLTQPPSASGT PGQRVTISC | SGSSSNIG- SNTV N | WYQQLPGTAPK LLIY | LNNQRPS | GVPDRFSGSKSGTSAS LAISGLQSEDEADYYC | SAWDDS LNGYV | FGTGT KVTVL |
| 29A11 | 92 | V1-16 | JL1 | WSVLTQPPSASGT PGQRVTISC | SGSSSNIG- SNTV N | WYQQLPGTAPK LLIY | LNNQRPS | GVPDRFSGSKSGTSAS LAISGLQSEDEADFYC | AAWDDS LNGYV | FGTGT KVTVL |
| 30H10 | 96 | V1-16 | JL1 | QSVLTQPPSASGT PGQRVTISC | SGSSSNIG- SNTV N | WYQQLPGTAPK LLIY | LNNQRPS | GVPGRFSGSKSGTSAS LAISGLQSESEADYYC | SAWDDS LNGYV | FGTGT KVTVL |
| 32C11 | 100 | V1-16 | JL1 | QSVLTQPPSASGT PGQRVTISC | SGSSSNIG- SNTV N | WYHQLPGTAPK LLIY | LNNQRPS | GVPDRFSGSKSGTAS LASIGLQSEDEADYYC | SAWDDS LNGYV | FGTGT KVTVL |
| | 129 | Germline | | QAVLTQPSSLSAS PGASASLTC | TLRSGINVG- TYR IY | WYQQKPGSPPQ YLLR | YKSDSDK | QQGSGVPSRFSGSKDA SANAGILLISGLQSED | EADYY GMIWH S###V | FGGGT KLTVL |
| 29A3 | 104 | V4-2 | JL3 | QAVLTQPSSLSAS PGASASLTC | TLRSGINVG- TYR IY | WYQQKPGSPPQ YLLR | YKSDSDQ | LQGSGVPSRFSGSKDA SANAGILLISGLQSED | EADYY CMVWH SNTWV | FGGGT KLTVL |
| | 130 | Germline | | QPVLTQSSSASAS LGSSVKLTC | TLSSGH- SSYIIA | WHQQQPGKAPR YLMK | LEGSGSY | NKGSGVPDRFSGSSSG ADRYLTISNLQFEDEA | DYYCE TWDSN TVV | FGGGT KLTVL |
| 1G6 | 108 | V5-4 | JL2 | QPVLTQSSSASAS LGSSVKLTC | TLSSGH- SSYIIA | WHQQQPGKAPR YLMK | LEGSGSY | NKGSGVPDRFSGSSSG ADRYLTISNLQFEDEA | DYYCE TWDSY TVV | FGGGT KLTVL |

TABLE 21b

Light chain analysis

| Chain Name | SEQ ID NO: | V | J | FR1 | CDR1 | FR2 | CDR2 | FR3 | CDR3 | FR4 |
|---|---|---|---|---|---|---|---|---|---|---|
| | 144 | Germline | | DIVMTQSPDSLA VSLGERATINC | KSSQSVLYS SNNKNYLA | WYQQKPGQ PPKLLIY | WASTRES | GVPDRFSGS GSGTDFTLT ISSLQAEDV AVYYC | QQYYST PWT | FGQGTKV EIK |
| 33E1 | 52 | B3 | JK1 | DIVMTQSPDSLA VSLGERATINC | KSSQSILYS SNNKNYLA | WYQRKPGQ PPILLIH | WASTRES | GVPDRFSGS GSRTDFTLT ISSLQAEDV AVYYC | QQYFIT PWT | FGQGTKV EIK |
| | 145 | Germline | | QSVLTQPPSAS GTPGQRVTISC | SGSSSNIGS NTVN | WYQQLPGT APKLLIY | SNNQRPS | GVPDRFSGS KSGTSASLA ISGLQSESE ADYYC | AAWDDS LNGYV | FGTGTKV TVL |
| 29A11 | 92 | VL 1c | JL1 | QSVLTQPPSAS GTPGQRVTISC | SGSSSNIGS NTVN | WYQQLPGT APKLLIY | LNNQRPS | GVPDRFSGS KSGTSASLA ISGLQSESE ADFYC | AAWDDS LNGYV | FGTGTKV TVL |
| 32B2 | 84 | VL 1c | JL1 | QSVLTQPPSAS GTPGQRVTISC | SGSSSNIGS NTVN | WYQQLPGT APKLLIY | LNNQRPS | GVPDRFSGS ISGTSASLA ISGLQSESE ADYYC | SAWDDS LNGYV | FGTGTKV TVL |

TABLE 21b-continued

| Light chain analysis | | | | | | | | | | |
|---|---|---|---|---|---|---|---|---|---|---|
| Chain Name | SEQ ID NO: | V | J | FR1 | CDR1 | FR2 | CDR2 | FR3 | CDR3 | FR4 |
| 30E3 | 88 | VL 1c | JL1 | QSVLTQPPSAS GTPGQRVTISC | SGSSSNIGS NTVN | WYQQLPGT APKLLIY | LNNQRPS | GVPDRFSGS KSGTSASLA ISGLQSESE ADYYC | SAWDDS LNGYN | FGTGTKV TVL |
| 30H10 | 96 | VL 1c | JL1 | QSVLTQPPSAS GTPGQRVTISC | SGSSSNIGS NTVN | WYQQLPGT APKLLIY | LNNQRPS | QVPGRFSGS KSGTSASLA ISGLQSESE ADYYC | SAWDDS LNGYV | FGTGTKV TVL |
| 32C11 | 100 | VL 1c | JL1 | QSVLTQPPSAS GTPGQRTVISC | SGSSSNIGS NTVN | WYHQLPGT APKLLIY | LNNQRPS KSGTSASLA | GVPDRFSGS LNGYV ISGLQSESE ADYYC | SAWDDS TVL | FGTGTKV |
| | 146 | Germline | | EIVLTQSPGTL SLSPGERATLS C | RASQSVSSS YLA | WYQQKPGQ APRLLIY | GASSRAT | GIPDRFSGS GSGTDFTLT ISRLEPEDF AVYYC | QQYGSS PIT | FGQGTRL EIK |
| 22B8 | 32 | VK A27 | JK5 | EIVLTQSPGTL SLSPGERAALS | RASQSISSS YLA | WYQQRPGQ APRLLIY | GASSRAT | GIPDRFNGS GSGTDFTLT ISRLEPEDF AVYYC | QQFGSS -IT | FGQGTRL EIK |
| 30A1 | 28 | VK A27 | JK5 | EIVLTQSPGTL SLSPGKRAALS | RASQSISSS YLA | WYQQKPGQ APRLLIY | GASSRAT | GIPDRFNGS GSGTDFTLT ISRLEPEDF AVYYC | QQLGSS -IT | RGQGTRL EIK |
| | 147 | Germline | | DIQMTQSPSSL SASVGDRVTIT C | RASQGIRND LG | WYQQKPGK APKRLIY | AASSLQS | GVPSRFSGS GSGTEFTLT ISSLQPEDF ATYYC | LQHNSY PWT | FGQGTKV EIK |
| 24B3 | 44 | VK A30 | JK1 | DIQMTQSPSSL SASVGDRVTIT C | RASQGIRSD LG | WYQQKPGK APKRLIY | ATSSLQS | GVPSRFSGS GSGTEFTLT ISSLQPEDF ATYYC | LQHNRY PWT | FGQGTKV EIK |
| 24C9 | 36 | VK A30 | JK1 | DIQMTQSPSSL SASVGDRVTIT C | RASQGIRND LG | WYQQKPGK APKRLIY | ATFSLQS | GVPSRFSGS GSGTEFTLT ISSLQPEDF ATYYC | LQHNRY PWT | FGQGTKV EIK |
| 32G7 | 40 | VK A30 | JK1 | DQIMTQSPSSL SASVGDRVTIT C | RASQDIRND LG | WYQQKPGK APKRLIY | AASSLQS | GVPSRFSGS GSGTEFTLT ISSLQPEDF ATYYC | QLHNSF PWT | FGQGTKV EIK |
| 33B1 | 48 | VK A30 | JK1 | DIQMTQSPSSL SASVGDRVTIT C | RASQGIRND LG | WYQQKPGK APKRLIY | ATSSLQS | GVPSRFSGS GSGTEFTLT ISSLQPEDF ATYYC | LHHNSF PWT | FGQGTKV EIK |
| | 148 | Germline | | QAVLTQPASLS ASPGASASLTC | TLRSGINVG TYRIY | WYQQKPGS PPQYLLR | YKSDSDKQQ GS | GVPSRFSGS KDASANAGI LLISGLQSE DEADYYC | MIWHSS ASV | FGGGTKL TVL |
| 29A3 | 104 | VL 5c | JL2 JL3 | +QAVLTQPSSLS ASPGASASLTC | TLRSGINVG TYRIY | WYQQKPGS PPQYLLR | YKSDSDQLQ GS | GVPSRFSGS KDASANAGI LLISGLQSE DEADYYC | MVWHSN TWV | FGGGTKL TVL |
| | 149 | Germline | | EIVLTQSPGTL SLSPGERATLS C | RASQSVSSS YLA | WYQQKPGQ APRLLIY | GASSRAT | GIPDRSSGS GSGTFTLT ISRLEPEDF AVYYC | QQYGSS PPLT | FGGGTKV EIK |
| 27A3 | 12 | VK A27 | JK4 | EIVLTQSPGTL SLSPGERATLS C | RASQSVSSS YLA | WYQQKPGQ APRLLIY | ATSNRAT | GIPDRFSGS GSGTDFTLT ISRLEPEDF AVYYC | QQHGSS PPLT | FGGGTKV EIK |

TABLE 21b-continued

| Light chain analysis | | | | | | | | | | |
|---|---|---|---|---|---|---|---|---|---|---|
| Chain Name | SEQ ID NO: | V | J | FR1 | CDR1 | FR2 | CDR2 | FR3 | CDR3 | FR4 |
| 27D10 | 16 | VK A27 | JK4 | EIVLTQSPGTL SLSPGERATLS C | RASQSVSSS YLA | WYQQKPGQ APRLLIY | GASSRAT | GIPDRFSGS GSGTDFTLT ISRLEPEDF AVYYC | QQYGSS PPLT | FGGGTKV EIK |
| 32F4 | 20 | VK A27 | JK4 | EIVLTQSPGTL WLSPGERATLS C | RTSQSVSSS YLA | WYQQKPGQ APRLLIY | GASSRAT | GVPDRFSGS GSGTDFSLT ISRLEPEDF AVYYC | QQYGSS PPLT | FGGGTKV EIK |
| 29D4 | 24 | VK A27 | JK4 | EIVLTQSPGTL SLSPGERATLS C | RASQSISRS YLA | WYQQKPGQ APRLLIY | GASSRAT | GIPDRFSGS GSGTDFTLT ISRLEPEDF AVYYC | QQYGSS PPLT | FGGGTKV EIK |
| | 150 | Germline | | DIQMTQSPSSV SASVGDRVTIT C | RASQGISSW LA | WYQQKPGK APKLLIY | AASSLQS | GVPSRFSGS GSGTDFTLT ISSLQPEDF ATYYC | QQANSF PFT | FGPGTKV DIK |
| 29F7 | 64 | VK L5 | JK3 | DIQMTQSPSSV FASVGDRVTIT C | RASQGISTW LA | WYQQKPGK APKFLIY | AASSLQS | GVPSRFSGS GSGTDFTLT ISSLQPDDF ATYYC | QQANNF PFT | FGPGTKV DIK |
| 29H3 | 56 | VK L5 | JK3 | DIQMTQSPSSV SASVGDRVTIT C | RASQGISSW LV | WYHQKPGK APKLLIY | GASSLQS | GVPSRFSGS GSGTDFTLT ISSLQPEDF ATYYC | QQANNF PFT | FGPGTKV DIK |
| 33D5 | 60 | VK L5 | JK3 | DIQMTQSPSSV SVSVGDRVTIT C | RASQGISSW LA | WYQQKPGK APKLLIY | AASSLQS | GVPSRFSGS GSGTDFTLT ISSLQPEDF ATYYC | QQANSF PFT | FGPFTKV DIK |
| | 151 | Germline | | DIQMTQSPSSL SASVGDRVTIT C | RASQSISSY LN | WYQQKPGK APKLLIY | AASSLQS | GVPSRFSGS GSGTDFTLT ISSLQPEDF ATYYC | QQSYST PLT | FGGGTKV EIK |
| 21A1 = 21H6 | 68 | VK O2 + O12 | JK4 | DIQMTQFSSSL SASVGDRVTIT C | RASQSISRY LN | WYQQKPGK APKLLIY | AASSLQS | GVPSRFNGS GSGTDFTLT ISSLQPEDF ATYYC | QQSYSA PLT | FGGGTKV EIK |
| 31E11 | 72 | VK O2 + O12 | JK4 | DIQMTQSPSSL SASVGDRVTIT C | RANQTISTF LN | WYQQNPGK APKLLIY | AASSLQS | GVPSRFSGS GSGTDFTLT ISSLQPEDF ATYYC | QQTYII PLT | FGGGTKV EIK |
| 33C3 | 76 | VK O2 + O12 | JK4 | DIQMTQYPLSL SASVGDRVTIT C | RASQSISSF LN | WYHQKPGK APKLLIY | GTSSLQS | GVPSRFSGS GSGTDFTLT ISSLQPEDF ATYYC | QQTYSI PLT | FGGGTNV EIK |
| 30F6 | 80 | VK O2 + O12 | JK4 | DIQMTQSPSSL SASVGDRVIIT C | RASQNISSY LI | WYQQKPGK APNHLIH | TTSSLQR | GVPSRFSGS GSGTDFTLT ISSLQPEDF ATYYC | QQSYSA PLT | FGGGTKV EIK |
| | 152 | Germline | | DIVMTQTPLSS PVTLGQPASIS C | RSSQSLVHS DGNTYLS | WLQQRPGQ PPRLLIY | KISNRFS | GVPDRFSGS GAGTDFTLK ISRVEAEDV GVYYC | MQATQF PLT | FGGGTKV EIK |
| 21H9 | 8 | VK A23 | JK4 | DIVMTQTPLSS PVTFGQPASIS C | RSSQSLVHS DGNTYLS | WLQQRPGQ PPRLLIY | KISNRFF | GVPDRFSGS GAGTDFTLK ISRVEAEDV GLYYC | MQSTQF PLT | FGGGTKV EIK |
| 30D7 | 4 | VK A23 | JK4 | DIVMTQTPLSS PVTLGQPASIS C | RSSQSLVHS DGNTYLS | WLQQGPGQ PPRLLIY | KISNRFF | GVPDRFSGS GAGTDFTLK IGRVEAEDV GLYYC | MQSTQF PLT | FGGGTKV EIK |

TABLE 21b-continued

| Light chain analysis | | | | | | | | | | |
|---|---|---|---|---|---|---|---|---|---|---|
| Chain Name | SEQ ID NO: | V | J | FR1 | CDR1 | FR2 | CDR2 | FR3 | CDR3 | FR4 |
| | 153 | Germline | | QPVLTQSSSAS ASLGSSVKLTC | TLSSGHSSY IIA | WHQQQPGK APRYLMK | LEGSGSYNK GS | GVPDRFSGS SSGADRYLT ISNLQLEDE ADYYC | ETWDSN TVV | FGGGTKL TVL |
| 1G6 | 108 | VL 4a | JL2 JL3 | +QPVLTQSSSAS ASLGSSVKLTC | TLSSGHSSY IIA | WHQQQPGK APRYLMK | LEGSGSYNK GS | GVPDRFSGS SSGADRYLT ISNLQFEDE ADYYC | ETWDSY TVV | FGGGTKL TVL |

Example 11

Potency Determination of KDR Antibodies

The potency of the candidate KDR antibodies was determined to discriminate candidate antibodies based on their ability to prevent the VEGF165-induced tyrosine phosphorylation of KDR in HUVEC cells. This assay was performed with two different conditions, one with a one hour pre-incubation of antibody with HUVEC cells at 4° C. and the second with a 24-hour pre-incubation of antibody with HUVEC cells at 37° C.

HUVEC cells were seeded at 25,000 cells/well in supplemented media (EMB-2+2% FCS) and incubated overnight at 37° C. The cells were then incubated overnight in media without supplement at 37° C. On day 3, 50 μL/well of candidate antibody titration or serum-free media (for control) was added to the HUVEC cells. The cells were pre-incubated with candidate antibody for either one hour at 4° C. or for 24 hours at 37° C. After the pre-incubation period, the cells were stimulated with 50 μL of 2 nM VEGF165 (Calbiochem) and subsequently lysed. Cell lysates were then assayed by ELISA.

Table 22 shows assay results for the candidate antibodies after a one hour pre-incubation period. Table 23 shows the results for the candidate antibodies after a 24 hour pre-incubation period.

TABLE 22

ELISA Results from Inhibition Potency Assay (1-hour Pre-incubation at 4° C.)

| | Activity at 133 nM (% Inhibition) | | |
|---|---|---|---|
| MAb ID | N = 1 | N = 2 | Average |
| 33D5 | 39% | 60% | 49% |
| 1G6 | 35% | 50% | 43% |
| 29A11 | 30% | 33% | 32% |
| 32G7 | 79% | 79% | 79% |
| 29D4 | 64% | 73% | 68% |
| 30E3 | 29% | 37% | 33% |
| 33B1 | 86% | 88% | 87% |
| 33C3 | 78% | 83% | 80% |
| 29F7 | 36% | 52% | 44% |
| 27A3 | 63% | 72% | 67% |
| 21H9 | 21% | 31% | 26% |
| 27D10 | 60% | 69% | 65% |
| 32F4 | 60% | 68% | 64% |
| 30D7 | 26% | 28% | 27% |
| 32B2 | 25% | 33% | 29% |
| 22B8 | 75% | 76% | 76% |
| 29H3 | 45% | 55% | 50% |
| 21H6 | 74% | 75% | 74% |
| 30F6 | 84% | 85% | 84% |
| 29A3 | 25% | 20% | 23% |

TABLE 22-continued

ELISA Results from Inhibition Potency Assay (1-hour Pre-incubation at 4° C.)

| | Activity at 133 nM (% Inhibition) | | |
|---|---|---|---|
| MAb ID | N = 1 | N = 2 | Average |
| 30H10 | 31% | 21% | 26% |
| 24B3 | 80% | 80% | 80% |
| 32C11 | 32% | 21% | 27% |
| 31E11 | 82% | 80% | 81% |
| 33E1 | 78% | 75% | 77% |
| 24C9 | 81% | no material | 81% |

TABLE 23

ELISA Results from Inhibition Potency Assay (24-hour Pre-incubation at 37° C.)

| | Activity at 133 nM (% Inhibition) | | |
|---|---|---|---|
| MAb ID | N = 1 | N = 2 | Average |
| 33D5 | 8% | −38% | −15% |
| 1G6 | 25% | 47% | 36% |
| 29A11 | 19% | 27% | 23% |
| 32G7 | 36% | 77% | 57% |
| 29D4 | 75% | 85% | 80% |
| 30E3 | 69% | 97% | 83% |
| 33B1 | 88% | 82% | 85% |
| 33C3 | 45% | 88% | 67% |
| 29F7 | 23% | 30% | 26% |
| 27A3 | 19% | 0% | 9% |
| 21H9 | −3% | 2% | −1% |
| 27D10 | 19% | −4% | 8% |
| 32F4 | 25% | 18% | 22% |
| 30D7 | 39% | 37% | 38% |
| 32B2 | 38% | 61% | 49% |
| 22B8 | 82% | 115% | 99% |
| 29H3 | 1% | 36% | 19% |
| 21H6 | 35% | 19% | 27% |
| 30F6 | 60% | 51% | 55% |
| 29A3 | 7% | 15% | 11% |
| 30H10 | 48% | 77% | 62% |
| 24B3 | 76% | 69% | 72% |
| 32C11 | 73% | 73% | 73% |
| 31E11 | 90% | 48% | 69% |
| 33E1 | 85% | 68% | 77% |
| 24C9 | 46% | no material | 46% |

Example 12

Characterization of KDR Antibodies to Deliver Agonist Signal

The next assay was conducted in order to characterize the ability of anti-KDR antibodies ability to deliver an agonist signal.

HUVEC cells were seeded at 25,000 cells/well in supplemented media (EMB-2+2% FCS) and incubated overnight at 37° C. The media was then replaced with supplement-free media (EMB-2), and the cells were incubated overnight at 37° C. On day 3, the supplement-free media was replaced with 50 μL/well of candidate antibody titration or serum-free media (for control), and the cells were incubated with candidate antibody for one hour at 4° C. After the pre-incubation period, the cells were stimulated with 2 nM VEGF-165 (Calbiochem) and subsequently lysed. Cell lysates were then assayed by ELISA.

Table 24 shows assay results for the candidate antibodies as a percentage of phosphorylation activity compared to that induced by VEGF-165.

TABLE 24

ELISA Results from Agonist Activity Assay

| MAb ID | % of Max VEGF KDR pTyr Activity (at 133 nM antibody concentration) N = 1 | N = 2 | Average |
|---|---|---|---|
| 33D5 | 20% | 15% | 17% |
| 1G6 | 17% | 10% | 13% |
| 29A11 | 15% | 10% | 12% |
| 32G7 | 11% | 6% | 9% |
| 29D4 | 15% | 12% | 13% |
| 30E3 | 11% | 8% | 10% |
| 33B1 | 7% | 7% | 7% |
| 33C3 | 6% | 10% | 8% |
| 29F7 | 19% | 12% | 16% |
| 27A3 | 22% | 17% | 19% |
| 21H9 | 16% | 13% | 15% |
| 27D10 | 19% | 17% | 18% |
| 30D7 | 12% | 12% | 12% |
| 32B2 | 12% | 10% | 11% |
| 22B8 | 9% | 5% | 7% |
| 29H3 | 20% | 11% | 16% |
| 21H6 | 10% | 12% | 11% |
| 30F6 | 14% | 13% | 13% |
| 29A3 | 15% | 17% | 16% |
| 30H10 | 12% | 13% | 12% |
| 24B3 | 12% | 15% | 14% |
| 32C11 | 9% | 11% | 10% |
| 31E11 | 4% | 6% | 5% |
| 33E1 | 5% | 10% | 8% |
| 24C9 | 13% | no material | 13% |
| 2 nM VEGF | 100% | 100% | 100% |
| Non-Simulated | 0% | 0% | 0% |
| IgG2 | 6% | 12% | 9% |
| IgG4 | 6% | 10% | 8% |

Example 13

Determination of Relative Potency of Purified Antibodies

Inhibition of VEGF165-Mediated Survival

The relative potencies of the purified candidate antibodies were examined for their ability to block survival of serum-deprived HUVEC cells as mediated by VEGF165. These assays were also performed at a antibody concentrations of 133 nM. All incubations with HUVEC cells took place at 37° C. and 5% $CO_2$.

HUVEC cells were seeded at 10,000 cells/well and incubated overnight in supplemented media (EBM-2+2% FCS+all supplements except VEGF, see Example 8). The cells were then washed and the candidate antibodies were added to the HUVEC cells and incubated for 2 hours. VEGF165 was added to the cells to a final concentration of 1 nM, and the cells were incubated for 4 days. Cell survival was then measured by addition of luminescent substrate and luminometer assay. Table 25 provides a listing of (n=2) luminometer readings indicating the percentage of HUVEC survival inhibition of VEGF165-mediated KDR activity.

TABLE 25

Inhibition of HUVEC Cell Survival by Purified Antibody (Measurement by VEGF165-Mediated KDR Activity)

| MAb ID | Activity at 133 nM Antibody Concentration (% Survival Inhibition) N = 1 | N = 2 | Average |
|---|---|---|---|
| 33D5 | 13% | −2% | 5% |
| 1G6 | 9% | −10% | 0% |
| 29A11 | 6% | −10% | −2% |
| 32G7 | 70% | 67% | 69% |
| 29D4 | 85% | 85% | 85% |
| 30E3 | −5% | −27% | −16% |
| 33B1 | 80% | 66% | 73% |
| 33C3 | 104% | 102% | 103% |
| 29F7 | 3% | −27% | −12% |
| 27A3 | 86% | 81% | 83% |
| 21H9 | −20% | −16% | −18% |
| 27D10 | 84% | 68% | 76% |
| 32F4 | 88% | 58% | 73% |
| 30D7 | −9% | −92% | −51% |
| 32B2 | −13% | −29% | −21% |
| 22B8 | 88% | 87% | 88% |
| 29H3 | −5% | −136% | −70% |
| 21H6 | 105% | 77% | 91% |
| 30F6 | 91% | 74% | 82% |
| 29A3 | −65% | −156% | −111% |
| 30H10 | −84% | −147% | −115% |
| 24B3 | 65% | 64% | 65% |
| 32C11 | −95% | −87% | −91% |
| 31E11 | 83% | 95% | 89% |
| 33E1 | 86% | 97% | 92% |
| 24C9 | 57% | no material | 57% |

Example 14

Determination of Relative Potency of Purified Antibodies

Inhibition of VEGF-Mediated Release of Prostaglandin

The relative potencies of the purified candidate antibodies were also examined for their ability to block release of 6-keto Prostaglandin $F_{1\alpha}$ from HUVEC cells as mediated by VEGF165. These assays were also performed at antibody concentrations of 133 nM. All incubations with HUVEC cells took place at 37° C. and 5% $CO_2$.

HUVEC cells were seeded at 20,000 cells/well and incubated for three days in supplemented media (EBM-2+2% FCS+all supplements except VEGF, see Example 8). The cells were then washed, and the candidate antibodies were added to the HUVEC cells and incubated for 2 hours at 4° C. VEGF165 was added to the cells to a final concentration of 1 nM, and the cells were incubated overnight at 37° C. and 5% $CO_2$. Supernatant samples from each well were then measured for release of VEGF165-mediated 6-keto Prostaglandin $F_{1\alpha}$. Table 26 shows the results as a percent inhibition of prostaglandin release.

TABLE 26

Inhibition of VEGF165-mediated 6-keto Prostaglandin $F_{1\alpha}$ release in HUVEC Cells by Purified Antibody

| | Activity at 133 nM Antibody Concentration (% Inhibition) | | |
|---|---|---|---|
| MAb ID | N = 1 | N = 2 | Average |
| 33D5 | 15% | 57% | 36% |
| 1G6 | 12% | 86% | 49% |
| 29A11 | 8% | 41% | 25% |
| 32G7 | 37% | 115% | 76% |
| 29D4 | 72% | 119% | 95% |
| 30E3 | 15% | 33% | 24% |
| 33B1 | 76% | 114% | 95% |
| 33C3 | 106% | 178% | 142% |
| 29F7 | 1% | 38% | 19% |
| 27A3 | 54% | 121% | 88% |
| 21H9 | 5% | 61% | 33% |
| 27D10 | 56% | 111% | 84% |
| 32F4 | 69% | 76% | 73% |
| 30D7 | 4% | 15% | 10% |
| 32B2 | 3% | 9% | 6% |
| 22B8 | 67% | 76% | 72% |
| 29H3 | 14% | 22% | 18% |
| 21H6 | 104% | 96% | 100% |
| 30F6 | 68% | 89% | 79% |
| 29A3 | 11% | 16% | 13% |
| 30H10 | 10% | no material | 10% |
| 24B3 | 66% | 70% | 68% |
| 32C11 | 6% | 11% | 9% |
| 31E11 | 130% | 98% | 114% |
| 33E1 | 128% | 98% | 113% |
| 24C9 | 91% | no material | 91% |

Based on the data provided the activity comparison experiments as described in this Example and in Examples 11-13 (Tables 22-26), fourteen antibody candidates were carried forward for further analysis. Table 27 provides a summary of the candidate antibodies selected for further study.

TABLE 27

Anti-KDR Candidate Antibodies Selected for Further Study

| Selected for further study | MAb ID |
|---|---|
| X | 21H6 |
| X | 22B8 |
| X | 24B3 |
| X | 27A3 |
| X | 27D10 |
| X | 29D4 |
| X | 29H3 |
| X | 30H10 |
| X | 31E11 |
| X | 32F4 |
| X | 32G7 |
| X | 33E1 |
| X | 33B1 |
| X | 33C3 |
| | 1G6 |
| | 21H9 |
| | 24C9 |
| | 29A11 |
| | 29A3 |
| | 29F7 |
| | 30E3 |
| | 30D7 |
| | 30F6 |
| | 32B2 |
| | 32C11 |
| | 33D5 |

Example 15

Cross-Reactivity of Purified KDR Antibodies to Human VEGF-Receptor-1 (Flt-1) and Mouse KDR (Flk-1)

The cross-reactivity of purified antibodies was tested against KDR mouse ortholog KDR mouse ortholog (mouse VEGFR2, or Flk-1) and human VEGFR1 (Flt-1). The ability of the antibodies to bind soluble KDR Ig4-7 domain and to the entire KDR extracellular domain (ECD) was also measured.

Cross-reactivity experiments were carried out and measured using an ELISA based assay as described in Example 6. Briefly, titrations of purified antibody (1:10 serial dilutions over 3 data points, starting concentration=1 μg/mL) were added into wells coated with human VEGFR1 (Flt-1, Cat. #321-FL/CF, R&D Systems, Inc.) at 5 μg/mL, mouse KDR (Flk-1, Cat. #443-KD/CF, R&D Systems, Inc.) at 5 μg/mL), soluble KDR Ig4-7 (supernatant, diluted 1:1), or whole KDR-ECD (Cat. # 676490, Calbiochem) at 5 μg/mL. Antibody controls included IgG1 and IgG4 (Sigma-Aldrich, Cat. #15154 and #14639, respectively). Table 28 provides the results of the ELISA cross-reactivity assay for each substrate.

TABLE 28

Purified Antibody ELISA Cross-Reactivity Assay Results

| | Substrate | | | | | | | | | | | | | | |
|---|---|---|---|---|---|---|---|---|---|---|---|---|---|---|---|
| | Flt-1 (5 μg/mL) Antibody Conc. (μg/mL) | | | Flk-1 (5 μg/mL) Antibody Conc. (μg/mL) | | | KDR Ig4-7 (1:1 diln.) Antibody Conc. (μg/mL) | | | KDR-ECD (5 ug/mL) Antibody Conc. (μg/mL) | | | 1% PBS/1% milk Antibody Conc. (μg/mL) | | |
| MAb ID | 1 | 0.1 | 0.01 | 1 | 0.1 | 0.01 | 1 | 0.1 | 0.01 | 1 | 0.1 | 0.01 | 1 | 0.1 | 0.01 |
| 27A3 | 2.483 | 1.954 | 1.023 | 2.571 | 1.764 | 0.742 | 0.078 | 0.075 | 0.080 | 1.973 | 0.111 | 0.093 | 3.109 | 2.080 | 0.611 |
| 32F4 | 2.383 | 2.013 | 1.086 | 2.623 | 1.998 | 0.802 | 0.114 | 0.079 | 0.076 | 1.934 | 0.132 | 0.090 | 3.182 | 2.334 | 0.653 |

TABLE 28-continued

Purified Antibody ELISA Cross-Reactivity Assay Results

| | Substrate | | | | | | | | | | | | | | |
|---|---|---|---|---|---|---|---|---|---|---|---|---|---|---|---|
| | Flt-1 (5 μg/mL) Antibody Conc. (μg/mL) | | | Flk-1 (5 μg/mL) Antibody Conc. (μg/mL) | | | KDR Ig4-7 (1:1 diln.) Antibody Conc. (μg/mL) | | | KDR-ECD (5 ug/mL) Antibody Conc. (μg/mL) | | | 1% PBS/1% milk Antibody Conc. (μg/mL) | | |
| MAb ID | 1 | 0.1 | 0.01 | 1 | 0.1 | 0.01 | 1 | 0.1 | 0.01 | 1 | 0.1 | 0.01 | 1 | 0.1 | 0.01 |
| 27D10 | 2.083 | 1.655 | 0.858 | 2.138 | 1.483 | 0.537 | 0.076 | 0.086 | 0.073 | 1.364 | 0.187 | 0.087 | 2.360 | 1.714 | 0.441 |
| 21H6 | 2.449 | 1.889 | 0.848 | 2.722 | 1.780 | 0.612 | 0.087 | 0.074 | 0.074 | 1.458 | 0.139 | 0.087 | 3.303 | 1.936 | 0.455 |
| 30H10 | 2.653 | 2.467 | 1.434 | 2.858 | 2.643 | 1.416 | 3.036 | 2.772 | 1.358 | 2.466 | 0.310 | 0.117 | 3.391 | 3.161 | 1.320 |
| 29H3 | 2.681 | 2.211 | 1.224 | 3.041 | 2.354 | 1.138 | 3.024 | 2.357 | 1.140 | 2.619 | 0.306 | 0.099 | 3.296 | 2.678 | 0.967 |
| 32G7 | 2.406 | 2.088 | 1.229 | 2.672 | 2.138 | 0.988 | 2.654 | 2.309 | 0.933 | 2.362 | 0.307 | 0.103 | 2.979 | 2.470 | 0.968 |
| 29D4 | 2.814 | 2.420 | 1.158 | 3.291 | 2.590 | 1.165 | 0.082 | 0.078 | 0.080 | 2.150 | 0.096 | 0.089 | 3.727 | 2.855 | 0.817 |
| 33E1 | 2.091 | 1.639 | 1.043 | 2.166 | 1.469 | 0.846 | 0.107 | 0.074 | 0.067 | 1.375 | 0.205 | 0.081 | 2.285 | 1.605 | 0.714 |
| 31E11 | 2.846 | 2.130 | 0.976 | 3.100 | 2.366 | 0.826 | 0.107 | 0.073 | 0.072 | 1.963 | 0.161 | 0.080 | 3.604 | 2.439 | 0.743 |
| 24B3 | 2.927 | 2.601 | 1.632 | 3.393 | 2.755 | 1.584 | 3.473 | 2.802 | 1.451 | 3.016 | 0.304 | 0.090 | 4.044 | 3.003 | 1.648 |
| 22B8 | 2.763 | 2.469 | 1.367 | 3.211 | 2.945 | 1.202 | 0.080 | 0.078 | 0.074 | 1.907 | 0.089 | 0.075 | 3.412 | 2.985 | 1.131 |
| 33C3 | 2.790 | 2.836 | 1.404 | 3.475 | 3.042 | 1.246 | 0.094 | 0.088 | 0.073 | 1.115 | 0.153 | 0.090 | 3.825 | 3.384 | 1.338 |
| 33B1 | 2.670 | 2.081 | 0.991 | 3.118 | 2.105 | 0.753 | 3.035 | 2.137 | 0.609 | 1.986 | 0.178 | 0.072 | 3.241 | 2.303 | 0.753 |
| IgG1 (Control) | 0.480 | 0.471 | 0.465 | 0.240 | 0.224 | 0.230 | 0.139 | 0.097 | 0.079 | 0.121 | 0.087 | 0.082 | 0.125 | 0.084 | 0.079 |
| IgG4 (Control) | 0.482 | 0.495 | 0.462 | 0.227 | 0.223 | 0.232 | 0.181 | 0.078 | 0.075 | 0.106 | 0.078 | 0.077 | 0.096 | 0.075 | 0.083 |

Example 16

Potency Comparison of Purified KDR Antibodies

Inhibition of VEGF-Induced KDR Tyrosine Phosphorylation

The relative potency of the purified antibodies was compared by measuring how well the antibodies blocked KDR phosphorylation in an endogenously KDR-expressing normal cell line (HUVEC). The assays were conducted using multiple antibody concentrations and included examination of antibody ability to block VEGF165-mediated KDR tyrosine phosphorylation, ability to block VEGF165-mediated survival of serum-deprived HUVEC, and inhibition of VEGF165-mediated release of 6-keto Prostaglandin $F_{1\alpha}$ from HUVEC cells. All incubations with HUVEC cells took place at 37° C. and 5% $CO_2$ except where indicated.

Assay to Measure Inhibition of VEGF165-mediated KDR Activity

HUVEC cells were seeded at 25,000 cells/well and incubated overnight in supplemented media (EBM-2+2% FCS+all supplements except VEGF). The cells were then washed and incubated in supplement-free media overnight. On the third day, the various purified antibodies (at 100 nM starting concentration and serially diluted 1:5 to 6 pM final concentration) were added to the HUVEC cells and incubated for one hour at 4° C. The media was then replaced by 50 μL of VEGF165 at 2 nM final concentration. After stimulation with VEGF165 for 10 minutes, the cells were lysed, and the cell lysates were measured for inhibition of VEGF165-mediated KDR activity. Table 29 indicates the level of inhibition of VEGF165-mediated KDR tyrosine phosphorylation as EC50 values and as percentage inhibition values.

TABLE 29

Inhibition of VEGF165-mediated KDR tyrosine phosphorylation

| | EC50 (nM) | | | Maximum Inhibition at 100 nM (% Inhibition) | | |
|---|---|---|---|---|---|---|
| MAb ID | N = 1 | N = 2 | Average | N = 1 | N = 2 | Average |
| 27A3 | 3.4 | 2.9 | 3.1 | 77% | 79% | 78% |
| 32F4 | 1.7 | 1.9 | 1.8 | 71% | 79% | 75% |
| 27D10 | 1.6 | 2.3 | 1.9 | 70% | 75% | 72% |
| 21H6 | 7.1 | 6.7 | 6.9 | 81% | 84% | 82% |
| 30H10 | 0.6 | 0.2 | 0.4 | 36% | 22% | 29% |
| 29H3 | 0.5 | 0.4 | 0.4 | 33% | 30% | 32% |
| 32G7 | 0.6 | 0.6 | 0.6 | 69% | 77% | 73% |
| 29D4 | 2.0 | 1.9 | 1.9 | 74% | 77% | 75% |
| 33E1 | 5.8 | 5.1 | 5.5 | 73% | 75% | 74% |
| 31E11 | 2.0 | 1.9 | 1.9 | 84% | 86% | 85% |
| 24B3 | 2.1 | 2.3 | 2.2 | 78% | 84% | 81% |
| 22B8 | 2.7 | 3.4 | 3.1 | 75% | 79% | 77% |
| 33C3 | 1.2 | 1.1 | 1.2 | 83% | 86% | 85% |
| 33B1 | 1.2 | 1.1 | 1.1 | 86% | 86% | 86% |

Assay to Measure Ability of Antibody to Block VEGF 165-mediated Survival of Serum-deprived HUVEC Cells HUVEC cells were seeded at 10,000 cells/well and incubated overnight in supplemented media (EBM-2+2% FCS+all supplements except VEGF). The cells were then washed and the various purified antibodies were added to the HUVEC cells (at 200 nM starting concentration and serially diluted 1:4 to 13 pM final concentration) and incubated for 2 hours at 4° C. VEGF165 was added to the cells to a final concentration of 1 nM, and the cells were incubated for three days. Cell survival was then measured by addition of luminescent substrate and luminometer assay. Table 30 indicates HUVEC survival by VEGF165-mediated KDR activity as EC50 values and as percent inhibition of survival.

TABLE 30

Survival of HUVEC Cells by VEGF165-mediated KDR Activity

| MAb ID | EC50 N = 1 | EC50 N = 2 | EC50 Average | Maximum Inhibition at 50 nM (% Inhibition) N = 1 | N = 2 | Average |
|---|---|---|---|---|---|---|
| 27A3 | 3.3 | 1.9 | 2.6 | 95% | 94% | 95% |
| 32F4 | 2.3 | 1.0 | 1.7 | 91% | 94% | 92% |
| 27D10 | 2.3 | 2.0 | 2.2 | 93% | 85% | 89% |
| 21H6 | 2.5 | 2.3 | 2.4 | 96% | 96% | 96% |
| 30H10 | *** | *** | *** | −9% | −1% | −5% |
| 29H3 | *** | *** | *** | 4% | 18% | 11% |
| 32G7 | 0.4 | 1.4 | 0.9 | 73% | 72% | 72% |
| 29D4 | 1.1 | 2.9 | 2.0 | 89% | 95% | 92% |
| 33E1 | 1.7 | 1.2 | 1.4 | 107% | 99% | 103% |
| 31E11 | 2.0 | 2.8 | 2.4 | 101% | 101% | 101% |
| 24B3 | 2.9 | 4.1 | 3.5 | 97% | 82% | 90% |
| 22B8 | 2.1 | 2.4 | 2.2 | 80% | 95% | 87% |
| 33C3 | 0.7 | 1.4 | 1.1 | 106% | 95% | 101% |
| 33B1 | 1.7 | 3.1 | 2.4 | 55% | 59% | 57% |

***EC50 data not presented as KDR was not sufficiently inhibited.

Assay to Measure Ability of Antibody to Inhibit VEGF165-mediated release of 6-keto Prostaglandin $F_{1\alpha}$ from HUVEC cells HUVEC cells were seeded at 20,000 cells/well and incubated for three days in supplemented media (EBM-2+2% FCS+all supplements except VEGF). The cells were then washed, and the candidate antibodies were added to the HUVEC cells (at 333 nM starting concentration and serially diluted 1:5 to 4 pM final concentration) and incubated for 2 hours at 4° C. VEGF165 was added to the cells to a final concentration of 1 nM, and the cells were incubated overnight. Supernatant samples from each well were then measured for release of VEGF165-mediated 6-keto Prostaglandin $F_{1\alpha}$. Table 31 shows the results as a EC50 values and as percent inhibition of prostaglandin release.

TABLE 31

Inhibition of VEGF165-mediated 6-keto Prostaglandin $F_{1\alpha}$ release in HUVEC Cells by Purified Antibody

| MAb ID | EC50 (nM) N = 1 | EC50 (nM) N = 2 | EC50 (nM) Average | Maximum Inhibition (% Inhibition) N = 1 (200 nM) | N = 2 (333 nM) | Average |
|---|---|---|---|---|---|---|
| 27A3 | 5.5 | 5.7 | 5.6 | 49% | 49% | 49% |
| 32F4 | 4.4 | 4.6 | 4.5 | 42% | 54% | 48% |
| 27D10 | 4.5 | 5.2 | 4.8 | 46% | 51% | 49% |
| 21H6 | 7.3 | 5.4 | 6.3 | 80% | 75% | 77% |
| 30H10 | *** | *** | *** | 0% | 6% | 3% |
| 29H3 | *** | *** | *** | 2% | 8% | 5% |
| 32G7 | 11.2 | 35.1 | 23.1 | 28% | 55% | 42% |
| 29D4 | 3.2 | 3.2 | 3.2 | 45% | 67% | 56% |
| 33E1 | 4.8 | 5.4 | 5.1 | 77% | 103% | 90% |
| 31E11 | 6.1 | 6.4 | 6.2 | 88% | 108% | 98% |
| 24B3 | 8.1 | 16.2 | 12.1 | 37% | 72% | 54% |
| 22B8 | 5.1 | 5.6 | 5.3 | 63% | 76% | 70% |
| 33C3 | 3.5 | 4.4 | 3.9 | 76% | 94% | 85% |
| 33B1 | 17.0 | 7673.0 | 3845.0 | 31% | 76% | 53% |

***EC50 data not presented as KDR was not sufficiently inhibited.

Example 17

Determination of Binding Affinity of Purified Antibodies

The binding affinities of the purified antibodies for endogenously-expressed KDR in HUVEC cells was measured. HUVEC cells were seeded at 150,000 cells/well and incubated with titrations of purified antibody for 4 hours at 4° C. The cells were then washed and incubated with goat anti-human IgG-Fc-Cy5+5 μg/mL 7-Amino-Actinomycin (7AAD) for 30 minutes at 4° C. Bound KDR was detected using FACS analysis. Table 32 lists the FACS data obtained from analysis of the HUVEC cells with purified antibodies.

TABLE 32

Binding Affinity/Avidity of Purified Antigens to KDR in HUVEC cells

| MAb ID | FACS Kd (nM) |
|---|---|
| 27A3 | 5.4 |
| 32F4 | 1.8 |
| 27D10 | 1.9 |
| 21H6 | 17.9 |
| 30H10 | 0.9 |
| 29H3 | 0.5 |
| 32G7 | 0.2 |
| 29D4 | 1.0 |
| 33E1 | 3.8 |
| 31E11 | 11.3 |
| 24B3 | 0.8 |
| 22B8 | 1.8 |
| 33C3 | 1.0 |
| 33B1 | 0.2 |

Based on the data provided potency experiments and data as described in this Example and in Examples 16 (Tables 29-32), eleven antibody candidates were carried forward for further analysis. Table 33 provides a summary of the candidate antibodies selected for further study.

TABLE 33

Anti-KDR Candidate Antibodies Selected for Further Study (Based on Potency Data)

| Selected for further study | MAb ID |
|---|---|
| X | 27A3 |
| X | 32F4 |
| X | 27D10 |
| X | 21H6 |
| X | 29D4 |
| X | 33E1 |
| X | 31E11 |
| X | 24B3 |
| X | 22B8 |
| X | 33C3 |
| X | 33B1 |
| | 30H10 |
| | 29H3 |
| | 32G7 |

Example 18

Cross-Reactivity of Purified KDR Antibodies to Non-Human Primates

KDR derived from cynomolgus monkey was cloned and expressed on the surface of HEK 293T cells. The binding of purified antibodies to cell-bound cynomolgus KDR (with parental cells as negative control) was tested by FACS analysis in this assay.

Cynomolgus KDR was cloned in 3 pieces. One piece was PCR amplified from cynomolgus lung cDNA, and the remaining two pieces were PCR amplified from cynomolgus kidney cDNA. The three PCR products were inserted into pCR3.1 Bid vector. HEK 293T cells were then transfected with cynomologus KDR expression vector or with empty pCR3.1 Bid vector. Transfected cells were seeded at 50,000 cells/well and incubated with 5 μg/mL of candidate antibody for one hour at 4° C. The cells were then washed and incubated with secondary antibody (Cy5-conjugated goat anti-human antibody, or Cy5-conjugated rabbit anti-goat antibody, plus 7-Amino-Actinomycin (7AAD)) for 15 minutes at 4° C. Binding between cynomolgus KDR and purified antibody was detected by FACS analysis. Table 34 provides a summary of the results for the assay.

TABLE 34

Cyno Cross-Reactivity Assay Results for Purified Antibodies

| MAb ID | FACS Geometric Mean Fluorescence Cyno KDR/293T Transfectants | FACS Geometric Mean Fluorescence Mock 293T Transfectants |
|---|---|---|
| 27A3 | 89.7 | 2.8 |
| 32F4 | 104.6 | 2.8 |
| 27D10 | 89.4 | 2.8 |
| 21H6 | 101.7 | 2.8 |
| 29D4 | 115.3 | 2.6 |
| 33E1 | 88.5 | 2.7 |
| 31E11 | 99.5 | 2.8 |
| 24B3 | 68.4 | 2.7 |
| 22B8 | 103.2 | 2.7 |
| 33C3 | 108.1 | 2.7 |
| 33B1 | 107.6 | 2.8 |

Example 19

Determination of Relative Potency of Purified Antibodies

Ability to Block VEGF Binding to KDR

The relative potency of the various antibodies was assayed by how well the antibodies blocked human VEGF binding to KDR. HEK 293T cells were transfected with human KDR (courtesy of Amgen Fremont, Fremont Calif.) or with empty pCR3.1 Bid vector. Transfected cells were then seeded at 50,000 cells/well and incubated with 5 μg/mL of candidate antibody for one hour at 4° C. The antibodies were subsequently removed, and the cells were and incubated VEGF165 (Cat. # 293-VE, R&D Systems, Inc.) at a concentration of 50 ng/mL for one hour at 4° C. The cells were then washed and incubated with goat anti-VEGF for one hour at 4° C. After washing, the cells were incubated with Cy5-conjugated rabbit anti-goat antibody plus 7AAD for 15 minutes at 4° C. Inhibition of VEGF binding to KDR was detected by FACS analysis. Table 35 provides a summary of the results for the assay.

TABLE 35

FACS Results for Inhibition of VEGF Binding to Human KDR

| MAb ID | FACS Geometric Mean Fluorescence | % Inhibition |
|---|---|---|
| 27A3 | 118 | 9% |
| 32F4 | 112 | 14% |
| 27D10 | 111 | 15% |
| 21H6 | 133 | −3% |
| 29D4 | 116 | 11% |
| 33E1 | 147 | −15% |
| 31E11 | 138 | −8% |
| 24B3 | 97 | 27% |
| 22B8 | 120 | 7% |
| 33C3 | 126 | 2% |
| 33B1 | 81 | 40% |
| 293T/KDR transfectants (control) | 129 | |
| 293T/mock transfectants (control) | 10 | |

The above results show these antibodies have a differentiated mode of action compared to IMC1121b (Lu et al, JBC 2003, 278, 43496).

Example 20

Determination of Relative Potency of Purified Antibodies

Ability to Block VEGF-C Mediated KDR Activity

The anti-KDR candidate antibodies were assayed for their ability to inhibit VEGF-C-mediated KDR tyrosine phosphorylation in HUVEC cells. HUVEC cells were seeded at 25,000 cells/well and incubated overnight in supplemented media (EBM-2+2% FCS+all supplements except VEGF). The cells were then washed and incubated in supplement-free media overnight. On the third day, the various purified antibodies were added to the HUVEC cells (at 1:10 serial dilution over three data points, starting concentration=100 nM) and incubated for 2 hours at 4° C. The supernatant volumes were then removed and replaced by 50 μo of VEGF-C at 50 nM final concentration for 10 minutes at 37° C. After stimulation VEGF-C, the cells were lysed, and the cell lysates were measured for inhibition of VEGF-C-mediated KDR activity by ELISA assay. Table 36 provides the results of the assay indicating the level of inhibition of VEGF-C-mediated KDR tyrosine phosphorylation.

TABLE 36

Inhibition of VEGF-C-mediated KDR Activity

| MAb ID | % Inhibition (N = 1) 100 nM | 10 nM | 1 nM | % Inhibition (N = 2) 100 nM | 10 nM | 1 nM | % Inhibition (Average) 100 nM | 10 nM | 1 nM |
|---|---|---|---|---|---|---|---|---|---|
| 27A3 | 73% | 75% | 40% | 77% | 80% | 38% | 75% | 78% | 39% |
| 32F4 | 75% | 76% | 55% | 86% | 79% | 31% | 81% | 77% | 43% |
| 27D10 | 76% | 73% | 52% | 84% | 79% | 50% | 80% | 76% | 51% |
| 21H6 | 93% | 78% | 23% | 95% | 90% | 34% | 94% | 84% | 28% |
| 29D4 | 74% | 71% | 42% | 79% | 72% | 25% | 76% | 71% | 34% |
| 33 E1 | 83% | 75% | 29% | 75% | 64% | 36% | 79% | 69% | 32% |

TABLE 36-continued

| Inhibition of VEGF-C-mediated KDR Activity | | | | | | | | | |
|---|---|---|---|---|---|---|---|---|---|
| | % Inhibition (N = 1) | | | % Inhibition (N = 2) | | | % Inhibition (Average) | | |
| MAb ID | 100 nM | 10 nM | 1 nM | 100 nM | 10 nM | 1 nM | 100 nM | 10 nM | 1 nM |
| 31 E11 | 84% | 81% | 47% | 84% | 85% | 33% | 84% | 83% | 40% |
| 24B3 | 67% | 61% | 26% | 75% | 62% | 34% | 71% | 62% | 30% |
| 22B8 | 71% | 74% | 38% | 77% | 56% | 17% | 74% | 65% | 27% |
| 33C3 | 84% | 87% | 71% | 86% | 89% | 61% | 85% | 88% | 66% |
| 33B1 | 64% | 61% | 45% | 73% | 62% | 53% | 68% | 62% | 49% |

Example 21

Determination of Binding Affinities of Purified Antibodies by Biacore

Each purified anti-KDR antibody was immobilized on a CM4 sensor chip within a Biacore 2000 using standard amine coupling. Immobilization levels were kept between 250 and 350 RU. The concentration of KDR was determined by UV-VIS spectroscopy using a molar absorptivity at 280 nm of 110, 440 $M^{-1}cm^{-1}$, which was calculated from the sequence of the protein using a method developed by Pace et al. (G. R. Grimsley and C. N. Pace (2003) in Current Protocols in Protein Science (John Wiley & Sons, Inc.), 3.1.1-3.1.9). The antigen KDR was diluted to a starting concentration of 52 nM and tested in a 3-fold dilution series in triplicate. The running buffer contained HBS-P with 0.1 mg/ml BSA and binding responses were collected at 23 degrees C. Bound complexes were regenerated with a 12 second pulse of 146 mM of phosphoric acid. The response data were globally fit with a simple 1:1 interaction model. The binding constants are provided in the table below. The number shown in parentheses is the standard error in the last significant figure.

| | ka (M−1s−1) | kd (s−1) | Kd |
|---|---|---|---|
| 27D10 | 5.176(6)e4 | 2.54(1)e−4 | 4.91(2) nM |
| 24B3 | 1.750(1)e5 | 1.907(8)e−4 | 1.089(4) nM |
| 33C3 | 1.0214(8)e5 | 9.3(1)e−5 | 910(10) pM |

ka (M−1s−1) = $k_{on}$,
kd (s−1) = $k_{off}$

Example 22

Determination of Cross Competition for KDR by Purified Anti-KDR Antibodies

Each purified anti-KDR antibody was tested for its ability to block binding of other anti-KDR antibodies to human KDR using a cell adhesion assay.

Wells of 96 well plates were coated over night at 4° C. with 33C3, 24B3 or 27D10 at a concentration of 10 μg/ml PBS. The wells were then blocked with PBS/3% BSA for an hour at 37° C. and washed with PBS. Titrations of purified anti-KDR antibody were tested against each coating antibody for cross competition to KDR, using a maximum concentration of 25 μg/ml. Isotype controls IgG1 and IgG2 (Sigma-Aldrich, Cat #I5154 and I5404 respectively) were included. Antibody titrations were prepared in serum free Hams F12 media at 10 times the final assay concentration and 10 μl was added to triplicate test wells. Porcine Aortic Endothelial cells transfected with human KDR were added at a density of 100,000 cells per well in 90 μl of serum free Hams F12 media. The plates were incubated at 37° C., 5% $CO_2$ for 1 hour. Non-adhered cells were flicked from the plates and the wells washed twice with PBS. The adhered cells were fixed with 100% ethanol for 30 minutes at room temperature and then stained with 0.1% crystal violet in 1.5% methanol, for 15 minutes at room temperature. Excess stain was washed off with water and the stain within the cells solubilised with 100 ul per well of 0.1% triton X-100 in double distilled water for 2 hours on an orbital platform. The OD at 570 nm was measured and the percent inhibition of binding by each antibody calculated.

The table indicates the cross competition between each of the antibodies for human KDR as percent inhibition of cell binding to coating antibody by 25 μg/ml of inhibiting antibody.

| | | Inhibiting Antibody | | | |
|---|---|---|---|---|---|
| | | 33C3 | 24B3 | 27D10 | IgG2 |
| Coating Antibody | 33C3 | 100 | 29 | 98 | 0 |
| | 24B3 | −9 | 102 | −14 | 0 |
| | 27D10 | 103 | 20 | 103 | 0 |

Example 23

KDR Inhibitory Antibodies Reduce Tube Formation In Vitro

KDR inhibitory antibodies were tested for the ability to reduce endothelial cell tube formation in an in vitro co-culture assay (TCS Cell Works Cat no. ZHA-1000). On day 1, Human Umbilical Vein Endothelial Cells (HUVECs) and human diploid fibroblasts were obtained as co-cultures in 24 well plates. KDR blocking antibodies were introduced to the cultures on day 1 and at regular intervals over an 11-day period at the following concentrations: 20 μg/mL, 5 μg/mL, 1.25 μg/mL and 0.3125 μg/mL. Media was replenished on days 4, 7 and 9. The co-culture model was maintained in either TCS Optimised medium (supplied with the co-culture assay) or in MCDB131 medium supplemented with 2% foetal calf serum (FCS), 1% glutamine and 1% penicillin/streptomycin (hereafter referred to as 2% FS MCDB131 medium). The co-culture model was maintained at 37° C. in a humidified 5% $CO_2$/95% air atmosphere.

Tubule formation was examined at day 11 following fixing and staining of tubules for CD31 using a tubule staining kit according to the manufacturors instructions (TCS Cell Works Cat no. ZHA-1225). Briefly, cells were fixed with ice-cold 70% ethanol for 30 minutes at room temperature (RT). Cells were blocked after which they were treated with anti-human CD31 for 60 minutes at RT. Plates were washed and treated with goat anti-mouse IgG conjugated with alkaline phosphatase (AP) for 60 minutes at RT. After incubation with the AP-conjugated secondary antibody, the plates were washed and 5-bromo-4-chloro-3-indolyl phosphate/nitro blue tetrazolium (BCIP/NBT) substrate was added for approximately 10 minutes. The development of a dark purple colour within 10 minutes reflected tubule formation. Plates were subsequently washed and left to air dry.

Quantification of tubule growth was conducted by whole-well image analysis methodology using a Zeiss KS400 3.0 Image Analyser. The morphological parameter measured in the quantification methodology was total tubule length. All tubule formations within each of the 24 wells were measured excluding a rim of 100 μm depth to avoid edge retraction artifact.

As illustrated in FIG. 1, it was observed that the antibodies are effective in inhibiting endothelial cell tube formation in vitro. The data indicate that the antibodies are active in a functional assay that models the angiogenic process.

Example 24

Determination of In Vivo Efficacy of Purified Antibodies

Figure 2:
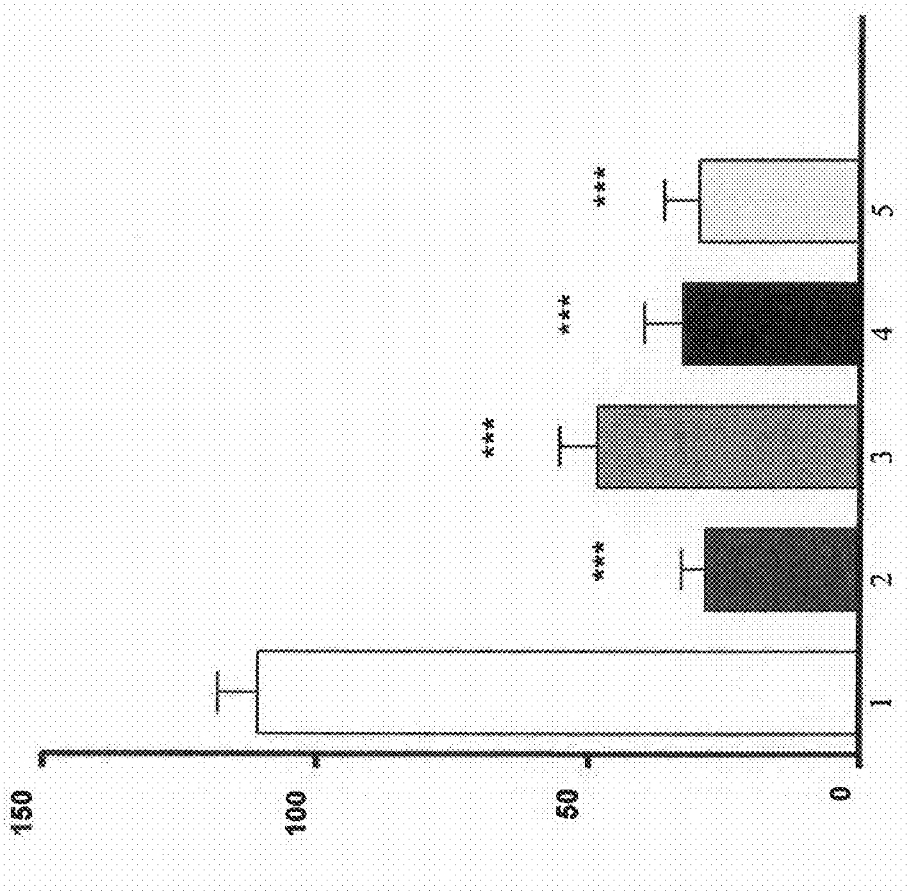
FIG. 2 is a bar chart showing the effect of inhibitory KDR antibodies on angiogenesis in vivo. Along the X axis 1=vehicle twice weekly; 2=24B3 10 mg/kg twice weekly; 3=24B3 1 mg/kg twice weekly; 4=33C3 10 mg/kg twice weekly; 5=33C3 1 mg/kg twice weekly. The Y axis shows vessel numbers.

Evaluation of the Antiangiogenic Efficacy in a Spheroid-Based In Vivo Angiogenesis Assay Human umbilical vein endothelial cell (HUVEC) spheroids were prepared as described earlier (Korff and Augustin: J Cell Biol 143: 1341-52, 1998) by pipetting 100 endothelial cells (EC) in a hanging drop on plastic dishes to allow overnight spheroid formation. The following day, using the method previously described (Alajati et al: Nature Methods 5:439-445, 2008), EC spheroids were harvested and mixed in a Matrigel/fibrin solution with single HUVECs to reach a final number of 100,000 ECs as spheroids and 200,000 single ECs per injected plug. VEGF-A and FGF-2 were added at a final concentration of 1000 ng/ml. Male SCID mice (5-8 weeks old) were subcutaneously injected with 500 μl of the cell/matrix suspension. The following day (day 1) treatment commenced. At day 21 the study was terminated. The matrix plugs were removed and fixed in 4% PFA. All matrix plugs were paraffin embedded and cut to a thickness of 8-10 μm for histological examination. Blood vessels were visualized by staining for human CD34 and smooth muscle actin (SMA) and the vessel density and pericyte coverage was determined As illustrated in FIG. 2, the antibodies are effective in inhibiting vessel formation in vivo. The data indicate that the antibodies are active in an in vivo assay of angiogenesis.

Example 25

Inhibition of Tumour Cell Growth in Human Patients

A group of human cancer patients diagnosed with pancreatic cancer is randomized into treatment groups. Each patient group is treated with weekly intravenous injections of fully human monoclonal antibodies against KDR as described herein. Each patient is dosed with an effective amount of the antibody ranging from 5 mg/kg/week to 15 mg/kg/week for 4-8 months. A control group is given only the standard chemotherapeutic regimen.

At periodic times during and after the treatment regimen, tumour burden is assessed by magnetic resonance imaging (MRI). It can be expected that the patients who have received weekly antibody treatments will show significant reductions in tumour size, time delay to progression or prolonged survival compared to patients that do not receive antibody treatment. In some treated patients, it can be expected that the tumours are no longer detectable. In contrast, it can be expected that tumour size increases or remains substantially the same in the control group.

Example 26

Inhibition of Colon Cancer in a Human Patient

A group of human cancer patients diagnosed with colon cancer is randomized into treatment groups. Each patient group is treated 3-weekly with intravenous injections of fully human monoclonal antibodies against KDR as described herein. Each patient is dosed with an effective amount of the antibody ranging from 5 mg/kg/week to 15 mg/kg/week for 4-8 months. A control group is given only the standard chemotherapeutic regimen. At periodic times during and after the treatment regimen, tumour burden is assessed by magnetic resonance imaging (MRI). It can be expected that the patients who have received 3-weekly antibody treatments show significant reductions in tumour size, time delay to progression or prolonged survival compared to patients that do not receive the antibody treatment. In some treated patients, it can be expected that the tumours are no longer detectable. In contrast, it can be expected that tumour size increases or remains substantially the same in the control group.

Example 27

Inhibition of Melanoma in a Human Patient

A group of human cancer patients diagnosed with melanoma is randomized into treatment groups. Each patient group is treated 3-weekly with intravenous injections of fully human monoclonal antibodies against KDR as described herein. Each patient is dosed with an effective amount of the antibody ranging from 5 mg/kg/week to 15 mg/kg/week for 4-8 months. A control group is given only the standard chemotherapeutic regimen. At periodic times during and after the treatment regimen, tumour burden is assessed by magnetic resonance imaging (MRI). It can be expected that the patients who have received 3-weekly antibody treatments with antibodies against KDR show significant reductions in melanoma, time delay to progression or prolonged survival compared to patients that do not receive the antibody treatment. In some treated patients, it can be expected that the melanoma lesions are no longer detectable. In contrast, it can be expected that melanoma increases or remains substantially the same in the control group.

Example 28

Inhibition of Chronic Myelogenous Leukemia (CML) in a Human Patient

A group of human cancer patients diagnosed with CML is randomized into treatment groups. Each patient group is treated 3-weekly with intravenous injections of fully human monoclonal antibodies against KDR as described herein. Each patient is dosed with an effective amount of the antibody ranging from 5 mg/kg/week to 15 mg/kg/week for 4-8 months. A control group is given only the standard chemotherapeutic regimen. At periodic times during and after the treatment regimen, tumour burden is assessed by magnetic resonance imaging (MRI). It can be expected that the patients who have received 3-weekly antibody treatments show significant reductions in CML, time delay to progression or prolonged survival compared to patients that do not receive the antibody treatment. In some treated patients, it can be expected that the CML is no longer detectable. In contrast, it can be expected that CML increases or remains substantially the same in the control group.

Example 29

Inhibition of Tumour Cell Growth in a Human Patient

A human patient is diagnosed with a malignant tumour. The patient is treated with weekly intravenous injections of fully human monoclonal antibodies against KDR as described herein for 8 weeks. At periodic times during and after the treatment regimen, tumour burden is assessed by magnetic resonance imaging (MRI). It can be expected that significant reductions in tumour size are found.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A monoclonal antibody or a binding fragment thereof as shown in Table 1.

2. The monoclonal antibody or binding fragment thereof of claim 1, wherein said monoclonal antibody or binding fragment thereof is 24B3 (SEQ ID NO. 42 and 44), 27D10 (SEQ ID NO. 14 and 16), or 33C3 (SEQ ID NO. 74 and 76), as shown in Table 1.

3. The monoclonal antibody or binding fragment thereof of claim 1, wherein the binding fragment thereof is selected from the group consisting of a Fab, Fab', F(ab')2, FV and dAb fragment.

4. A method of treating a malignant tumour in a human, comprising: selecting a human in need of treatment for a malignant tumour; and administering to said human a therapeutically effective dose of the monoclonal antibody of claim 1.

* * * * *

UNITED STATES PATENT AND TRADEMARK OFFICE

CERTIFICATE OF CORRECTION

PATENT NO. : 8,119,130 B2
APPLICATION NO. : 12/669724
DATED : February 21, 2012
INVENTOR(S) : Barry et al.

It is certified that error appears in the above-identified patent and that said Letters Patent is hereby corrected as shown below:

On the Face Page, in Field (56), under “OTHER PUBLICATIONS”, in Column 1, Line 1, delete “et al,” and insert -- et al., --, therefor.

On the Face Page, in Field (56), under “OTHER PUBLICATIONS”, in Column 1, Line 3, delete “et al,” and insert -- et al., --, therefor.

On the Face Page, in Field (56), under “OTHER PUBLICATIONS”, in Column 1, Line 4, delete “et al, Mol. Immunol” and insert -- et al., Mol. Immunol --, therefor.

On the Face Page, in Field (56), under “OTHER PUBLICATIONS”, in Column 2, Line 4, delete “lastest” and insert -- latest --, therefor.

On the Face Page, in Field (56), under “OTHER PUBLICATIONS”, in Column 2, Line 39, delete “Opinon” and insert -- Opinion --, therefor.

In Column 234, Line 1, in Claim 3, delete “FV” and insert -- Fv --, therefor.

Signed and Sealed this
Fifteenth Day of May, 2012

David J. Kappos
*Director of the United States Patent and Trademark Office*

SEQUENCE LISTING

```
<160> NUMBER OF SEQ ID NOS: 153

<210> SEQ ID NO 1
<211> LENGTH: 384
<212> TYPE: DNA
<213> ORGANISM: Homo sapiens

<400> SEQUENCE: 1

caggtgccgc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcagtt atatggtatg atggaagtaa taaatactat     180

gcagactccg tgaagggccg attcaccatc tccagagaca attccaagaa tacgctgtat     240

ctgcaaatga acagcctgag agccgaggac acggctgtat attactgtgc gagaggcgtt     300

actatggttc ggggagttat tatagcgcgc tactactacg gtttggacgt ctggggccaa     360

gggaccacgg tcaccgtctc ctca                                            384


<210> SEQ ID NO 2
<211> LENGTH: 128
<212> TYPE: PRT
<213> ORGANISM: Homo sapiens

<400> SEQUENCE: 2

Gln Val Pro Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Thr Met Val Arg Gly Val Ile Ile Ala Arg Tyr Tyr
            100                 105                 110
```

Tyr Gly Leu Asp Val Trp Gly Gln Gly Thr Thr Val Thr Val Ser Ser
115 120 125

<210> SEQ ID NO 3
<211> LENGTH: 336
<212> TYPE: DNA
<213> ORGANISM: Homo sapiens

<400> SEQUENCE: 3
gatattgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taatcggttc 180
tttggggtcc cagacagatt cagtggcagt ggggcaggga cagatttcac actgaaaatc 240
ggcagggtgg aggctgagga tgtcgggctt tattactgca tgcagtctac acaatttcct 300
ctcactttcg gcggagggac caaggtggag atcaaa 336

<210> SEQ ID NO 4
<211> LENGTH: 112
<212> TYPE: PRT
<213> ORGANISM: Homo sapiens

<400> SEQUENCE: 4

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Phe Gly Val Pro
50 55 60

Asp Arg Phe Ser Gly Ser Gly Ala Gly Thr Asp Phe Thr Leu Lys Ile
65 70 75 80

Gly Arg Val Glu Ala Glu Asp Val Gly Leu Tyr Tyr Cys Met Gln Ser
85 90 95

Thr Gln Phe Pro Leu Thr Phe Gly Gly Gly Thr Lys Val Glu Ile Lys
100 105 110

<210> SEQ ID NO 5
<211> LENGTH: 384
<212> TYPE: DNA
<213> ORGANISM: Homo Sapiens

<400> SEQUENCE: 5
caggtgccgc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgcagggccg attcaccatc tccagagaca attccaagaa tacgctgtat 240
ctgcaaatga acagcctgag agccgaggac acggctgtat attactgtgc gagaggcgtt 300
actatggttc ggggacttat tatagcgcgc tactactacg gtttggacgt ctggggccaa 360
gggaccacgg tcaccgtctc ctca 384

<210> SEQ ID NO 6
<211> LENGTH: 128
<212> TYPE: PRT
<213> ORGANISM: Homo Sapiens

<400> SEQUENCE: 6

Gln Val Pro Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Thr Met Val Arg Gly Leu Ile Ile Ala Arg Tyr Tyr
            100                 105                 110

Tyr Gly Leu Asp Val Trp Gly Gln Gly Thr Thr Val Thr Val Ser Ser
        115                 120                 125

<210> SEQ ID NO 7
<211> LENGTH: 336
<212> TYPE: DNA
<213> ORGANISM: Homo Sapiens

<400> SEQUENCE: 7
gatattgtga tgacccagac tccactctcc tcacctgtca cttttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taatcggttc 180
tttggggtcc cagacagatt cagtggcagt ggggcaggga cagatttcac actgaaaatc 240
agcagggtgg aggctgagga tgtcgggctt tattactgca tgcagtctac acaatttcct 300
ctcactttcg gcggagggac caaggtggag atcaaa 336

<210> SEQ ID NO 8
<211> LENGTH: 112
<212> TYPE: PRT
<213> ORGANISM: Homo Sapiens

<400> SEQUENCE: 8

Asp Ile Val Met Thr Gln Thr Pro Leu Ser Ser Pro Val Thr Phe Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Met Gln Ser
                85                  90                  95

Thr Gln Phe Pro Leu Thr Phe Gly Gly Gly Thr Lys Val Glu Ile Lys
            100                 105                 110

<210> SEQ ID NO 9
<211> LENGTH: 360
<212> TYPE: DNA
<213> ORGANISM: Homo Sapiens

<400> SEQUENCE: 9

```
cagctgcagc tgcaggagtc gggcccagga ctggtgaagc cttcggagac cctgtccctc      60
acctgcactg tctctggtgg ctccatcagc agtaggagtg actactgggg ctggatccgg     120
cagcccccag ggaagggact ggagtggatt gggactatct attatagtgg ggacacctac     180
tacaacccgt ccctcaagag tcgagtcacc atatccgtag acacgtccaa gaaccagttc     240
tccctgaagt tgagctctgt gaccgccgca gacacggctg tgtattactg tgcgagacaa     300
cagctggtcc tctactactt tgactactgg ggccagggaa ccctggtcac cgtctcctca     360
```

<210> SEQ ID NO 10
<211> LENGTH: 120
<212> TYPE: PRT
<213> ORGANISM: Homo sapiens

<400> SEQUENCE: 10

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Ser Asp Tyr Trp Gly Trp Ile Arg Gln Pro Pro Gly Lys Gly Leu Glu
        35                  40                  45

Trp Ile Gly Thr Ile Tyr Tyr Ser Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gln Leu Val Leu Tyr Tyr Phe Asp Tyr Trp Gly Gln
            100                 105                 110

Gly Thr Leu Val Thr Val Ser Ser
        115                 120
```

<210> SEQ ID NO 11
<211> LENGTH: 327
<212> TYPE: DNA
<213> ORGANISM: Homo Sapiens

<400> SEQUENCE: 11

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg cccccaggct cctcatctat gctacatcca acagggccac tggcatccca     180
gacaggttca gtggcagtgg gtctgggaca gacttcactc tcaccatcag cagactggag     240
cctgaagatt ttgcagtgta ttactgtcag cagcatggta gctcacctcc gctcactttc     300
ggcgggggga ccaaggtgga gatcaaa                                         327
```

<210> SEQ ID NO 12
<211> LENGTH: 109
<212> TYPE: PRT
<213> ORGANISM: Homo Sapiens

<400> SEQUENCE: 12

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
35 40 45

Ile Tyr Ala Thr Ser Asn Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln His Gly Ser Ser Pro
85 90 95

Pro Leu Thr Phe Gly Gly Gly Thr Lys Val Glu Ile Lys
100 105

<210> SEQ ID NO 13
<211> LENGTH: 360
<212> TYPE: DNA
<213> ORGANISM: Homo Sapiens

<400> SEQUENCE: 13
cagctgcagc tgcaggagtc gggcccagga ctggtgaagc cttcggagac cctgtccctc 60
acctgcactg tctctggtgg ctccatcagc agtagaagtg actactgggg ctggatccgc 120
cagcccccag ggaaggggct ggagtggatt gggactatct attatagtgg gagcaccttc 180
tacaacccgt ccctcaagag tcgagtcacc atatccgtag acacgtccaa gaaccagttc 240
tccctgaagc tgagctctgt gaccgccgca gacacggctg tgtattactg tgcgcgacaa 300
cagctggtcc tctactactt tgactactgg ggccagggaa ccctggtcac cgtctcctca 360

<210> SEQ ID NO 14
<211> LENGTH: 120
<212> TYPE: PRT
<213> ORGANISM: Homo Sapiens

<400> SEQUENCE: 14

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Arg
20 25 30

Ser Asp Tyr Trp Gly Trp Ile Arg Gln Pro Pro Gly Lys Gly Leu Glu
35 40 45

Trp Ile Gly Thr Ile Tyr Tyr Ser Gly Ser Thr Phe Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gln Gln Leu Val Leu Tyr Tyr Phe Asp Tyr Trp Gly Gln
100 105 110

Gly Thr Leu Val Thr Val Ser Ser
115 120

<210> SEQ ID NO 15
<211> LENGTH: 327
<212> TYPE: DNA
<213> ORGANISM: Homo Sapiens

<400> SEQUENCE: 15
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctcc gctcactttc 300
ggcggaggga ccaaggtgga gatcaaa 327

<210> SEQ ID NO 16
<211> LENGTH: 109
<212> TYPE: PRT
<213> ORGANISM: Homo Sapiens

<400> SEQUENCE: 16

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Pro Leu Thr Phe Gly Gly Gly Thr Lys Val Glu Ile Lys
100 105

<210> SEQ ID NO 17
<211> LENGTH: 360
<212> TYPE: DNA
<213> ORGANISM: Homo Sapiens

<400> SEQUENCE: 17
caactgcagc tgcaggagtc gggcccagga ctggtgaagc cttcggggac cctgtccctc 60
agctgcactg tctctggtgg ctccatcagc agtagaagtg actactgggg ctggatccgc 120
cagcccccag ggaaggggct ggagtggatt gggactatct attatagtgg gaacaccttc 180
tacaacccgt ccctcaagag tcgagtcacc atatccgtag acacgtccaa gaagcagttc 240
tccctgaagc tgagctctgt gaccgccgca gacacggctg tctattactg tgcgcgacaa 300
cagctggtcc tctactactt tgactactgg ggccagggaa ccctggtcac cgtctcctca 360

<210> SEQ ID NO 18
<211> LENGTH: 120
<212> TYPE: PRT
<213> ORGANISM: Homo Sapiens

<400> SEQUENCE: 18

Gln Leu Gln Leu Gln Glu Ser Gly Pro Gly Leu Val Lys Pro Ser Gly
1 5 10 15

Thr Leu Ser Leu Ser Cys Thr Val Ser Gly Gly Ser Ile Ser Ser Arg
20 25 30

Ser Asp Tyr Trp Gly Trp Ile Arg Gln Pro Pro Gly Lys Gly Leu Glu
35 40 45

Trp Ile Gly Thr Ile Tyr Tyr Ser Gly Asn Thr Phe Tyr Asn Pro Ser
50 55 60

Leu Lys Ser Arg Val Thr Ile Ser Val Asp Thr Ser Lys Lys Gln Phe
65 70 75 80

```
Ser Leu Lys Leu Ser Ser Val Thr Ala Ala Asp Thr Ala Val Tyr Tyr
                85                  90                  95

Cys Ala Arg Gln Gln Leu Val Leu Tyr Tyr Phe Asp Tyr Trp Gly Gln
            100                 105                 110

Gly Thr Leu Val Thr Val Ser Ser
        115                 120


<210> SEQ ID NO 19
<211> LENGTH: 327
<212> TYPE: DNA
<213> ORGANISM: Homo Sapiens

<400> SEQUENCE: 19

gaaattgtgt tgacgcagtc tccaggcacc ctgtctttgt ctccagggga aagagccacc     60

ctctcctgca ggaccagtca gagtgttagc agcagctact tagcctggta tcagcagaaa    120

cctggccagg ctcccaggct cctcatctat ggtgcatcca gcagggccac tggcgtccca    180

gacaggttca gtggcagtgg gtctgggaca gacttctctc tcaccatcag caggctggag    240

cctgaagatt ttgcagtgta ttactgtcag caatatggta gctcacctcc gctcactttc    300

ggcggaggga ccaaggtgga gatcaaa                                         327


<210> SEQ ID NO 20
<211> LENGTH: 109
<212> TYPE: PRT
<213> ORGANISM: Homo Sapiens

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105


<210> SEQ ID NO 21
<211> LENGTH: 360
<212> TYPE: DNA
<213> ORGANISM: Homo sapiens

<400> SEQUENCE: 21

cagctgcagc tgcaggagtc gggcccagga ctggtgaagc cttcggagac cctgtccctc     60

acctgcactg tctctggtgg ctccatcagc agtagaagta actactgggg ctggatccgc    120

cagcccccag ggaagggact ggagtggatt gggactatct attatagtgg gcacacctac    180

tacaacccgt ccctcaagag tcgagtcagc atatccgtag acacgtccaa gaaccagttc    240

tccctgaagt tgagctctgt gaccgccaca gacacggctc tgtattactg tgcgagacaa    300

cagctggtcc tctactactt tgaatactgg ggccagggaa ccctggtcac cgtctcctca    360


<210> SEQ ID NO 22
```

<211> LENGTH: 120
<212> TYPE: PRT
<213> ORGANISM: Homo Sapiens

<400> SEQUENCE: 22

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Ser Asn Tyr Trp Gly Trp Ile Arg Gln Pro Pro Gly Lys Gly Leu Glu
        35                  40                  45

Trp Ile Gly Thr Ile Tyr Tyr Ser Gly His Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Thr Asp Thr Ala Leu Tyr Tyr
                85                  90                  95

Cys Ala Arg Gln Gln Leu Val Leu Tyr Tyr Phe Glu Tyr Trp Gly Gln
            100                 105                 110

Gly Thr Leu Val Thr Val Ser Ser
        115                 120
```

<210> SEQ ID NO 23
<211> LENGTH: 327
<212> TYPE: DNA
<213> ORGANISM: Homo sapiens

<400> SEQUENCE: 23

```
gaaattgtgt tgacgcagtc tccaggcacc ctgtctttgt ctccagggga aagagccacc      60

ctctcctgca gggccagtca gagtattagc agaagttact tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtata ttactgtcag cagtatggta gttcacctcc gctcactttc     300

ggcggaggga ccaaggtgga gatcaaa                                         327
```

<210> SEQ ID NO 24
<211> LENGTH: 109
<212> TYPE: PRT
<213> ORGANISM: Homo Sapiens

<400> SEQUENCE: 24

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105
```

<210> SEQ ID NO 25
<211> LENGTH: 360
<212> TYPE: DNA
<213> ORGANISM: Homo Sapiens

<400> SEQUENCE: 25
cagctgcagc tgcaggagtc gggcccagga ctggtgaagc cttcggagac cctgtccctc 60
acctgcactg tctctggtgg ctccatcagc agtcctaatt actactgggg ctggatccgc 120
cagcccccag gaaaggggct ggagtggatt gggactatct attatagtgg gaacaccttc 180
tacaacccgt ccctcaagag tcgagtcacc atatccgtag acacgtccaa gaaccagttc 240
tccctgaagc tgagctctgt gaccgccgca gacacggctg tgtattactg tgcgactcag 300
cagctggtcc tctactactt tgacttctgg ggccagggaa ccctggtcac cgtctcctca 360

<210> SEQ ID NO 26
<211> LENGTH: 120
<212> TYPE: PRT
<213> ORGANISM: Homo Sapiens

<400> SEQUENCE: 26

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Pro
20 25 30

Asn Tyr Tyr Trp Gly Trp Ile Arg Gln Pro Pro Gly Lys Gly Leu Glu
35 40 45

Trp Ile Gly Thr Ile Tyr Tyr Ser Gly Asn Thr Phe Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Thr Gln Gln Leu Val Leu Tyr Tyr Phe Asp Phe Trp Gly Gln
100 105 110

Gly Thr Leu Val Thr Val Ser Ser
115 120

<210> SEQ ID NO 27
<211> LENGTH: 321
<212> TYPE: DNA
<213> ORGANISM: Homo Sapiens

<400> SEQUENCE: 27
gaaattgtgt tgacgcagtc tccaggcacc ctgtctttgt ctccagggaa aagagccgcc 60
ctctcctgca gggccagtca gagtattagc agcagctatt tagcctggta ccaacagaaa 120
cctggccagg ctcccaggct cctcatctat ggtgcatcca gcagggccac tggcatccca 180
gacaggttca atggcagtgg gtctgggaca gacttcactc tcaccatcag cagactggag 240
cctgaagatt ttgcagtgta ttactgtcag cagcttggta gttcgatcac cttcggccaa 300
gggacacgac tggagattaa a 321

<210> SEQ ID NO 28
<211> LENGTH: 107
<212> TYPE: PRT
<213> ORGANISM: Homo Sapiens

<400> SEQUENCE: 28

Glu Ile Val Leu Thr Gln Ser Pro Gly Thr Leu Ser Leu Ser Pro Gly

-continued

```
1               5                   10                  15

Lys Arg Ala Ala Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Asn
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Gly Ser Ser Ile
                85                  90                  95

Thr Phe Gly Gln Gly Thr Arg Leu Glu Ile Lys
            100                 105
```

<210> SEQ ID NO 29
<211> LENGTH: 360
<212> TYPE: DNA
<213> ORGANISM: Homo Sapiens

<400> SEQUENCE: 29

```
cagctgcagc tgcaggagtc gggcccagga ctggtgaagc cttcggagac cctgtccctc     60

acctgcactg tctctggtgg ctccatcagc agtcgttatt actactgggg ctgggtccgc    120

cagcccccag gaaaggggct ggagtggatt gggactatct attatagtgg gcacacctac    180

tacaacccgt ccctcaagac tcgcgtcacc atatccgtag acacgtccaa gaaccagttc    240

tccctgaagc tgatctctgt gaccgccgca gacacggctg tgtattactg tgcgactcag    300

cagctggtac tctactactt tgacttctgg ggccagggaa ccctggtcac cgtctcctca    360
```

<210> SEQ ID NO 30
<211> LENGTH: 120
<212> TYPE: PRT
<213> ORGANISM: Homo Sapiens

<400> SEQUENCE: 30

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Tyr Tyr Tyr Trp Gly Trp Val Arg Gln Pro Pro Gly Lys Gly Leu Glu
        35                  40                  45

Trp Ile Gly Thr Ile Tyr Tyr Ser Gly His Thr Tyr Tyr Asn Pro Ser
    50                  55                  60

Leu Lys Thr Arg Val Thr Ile Ser Val Asp Thr Ser Lys Asn Gln Phe
65                  70                  75                  80

Ser Leu Lys Leu Ile Ser Val Thr Ala Ala Asp Thr Ala Val Tyr Tyr
                85                  90                  95

Cys Ala Thr Gln Gln Leu Val Leu Tyr Tyr Phe Asp Phe Trp Gly Gln
            100                 105                 110

Gly Thr Leu Val Thr Val Ser Ser
        115                 120
```

<210> SEQ ID NO 31
<211> LENGTH: 321
<212> TYPE: DNA
<213> ORGANISM: Homo Sapiens

<400> SEQUENCE: 31

```
gaaattgtgt tgacgcagtc tccaggcacc ctgtctttgt ctccagggga aagagccgcc     60

ctctcctgca gggccagtca gagtattagc agcagctact tagcctggta ccagcagaga    120

cctggccagg ctcccaggct cctcatttat ggtgcatcta gcagggccac tggcatccca    180

gacaggttca acggcagtgg gtctgggaca gacttcactc tcaccatcag cagactggag    240

cctgaagatt ttgcagtgta ttactgtcag cagtttggta gctcgatcac cttcggccaa    300

gggacacgac tggagattaa a                                              321
```

<210> SEQ ID NO 32
<211> LENGTH: 107
<212> TYPE: PRT
<213> ORGANISM: Homo Sapiens

<400> SEQUENCE: 32

```
Glu Ile Val Leu Thr Gln Ser Pro Gly Thr Leu Ser Leu Ser Pro Gly
1               5                   10                  15

Glu Arg Ala Ala Leu Ser Cys Arg Ala Ser Gln Ser Ile Ser Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Asn
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Ile
                85                  90                  95

Thr Phe Gly Gln Gly Thr Arg Leu Glu Ile Lys
            100                 105
```

<210> SEQ ID NO 33
<211> LENGTH: 348
<212> TYPE: DNA
<213> ORGANISM: Homo Sapiens

<400> SEQUENCE: 33

```
gaggtgcagc tggtggagtc tgggggaggc ctggtcaagc ctgggggggtc cctgagactc     60

tcctgtgcag cctctggatt caccttcagt acctatagca tgaactgggt ccgccaggct    120

ccaggcaagg ggctggagtg ggtctcattc attagtggta gaagtagtta catatactac    180

gcagactcag tgaagggccg attcaccatc tccagagaca acgccaagaa ctcactgtat    240

ctgcaaatga acagcctgag agccgaggac acggctgtgt attactgttc gaaagatgat    300

tggttcgagg agttatgggg ccagggaacc ctggtcaccg tctcctca                 348
```

<210> SEQ ID NO 34
<211> LENGTH: 116
<212> TYPE: PRT
<213> ORGANISM: Homo Sapiens

<400> SEQUENCE: 34

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Phe Ile Ser Gly Arg Ser Ser Tyr Ile Tyr Tyr Ala Asp Ser Val
    50                  55                  60
```

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ser Lys Asp Asp Trp Phe Glu Glu Leu Trp Gly Gln Gly Thr Leu Val
100 105 110

Thr Val Ser Ser
115

<210> SEQ ID NO 35
<211> LENGTH: 321
<212> TYPE: DNA
<213> ORGANISM: Homo Sapiens

<400> SEQUENCE: 35
gacatccaga tgacccagtc tccatcctcc ctgtctgcat ctgtcggaga cagagtcacc 60
atcacttgcc gggcaagtca gggcattaga aatgatttag gctggtatca gcagaaacca 120
gggaaagccc ctaagcgcct gatctatgct acattcagtt tgcaaagtgg ggtcccatca 180
aggttcagcg gcagtggctc tgggacagaa ttcactctca caatcagcag cctgcagcct 240
gaagattttg caacttatta ctgtctacag cataatcgtt acccgtggac gttcggccaa 300
gggaccaagg tggaaatcaa a 321

<210> SEQ ID NO 36
<211> LENGTH: 107
<212> TYPE: PRT
<213> ORGANISM: Homo Sapiens

<400> SEQUENCE: 36

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Thr Phe Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Arg Tyr Pro Trp
85 90 95

Thr Phe Gly Gln Gly Thr Lys Val Glu Ile Lys
100 105

<210> SEQ ID NO 37
<211> LENGTH: 348
<212> TYPE: DNA
<213> ORGANISM: Homo Sapiens

<400> SEQUENCE: 37
gaggtgcagc tggtggagtc tgggggaggc ctggtcaagc ctgggggtc cctgagactc 60 tcctgtgcag cctctggatt caccatcagt agctatagca tgaactgggt ccgccaggct 120
ccagggaagg ggctggagtg ggtctcattc attagtagta gaagtaatta catatactac 180
gcagactcag tgaagggccg attcaccatc tccagagaca acgccaagaa ctcactgtat 240
ctgcaaatga acagcctgag agccgaggac acggctgtgt attactgttc gaaagatgat 300
tggttcgagg agttatgggg ccagggaacc ctggtcaccg tctcctca 348

<210> SEQ ID NO 38
<211> LENGTH: 116
<212> TYPE: PRT
<213> ORGANISM: Homo Sapiens

<400> SEQUENCE: 38

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Ile Ser Ser Tyr
20 25 30

Ser Met Asn Trp Val Arg Gln Ala Pro Gly Lys Gly Leu Glu Trp Val
35 40 45

Ser Phe Ile Ser Ser Arg Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ser Lys Asp Asp Trp Phe Glu Glu Leu Trp Gly Gln Gly Thr Leu Val
100 105 110

Thr Val Ser Ser
115

<210> SEQ ID NO 39
<211> LENGTH: 321
<212> TYPE: DNA
<213> ORGANISM: Homo Sapiens

<400> SEQUENCE: 39
gacatccaga tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagcgcct gatctatgct gcatccagtt tacaaagtgg ggtcccatca 180
aggttcagcg gcagtggatc tgggacagaa ttcactctca caatcagcag cctgcagcct 240
gaagattttg caacttatta ctgtctacag cataatagtt tcccgtggac gttcggccaa 300
gggaccaagg tggaaatcaa a 321

<210> SEQ ID NO 40
<211> LENGTH: 107
<212> TYPE: PRT
<213> ORGANISM: Homo Sapiens

<400> SEQUENCE: 40

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Ser Phe Pro Trp
85 90 95

-continued

Thr Phe Gly Gln Gly Thr Lys Val Glu Ile Lys
100 105

<210> SEQ ID NO 41
<211> LENGTH: 348
<212> TYPE: DNA
<213> ORGANISM: Homo Sapiens

<400> SEQUENCE: 41
gaggtgcagc tggtggagtc tgggggaggc ctggtcaagc ctgggggtc cctgagactc 60 tcctgtgcag cctctggatt caccttcagt acctatagca tgaactgggt ccgccaggct 120
ccaggcaagg ggctggagtg ggtctcattc attagtggta gaagtagtta catatactac 180
gcagactcag tgaagggccg attcaccatc tccagagaca acgccaagaa ctcactgtat 240
ctgcaaatga acagcctgag agccgaggac acggctgtgt attactgttc gaaagatgat 300
tggttcgagg agttatgggg ccagggaacc ctggtcaccg tctcctct 348

<210> SEQ ID NO 42
<211> LENGTH: 116
<212> TYPE: PRT
<213> ORGANISM: Homo Sapiens

<400> SEQUENCE: 42

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ser Met Asn Trp Val Arg Gln Ala Pro Gly Lys Gly Leu Glu Trp Val
35 40 45

Ser Phe Ile Ser Gly Arg Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ser Lys Asp Asp Trp Phe Glu Glu Leu Trp Gly Gln Gly Thr Leu Val
100 105 110

Thr Val Ser Ser
115

<210> SEQ ID NO 43
<211> LENGTH: 321
<212> TYPE: DNA
<213> ORGANISM: Homo Sapiens

<400> SEQUENCE: 43
gacatccaga tgacccagtc tccatcctcc ctgtctgcat ctgtcggaga cagagtcacc 60
atcacttgcc gggcaagtca gggcattaga agtgatttag gctggtatca gcagaaacca 120
gggaaagccc ctaagcgcct gatctatgct acatccagtt tgcaaagtgg ggtcccatca 180
aggttcagcg gcagtggctc tgggacagaa ttcactctca caatcagcag cctgcagcct 240
gaagattttg caacttatta ctgtctacag cataatcgtt acccgtggac gttcggccaa 300
gggaccaagg tggaaatcaa a 321

<210> SEQ ID NO 44
<211> LENGTH: 107
<212> TYPE: PRT
<213> ORGANISM: Homo Sapiens

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Arg Tyr Pro Trp
                85                  90                  95

Thr Phe Gly Gln Gly Thr Lys Val Glu Ile Lys
            100                 105
```

<210> SEQ ID NO 45
<211> LENGTH: 348
<212> TYPE: DNA
<213> ORGANISM: Homo Sapiens

<400> SEQUENCE: 45

```
gaggtgcagc tggtggagtc tgggggaggc ctggtcaagc ctgggggtc cctgagactc      60

tcctgtgcag cctctggatt caccttcagt agctatacca tgaactgggt ccgccaggct    120

ccagggaagg ggctggagtg ggtctcattc attgatagta gaagtagtta catatactac    180

gcagactcag tgaagggccg attcaccatc tccagagaca acgccaagaa ctcactgtat    240

ctgcaaatga acagcctgag agccgaggac acggctgtgt attactgttc gaaagatgat    300

tggttcgagg agttatgggg ccagggaacc ctggtcaccg tctcctca                348
```

<210> SEQ ID NO 46
<211> LENGTH: 116
<212> TYPE: PRT
<213> ORGANISM: Homo Sapiens

<400> SEQUENCE: 46

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Phe Ile Asp Ser Arg Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Lys Asp Asp Trp Phe Glu Glu Leu Trp Gly Gln Gly Thr Leu Val
            100                 105                 110

Thr Val Ser Ser
        115
```

<210> SEQ ID NO 47
<211> LENGTH: 321
<212> TYPE: DNA

<213> ORGANISM: Homo Sapiens

<400> SEQUENCE: 47
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct acatccagtt tacaaagtgg ggtcccatca 180
aggttcagcg gcagtggatc tgggacagaa ttcactctca caatcagcag cctgcagcct 240
gaagattttg caacttatta ctgtctacac cataatagtt tcccgtggac gttcggccaa 300
gggaccaagg tggaaatcaa a 321

<210> SEQ ID NO 48
<211> LENGTH: 107
<212> TYPE: PRT
<213> ORGANISM: Homo Sapiens

<400> SEQUENCE: 48

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Thr Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu His His Asn Ser Phe Pro Trp
85 90 95

Thr Phe Gly Gln Gly Thr Lys Val Glu Ile Lys
100 105

<210> SEQ ID NO 49
<211> LENGTH: 369
<212> TYPE: DNA
<213> ORGANISM: Homo Sapiens

<400> SEQUENCE: 49
caggtgcagc tgcaggagtc gggcccagga ctggtgaagc cttcacagac cctgtccctc 60
acctgcactg tctctggtgg ctccatcagc agtggtgatc actactggag ctggatccgc 120
cagcacccag ggaagggcct ggagtggatt gggcacatct attacagtgg gagcaccgat 180
tacaacccgt ccctcaagag tcgagttacc atatcagtag acacgtctaa gaaccatttc 240
tccctgaagc tgaactctgt gactgccgcg gacacggccg tgtattactg tgcgaggacg 300
aatagcagca gctggtccga ctggtacttc gatctctggg gccgtggcac cctggtcact 360
gtctcctca 369

<210> SEQ ID NO 50
<211> LENGTH: 123
<212> TYPE: PRT
<213> ORGANISM: Homo Sapiens

<400> SEQUENCE: 50

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

```
Asp His Tyr Trp Ser Trp Ile Arg Gln His Pro Gly Lys Gly Leu Glu
        35                  40                  45

Trp Ile Gly His Ile Tyr Tyr Ser Gly Ser Thr Asp Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Asn Ser Val Thr Ala Ala Asp Thr Ala Val Tyr Tyr
                85                  90                  95

Cys Ala Arg Thr Asn Ser Ser Ser Trp Ser Asp Trp Tyr Phe Asp Leu
            100                 105                 110

Trp Gly Arg Gly Thr Leu Val Thr Val Ser Ser
        115                 120


<210> SEQ ID NO 51
<211> LENGTH: 339
<212> TYPE: DNA
<213> ORGANISM: Homo Sapiens

<400> SEQUENCE: 51

gacatcgtga tgacccagtc tccagactcc ctggctgtgt ctctgggcga gagggccacc      60

atcaactgca agtccagcca gagtatttta tacagctcca acaataagaa ctacttagct     120

tggtaccagc ggaaaccagg acagcctccg atactgctca ttcactgggc ttctacccgg     180

gaatccgggg tccctgaccg attcagtggc agcgggtctc ggaccgattt cactctcacc     240

atcagcagcc tgcaggctga agatgtggcc gtttattact gtcagcaata ttttattact     300

ccgtggacgt tcggccaagg gaccaaggtg gaaatcaaa                            339


<210> SEQ ID NO 52
<211> LENGTH: 113
<212> TYPE: PRT
<213> ORGANISM: Homo Sapiens

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Asn Lys Asn Tyr Leu Ala Trp Tyr Gln Arg Lys Pro Gly Gln
        35                  40                  45

Pro Pro Ile Leu Leu Ile His Trp Ala Ser Thr Arg Glu Ser Gly Val
    50                  55                  60

Pro Asp Arg Phe Ser Gly Ser Gly Ser Arg Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ile Thr Pro Trp Thr Phe Gly Gln Gly Thr Lys Val Glu Ile
            100                 105                 110

Lys


<210> SEQ ID NO 53
<211> LENGTH: 360
<212> TYPE: DNA
<213> ORGANISM: Homo Sapiens

<400> SEQUENCE: 53

caggtgcagc tggtgcagtc tggggctgag gtgaagaagc ccggtgcctc agtgaaggtc      60
```

```
tcctgcaagg cttctggata caccttcacc agttatgata tcaactgggt gcgacaggcc    120

actggacaag ggcttgagtg gatgggatgg atgaacccta acagtggtaa gacaggctat    180

gcacagaagt tccagggcag agtcaccatg accaggaaca cctccataaa tacagcctac    240

atggagctga gcagcctgag atctgaggac acggccgtgt attactgtgc gagaggcggg    300

tatagcaact tggggtggtt cgacccctgg ggccagggaa ccctggtcac cgtctcctca    360


<210> SEQ ID NO 54
<211> LENGTH: 120
<212> TYPE: PRT
<213> ORGANISM: Homo Sapiens

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Lys Thr Gly Tyr Ala Gln Lys Phe
    50                  55                  60

Gln Gly Arg Val Thr Met Thr Arg Asn Thr Ser Ile Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Asn Leu Gly Trp Phe Asp Pro Trp Gly Gln
            100                 105                 110

Gly Thr Leu Val Thr Val Ser Ser
        115                 120


<210> SEQ ID NO 55
<211> LENGTH: 321
<212> TYPE: DNA
<213> ORGANISM: Homo Sapiens

<400> SEQUENCE: 55

gacatccaga tgacccagtc tccatcttcc gtgtctgcat ctgttggaga cagagtcacc     60

atcacttgtc gggcgagtca gggtattagc agctggttag tctggtatca ccagaaacca    120

gggaaagccc ctaaactcct gatctatggt gcatccagtt tgcaaagtgg ggtcccatca    180

aggttcagcg gcagtggatc tgggacagat ttcactctca ccatcagcag cctgcagcct    240

gaagattttg caacttacta ttgtcaacag gctaacaatt tcccattcac tttcggccct    300

gggaccaaag tggatatcaa a                                              321


<210> SEQ ID NO 56
<211> LENGTH: 107
<212> TYPE: PRT
<213> ORGANISM: Homo Sapiens

<400> SEQUENCE: 56

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr His Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
                85                  90                  95

Thr Phe Gly Pro Gly Thr Lys Val Asp Ile Lys
            100                 105


<210> SEQ ID NO 57
<211> LENGTH: 360
<212> TYPE: DNA
<213> ORGANISM: Homo Sapiens

<400> SEQUENCE: 57

caggtgcagc tggtgcagtc tggggctgag gtgaagaagc ctggggcctc agtgaaggtc      60

tcctgcaagg cttctggata caccttcggc agttatgata tcaactgggt gcgacaggcc     120

accggacaag ggcttgagtg gatgggatgg atgaacccta acagtggtaa cacaggctat     180

gcacaaaagt tccagggcag agtcaccctg accaggaaca cctccataag aacagtctac     240

atggaattga gcagcctgag atctgaggac acggccgtgt attactgtgc gagaggcggt     300

tatagtaact tggggtggtt cgacccctgg ggccagggaa gcctggtcac cgtctcctca     360


<210> SEQ ID NO 58
<211> LENGTH: 120
<212> TYPE: PRT
<213> ORGANISM: Homo Sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Leu Thr Arg Asn Thr Ser Ile Arg Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Asn Leu Gly Trp Phe Asp Pro Trp Gly Gln
            100                 105                 110

Gly Ser Leu Val Thr Val Ser Ser
        115                 120


<210> SEQ ID NO 59
<211> LENGTH: 321
<212> TYPE: DNA
<213> ORGANISM: Homo Sapiens

<400> SEQUENCE: 59

gacatccaga tgacccagtc tccatcttcc gtgtctgtat ctgtaggaga cagagtcacc      60

atcacttgtc gggcgagtca gggtattagc agctggttag cctggtatca gcagaaacca     120

gggaaagccc ctaagctcct gatctatgct gcatccagtt tgcaaagtgg ggtcccatca     180

aggttcagcg gcagtggatc tgggacagat ttcactctca ccatcagcag cctgcagcct     240

gaagattttg caacttacta ttgtcaacag gctaacagtt tcccattcac tttcggccct     300
```

gggaccaaag tggatatcaa a 321

<210> SEQ ID NO 60
<211> LENGTH: 107
<212> TYPE: PRT
<213> ORGANISM: Homo Sapiens

<400> SEQUENCE: 60

Asp Ile Gln Met Thr Gln Ser Pro Ser Ser Val Ser Val Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Phe
85 90 95

Thr Phe Gly Pro Gly Thr Lys Val Asp Ile Lys
100 105

<210> SEQ ID NO 61
<211> LENGTH: 360
<212> TYPE: DNA
<213> ORGANISM: Homo Sapiens

<400> SEQUENCE: 61
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgaatg gatgggatgg atgaacccta acagtggtaa aacaggctat 180
gcacagaagt tccagggcag agtcaccatg accaggagca cctccataag cacagcctac 240
atggagctga gcagtctgag atctgaggac acggccgtgt attactgtgc gagaggcggg 300
tatagcaact tggggtggtt cgacccctgg ggccagggaa ccctggtcac cgtctcctca 360

<210> SEQ ID NO 62
<211> LENGTH: 120
<212> TYPE: PRT
<213> ORGANISM: Homo Sapiens

<400> SEQUENCE: 62

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Thr Gly Gln Gly Leu Glu Trp Met
35 40 45

Gly Trp Met Asn Pro Asn Ser Gly Lys Thr Gly Tyr Ala Gln Lys Phe
50 55 60

Gln Gly Arg Val Thr Met Thr Arg Ser Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Tyr Ser Asn Leu Gly Trp Phe Asp Pro Trp Gly Gln
100 105 110

Gly Thr Leu Val Thr Val Ser Ser
115 120

<210> SEQ ID NO 63
<211> LENGTH: 321
<212> TYPE: DNA
<213> ORGANISM: Homo Sapiens

<400> SEQUENCE: 63
gacatccaga tgacccagtc tccatcttcc gtgtttgcat ctgtaggaga cagagtcacc 60
atcacttgtc gggcgagtca gggtattagc acctggttag cctggtatca gcagaaacca 120
gggaaagccc ctaagttcct gatctatgct gcatccagtt tgcaaagtgg ggtcccatca 180
aggttcagcg gcagtggatc tgggacagat ttcactctca ccatcagcag cctgcagcct 240
gacgattttg caacttacta ttgtcaacag gctaacaatt tcccattcac tttcggccct 300
gggaccaaag tggatatcaa a 321

<210> SEQ ID NO 64
<211> LENGTH: 107
<212> TYPE: PRT
<213> ORGANISM: Homo Sapiens

<400> SEQUENCE: 64

Asp Ile Gln Met Thr Gln Ser Pro Ser Ser Val Phe Ala Ser Val Gly
1 5 10 15

Asp Arg Val Thr Ile Thr Cys Arg Ala Ser Gln Gly Ile Ser Thr Trp
20 25 30

Leu Ala Trp Tyr Gln Gln Lys Pro Gly Lys Ala Pro Lys Phe Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Asp Asp Phe Ala Thr Tyr Tyr Cys Gln Gln Ala Asn Asn Phe Pro Phe
85 90 95

Thr Phe Gly Pro Gly Thr Lys Val Asp Ile Lys
100 105

<210> SEQ ID NO 65
<211> LENGTH: 369
<212> TYPE: DNA
<213> ORGANISM: Homo Sapiens

<400> SEQUENCE: 65
caggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac ataagtaata gtggtattac catatactac 180
gcagactctg tgaagggccg attcaccatc tccagggaca acgccaagaa ctcactgtat 240
ctgcaaatga acagcctgag agccggggac acggccgtgt attactgtgc gagagaggag 300
tggtatagca gtaggtggta caggaatttt gactactggg gccagggaac cctggtcacc 360
gtctcctct 369

<210> SEQ ID NO 66
<211> LENGTH: 123
<212> TYPE: PRT
<213> ORGANISM: Homo Sapiens

<400> SEQUENCE: 66

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Asn Ser Gly Ile Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Arg Glu Glu Trp Tyr Ser Ser Arg Trp Tyr Arg Asn Phe Asp Tyr
            100                 105                 110

Trp Gly Gln Gly Thr Leu Val Thr Val Ser Ser
        115                 120
```

<210> SEQ ID NO 67
<211> LENGTH: 321
<212> TYPE: DNA
<213> ORGANISM: Homo Sapiens

<400> SEQUENCE: 67

```
gacatccaga tgacccagtt ttcatcctcc ctgtccgcat ctgtgggaga cagagtcacc      60

atcacttgcc gggcaagtca gagcattagc aggtatttaa attggtatca gcagaaacca     120

gggaaagccc ctaaactcct gatctatgct gcatccagtt tgcaaagtgg ggtcccatca     180

aggttcaatg gcagtggatc tgggacagac ttcactctca ccatcagcag tcttcaacct     240

gaagattttg caacttacta ttgtcaacag agttacagtg ccccgctcac tttcggcgga     300

gggaccaagg tagagatcaa a                                               321
```

<210> SEQ ID NO 68
<211> LENGTH: 107
<212> TYPE: PRT
<213> ORGANISM: Homo Sapiens

<400> SEQUENCE: 68

```
Asp Ile Gln Met Thr Gln Phe Ser Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Asn Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Leu
                85                  90                  95

Thr Phe Gly Gly Gly Thr Lys Val Glu Ile Lys
            100                 105
```

<210> SEQ ID NO 69
<211> LENGTH: 369
<212> TYPE: DNA

<213> ORGANISM: Homo Sapiens

<400> SEQUENCE: 69
caggtgcagt tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatat attagtatta gtggtagtac catatactac 180
gcagactctg tgaagggccg attcaccatc tccagggaca acgccaagaa ctcactgtat 240
ctgcaaatga acagcctgag agccgaggac acggccgtat attactgtgc gagagacgat 300
ttttggagtg gttattactt caactggttc gacccctggg gccagggaac cctggtcacc 360
gtctcctca 369

<210> SEQ ID NO 70
<211> LENGTH: 123
<212> TYPE: PRT
<213> ORGANISM: Homo Sapiens

<400> SEQUENCE: 70

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ile Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Phe Trp Ser Gly Tyr Tyr Phe Asn Trp Phe Asp Pro
100 105 110

Trp Gly Gln Gly Thr Leu Val Thr Val Ser Ser
115 120

<210> SEQ ID NO 71
<211> LENGTH: 321
<212> TYPE: DNA
<213> ORGANISM: Homo Sapiens

<400> SEQUENCE: 71
gacatccaga tgacccagtc tccatcctcc ctgtctgcat ctgttggaga cagagtcacc 60
atcacttgcc gggcaaatca gaccattagc accttttttaa attggtatca gcagaaccca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag acttacatta ttccgctcac tttcggcgga 300
gggaccaagg tggagatcaa a 321

<210> SEQ ID NO 72
<211> LENGTH: 107
<212> TYPE: PRT
<213> ORGANISM: Homo Sapiens

<400> SEQUENCE: 72

Asp Ile Gln Met Thr Gln Ser Pro Ser Ser Leu Ser Ala Ser Val Gly
1 5 10 15

```
Asp Arg Val Thr Ile Thr Cys Arg Ala Asn Gln Thr Ile Ser Thr Phe
            20                  25                  30

Leu Asn Trp Tyr Gln Gln Asn Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ile Ile Pro Leu
                85                  90                  95

Thr Phe Gly Gly Gly Thr Lys Val Glu Ile Lys
            100                 105
```

<210> SEQ ID NO 73
<211> LENGTH: 369
<212> TYPE: DNA
<213> ORGANISM: Homo Sapiens

<400> SEQUENCE: 73

```
caggtgcagc tggtggagtc tgggggaggc ttggtcaagc ctggagagtc cctgagactc      60

tcctgtgcag cctctggatt caccttcagt gactactaca tgagctggat ccgccaggct     120

ccagggaagg ggctggagtg ggtttcatac attagtcatg gtggtagtac catatactac     180

gcagactctg tgaagggccg attcaccatc tccagggaca acgccaagaa ctcactgtat     240

ctgcaaatga acagcctgag agtcgaggac acggccgtgt atttctgtgc gagagacgat     300

ttttggagtg gttattactt caactggttc gacccctggg gccagggagc cctggtcacc     360

gtctcctca                                                             369
```

<210> SEQ ID NO 74
<211> LENGTH: 123
<212> TYPE: PRT
<213> ORGANISM: Homo Sapiens

<400> SEQUENCE: 74

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser His Gly Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Phe Cys
                85                  90                  95

Ala Arg Asp Asp Phe Trp Ser Gly Tyr Tyr Phe Asn Trp Phe Asp Pro
            100                 105                 110

Trp Gly Gln Gly Ala Leu Val Thr Val Ser Ser
        115                 120
```

<210> SEQ ID NO 75
<211> LENGTH: 321
<212> TYPE: DNA
<213> ORGANISM: Homo Sapiens

<400> SEQUENCE: 75

```
gacatccaga tgactcagta tccattgtcc ctgtctgcat ctgtcggaga cagagtcacc      60

atcacttgcc gggcaagtca gagcattagt agttttttaa attggtatca ccagaaacca    120

gggaaagccc ctaagctcct gatctatggg acatccagtt tgcaaagtgg ggtcccatca    180

aggttcagtg gcagtggatc tgggacagat ttcactctca ccatcagcag tctgcaacct    240

gaagattttg caacttacta ctgtcaacag acttacagta tccccctcac tttcggcgga    300

gggaccaatg tagagatcaa a                                              321
```

<210> SEQ ID NO 76
<211> LENGTH: 107
<212> TYPE: PRT
<213> ORGANISM: Homo Sapiens

<400> SEQUENCE: 76

```
Asp Ile Gln Met Thr Gln Tyr Pro Leu Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr His Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ile Pro Leu
                85                  90                  95

Thr Phe Gly Gly Gly Thr Asn Val Glu Ile Lys
            100                 105
```

<210> SEQ ID NO 77
<211> LENGTH: 366
<212> TYPE: DNA
<213> ORGANISM: Homo Sapiens

<400> SEQUENCE: 77

```
caggtacagc tggtggagtc tgggggaggc gtggtccagc ctgggaggtc cctgagactc      60

tcctgtgcag cgtctggatt caccttcagt acctatggca tgcactgggt ccgccaggct    120

ccaggcaagg ggctggagtg ggtggcagtt atatggtatg atggaagtaa taaatactat    180

gcagactccg tgaagggccg attcaccatc tccagagaca attccaagaa cacgctgtat    240

ctgcaaatga acagcctgag agccgaagac acggctgtgt attactgtgc gtgttcttat    300

tggaacgacg actactatta cggtatggac gtctggggcc aagggaccac ggtcaccgtc    360

tcctca                                                              366
```

<210> SEQ ID NO 78
<211> LENGTH: 122
<212> TYPE: PRT
<213> ORGANISM: Homo Sapiens

<400> SEQUENCE: 78

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45
```

-continued

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Cys Ser Tyr Trp Asn Asp Asp Tyr Tyr Tyr Gly Met Asp Val Trp
100 105 110

Gly Gln Gly Thr Thr Val Thr Val Ser Ser
115 120

<210> SEQ ID NO 79
<211> LENGTH: 321
<212> TYPE: DNA
<213> ORGANISM: Homo Sapiens

<400> SEQUENCE: 79
gacatccaga tgacccagtc tccatcctcc ctgtctgcat ctgtaggaga cagagtcatc 60
atcacttgcc gggcaagtca gaacattagc agctatttaa tttggtatca gcagaaacca 120
gggaaagccc ctaacctcct aatccatact acgtccagtt tgcaacgtgg ggtcccatca 180
aggttcagtg gcagtggatc tgggactgat ttcactctca ccatcagcag tctgcaacct 240
gaagattttg caacttacta ctgtcaacag agttacagtg ccccgctcac tttcggcgga 300
gggaccaagg tggagatcaa a 321

<210> SEQ ID NO 80
<211> LENGTH: 107
<212> TYPE: PRT
<213> ORGANISM: Homo Sapiens

<400> SEQUENCE: 80

Asp Ile Gln Met Thr Gln Ser Pro Ser Ser Leu Ser Ala Ser Val Gly
1 5 10 15

Asp Arg Val Ile Ile Thr Cys Arg Ala Ser Gln Asn Ile Ser Ser Tyr
20 25 30

Leu Ile Trp Tyr Gln Gln Lys Pro Gly Lys Ala Pro Asn Leu Leu Ile
35 40 45

His Thr Thr Ser Ser Leu Gln Arg Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ala Pro Leu
85 90 95

Thr Phe Gly Gly Gly Thr Lys Val Glu Ile Lys
100 105

<210> SEQ ID NO 81
<211> LENGTH: 342
<212> TYPE: DNA
<213> ORGANISM: Homo Sapiens

<400> SEQUENCE: 81
gaggtgcagc tgttggagtc tgggggaggc ttggtacagc ctggggggtc cctgagactc 60
tcctgtgcag cctctggatt cacctttagc aactatgcca tgagctgggt ccgccaggct 120
ccagggaagg ggctggactg ggtctcagct attagtggtc gtggtggtag cacatactac 180
gcagactccg tgaagggccg gttcaccatc tccagagaca attccaagaa cacgctgttt 240
ctgctaatga acagcctgag agccgaggac acggccgtat attactgtgc gaaagcttca 300
ggggacgact ggggccaggg aaccctggtc accgtctcct ct 342

<210> SEQ ID NO 82
<211> LENGTH: 114
<212> TYPE: PRT
<213> ORGANISM: Homo Sapiens

<400> SEQUENCE: 82

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Asp Trp Val
35 40 45

Ser Ala Ile Ser Gly Arg Gly Gly Ser Thr Tyr Tyr Ala Asp Ser Val
50 55 60

Lys Gly Arg Phe Thr Ile Ser Arg Asp Asn Ser Lys Asn Thr Leu Phe
65 70 75 80

Leu Leu Met Asn Ser Leu Arg Ala Glu Asp Thr Ala Val Tyr Tyr Cys
85 90 95

Ala Lys Ala Ser Gly Asp Asp Trp Gly Gln Gly Thr Leu Val Thr Val
100 105 110

Ser Ser

<210> SEQ ID NO 83
<211> LENGTH: 330
<212> TYPE: DNA
<213> ORGANISM: Homo Sapiens

<400> SEQUENCE: 83
cagtctgtgc tgactcagcc accctcagcg tctgggaccc ccggacagag ggtcaccatc 60
tcttgttctg gaagcagctc caacatcgga agtaatactg taaactggta ccagcagctc 120
ccaggaacgg cccccaaact cctcatctat cttaataatc agcggccctc aggggtccct 180
gaccgattct ctggctccaa gtctggcacc tcagcctccc tggccatcag tgggctccag 240
tctgaggatg aggctgatta ttactgttca gcatgggatg acagcctgaa tggttatgtc 300
ttcggaactg ggaccaaggt caccgtccta 330

<210> SEQ ID NO 84
<211> LENGTH: 110
<212> TYPE: PRT
<213> ORGANISM: Homo Sapiens

<400> SEQUENCE: 84

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Leu Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ala Trp Asp Asp Ser Leu 85 90 95

Asn Gly Tyr Val Phe Gly Thr Gly Thr Lys Val Thr Val Leu
100 105 110

<210> SEQ ID NO 85
<211> LENGTH: 342
<212> TYPE: DNA
<213> ORGANISM: Homo Sapiens

<400> SEQUENCE: 85
gaggtgcagc tgttggagtc tgggggaggc ttggttcagc ctggggggtc cctgagactc 60
tcctgtgcag cctctggatt cacctttagc aactatgcct tgagctgggt ccgccaggct 120
ccagggaagg ggctggagtg ggtctcagct attagtggaa gtggtcgtaa cacatactac 180
gcagactccg tgaagggccg gttcaccctc tccagagaca attccaagaa cacgctgttt 240
ctgcaaatga acagcctgag agccgaggac acggccgtat attactgtgc gaaagcctca 300
ggggacaact ggggccaggg aaccctggtc accgtctcct ca 342

<210> SEQ ID NO 86
<211> LENGTH: 114
<212> TYPE: PRT
<213> ORGANISM: Homo Sapiens

<400> SEQUENCE: 86

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Leu Ser Trp Val Arg Gln Ala Pro Gly Lys Gly Leu Glu Trp Val
35 40 45

Ser Ala Ile Ser Gly Ser Gly Arg Asn Thr Tyr Tyr Ala Asp Ser Val
50 55 60

Lys Gly Arg Phe Thr Leu Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Lys Ala Ser Gly Asp Asn Trp Gly Gln Gly Thr Leu Val Thr Val
100 105 110

Ser Ser

<210> SEQ ID NO 87
<211> LENGTH: 330
<212> TYPE: DNA
<213> ORGANISM: Homo Sapiens

<400> SEQUENCE: 87
cagtctgtgc tgactcagcc accctcagcg tctgggaccc ccggacagag ggtcaccatc 60
tcttgttctg gaagcagctc caacatcgga agtaatactg taaactggta ccagcagctc 120
ccaggaacgg cccccaaact cctcatctat cttaataatc agcggccctc aggggtccct 180
gaccgattct ctggctccaa gtctggcacc tcagcctccc tggccatcag tgggctccag 240
tctgaggatg aggctgatta ttactgttca gcatgggatg acagcctgaa tggttatgtc 300
ttcggaactg ggaccaaggt caccgtccta 330

<210> SEQ ID NO 88
<211> LENGTH: 110
<212> TYPE: PRT

<213> ORGANISM: Homo Sapiens

<400> SEQUENCE: 88

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Leu Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ala Trp Asp Asp Ser Leu
85 90 95

Asn Gly Tyr Val Phe Gly Thr Gly Thr Lys Val Thr Val Leu
100 105 110

<210> SEQ ID NO 89
<211> LENGTH: 342
<212> TYPE: DNA
<213> ORGANISM: Homo Sapiens

<400> SEQUENCE: 89
gaggtgcagc tgttggagtc tgggggaggc ttggtacagc ctggggggtc cctgagactc 60
tcctgtgcag cctctggatt cacctttagc aactatgcca tgaactgggt ccgccaggct 120
ccagggaagg ggctggagtg ggtctcagct attagtggtg gtggtggtaa cacatactac 180
gcagactccg tgaagggccg gttcaccatc tccagagaca attccaagaa cacgctgtat 240
ctgcaaatga acaggctgag agccgaggac acggccgtat attactgtgc gaaagcttca 300
ggggacgact ggggccaggg aaccttggtc accgtctcct ca 342

<210> SEQ ID NO 90
<211> LENGTH: 114
<212> TYPE: PRT
<213> ORGANISM: Homo Sapiens

<400> SEQUENCE: 90

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Asn Trp Val Arg Gln Ala Pro Gly Lys Gly Leu Glu Trp Val
35 40 45

Ser Ala Ile Ser Gly Gly Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Arg Leu Arg Ala Glu Asp Thr Ala Val Tyr Tyr Cys
85 90 95

Ala Lys Ala Ser Gly Asp Asp Trp Gly Gln Gly Thr Leu Val Thr Val
100 105 110

Ser Ser

<210> SEQ ID NO 91
<211> LENGTH: 330
<212> TYPE: DNA

<213> ORGANISM: Homo Sapiens

<400> SEQUENCE: 91

```
cagtctgtgc tgactcagcc accctcagcg tctgggaccc ccgggcagag ggtcaccatc     60

tcttgttctg gaagcagctc caacatcgga agtaatactg taaactggta ccagcaactc    120

ccaggaacgg cccccaaact cctcatctat cttaataatc agcggccctc aggggtccct    180

gaccgattct ctggctccaa gtctggcacc tcagcctccc tggccatcag tgggctccag    240

tctgaggatg aggctgattt ttactgtgca gcatgggatg acagcctgaa tggttatgtc    300

ttcggaactg ggaccaaggt caccgtccta                                     330
```

<210> SEQ ID NO 92
<211> LENGTH: 110
<212> TYPE: PRT
<213> ORGANISM: Homo Sapiens

<400> SEQUENCE: 92

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Phe Tyr Cys Ala Ala Trp Asp Asp Ser Leu
                85                  90                  95

Asn Gly Tyr Val Phe Gly Thr Gly Thr Lys Val Thr Val Leu
            100                 105                 110
```

<210> SEQ ID NO 93
<211> LENGTH: 342
<212> TYPE: DNA
<213> ORGANISM: Homo Sapiens

<400> SEQUENCE: 93

```
gaggtgcagc tgttggagtc tgggggaggc ttggtacagc ctggggggtc cctgagactc     60

tcctgtgcag cctctggatt cacctttagc aactatgcca tgagctgggt ccgccaggct    120

ccagggaagg ggctggagtg ggtctcagct attagtggta gtggtggtat cacatactac    180

gcagactccg tgaagggccg gttcaccatc tccagagaca attccaagaa cacgctgttt    240

ctgcaaatga acagcctgag agccgaggac acggccgtat attactgtgc gaaagcctca    300

ggggacaact ggggccaggg aaccctggtc agcgtctcct ca                       342
```

<210> SEQ ID NO 94
<211> LENGTH: 114
<212> TYPE: PRT
<213> ORGANISM: Homo Sapiens

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
```

```
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Ala Ser Gly Asp Asn Trp Gly Gln Gly Thr Leu Val Ser Val
            100                 105                 110

Ser Ser


<210> SEQ ID NO 95
<211> LENGTH: 330
<212> TYPE: DNA
<213> ORGANISM: Homo Sapiens

<400> SEQUENCE: 95

cagtctgtgc tgactcagcc accctcagcg tctgggaccc ccggacagag ggtcaccatc      60

tcttgttctg gaagcagctc caacatcgga agtaatactg taaactggta ccagcagctc     120

ccaggaacgg cccccaaact cctcatctat cttaataatc agcggccctc aggggtccct     180

ggccgattct ctggctccaa gtctggcacc tcagcctccc tggccatcag tgggctccag     240

tctgaggatg aggctgatta ttactgttca gcatgggatg acagcctgaa tggttatgtc     300

ttcggaactg gaaccaaggt caccgtccta                                      330


<210> SEQ ID NO 96
<211> LENGTH: 110
<212> TYPE: PRT
<213> ORGANISM: Homo Sapiens

<400> SEQUENCE: 96

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Gly Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asp Ser Leu
                85                  90                  95

Asn Gly Tyr Val Phe Gly Thr Gly Thr Lys Val Thr Val Leu
            100                 105                 110


<210> SEQ ID NO 97
<211> LENGTH: 342
<212> TYPE: DNA
<213> ORGANISM: Homo Sapiens

<400> SEQUENCE: 97

gaggtgcagc tgttggagtc tgggggaacc ttggtacagc ctggggggtc cctgagactc      60

tcctgtgcag cctctggatt cacctttagc aactatgcca tgagctgggt ccgtcaggct     120

ccagggaagg ggctggagtg ggtctcagct attagtggtc gtgctggtag cacatactac     180

gcagactccg tgaagggccg gttcaccatc tccagagaca attccaagaa cacgctgttt     240
```

ctgcaaatga acagcctgag agccgaggac acggccgtat attactgtgc gaaagcttca 300
ggggacgact ggggccaggg aaccctggtc accgtctcct ca 342

<210> SEQ ID NO 98
<211> LENGTH: 114
<212> TYPE: PRT
<213> ORGANISM: Homo Sapiens

<400> SEQUENCE: 98

Glu Val Gln Leu Leu Glu Ser Gly Gly Thr Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Ala Ile Ser Gly Arg Ala Gly Ser Thr Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Lys Ala Ser Gly Asp Asp Trp Gly Gln Gly Thr Leu Val Thr Val
100 105 110

Ser Ser

<210> SEQ ID NO 99
<211> LENGTH: 330
<212> TYPE: DNA
<213> ORGANISM: Homo Sapiens

<400> SEQUENCE: 99
cagtctgtgc tgactcagcc accctcagcg tctgggaccc ccggacagag ggtcaccatc 60
tcttgttctg gaagcagctc caacatcgga agtaatactg taaactggta ccatcagctc 120
ccaggaacgg cccccaaact cctcatctat cttaataatc agcggccctc aggggtccct 180
gaccgattct ctggctccaa gtctggcacc tcagcctccc tggccatcag tgggctccag 240
tctgaggatg aggctgatta ttactgttca gcatgggatg acagcctgaa tggttatgtc 300
ttcggaactg ggaccaaggt caccgtccta 330

<210> SEQ ID NO 100
<211> LENGTH: 110
<212> TYPE: PRT
<213> ORGANISM: Homo Sapiens

<400> SEQUENCE: 100

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr His Gln Leu Pro Gly Thr Ala Pro Lys Leu Leu
35 40 45

Ile Tyr Leu Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ala Trp Asp Asp Ser Leu 85 90 95

Asn Gly Tyr Val Phe Gly Thr Gly Thr Lys Val Thr Val Leu
100 105 110

<210> SEQ ID NO 101
<211> LENGTH: 360
<212> TYPE: DNA
<213> ORGANISM: Homo Sapiens

<400> SEQUENCE: 101
caggtgcagc tgcaggagtc gggcccagga ctggtgaagc cttcggagac cctgtccctc 60
acctgcactg tctctggtgg ctccatcagt agttacttct ggagctggat ccggcagccc 120
gccgggaagg gactggagtg gattgggcgt atctatttca gtgggcgcac caactacaac 180
ccctccctca agagtcgggt caccatgtca gtagagacgt ccaagaacca gttctccctg 240
aagctgaact ctgtgaccgc cgcggacacg gccgtgtatt attgtgcgag agatggaggg 300
tggaactacg acgttgcctt tgactactgg ggccagggaa ccctggtcac cgtctcctca 360

<210> SEQ ID NO 102
<211> LENGTH: 120
<212> TYPE: PRT
<213> ORGANISM: Homo Sapiens

<400> SEQUENCE: 102

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Phe Trp Ser Trp Ile Arg Gln Pro Ala Gly Lys Gly Leu Glu Trp Ile
35 40 45

Gly Arg Ile Tyr Phe Ser Gly Arg Thr Asn Tyr Asn Pro Ser Leu Lys
50 55 60

Ser Arg Val Thr Met Ser Val Glu Thr Ser Lys Asn Gln Phe Ser Leu
65 70 75 80

Lys Leu Asn Ser Val Thr Ala Ala Asp Thr Ala Val Tyr Tyr Cys Ala
85 90 95

Arg Asp Gly Gly Trp Asn Tyr Asp Val Ala Phe Asp Tyr Trp Gly Gln
100 105 110

Gly Thr Leu Val Thr Val Ser Ser
115 120

<210> SEQ ID NO 103
<211> LENGTH: 345
<212> TYPE: DNA
<213> ORGANISM: Homo Sapiens

<400> SEQUENCE: 103
caggctgtgc tgactcagcc gtcttccctc tctgcatctc ctggagcatc agccagtctc 60
acctgcacct tacgcagtgg catcaatgtt ggtacctaca ggatatactg gtaccagcag 120
aagccaggga gtcctcccca gtatctcctg aggtacaaat cagactcaga tcagcttcag 180
ggctctggag tccccagccg cttctctgga tccaaagatg cttcggccaa tgcagggatt 240
ttactcatct ctgggctcca gtctgaggat gaggctgact attactgtat ggtttggcac 300
agcaacactt gggtgttcgg cggagggacc aagctgaccg tccta 345

<210> SEQ ID NO 104
<211> LENGTH: 115

<212> TYPE: PRT
<213> ORGANISM: Homo Sapiens

<400> SEQUENCE: 104

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Gln Leu Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Val Trp His Ser Asn Thr Trp Val Phe Gly Gly Gly Thr Lys Leu
            100                 105                 110

Thr Val Leu
        115

<210> SEQ ID NO 105
<211> LENGTH: 366
<212> TYPE: DNA
<213> ORGANISM: Homo Sapiens

<400> SEQUENCE: 105
caggtacagc tggtggagtc tgggggaggc gtggtccagc ctgggaggtc cctgagactc      60
tcctgtgcag cgtctggatt caccttcagt acctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaagac acggctgtgt attactgtgc gtgttcttat     300
tggaacgacg actactatta cggtatggac gtctggggcc aagggaccac ggtcaccgtc     360
tcctca                                                                366

<210> SEQ ID NO 106
<211> LENGTH: 122
<212> TYPE: PRT
<213> ORGANISM: Homo Sapiens

<400> SEQUENCE: 106

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Cys Ser Tyr Trp Asn Asp Asp Tyr Tyr Tyr Gly Met Asp Val Trp
            100                 105                 110

Gly Gln Gly Thr Thr Val Thr Val Ser Ser
115 120

<210> SEQ ID NO 107
<211> LENGTH: 333
<212> TYPE: DNA
<213> ORGANISM: Homo Sapiens

<400> SEQUENCE: 107
cagcctgtgc tgactcaatc atcctctgcc tctgcttccc tgggatcctc ggtcaagctc 60
acctgcactc tgagcagtgg gcacagtagc tacatcatcg catggcatca gcagcagcca 120
gggaaggccc ctcggtactt gatgaagctt gaaggtagtg gaagctacaa caaggggagc 180
ggagttcctg atcgcttctc aggctccagc tctggggctg accgctacct caccatctcc 240
aacctccagt ttgaggatga ggctgattat tactgtgaga cctgggacag ttacactgtg 300
gtattcggcg gagggaccaa gctgaccgtc cta 333

<210> SEQ ID NO 108
<211> LENGTH: 111
<212> TYPE: PRT
<213> ORGANISM: Homo Sapiens

<400> SEQUENCE: 108

Gln Pro Val Leu Thr Gln Ser Ser Ser Ala Ser Ala Ser Leu Gly Ser
1 5 10 15

Ser Val Lys Leu Thr Cys Thr Leu Ser Ser Gly His Ser Ser Tyr Ile
20 25 30

Ile Ala Trp His Gln Gln Gln Pro Gly Lys Ala Pro Arg Tyr Leu Met
35 40 45

Lys Leu Glu Gly Ser Gly Ser Tyr Asn Lys Gly Ser Gly Val Pro Asp
50 55 60

Arg Phe Ser Gly Ser Ser Ser Gly Ala Asp Arg Tyr Leu Thr Ile Ser
65 70 75 80

Asn Leu Gln Phe Glu Asp Glu Ala Asp Tyr Tyr Cys Glu Thr Trp Asp
85 90 95

Ser Tyr Thr Val Val Phe Gly Gly Gly Thr Lys Leu Thr Val Leu
100 105 110

<210> SEQ ID NO 109
<211> LENGTH: 115
<212> TYPE: PRT
<213> ORGANISM: Homo Sapiens

<400> SEQUENCE: 109

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Thr Gly Gln Gly Leu Glu Trp Met
35 40 45

Gly Trp Met Asn Pro Asn Ser Gly Asn Thr Gly Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Tyr Ser Trp Phe Asp Pro Trp Gly Gln Gly Thr Leu Val Thr
100 105 110

Val Ser Ser
115

<210> SEQ ID NO 110
<211> LENGTH: 121
<212> TYPE: PRT
<213> ORGANISM: Homo Sapiens

<400> SEQUENCE: 110

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Phe Trp Ser Gly Tyr Asn Trp Phe Asp Pro Trp Gly
100 105 110

Gln Gly Thr Leu Val Thr Val Ser Ser
115 120

<210> SEQ ID NO 111
<211> LENGTH: 118
<212> TYPE: PRT
<213> ORGANISM: Homo Sapiens

<400> SEQUENCE: 111

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Tyr Ser Ser Gly Trp Tyr Phe Asp Tyr Trp Gly Gln Gly Thr
100 105 110

Leu Val Thr Val Ser Ser
115

<210> SEQ ID NO 112
<211> LENGTH: 109
<212> TYPE: PRT
<213> ORGANISM: Homo Sapiens

<400> SEQUENCE: 112

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr

```
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Trp Phe Trp Gly Gln Gly Thr Leu Val Thr Val Ser Ser
            100                 105


<210> SEQ ID NO 113
<211> LENGTH: 109
<212> TYPE: PRT
<213> ORGANISM: Homo Sapiens

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105


<210> SEQ ID NO 114
<211> LENGTH: 114
<212> TYPE: PRT
<213> ORGANISM: Homo Sapiens

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Thr Asp Tyr Trp Gly Gln Gly Thr Leu Val Thr Val
            100                 105                 110

Ser Ser


<210> SEQ ID NO 115
<211> LENGTH: 117
```

<212> TYPE: PRT
<213> ORGANISM: Homo Sapiens

<400> SEQUENCE: 115

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Trp Asn Tyr Tyr Tyr Gly Met Asp Val Trp Gly Gln Gly Thr Thr
100 105 110

Val Thr Val Ser Ser
115

<210> SEQ ID NO 116
<211> LENGTH: 124
<212> TYPE: PRT
<213> ORGANISM: Homo Sapiens

<400> SEQUENCE: 116

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Met Val Arg Gly Val Ile Ile Tyr Tyr Tyr Gly Met Asp
100 105 110

Val Trp Gly Gln Gly Thr Thr Val Thr Val Ser Ser
115 120

<210> SEQ ID NO 117
<211> LENGTH: 114
<212> TYPE: PRT
<213> ORGANISM: Homo Sapiens

<400> SEQUENCE: 117

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Trp Asn Tyr Phe Asp Tyr Trp Gly Gln Gly Thr Leu Val Thr Val
100 105 110

Ser Ser

<210> SEQ ID NO 118
<211> LENGTH: 118
<212> TYPE: PRT
<213> ORGANISM: Homo Sapiens

<400> SEQUENCE: 118

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Ser Ser Ser Trp Trp Tyr Phe Asp Leu Trp Gly Arg Gly Thr
100 105 110

Leu Val Thr Val Ser Ser
115

<210> SEQ ID NO 119
<211> LENGTH: 116
<212> TYPE: PRT
<213> ORGANISM: Homo Sapiens

<400> SEQUENCE: 119

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Gln Leu Val Tyr Phe Asp Tyr Trp Gly Gln Gly Thr Leu Val
100 105 110

Thr Val Ser Ser
115

<210> SEQ ID NO 120
<211> LENGTH: 117
<212> TYPE: PRT

<213> ORGANISM: Homo Sapiens

<400> SEQUENCE: 120

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gln Leu Val Tyr Phe Asp Tyr Trp Gly Gln Gly Thr Leu
100 105 110

Val Thr Val Ser Ser
115

<210> SEQ ID NO 121
<211> LENGTH: 112
<212> TYPE: PRT
<213> ORGANISM: Homo Sapiens

<400> SEQUENCE: 121

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Met Gln Ala
85 90 95

Thr Gln Phe Pro Leu Thr Phe Gly Gly Gly Thr Lys Val Glu Ile Lys
100 105 110

<210> SEQ ID NO 122
<211> LENGTH: 109
<212> TYPE: PRT
<213> ORGANISM: Homo Sapiens

<400> SEQUENCE: 122

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

```
Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105


<210> SEQ ID NO 123
<211> LENGTH: 105
<212> TYPE: PRT
<213> ORGANISM: Homo Sapiens

<400> SEQUENCE: 123

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ile Thr Phe
                85                  90                  95

Gly Gln Gly Thr Arg Leu Glu Ile Lys
            100                 105


<210> SEQ ID NO 124
<211> LENGTH: 107
<212> TYPE: PRT
<213> ORGANISM: Homo Sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105


<210> SEQ ID NO 125
<211> LENGTH: 113
<212> TYPE: PRT
<213> ORGANISM: Homo Sapiens

<400> SEQUENCE: 125

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45
```

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 126
<211> LENGTH: 107
<212> TYPE: PRT
<213> ORGANISM: Homo Sapiens

<400> SEQUENCE: 126

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 127
<211> LENGTH: 105
<212> TYPE: PRT
<213> ORGANISM: Homo Sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Thr Phe
                85                  90                  95

Gly Gly Gly Thr Lys Val Glu Ile Lys
            100                 105

<210> SEQ ID NO 128
<211> LENGTH: 110
<212> TYPE: PRT
<213> ORGANISM: Homo Sapiens

<400> SEQUENCE: 128

-continued

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 129
<211> LENGTH: 112
<212> TYPE: PRT
<213> ORGANISM: Homo Sapiens

<400> SEQUENCE: 129

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Val Phe Gly Gly Gly Thr Lys Leu Thr Val Leu
            100                 105                 110

<210> SEQ ID NO 130
<211> LENGTH: 111
<212> TYPE: PRT
<213> ORGANISM: Homo Sapiens

<400> SEQUENCE: 130

Gln Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp His Gln Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Arg Tyr Leu Thr Ile Ser
65                  70                  75                  80

Asn Leu Gln Phe Glu Asp Glu Ala Asp Tyr Tyr Cys Glu Thr Trp Asp
                85                  90                  95

Ser Asn Thr Val Val Phe Gly Gly Gly Thr Lys Leu Thr Val Leu
            100                 105                 110

<210> SEQ ID NO 131
<211> LENGTH: 114
<212> TYPE: PRT
<213> ORGANISM: Homo Sapiens

<400> SEQUENCE: 131

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Gly Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ser Lys Val Ala Thr Asp Tyr Trp Gly Gln Gly Thr Leu Val Thr Val
100 105 110

Ser Ser

<210> SEQ ID NO 132
<211> LENGTH: 119
<212> TYPE: PRT
<213> ORGANISM: Homo Sapiens

<400> SEQUENCE: 132

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ser Ser Ser Trp Trp Tyr Phe Asp Leu Trp Gly Arg Gly
100 105 110

Thr Leu Val Thr Val Ser Ser
115

<210> SEQ ID NO 133
<211> LENGTH: 114
<212> TYPE: PRT
<213> ORGANISM: Homo Sapiens

<400> SEQUENCE: 133

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Asp Tyr Trp Gly Gln Gly Thr Leu Val Thr Val
            100                 105                 110

Ser Ser


<210> SEQ ID NO 134
<211> LENGTH: 118
<212> TYPE: PRT
<213> ORGANISM: Homo Sapiens

<400> SEQUENCE: 134

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gln Leu Val Tyr Phe Asp Tyr Trp Gly Gln Gly Thr
            100                 105                 110

Leu Val Thr Val Ser Ser
        115


<210> SEQ ID NO 135
<211> LENGTH: 118
<212> TYPE: PRT
<213> ORGANISM: Homo Sapiens

<400> SEQUENCE: 135

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gln Leu Val Tyr Phe Asp Tyr Trp Gly Gln Gly Thr
            100                 105                 110

Leu Val Thr Val Ser Ser
        115


<210> SEQ ID NO 136
```

<211> LENGTH: 114
<212> TYPE: PRT
<213> ORGANISM: Homo Sapiens

<400> SEQUENCE: 136

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Gly Glu Leu Trp Gly Gln Gly Thr Leu Val Thr Val
            100                 105                 110

Ser Ser
```

<210> SEQ ID NO 137
<211> LENGTH: 114
<212> TYPE: PRT
<213> ORGANISM: Homo Sapiens

<400> SEQUENCE: 137

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Asn Tyr Phe Asp Tyr Trp Gly Gln Gly Thr Leu Val Thr Val
            100                 105                 110

Ser Ser
```

<210> SEQ ID NO 138
<211> LENGTH: 116
<212> TYPE: PRT
<213> ORGANISM: Homo Sapiens

<400> SEQUENCE: 138

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60
```

```
Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Trp Phe Asp Pro Trp Gly Gln Gly Thr Leu Val
            100                 105                 110

Thr Val Ser Ser
        115


<210> SEQ ID NO 139
<211> LENGTH: 119
<212> TYPE: PRT
<213> ORGANISM: Homo Sapiens

<400> SEQUENCE: 139

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Ser Gly Trp Tyr Tyr Phe Asp Tyr Trp Gly Gln Gly
            100                 105                 110

Thr Leu Val Thr Val Ser Ser
        115


<210> SEQ ID NO 140
<211> LENGTH: 121
<212> TYPE: PRT
<213> ORGANISM: Homo Sapiens

<400> SEQUENCE: 140

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Trp Ser Gly Tyr Tyr Asn Trp Phe Asp Pro Trp Gly
            100                 105                 110

Gln Gly Thr Leu Val Thr Val Ser Ser
        115                 120


<210> SEQ ID NO 141
<211> LENGTH: 124
<212> TYPE: PRT
```

<213> ORGANISM: Homo Sapiens

<400> SEQUENCE: 141

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Thr Met Val Arg Gly Val Ile Ile Tyr Tyr Tyr Gly Met Asp
100 105 110

Val Trp Gly Gln Gly Thr Thr Val Thr Val Ser Ser
115 120

<210> SEQ ID NO 142
<211> LENGTH: 119
<212> TYPE: PRT
<213> ORGANISM: Homo Sapiens

<400> SEQUENCE: 142

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Trp Asn Asp Tyr Tyr Tyr Gly Met Asp Val Trp Gly Gln Gly
100 105 110

Thr Thr Val Thr Val Ser Ser
115

<210> SEQ ID NO 143
<211> LENGTH: 114
<212> TYPE: PRT
<213> ORGANISM: Homo Sapiens

<400> SEQUENCE: 143

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Thr Asp Tyr Trp Gly Gln Gly Thr Leu Val Thr Val
            100                 105                 110

Ser Ser


<210> SEQ ID NO 144
<211> LENGTH: 113
<212> TYPE: PRT
<213> ORGANISM: Homo Sapiens

<400> SEQUENCE: 144

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys


<210> SEQ ID NO 145
<211> LENGTH: 110
<212> TYPE: PRT
<213> ORGANISM: Homo Sapiens

<400> SEQUENCE: 145

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110


<210> SEQ ID NO 146
<211> LENGTH: 108
<212> TYPE: PRT
<213> ORGANISM: Homo Sapiens

<400> SEQUENCE: 146

Glu Ile Val Leu Thr Gln Ser Pro Gly Thr Leu Ser Leu Ser Pro Gly
```

-continued

```
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105


<210> SEQ ID NO 147
<211> LENGTH: 107
<212> TYPE: PRT
<213> ORGANISM: Homo Sapiens

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105


<210> SEQ ID NO 148
<211> LENGTH: 115
<212> TYPE: PRT
<213> ORGANISM: Homo Sapiens

<400> SEQUENCE: 148

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser Val Phe Gly Gly Gly Thr Lys Leu
            100                 105                 110

Thr Val Leu
        115
```

<210> SEQ ID NO 149
<211> LENGTH: 109
<212> TYPE: PRT
<213> ORGANISM: Homo Sapiens

<400> SEQUENCE: 149

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105
```

<210> SEQ ID NO 150
<211> LENGTH: 107
<212> TYPE: PRT
<213> ORGANISM: Homo Sapiens

<400> SEQUENCE: 150

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105
```

<210> SEQ ID NO 151
<211> LENGTH: 107
<212> TYPE: PRT
<213> ORGANISM: Homo Sapiens

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Val Glu Ile Lys
100 105

<210> SEQ ID NO 152
<211> LENGTH: 112
<212> TYPE: PRT
<213> ORGANISM: Homo Sapiens

<400> SEQUENCE: 152

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Met Gln Ala
85 90 95

Thr Gln Phe Pro Leu Thr Phe Gly Gly Gly Thr Lys Val Glu Ile Lys
100 105 110

<210> SEQ ID NO 153
<211> LENGTH: 111
<212> TYPE: PRT
<213> ORGANISM: Homo Sapiens

<400> SEQUENCE: 153

Gln Pro Val Leu Thr Gln Ser Ser Ser Ala Ser Ala Ser Leu Gly Ser
1 5 10 15

Ser Val Lys Leu Thr Cys Thr Leu Ser Ser Gly His Ser Ser Tyr Ile
20 25 30

Ile Ala Trp His Gln Gln Gln Pro Gly Lys Ala Pro Arg Tyr Leu Met
35 40 45

Lys Leu Glu Gly Ser Gly Ser Tyr Asn Lys Gly Ser Gly Val Pro Asp
50 55 60

Arg Phe Ser Gly Ser Ser Ser Gly Ala Asp Arg Tyr Leu Thr Ile Ser
65 70 75 80

Asn Leu Gln Leu Glu Asp Glu Ala Asp Tyr Tyr Cys Glu Thr Trp Asp
85 90 95

Ser Asn Thr Val Val Phe Gly Gly Gly Thr Lys Leu Thr Val Leu
100 105 110